US011472806B2

(12) United States Patent
Blayo et al.

(10) Patent No.: US 11,472,806 B2
(45) Date of Patent: Oct. 18, 2022

(54) SUBSTITUTED HETEROCYCLIC COMPOUNDS AS ALLOSTERIC MODULATORS OF GROUP II METABOTROPIC GLUTAMATE RECEPTORS

(71) Applicant: Domain Therapeutics, Illkirch Graffenstaden (FR)

(72) Inventors: Anne-Laure Blayo, Souffelweyersheim (FR); Thomas Catelain, Strasbourg (FR); Ismet Dorange, Stockholm (SE); Cédric Genet, Kientzheim (FR); Baptiste Manteau, Ways (BE); Stanislas Mayer, Eschau (FR); Stephan Schann, Illkirch (FR)

(73) Assignee: Domain Therapeutics, Illkirch Graffenstaden (FR)

( * ) Notice: Subject to any disclaimer, the term of this patent is extended or adjusted under 35 U.S.C. 154(b) by 0 days.

(21) Appl. No.: 16/612,866

(22) PCT Filed: May 14, 2018

(86) PCT No.: PCT/EP2018/062409
§ 371 (c)(1),
(2) Date: Nov. 12, 2019

(87) PCT Pub. No.: WO2018/206820
PCT Pub. Date: Nov. 15, 2018

(65) Prior Publication Data
US 2020/0140438 A1 May 7, 2020

(30) Foreign Application Priority Data
May 12, 2017 (EP) ..................................... 17170865

(51) Int. Cl.
*C07D 471/14* (2006.01)
*C07D 223/18* (2006.01)
(Continued)

(52) U.S. Cl.
CPC ......... *C07D 471/14* (2013.01); *C07D 223/18* (2013.01); *C07D 401/10* (2013.01);
(Continued)

(58) Field of Classification Search
CPC .. C07D 471/14; C07D 233/18; C07D 401/10; C07D 401/14; C07D 471/04; C07D 487/04; C07D 487/14; C07D 495/04
See application file for complete search history.

(56) References Cited

U.S. PATENT DOCUMENTS 4,153,799 A    5/1979  Gilman et al.
4,863,920 A    9/1989  Hunkeler et al.
2015/0105381 A1 4/2015  Mayer et al.

FOREIGN PATENT DOCUMENTS

CN       104540828     4/2015
WO    WO 2008/021545   2/2008
(Continued)

OTHER PUBLICATIONS

Anzini et al., "5,6-Dihydro-5-{4-[4-(2-methoxyphenyl)-1-piperazinyl]butyl}-4H-pyrrolo[1,2-a] {1,4} benzodiazepine-4,6-dione and related compounds as new 5-HT1A receptor ligands", *Medicinal Chemistry Research*, Birkhaeuser, Boston, US, XP009188082, vol. 3(4) pp. 249-256 (Jan. 1, 1993).

(Continued)

*Primary Examiner* — Alicia L Otton
(74) *Attorney, Agent, or Firm* — Parker Highlander PLLC

(57) ABSTRACT

The present invention provides novel heterocyclic compounds of the general formula (I), including novel compounds of formula (Ia), and pharmaceutical compositions containing them. Moreover, the compounds of formula (I) or (Ia) and the pharmaceutical compositions containing them are provided for use in the treatment and/or prophylaxis of conditions associated with altered glutamatergic signalling and/or functions, and/or conditions which can be affected by alteration of glutamate level or signalling in mammals. The compounds of formula (I) or (Ia) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders. The present invention further provides compounds of formula (I) or (Ia) that are modulators of metabotropic glutamate receptors (mGluRs), particularly positive allosteric modulators of mGluRs, and more specifically positive allosteric modulators of mGluR3.

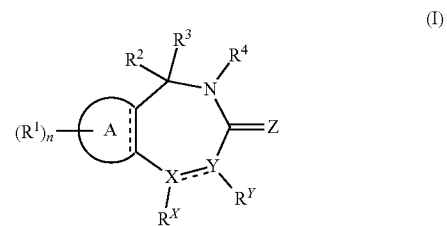

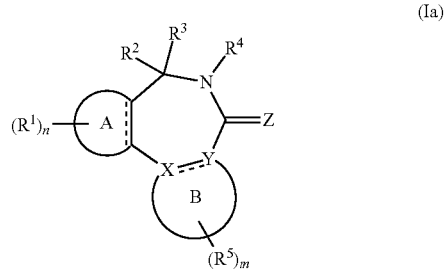

14 Claims, No Drawings

(51) Int. Cl.
| | |
|---|---|
| C07D 401/10 | (2006.01) |
| C07D 401/14 | (2006.01) |
| C07D 471/04 | (2006.01) |
| C07D 487/04 | (2006.01) |
| C07D 487/14 | (2006.01) |
| C07D 495/04 | (2006.01) |
| G01N 33/68 | (2006.01) |

(52) U.S. Cl.
CPC ......... *C07D 401/14* (2013.01); *C07D 471/04* (2013.01); *C07D 487/04* (2013.01); *C07D 487/14* (2013.01); *C07D 495/04* (2013.01); *G01N 33/6872* (2013.01)

(56) References Cited

FOREIGN PATENT DOCUMENTS

| WO | WO 2008/082887 | 7/2008 |
|---|---|---|
| WO | WO 2013/192347 | 12/2013 |
| WO | WO 2014/117919 | 8/2014 |
| WO | WO 2016-046404 | 3/2016 |
| WO | WO 2017/081483 | 5/2017 |

OTHER PUBLICATIONS

Bertelli et al., "1,2,3-Triazolo[1,5-a][1,4]- and 1,2,3-triazolo[1,5-a][1,5]benzodiazepine derivatives: Synthesis and benzodiazepine receptor binding", *IL Farmaco*, XP055242581, vol. 53(4), pp. 305-311 (Apr. 1, 1998).

Cannon, "Chapter Nineteen in Burger's Medicinal Chemistry and Drug Discovery," Fifth Edition, vol. 1: Principles and Practice, Wiley-Interscience 1995, pp. 783-802, 784.

Dick RM, "Chapter 2. Pharmacodynamics: The Study of Drug Action," In Ouellette R, Joyce JA. Pharmacology for Nurse Anesthesiology. Jones & Bartlett Learning: pp. 17-26, 2011.

Patani and LaVoie, "Biosisosterism: A Rational Approach in Drug Design,"Chemical Reviews, 1996, No. 96, No. 8, pp. 3147-3176.

PCT International Search Report and Written Opinion issued in International Application No. PCT/EP2018/062409, dated Jul. 9, 2018.

PCT International Search Report and Written Opinion issued in International Application No. PCT/GB2016/053550, dated Jan. 19, 2017.

Wang et al., "Facile synthesis of 1,4-benzodiazepin-3-ones from o-bromobenzylamines and amino acids via a cascade coupling/condensation process", *Tetrahedron*, Elsevier Science Publishers, Amsterdam, NL, XP026652574, vol. 65(44), pp. 8956-8960 (Oct. 31, 2009).

Wang et al., "Facile synthesis of 6,12b-diaza-dibenzo[a,h]azulen-7-ones and benzo[f]pyrrolo[1,2-a][1,4]diazepin-4-ones via CuI/l-proline catalyzed intramolecular N-arylation," *Tetrahedron Letters*, 52:541-543, 2011.

Wang et al., "Synthesis of benzo [6,7] [1,4] diazepino [1,2-b] indazol-7(6H)-ones and benzo [f] pyrazolo [1,5-a] [1,4] diazepin-4-one s via CuI/l-proline catalyzed intramolecular N2-arylation", *Tetrahedron Letters*, XP055242623, vol. 56(8), pp. 1030-1033, (Feb. 1, 2015).

SUBSTITUTED HETEROCYCLIC COMPOUNDS AS ALLOSTERIC MODULATORS OF GROUP II METABOTROPIC GLUTAMATE RECEPTORS

This application is a national phase application under 35 U.S.C. § 371 of International Application No. PCT/EP2018/062409, filed May 14, 2018, which claims priority to European Application No. 17170865.4, filed May 12, 2017, the entire contents of each of which are hereby incorporated by reference.

The present invention provides novel heterocyclic compounds of the general formula (I), including novel compounds of formula (Ia), and pharmaceutical compositions containing them. Moreover, the compounds of formula (I) or (Ia) and the pharmaceutical compositions containing them are provided for use in the treatment and/or prophylaxis of conditions associated with altered glutamatergic signalling and/or functions, and/or conditions which can be affected by alteration of glutamate level or signalling in mammals. The compounds of formula (I) or (Ia) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders. The present invention further provides compounds of formula (I) or (Ia) that are modulators of metabotropic glutamate receptors (mGluRs), particularly positive allosteric modulators of mGluRs, and more specifically positive allosteric modulators of mGluR3.

Glutamatergic pathways have been shown to be involved in the physiopathology of a number of neuronal damages and injuries. Many nervous system disorders including epilepsy and chronic or acute degenerative processes such as for example Alzheimer's disease, Huntington's disease, Parkinson's disease and amyotrophic lateral sclerosis (Mattson M P., *Neuromolecular Med.*, 3(2), 65-94, 2003), but also AIDS-induced dementia, multiple sclerosis, spinal muscular atrophy, retinopathy, stroke, ischemia, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatal dopaminergic neurons, could be mediated by over-stimulation of the glutamate receptors (Stephans S E and Yamamoto B K, *Synapse* 17(3), 203-9, 1994). Antidepressant and anxiolytic-like effects of compounds acting on glutamate have also been observed in mice, suggesting that glutamatergic transmission is implicated in the pathophysiology of affective disorders such as major depression, schizophrenia and anxiety (Palucha A et al., *Pharmacol. Ther.* 115(1), 116-47, 2007; Cryan J F et al., *Eur. J. Neurosc.* 17(11), 2409-17, 2003; Conn P J et al., *Trends Pharmacol. Sci.* 30(1), 25-31, 2009). Consequently, any compound able to modulate glutamatergic signalling or function could constitute a promising therapeutic agent for many disorders of the nervous system.

Moreover, compounds modulating glutamate level or signalling may be of great therapeutic value for diseases and/or disorders not directly mediated by glutamate levels and/or glutamate receptors malfunctioning, but which could be affected by alteration of glutamate levels or signalling.

In the central nervous system (CNS), L-glutamate (Glu) is the main excitatory neurotransmitter and is referred to as an excitatory amino-acid (EAA), and gamma-aminobutyric acid (GABA) is the main inhibitory neurotransmitter. The balance between excitation and inhibition is of utmost importance to CNS functions, and dysfunctions of either of the two can be related to various neurodegenerative or neurological disorders.

Glutamate is ubiquitously distributed in the nervous system in high concentrations, especially in the brain and spinal cord of mammals, where it is working at a variety of excitatory synapses and is thus involved in virtually all physiological functions such as motor control, vision, central control of heart, and processes of learning and memory. However, a large number of studies have established that cellular communication involving glutamate can also lead to a mechanism of cell destruction. This combination of neuroexcitatory activities and neurotoxic properties is called excitotoxicity.

Glutamate operates through two classes of receptors (Bräuner-Osborne H et al., *J. Med. Chem.* 43(14), 2609-45, 2000). The first class is directly coupled to the opening of cation channels in the cellular membrane of the neurons, namely the ionotropic glutamate receptors (iGluRs). The iGluRs are divided in three subtypes, which are named according to the depolarizing action of their selective agonists: N-methyl-D-aspartate (NMDA), α-amino-3-hydroxy-5-methylisoxazole-4-propionic acid (AMPA), and kainic acid (KA). The second class consists of G-protein coupled receptors (GPCRs) called metabotropic glutamate receptors (mGluRs). These mGluRs are localized both pre- and post-synaptically. They are coupled to multiple second messenger systems and their roles is to regulate the activity of ionic channels or enzymes producing second messengers via G-proteins binding the GTP (Nicoletti F et al.; *Neuropharmacol.*, 60(7-8), 1017-41, 2011). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation and long-term depression of synaptic transmission, regulation of baroreceptive reflexes, spatial learning, motor learning, and postural and kinetic integration. To date, eight mGluRs have been cloned and classified in three groups according to their sequence homologies, pharmacological properties and signal transduction mechanisms. Group I is constituted of mGluR1 and mGluR5, group II of mGluR2 and mGluR3 and group III of mGluR4, mGluR6, mGluR7 and mGluR8 (Schoepp D D et al., *Neuropharmacology*, 38(10), 1431-76, 1999).

mGluR modulators can be classified in two families depending on their site of interaction with the receptor (see Bräuner-Osborne H et al., *J. Med. Chem.* 43(14), 2609-45, 2000 for review). The first family consists of orthosteric modulators (or competitive modulators) able to interact with the glutamate binding-site of the mGluRs, which is localized in the large extra-cellular N-terminal part of the receptor (about 560 amino acids). Therefore, they are glutamate analogs and constitute a highly polar family of ligand. Examples of orthosteric modulators are S-DHPG or LY-367385 for group I mGluRs, LY-354740 or LY-379268 for group II mGluRs and ACPT-I or L-AP4 for group III mGluRs. The second family of mGluRs modulators consists of allosteric modulators that interact with a topologically different site from the orthosteric site of the receptor (see Bridges T M et al., *ACS Chem Biol*, 3(9), 530-41, 2008 for review). Their action results in a modulation of the effects induced by the endogenous ligand glutamate. Examples of such allosteric modulators are Ro-674853, MPEP or JNJ16259685 for group I mGluRs and CBiPES, BINA or LY487379 for group II mGluRs and PHCCC, VU0155041 or VU0359516 for group III mGluRs.

By interacting with allosteric binding sites, mGluR allosteric modulators stabilize a receptor conformation and equilibrium shift that increases or decreases the affinity and/or efficacy of an orthosteric agonist of the receptor, without activating the receptor on its own (Bridges T M et al., *ACS Chem Biol*, 3(9), 530-41, 2008). Such modulators are respectively termed positive allosteric modulators (PAMs) and negative allosteric modulators (NAMs).

Group II mGluR activation or potentiation has been shown to be associated with positive effects in animal models of anxiety (Swanson C J., *Nat Rev Drug Discov*, 4, 131-44, 2005), schizophrenia (Conn P J et al., *Trends in Pharmacol Sci*, 30, 25-31, 2009), memory-deficit of schizophrenia (Pitsikas N and Markou A, *Neuropharmacology*, 2014, 85, 27-35), drug-addiction (Adewale A S et al.; *J Pharmacol Exp Ther*, 318, 922-31, 2006—Justinova Z et al., *Biol. Psychiatry*, 2015), chronic pain (Jones C K et al.; *Neuropharmacology*, 49 (Suppl 1), 206-18, 2005), epilepsy (Caulder E H et al., *Epilepsy Res.*, 2014, 108(2), 171-81), Huntington's disease (Reiner A et al, *Brain Research*, 2012, 161-72—Reiner A et al, *Neurobiology of disease*, 2012, 47, 75-91), Parkinson's disease (Battaglia G et al, *PLoS ONE*, 2009, 4(8), e6591—Battaglia G et al., *Neuropharmacology*, 2003, 45, 155-66) or ALS (Battaglia G et al., *Neurobiology of disease*, 2015, 74, 126-36).

Neuroprotective role of mGluR3 was described by the teams of Ferdinando Nicoletti in Italy (Corti C, et al., *J. Neurosci*, 2007, 27(31), 8297-308. Battaglia G, et al., *PLoS ONE*, 2009, 4(8), e6591). They showed that activation of mGluR3, but not mGluR2 that seems to be neurotoxic (Caraci F. et al., *Mol. Pharmacol.*, 2011, 79(3), 618-26), can 1) induce production of growth factors such as transforming growth factor β (TGF-β) and glial cell line-derived neurotrophic factor (GDNF), 2) exert neuroprotection in vitro in models of excitotoxicity and 3) protect nigro-striatal neurons in the experimental animal model of parkinsonism induced by 1-methyl-4-phenyl-1,2,3-6-tetrahydropyiridine (MPTP). Great potential of GDNF for both symptomatic and neuroprotective treatments of Parkinson's disease (PD) has already been demonstrated (Vastag, B., *Nature*, 2010, 466 (7309), 916-8). For example, it was shown that GDNF together with TGF-β exert neuroprotection in the MPTP mice model (Schober A., et al. *Neurobiol Dis*, 2006, 25(2), 378-91) or that intraputaminal infusion of GDNF attenuates parkinsonian symptoms in two clinical trials (Gill S S., *Nat Med*, 2003, 9(5), 589-95 and Slevin J T. *J. Neurosurg*. 2005, 102, 216-222). Moreover, GDNF was also shown to exert positive effects in other neurodegenerative disorders such as Alzheimer's disease (Revilla S et al., *CNS Neurosci. Ther.*, 2014, 20(11), 961-72—Pertusa M et al., *Neurobiology Aging*, 2008, 29(9), 1366-79) or Huntington's disease (Ebert A B et al., *Exp. Neurol.*, 2010, 224(1), 155-62).

Several examples of group II mGluR PAMs have already been described in research articles and patent literature (see Trabanco A A, et al., *Curr Med Chem*, 2011, 18(1), 47-68 for review). These molecules exhibit either dual mGluR2/mGluR3 PAM activity, or selective mGluR2 PAM activity. However, there is still an urgent need for novel mGluR3 PAMs, particularly PAMs that are selective for mGluR3 over mGluR2.

Syntheses of various specific pyrrolo-1,4-benzodiazepinone, imidazolo-1,4-benzodiazepinone, pyrrolidino-1,4-benzodiazepinone and pyrazolo-1,4-benzodiazepinone compounds are described in five articles dealing with organic chemistry only: Wang H et al., *Tetrahedron*, 2009, 65, 8956-8960; Wang H J et al., *Tet. Lett.*, 2011, 52, 541-543; Norris D et al., *Tet. Lett*, 2001, 42, 4297-4299; Faigl F et al., *Chirality*, 2012, 24, 532-542; and Wang H J et al., *Tet. Lett.*, 2015, 56, 1030-1033. The compounds described in these publications are not disclosed to exhibit any biological activity.

Certain pyrrolo-1,4-benzodiazepinone compounds and analogues are described in US 2008/161292 and in Miyashiro J et al., *Bioorg. Med. Chem. Lett.* 2009, 19, 4050-4054. A series of pyrazolo-1,4-benzodiazepines is furthermore described in U.S. Pat. No. 4,130,716 and U.S. Pat. No. 4,153,799. Further diazepine derivatives and other compounds are disclosed in: Bertelli L et al., 11 Farmaco, 1998, 53, 305-311; Anzini M et al., *Med. Chem. Res.*, 1993, 3, 249-256; Vachhani D D et al., *Eur. J. Org. Chem.*, 2013, 7, 1223-1227; Beaumont S et al., *Eur. J. Org. Chem.* 2008, 30, 5162-5175; Gream G E et al., *Journal of the Chemical Society D: Chemical Communications*, 1970, 15, 895-896; Gschwend H W et al., *J. Org. Chem.*, 1982, 47(19), 3652-3657; Gu X et al., *Eur. J. Med. Chem.*, 2012, 51, 137-144; Hadden M et al., *Bioorg. Med. Chem. Lett.*, 2010, 20(9), 2912-2915; Jeffrey J L et al., *Angew. Chem. Int. Ed. Engl.*, 2013, 52(8), 2194-2197; Keller L et al., *J. Med. Chem.*, 2008, 51(12), 3414-3421; Leleu S et al., *Tetrahedron: Asymmetry*, 2004, 15(24), 3919-3928; Liu J et al., *J. Org. Chem.*, 2016, 81(20), 9695-9706; Moustaid K et al., *Can. J. Chem.*, 1992, 70(3), 802-808; Ohno A et al., *J. Am. Chem. Soc.*, 1994, 116(18), 8133-8137; Ohno A et al., *Bull. Chem. Soc. Jpn.*, 1996, 69(6), 1679-1685; Ohno A et al., *J. Am. Chem. Soc.*, 1998, 120(6), 1186-1192; Ohno A et al., *Tetrahedron Letters*, 1999; 40(24), 4577-4580; Ohno A et al., *J. Org. Chem.*, 2000, 65(20), 6381-6387; Ohno A et al., *Tetrahedron Letters*, 2001, 42(3), 399-401; Pons V et al., *ACS Med. Chem. Lett.*, 2011, 2(8), 565-570; Putey A et al., *Tetrahedron*, 2007, 63(4), 867-879; Putey A et al., *J. Med. Chem.*, 2009, 52(19), 5916-5925; Taylor E C et al., *J. Am. Chem. Soc.*, 1980, 102(21), 6513-6519; Thomas H G et al., *J. Heterocyclic Chem.*, 1984, 21(4), 1057-1062; Vasse J L et al., *Tetrahedron Letters*, 2001, 42(28), 4613-4616; Vasse J L et al., *Chem. Commun.* (Camb)., 2002, 19, 2256-2257; U.S. Pat. Nos. 3,551,414; 3,668,232; 3,681,343; 4,863,920; US 2003/0017200; US 2006/0046983; WO 93/20695; WO 2007/092000; WO 2008/039520; WO 2009/158011; WO 2010/132601; and WO 2013/192347.

WO 2014/117919 discloses substituted pyridine derivatives as positive allosteric modulators of metabotropic glutamate receptor subtype 3 (mGluR3). The compounds disclosed in this reference are structurally remote from those of the present invention.

The present invention provides novel compounds that exhibit highly potent positive allosteric modulator activity on mGluR3 as well as advantageous pharmacokinetic properties, which renders them particularly suitable as therapeutic agents. The invention further provides compounds that are mGluR3 PAMs showing an advantageous selectivity for mGluR3 over mGluR2. The present invention thus solves the problem of providing improved means and methods for the medical intervention in diseases, disorders and conditions associated with altered glutamatergic signalling and/or functions as well as conditions which can be affected by alteration of glutamate level or signalling, including in particular the treatment and/or prophylaxis of acute and chronic neurological and/or psychiatric disorders.

Accordingly, in a first aspect, the present invention provides a compound of the following general formula (I):

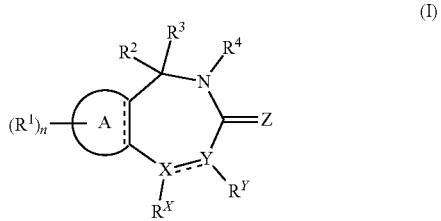

(I)

or a pharmaceutically acceptable salt, solvate or prodrug thereof, for use as a medicament (particularly for use in the treatment and/or prophylaxis of a condition associated with altered glutamatergic signalling and/or functions, and/or a condition which can be affected by alteration of glutamate level or signalling, such as Parkinson's disease).

In formula (I), A is aryl or heteroaryl.

X and Y are each independently N or C.

Z is O, S or N(—$R^z$).

Each ==== is independently a single bond or a double bond. The bond ==== between X and Y is a single bond if one or both of X and Y is/are N.

$R^X$ is a group $R^{X1}$, and $R^Y$ is a group $R^{Y1}$; or $R^X$ and $R^Y$ are mutually linked to form, together with the atoms X and Y that they are attached to, an aryl or heteroaryl group, wherein said aryl or heteroaryl group is optionally substituted with one or more groups $R^5$.

$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{60}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl.

Each $R^1$ is independently a group -$L^1$-$R^{11}$.

Each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —O$R^{12}$, —N$R^{12}R^{12}$, —CO$R^{12}$, —COO$R^{12}$, —OCO$R^{12}$, —CON$R^{12}R^{12}$, —N$R^{12}$CO$R^{12}$, —S$R^{12}$, —SO$R^{12}$, —SO$_2R^{12}$, —SO$_2$N$R^{12}R^{12}$, and —N$R^{12}$SO$_2R^{12}$, and further wherein one or more —CH$_2$— units comprised in said alkylene, said alkenylene or said alkynylene are each optionally replaced by a group independently selected from —O—, —N$R^{12}$—, —CO—, —S—, —SO—, and —SO$_2$—.

Each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —N$R^{12}R^{12}$, —O$R^{12}$, —S$R^{12}$, —SO$R^{12}$, —SO$_2R^{12}$, —CO$R^{12}$, —COO$R^{12}$, —OCO$R^{12}$, —CON$R^{12}R^{12}$, —N$R^{12}$CO$R^{12}$, —SO$_2$N$R^{12}R^{12}$, —N$R^{12}$SO$_2R^{12}$, and —SO$_3R^{12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{11}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO ($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO ($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{11}$-$R^{13}$.

Each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —N$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

Each $L^{11}$ is independently selected from a bond, $C_1$-$C_{10}$ alkylene, $C_2$-$C_{10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—.

Each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O ($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl.

n is an integer of 0 to 4.

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —SO$_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if one or both of $R^2$ and $R^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; or $R^2$ and $R^3$ together form a divalent group selected from =O, =S, =NH and =N($C_1$-$C_{10}$ alkyl).

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl.

Each $R^5$ is independently a group -$L^5$-$R^{51}$.

Each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—.

Each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —OR$^{52}$, —COR$^{52}$, —COOR$^{52}$, —OCOR$^{52}$, —CONR$^{52}$R$^{52}$, —NR$^{52}$OCOR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_1$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($CO_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$.

Each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_{1-10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to).

Each $L^{51}$ is independently selected from a bond, $C_1$-$C_{10}$ alkylene, $C_2$-$C_{10}$ alkenylene, and $C_2$-$C_{10}$ alkynylene, wherein one or more —OH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—.

Each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

$R^{X1}$ and $R^{Y1}$ are each independently a group -$L^{X11}$-$R^{X11}$.

Each $L^{X11}$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{X12}$, —$NR^{X12}R^{X12}$, —$COR^{X12}$, —$COOR^{X12}$, —$OCOR^{X12}$, —$CONR^{X12}R^{X12}$, —$NR^{X12}COR^{X12}$, —$SR^{X12}$, —$SOR^{X12}$, —$SO_2R^{X12}$, —$SO_2NR^{X12}R^{X12}$, and —$NR^{X12}SO_2R^{X12}$, and further wherein one or more —$CH_2$— units comprised in said alkylene, said alkenylene or said alkynylene are each optionally replaced by a group independently selected from —O—, —$NR^{X12}$—, —CO—, —S—, —SO—, and —$SO_2$—.

Each $R^{X11}$ is independently selected from hydrogen, aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{X12}R^{X12}$, —$OR^{X12}$, —$SR^{X12}$, —$SOR^{X12}$, —$SO_2R^{X12}$, —$COR^{X12}$, —$COOR^{X12}$, —$OCOR^{X12}$, —$CONR^{X12}R^{X12}$, —$NR^{X12}COR^{X12}$, —$SO_2NR^{X12}R^{X12}$, —$NR^{X12}SO_2R^{X12}$, and —$SO_3R^{X12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{X12}$-$R^{X13}$, and further wherein, if $R^{X12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{X12}$-$R^{X13}$.

Each $R^{X12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and wherein if $R^{X12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Each $L^{X12}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Each $R^{X13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

In accordance with the present invention, if A in formula (I) is phenyl, X is N, Y is C, the bond ═══ between X and Y is a single bond, and $R^X$ and $R^Y$ are mutually linked to form a heteroaryl group (which may optionally be substituted with one or more groups $R^5$), then said heteroaryl group is not a 5-membered monocyclic heteroaryl group consisting of carbon and nitrogen ring atoms.

Furthermore, if A in formula (I) is phenyl, $R^2$ and $R^3$ are each hydrogen, $R^4$ is methyl, Z is O, X and Y are each C, and the bond ═══ between X and Y is a double bond, then $R^X$ and $R^Y$ are not mutually linked to form a thiazolyl group that is substituted with one group -$L^5$-$R^{51}$, wherein $L^5$ is different from a bond and wherein $R^{51}$ is an optionally substituted aryl or an optionally substituted heteroaryl.

It is particularly preferred that the compound of the general formula (I) is a compound of the following general formula (Ia):

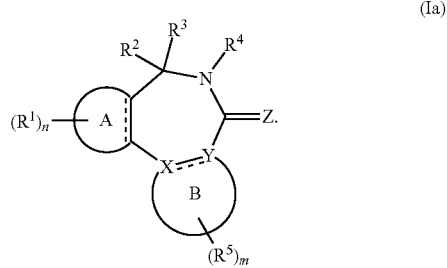

(Ia)

Accordingly, in the first aspect, the present invention relates, in particular, to a compound of formula (Ia) or a pharmaceutically acceptable salt, solvate or prodrug thereof for use as a medicament (particularly for use in the treatment and/or prophylaxis of a condition associated with altered glutamatergic signalling and/or functions, and/or a condition which can be affected by alteration of glutamate level or signalling, such as Parkinson's disease).

In formula (Ia), the ring group B (which includes the ring atoms X and Y) is an aryl or heteroaryl group, and m is an integer of 0 to 3.

The further groups/variables in formula (Ia), including in particular =====, A, X, Y, Z, $R^1$, $R^2$, $R^3$, $R^4$, $R^5$ and n, have the same meanings, including the same preferred meanings, as described and defined herein for the corresponding groups/variables in formula (I).

Moreover, in accordance with the definition of the compounds of formula (I), if A in formula (Ia) is phenyl, X is N, Y is C, the bond ===== between X and Y is a single bond, and B is a heteroaryl group, then said heteroaryl group is not a 5-membered monocyclic heteroaryl group consisting of carbon and nitrogen ring atoms.

Furthermore, if A in formula (Ia) is phenyl, $R^2$ and $R^3$ are each hydrogen, $R^4$ is methyl, Z is O, X and Y are each C, the bond ===== between X and Y is a double bond, m is 1, $L^5$ is different from a bond, and $R^{51}$ is an optionally substituted aryl or an optionally substituted heteroaryl, then B is not a thiazolyl group.

The present invention further provides novel compounds. In particular, in a second aspect, the invention relates to a compound of formula (I) or a pharmaceutically acceptable salt, solvate or prodrug thereof (preferably to a compound of formula (Ia) or a pharmaceutically acceptable salt, solvate or prodrug thereof), as described and defined in the first aspect of the invention, wherein:
(i) the groups $R^2$ and $R^3$ are mutually linked to form, together with the carbon atom that they are attached to, a cycloalkyl or a heterocycloalkyl; or
(ii) the ring group A is heteroaryl, said heteroaryl being different from pyrimidinyl and from 1,3-benzodioxolyl, and wherein the following compounds are excluded from formula (I) (and from formula (Ia), respectively):

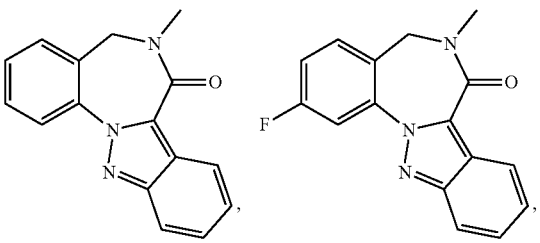

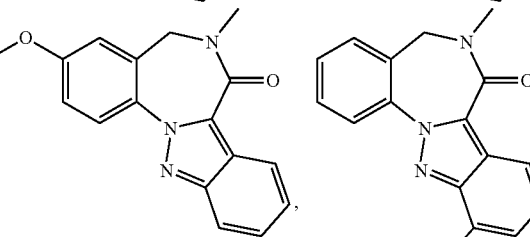

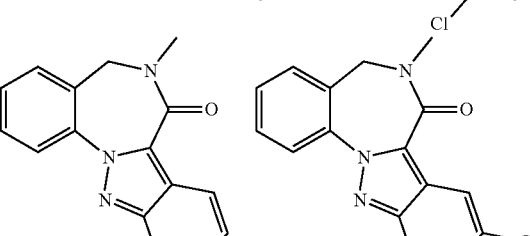

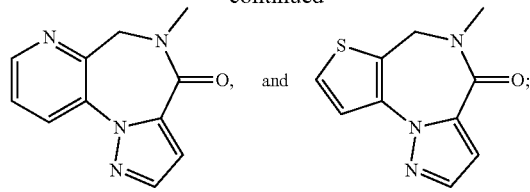

or
(iii) the ring group B in formula (Ia) is a heteroaryl group, said heteroaryl group being different from indolyl and from 1,3-benzodioxolyl,
wherein, if A is phenyl, X and Y are each C, Z is O, $R^2$ and $R^3$ are each hydrogen, $R^4$ is methyl or tert-butyl, n is 0 or 1, $R^1$ (if present) is methyl, m is 0 or 1, and $R^5$ (if present) is methyl, then B is not pyridinyl,
and wherein, if A is phenyl, X and Y are each C, the bond ===== between X and Y is a double bond, Z is O, one of $R^2$ and $R^3$ is hydrogen and the other one of $R^2$ and $R^3$ is methyl, $R^4$ is isopropyl, and n is 0, then B is not quinolinyl or 1,4-dihydroquinolinyl, and further wherein the following compounds are excluded from formula (Ia):

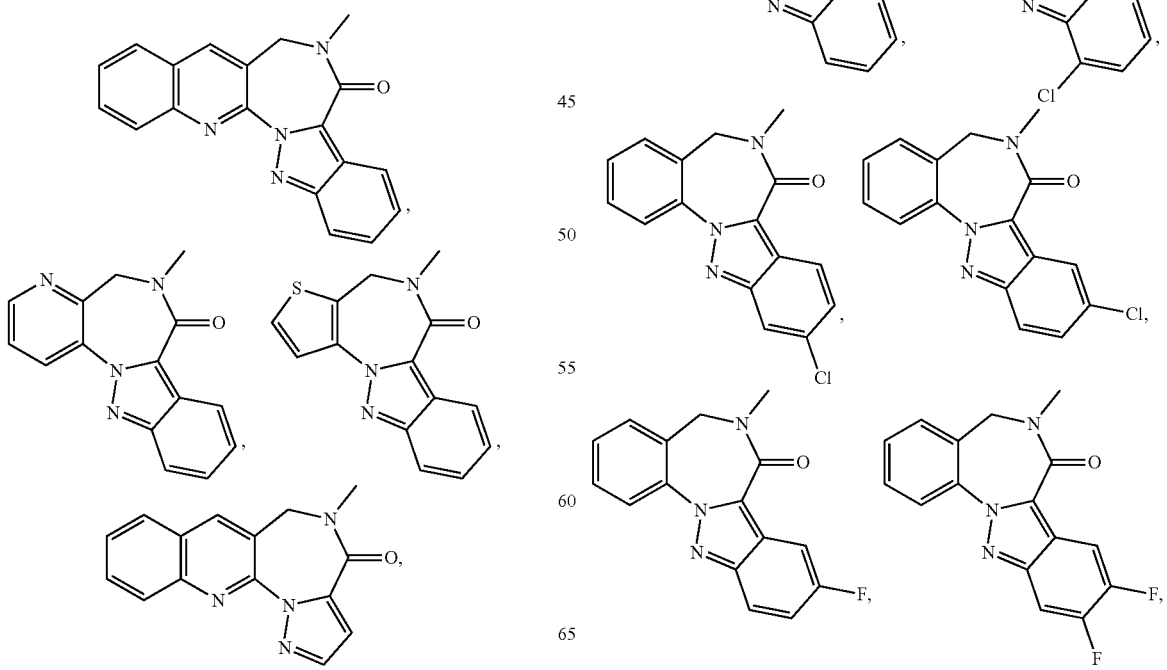

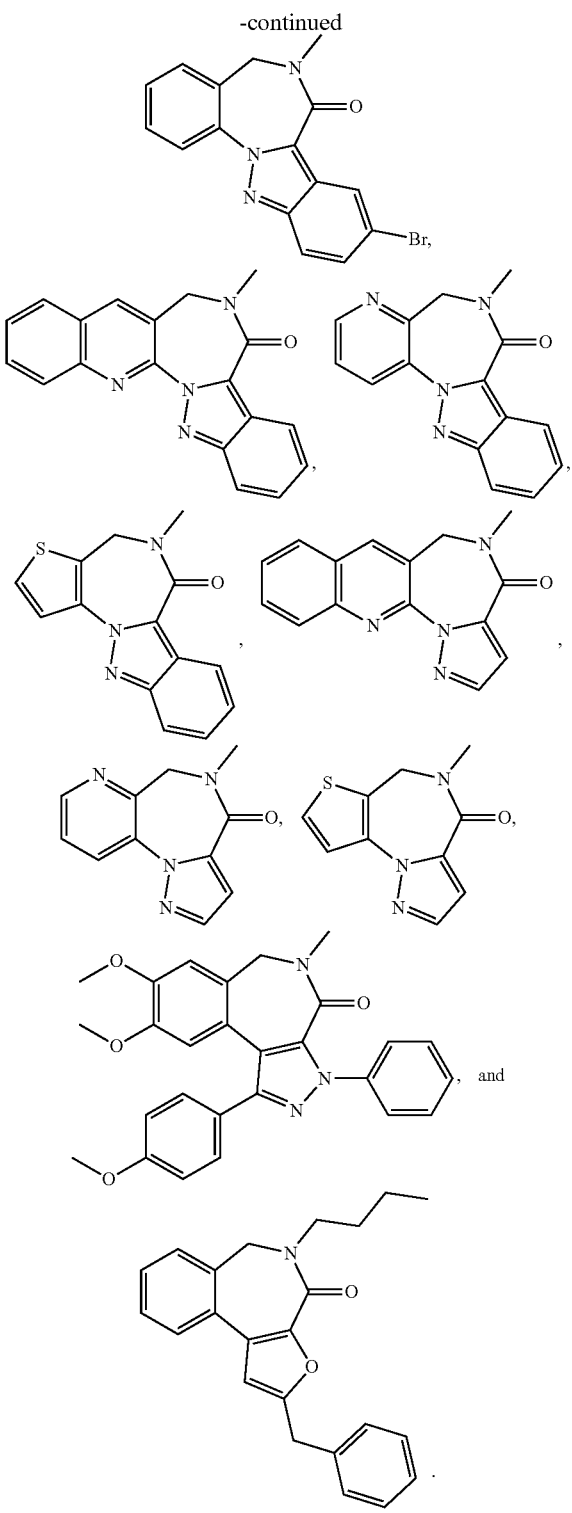

Moreover, the invention provides a pharmaceutical composition comprising a compound of formula (I) or (Ia), as described and defined in the first or second aspect of the invention, or a pharmaceutically acceptable salt, solvate or prodrug thereof, and optionally a pharmaceutically acceptable excipient. Accordingly, the invention also relates to a compound of formula (I) or (Ia) or a pharmaceutically acceptable salt, solvate or prodrug thereof, as defined in the first or second aspect of the invention, or a pharmaceutical composition comprising any of the aforementioned entities and optionally a pharmaceutically acceptable excipient, for use as a medicament.

The present invention furthermore relates to the compounds of formula (I) or (Ia) as well as their pharmaceutically acceptable salts, solvates and prodrugs, as defined in the first or second aspect of the invention, for use in the treatment and/or prophylaxis of conditions associated with altered glutamatergic signalling and/or functions, and/or conditions which can be affected by alteration of glutamate level or signalling. The invention likewise relates to a pharmaceutical composition comprising a compound of formula (I) or (Ia), as defined in the first or the second aspect of the invention, or a pharmaceutically acceptable salt, solvate or prodrug thereof, and optionally a pharmaceutically acceptable excipient, for use in the treatment and/or prophylaxis of conditions associated with altered glutamatergic signalling and/or functions, and/or conditions which can be affected by alteration of glutamate level or signalling.

The present invention also relates to the use of a compound of formula (I) or (Ia), as defined in the first or second aspect of the invention, or a pharmaceutically acceptable salt, solvate or prodrug thereof, for the preparation of a medicament for the treatment and/or prophylaxis of conditions associated with altered glutamatergic signalling and/or functions, and/or conditions which can be affected by alteration of glutamate level or signalling.

The invention further provides a method of treating and/or preventing conditions associated with altered glutamatergic signalling and/or functions, and/or conditions which can be affected by alteration of glutamate level or signalling in a mammal. Accordingly, the invention relates to a method of treating and/or preventing a disease or disorder, in particular a condition associated with altered glutamatergic signalling and/or functions, and/or a condition which can be affected by alteration of glutamate level or signalling, the method comprising the administration of a compound of formula (I) or (Ia), as defined in the first or second aspect of the invention, or a pharmaceutically acceptable salt, solvate or prodrug thereof, or a pharmaceutical composition comprising any of the aforementioned entities and optionally a pharmaceutically acceptable excipient, to a subject (preferably a mammal, more preferably a human) in need of such treatment or prevention. It will be understood that a therapeutically effective amount of the compound of formula (I) or (Ia) or the pharmaceutically acceptable salt, solvate or prodrug thereof, or of the pharmaceutical composition, is to be administered in accordance with this method.

The compounds of formula (I) or (Ia) as defined in the first or second aspect of the invention can be used as modulators of mGluRs of the nervous system, preferably as allosteric modulators of the mGluRs, and most preferably as positive allosteric modulators (PAMs) of mGluR3. The positive allosteric modulator activity of a compound on mGluR3 can be evaluated using methods known in the art, e.g., using the $Ca^{2+}$ assay described in Example 89, As noted above, the invention relates to the compounds of formula (I) or (Ia) as defined in the first or second aspect, their pharmaceutically acceptable salts, solvates and prodrugs, as well as pharmaceutical compositions comprising any of the aforementioned entities and optionally a pharmaceutically acceptable excipient, for use in the treatment and/or prophylaxis of conditions associated with altered glutamatergic signalling and/or functions, and/or conditions which can be affected by alteration of glutamate level or signalling.

The conditions associated with altered glutamatergic signalling and/or functions, and/or conditions which can be affected by alteration of glutamate level or signalling, that can be treated and/or prevented with the compounds or the pharmaceutical compositions according to the invention, include in particular: epilepsy, including newborn, infantile, childhood and adult syndromes, partial (localization-related) and generalized epilepsies, with partial and generalized, convulsive and non-convulsive seizures, with and without impairment of consciousness, and status epilepticus; Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Motor neuron disease or amyotrophic lateral sclerosis (ALS); Other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; Disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; Multiple sclerosis and other demyelinating diseases of the nervous system; Infantile cerebral palsy (spastic), monoplegic, paraplegic or tetraplegic; Hemiplegia and hemiparesis, flaccid or spastic, and other paralytic syndromes; Cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; Migraine, including classical migraine and variants such as cluster headache; Headache; Myoneural disorders including myasthenia gravis, acute muscle spasms, myopathies including muscular dystrophies, mytotonias and familial periodic paralysis; Disorders of the eye and visual pathways, including retinal disorders, and visual disturbances; Intracranial trauma/injury and their sequels; Trauma/injury to nerves and spinal cord and their sequels; Poisoning and toxic effects of nonmedicinal substances; Accidental poisoning by drugs, medicinal substances and biologicals acting on the central, peripheral and autonomic system; Neurological and psychiatric adverse effects of drugs, medicinal and biological substances; Disturbance of sphincter control and sexual function; Mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; Delirium and other cognitive disorders; Substance related disorders including: alcohol-related disorders, nicotine-related disorders, disorders related to cocaine, opioids, cannabis, hallucinogens and other drugs; Schizophrenia and other psychotic disorders; Mood disorders, including depressive disorders and bipolar disorders; Anxiety disorders, including panic disorders, phobias, obsessive-compulsive disorders, stress disorders, generalized anxiety disorders; Eating disorders, including anorexia and bulimia; Sleep disorders, including dyssomnias (insomnia, hypersomnia, narcolepsy, breathing related sleep disorder) and parasomnias; Medication-induced movement disorders (including neuroleptic-induced parkinsonism and tardive dyskinesia); Endocrine and metabolic diseases including diabetes, disorders of the endocrine glands, hypoglycaemia; Acute and chronic pain; Nausea and vomiting; Irritable bowel syndrome; or cancers.

In particular, the conditions associated with altered glutamatergic signalling and/or functions, and/or conditions which can be affected by alteration of glutamate level or signalling to be treated and/or prevented by the compounds or the pharmaceutical compositions according to the invention, include: epilepsy (including, e.g., newborn, infantile, childhood and adult syndromes, partial (localization-related) and generalized epilepsies, with partial and generalized, convulsive and non-convulsive seizures, with and without impairment of consciousness, and status epilepticus); dementias (including, e.g., dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease, and atypical subacute spongiform encephalopathy); parkinsonism and movement disorders (including, e.g., Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus); motor neuron disease; amyotrophic lateral sclerosis; neurodegenerative and/or hereditary disorders of the nervous system (including, e.g., spinocerebrellar degenerations such as Friedrich's ataxia and other hereditary cerebellar ataxias, predominantly spinal muscular atrophies, hereditary neuropathies, and phakomatoses); disorders of the peripheral nervous system (including, e.g., trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, and inflammatory and toxic neuropathies); infantile cerebral palsy; hemiplegia and hemiparesis, and other paralytic syndromes; cerebrovascular disorders (including, e.g., subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting); migraine (including, e.g., classical migraine and variants such as cluster headache); headache; myoneural disorders (including, e.g., myasthenia gravis, acute muscle spasms, myopathies including muscular dystrophies, mytotonias and familial periodic paralysis); disorders of the eye and visual pathways (including, e.g., retinal disorders, and visual disturbances); intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders (including, e.g., alcohol-related disorders, nicotine-related disorders, disorders related to cocaine, opioids, cannabis, hallucinogens or other drugs); schizophrenia and other psychotic disorders; mood disorders (including, e.g., depressive disorders and bipolar disorders); anxiety disorders (including, e.g., panic disorders, phobias, obsessive-compulsive disorders, stress disorders, generalized anxiety disorders); eating disorders (including, e.g., anorexia and bulimia); sleep disorders (including, e.g., dyssomnias (insomnia, hypersomnia, narcolepsy, breathing related sleep disorder) and parasomnias); medication-induced movement disorders (including, e.g., neuroleptic-induced parkinsonism and tardive dyskinesia); acute and chronic pain; nausea and vomiting; or irritable bowel syndrome.

The conditions associated with altered glutamatergic signalling and/or functions, and/or conditions which can be affected by alteration of glutamate level or signalling to be treated and/or prevented by the compounds or the pharmaceutical compositions according to the invention, are preferably selected from: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Acute and chronic pain; Anxiety disorders, including panic disorders, phobias, obsessive-compulsive disorders, stress disorders and generalized anxiety disorders; Schizophrenia and other psychotic disorders; or Mood disorders, including depressive disorders and bipolar disorders.

The present invention particularly relates to a compound of formula (I) or (Ia) as defined in the first or second aspect, or a pharmaceutically acceptable salt, solvate or prodrug thereof, or a pharmaceutical composition comprising any of the aforementioned entities and optionally a pharmaceutically acceptable excipient, for use in the treatment or prevention/prophylaxis of Parkinson's disease.

The present invention furthermore provides a method for identifying an agent that binds to metabotropic glutamate receptor 3 (mGluR3), or in other words for determining the capability of one or more test agent(s) to bind to mGluR3, the method comprising the following steps: (a) contacting mGluR3 with a compound of formula (I) or (Ia) as defined in the first or second aspect of the invention, or a pharmaceutically acceptable salt, solvate or prodrug thereof, wherein the compound is labeled, preferably radio-labeled or fluorescence-labeled, under conditions that permit binding of the compound to mGluR3, thereby generating a bound, labeled compound; (b) detecting a signal that corresponds to the amount of the bound, labeled compound in the absence of test agent; (c) contacting the bound, labeled compound with a test agent; (d) detecting a signal that corresponds to the amount of the bound labeled compound in the presence of test agent; and (e) comparing the signal detected in step (d) to the signal detected in step (b) to determine whether the test agent binds to mGluR3. As will be understood, a substantially unchanged signal detected in step (d) in comparison with the signal detected in step (b) indicates that the test agent does not bind to the receptor, or binds to the receptor less strongly than the compound of formula (I) or (Ia). A decreased or increased signal detected in step (d) in comparison with the signal detected in step (b) indicates that the test agent binds to the receptor. Thus, agents that bind to mGluR3 can be identified among the test agents employed in this method. It will further be understood that it is preferred to remove unbound labeled compounds, e.g. in a washing step, before carrying out steps (b) and (d).

The mGluR3 that is used in the above method may be a human form, e.g., a protein of the accession number NP_000831.2, or a protein having at least 80% (preferably at least 90%, more preferably at least 95%, even more preferably at least 99%) amino acid identity to said protein of the accession number NP_000831.2, or a non-human form, including e.g. a mouse form or a homolog thereof found in a different species (e.g. in a different mammalian species), or a mutein of any of the aforementioned entities wherein the mutein retains the mGluR3 activity. Said mutein can preferably be obtained by substitution, insertion, addition and/or deletion of one or more (such as, e.g., 1 to 20, including 1 to 10 or 1 to 3) amino acid residues of said aforementioned entities. The mGluR3 to be used in the above method may also be a functional fragment of any of the aforementioned entities (including said muteins), i.e. a fragment which retains the mGluR3 activity of the respective aforementioned entity or, in other words, a fragment having essentially the same biological activity (i.e., at least about 60% activity, preferably at least about 70% activity, more preferably at least about 80% activity, even more preferably at least about 90% activity) as the respective aforementioned entity. A skilled person is readily in a position to determine whether mGluR3 activity is retained using techniques known in the art, e.g., knock-out and rescue experiments. Preferably, the mGluR3 to be used in the above method is human mGluR3.

The present invention also relates to the use of a compound of formula (I) or (Ia), as defined in the first or second aspect, or a pharmaceutically acceptable salt, solvate or prodrug thereof as a positive allosteric modulator of metabotropic glutamate receptor 3 (i.e., as an mGluR3 PAM) in research, particularly as a research tool compound. Accordingly, the invention refers to the in vitro use of a compound of formula (I) or (Ia) as defined in the first or second aspect, or a pharmaceutically acceptable salt, solvate or prodrug thereof as an mGluR3 PAM and, in particular, to the in vitro use of a compound of formula (I) or (Ia) or a pharmaceutically acceptable salt, solvate or prodrug thereof as a research tool compound acting as an mGluR3 PAM. The invention likewise relates to an in vitro method of modulating mGluR3, the method comprising the application of a compound of formula (I) or (Ia) as defined in the first or second aspect of the invention, or a pharmaceutically acceptable salt, solvate or prodrug thereof, as an mGluR3 PAM. The present invention further provides an in vitro method of modulating mGluR3, comprising the use of a compound of formula (I) or (Ia) or a pharmaceutically acceptable salt, solvate or prodrug thereof as an mGluR3 PAM. The mGluR3 is preferably human mGluR3 (e.g., a protein of the accession number NP_000831.2), i.e., the present invention preferably relates to the in vitro use of a compound of formula (I) or (Ia) or a pharmaceutically acceptable salt, solvate or prodrug thereof as a positive allosteric modulator of human mGluR3 and, in particular, as a research tool compound acting as a positive allosteric modulator of human mGluR3. The invention likewise relates to an in vitro method of modulating human mGluR3, the method comprising the application of a compound of formula (I) or (Ia) or a pharmaceutically acceptable salt, solvate or prodrug thereof as a human mGluR3 PAM. It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc.

The compounds of formulae (I) and (Ia) according to the present invention will be described in more detail in the following. Unless specifically indicated otherwise, the following explanations apply both to the compounds of formula (I) and the compounds of formula (Ia), and they likewise apply to both the first aspect and the second aspect of the invention.

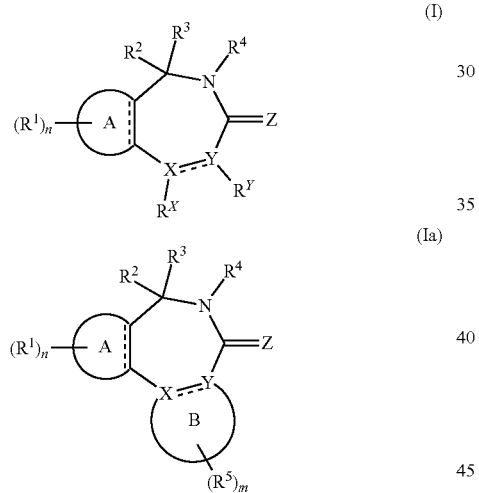

In formulae (I) and (Ia), each ==== is independently a single bond or a double bond. The bond ==== between the ring atoms X and Y is a single bond if one or both of X and Y is/are N (i.e., if X and/or Y is/are nitrogen).

A is aryl or heteroaryl. It will be understood that the ring group A is fused to the 7-membered ring containing the ring atoms X and Y, i.e., two carbon ring atoms are common to ring A and to said 7-membered ring, as also depicted in formulae (I) and (Ia).

Preferably, A is phenyl or monocyclic heteroaryl. More preferably, A is phenyl or a monocyclic 5- or 6-membered heteroaryl (particularly phenyl or a monocyclic 6-membered heteroaryl). Even more preferably, A is phenyl or a monocyclic 5- or 6-membered heteroaryl, wherein 1, 2 or 3 ring atoms of said 5-membered heteroaryl are nitrogen atoms and the remaining ring atoms are carbon atoms, and wherein 1, 2, 3 or 4 ring atoms of said 6-membered heteroaryl are nitrogen atoms and the remaining ring atoms are carbon atoms. Yet even more preferably, A is phenyl or a monocyclic 6-membered heteroaryl, wherein 1, 2, 3 or 4 ring atoms (particularly 1 or 2 ring atoms) of said heteroaryl are nitrogen atoms and the remaining ring atoms are carbon atoms (such as, e.g., pyridinyl, pyrimidinyl, pyrazinyl, or pyridazinyl).

Corresponding examples of preferred groups A are shown in the following (where the substituent(s) $R^1$ that may be attached to ring A are also depicted):

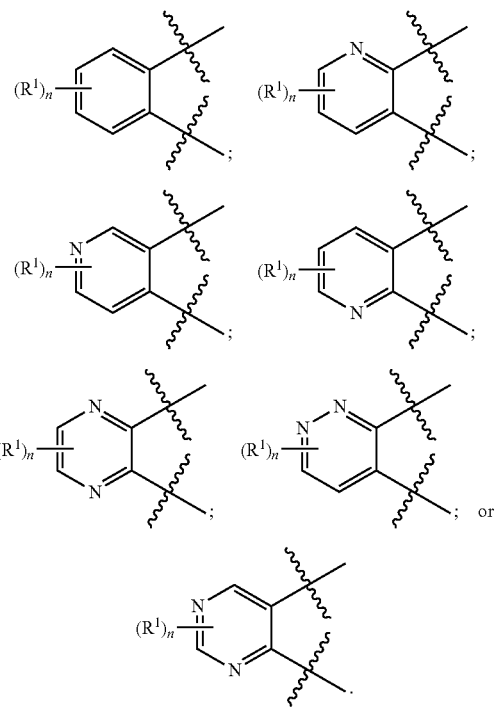

Examples of particularly preferred ring groups A are shown in the following:

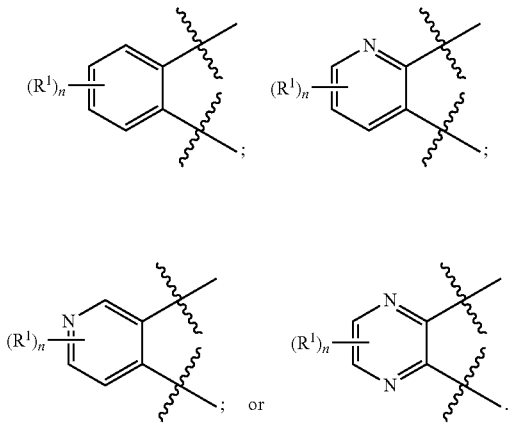

It will be understood that the above-depicted groups A are shown in the same orientation in which they are intended to be present in formula (I) or (Ia). Accordingly, if group A in formula (I) is, for example, the group

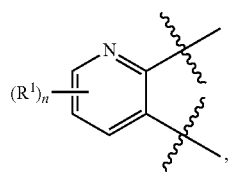

then the resulting compound of formula (I) has the following structure (the same analogously applies to the compounds of formula (Ia)):

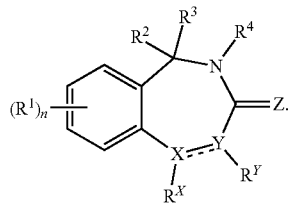

Even more preferably, A is phenyl (i.e., a group

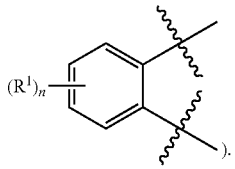

).

X and Y are each independently N or C. Accordingly, the ring atoms X and Y are each independently a nitrogen ring atom or a carbon ring atom.

Preferably, one of X and Y is C, and the other one of X and Y is N or C. More preferably, Y is C. Accordingly, it is particularly preferred that X is N and Y is C, or that X and Y are each C. Even more preferably, X and Y are each C.

$R^X$ is a group $R^{X1}$, and $R^Y$ is a group $R^{Y1}$; or $R^X$ and $R^Y$ are mutually linked to form, together with the atoms X and Y that they are attached to, an aryl or heteroaryl group, wherein said aryl or heteroaryl group is optionally substituted with one or more groups $R^5$.

It is preferred that $R^X$ and $R^Y$ are mutually linked to form, together with the atoms X and Y that they are attached to, an aryl or heteroaryl group, wherein said aryl or heteroaryl group is optionally substituted with one or more (e.g., one, two or three) groups $R^5$. It will be understood that in this case the ring atoms X and Y are common to both the 7-membered ring depicted in formula (I) and to the aforementioned aryl or heteroaryl group; in other words, the aryl or heteroaryl group that is formed through the linkage of the groups $R^X$ and $R^Y$ is condensed to the 7-membered ring depicted in formula (I).

Accordingly, it is particularly preferred that the compound of formula (I) is a compound of the following formula (Ia):

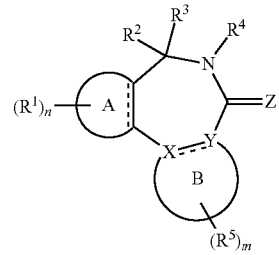

or a pharmaceutically acceptable salt, solvate or prodrug thereof, wherein the ring group B is an aryl or heteroaryl group, wherein m is an integer of 0 to 3, and wherein the further ===== groups/variables in formula (Ia), including in particular =====, A, X, Y, Z, $R^1$, $R^2$, $R^3$, $R^4$, $R^5$ and n, have the same meanings, including the same preferred meanings, as described and defined herein for the corresponding groups/variables in formula (I).

The compounds of formula (Ia) are highly advantageous, particularly with respect to their modulator activity on mGluR3. Thus, compounds of formula (Ia) are advantageously potent mGluR3 PAMs.

It is preferred that the ring group B in formula (Ia) and, likewise, the aryl or heteroaryl group that is formed through the linkage of the groups $R^X$ and $R^Y$ in formula (I)—which are collectively referred to as "ring group B" (or "B") in the following—is phenyl or monocyclic heteroaryl. More preferably, B is phenyl or a monocyclic 5- or 6-membered heteroaryl (such as, e.g., pyrrolyl, pyrazolyl, thiophenyl, or pyridinyl). Even more preferably, B is phenyl or a monocyclic 5- or 6-membered heteroaryl (such as, e.g., pyrrolyl, pyrazolyl, thiophenyl, or pyridinyl) in which both ring atoms X and Y are carbon atoms. Moreover, B may, e.g., be different from thiazolyl.

Examples of preferred ring groups B (or, in the case of a compound of formula (I), examples of preferred aryl or heteroaryl groups formed through the linkage of $R^X$ and $R^Y$) are shown in the following (where the substituent(s) $R^5$ that may be attached to ring B are also depicted):

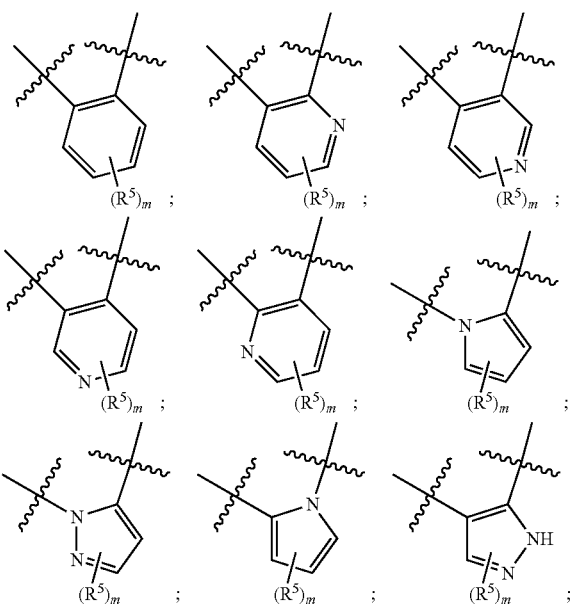

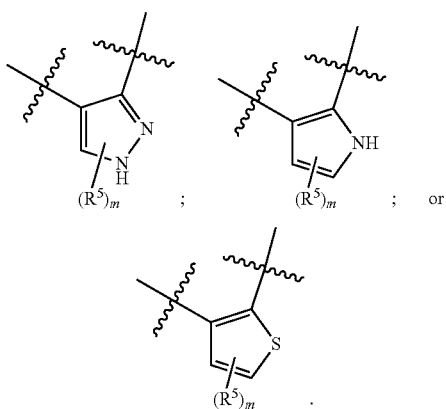

Particularly preferred examples of ring B are shown in the following:

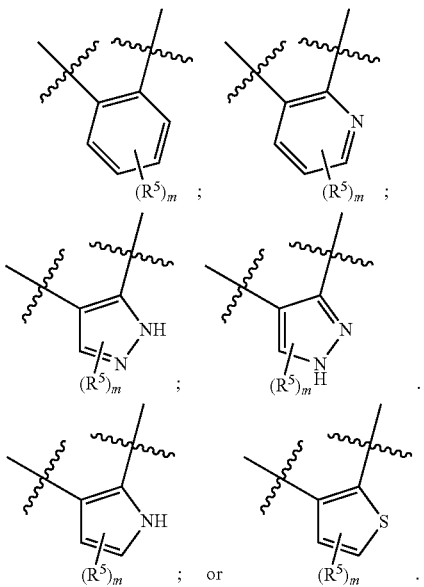

It will be understood that the above-depicted groups B are shown in the same orientation in which they are intended to be present in formula (Ia) (or in which the corresponding aryl or heteroaryl groups formed through the linkage of $R^X$ and $R^Y$ are intended to be present in formula (I). Accordingly, if group B in formula (Ia) is, for example, the group

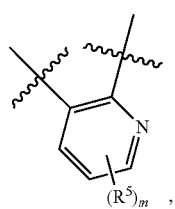

then the resulting compound of formula (Ia) has the following structure (the same analogously applies to the compounds of formula (I)):

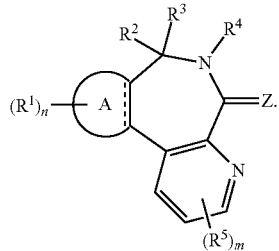

Even more preferred examples of ring B are shown in the following:

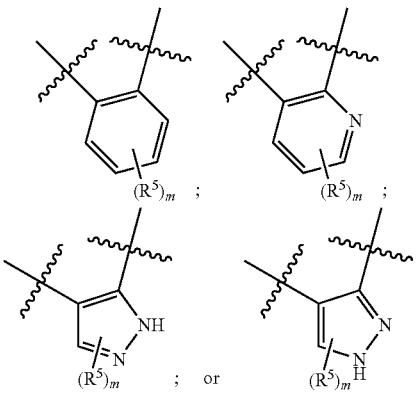

Yet even more preferred examples of ring B are shown in the following:

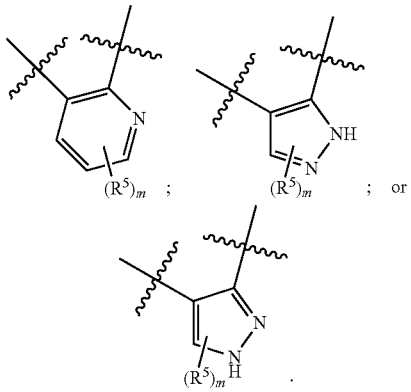

As explained above, it is preferred that the groups $R^X$ and $R^Y$ in formula (I) are mutually linked (and thus form an aryl or heteroaryl group). However, if $R^X$ and $R^Y$ are not mutually linked, then $R^X$ is a group $R^{X1}$, and $R^Y$ is a group $R^{Y1}$.

$R^{X1}$ and $R^{Y1}$ are each independently a group $-L^{X11}-R^{X11}$.

Each $L^{X11}$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups (e.g., one, two, or three groups) independently selected from halogen, $C_1$-$C_{10}$ haloalkyl, —CN, —OR$^{X12}$, —NR$^{X12}$R$^{X12}$, —COR$^{X12}$, —COOR$^{X12}$, —OCOR$^{X12}$, —CONR$^{X12}$R$^{X12}$, —NR$^{X12}$COR$^{X12}$, —SR$^{X12}$, —SOR$^{X12}$, —SO$_2$R$^{X12}$, —SO$_2$NR$^{X12}$R$^{X12}$, and —NR$^{X12}$SO$_2$R$^{X12}$ and further wherein one or more —CH$_2$— units (e.g., one, two, or three —CH$_2$— units) comprised in said alkylene, said alkenylene or said alkynylene are each optionally replaced by a group independently selected from —O—, —NR$^{X12}$—, —CO—, —S—, —SO—, and —SO$_2$—.

Preferably, each L$^{X11}$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OR$^{X12}$, —NR$^{X12}$R$^{X12}$, —COR$^{X12}$, —COOR$^{X12}$, —OCOR$^{X12}$, —CONR$^{X12}$R$^{X12}$, —NR$^{X12}$COR$^{12}$, —SR$^{X12}$, —SOR$^{X12}$, —SO$_2$R$^{X12}$, —SO$_2$NR$^{X12}$R$^{X12}$, and —NR$^{X12}$SO$_2$R$^2$, and further wherein one or more —CH$_2$— units (e.g., one, two, or three —CH$_2$— units) comprised in said alkylene are each optionally replaced by a group independently selected from —O—, —NR$^{X12}$—, —CO—, —S—, —SO—, and —SO$_2$—. In particular, each L$^{X11}$ may, e.g., be independently selected from a bond and C$_1$-C$_4$ alkylene (e.g., methylene or ethylene).

Each R$^{X11}$ is independently selected from hydrogen, aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{X12}$R$^{X12}$, —OR$^{X12}$, —SR$^{X12}$, —SOR$^2$, —SO$_2$R$^{X12}$, —COR$^{X12}$, —COOR$^{X12}$, —OCOR$^{X12}$, —CONR$^{X12}$R$^{X12}$, —NR$^{X12}$COR$^{X12}$, —SO$_2$NR$^{X12}$R$^{X12}$, —NR$^{X12}$SO$_2$R$^{X12}$, and —SO$_3$R$^{X12}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO (C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{X12}$-R$^{X13}$, and further wherein, if R$^{X11}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups (e.g., one, two or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO (C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{X12}$-R$^{X13}$.

Preferably, each R$^{X11}$ is independently selected from hydrogen, aryl, heteroaryl, cycloalkyl, heterocycloalkyl, cycloalkenyl, heterocycloalkenyl, halogen, C$_1$-C$_4$ haloalkyl, —CN, C$_1$-C$_4$ alkyl, —NH$_2$, —NH(C$_1$-C$_4$ alkyl), —N(C$_1$-C$_4$ alkyl)(C$_1$-C$_4$ alkyl), —OH, —O(C$_1$-C$_4$ alkyl), and —CO(C$_1$-C$_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_4$ haloalkyl, —CN, C$_1$-C$_4$ alkyl, —OH, —O(C$_1$-C$_4$ alkyl), —(C$_1$-C$_4$ alkylene)-OH, —(C$_1$-C$_4$ alkylene)-O(C$_1$-C$_4$ alkyl), —NH$_2$, —NH(C$_1$-C$_4$ alkyl), —N(C$_1$-C$_4$ alkyl)(C$_1$-C$_4$ alkyl), —CHO, —CO(C$_1$-C$_4$ alkyl), —COOH, tetrazolyl, —COO(C$_1$-C$_4$ alkyl), —OCO(C$_1$-C$_4$ alkyl), —CO—NH$_2$, —CO—NH(C$_1$-C$_4$ alkyl), —CO—N(C$_1$-C$_4$ alkyl)(C$_1$-C$_4$ alkyl), —NH—CO—(C$_1$-C$_4$ alkyl), —N(C$_1$-C$_4$ alkyl)-CO—(C$_1$-C$_4$ alkyl), —SO$_2$—NH(C$_1$-C$_4$ alkyl), —SO$_2$—N(C$_1$-C$_4$ alkyl)(C$_1$-C$_4$ alkyl), —NH—SO$_2$—(C$_1$-C$_4$ alkyl), —N(C$_1$-C$_4$ alkyl)-SO$_2$—(C$_1$-C$_4$ alkyl), cycloalkyl, heterocycloalkyl, aryl, and heteroaryl, and further wherein, if R$^{X11}$ is C$_1$-C$_4$ alkyl, then said alkyl is optionally substituted with one or more groups (e.g., one, two or three groups) independently selected from halogen, C$_1$-C$_4$ haloalkyl, —CN, —OH, —O(C$_1$-C$_4$ alkyl), —NH$_2$, —NH(C$_1$-C$_4$ alkyl), —N(C$_1$-C$_4$ alkyl)(C$_1$-C$_4$ alkyl), —CHO, —CO(C$_1$-C$_4$ alkyl), —COOH, tetrazolyl, —COO (C$_1$-C$_4$ alkyl), —OCO(C$_1$-C$_4$ alkyl), —CO—NH$_2$, —CO—NH(C$_1$-C$_4$ alkyl), —CO—N(C$_1$-C$_4$ alkyl)(C$_1$-C$_4$ alkyl), —NH—CO—(C$_1$-C$_4$ alkyl), —N(C$_1$-C$_4$ alkyl)-CO—(C$_1$-C$_4$ alkyl), —SO$_2$—NH$_2$, —SO$_2$—NH(C$_1$-C$_4$ alkyl), —SO$_2$—N(C$_1$-C$_4$ alkyl)(C$_1$-C$_4$ alkyl), —NH—SO$_2$—(C$_1$-C$_4$ alkyl), —N(C$_1$-C$_4$ alkyl)-SO$_2$—(C$_1$-C$_4$ alkyl), cycloalkyl, heterocycloalkyl, aryl, and heteroaryl. In particular, each R$^{X11}$ may, e.g., be selected independently from hydrogen, aryl (e.g., phenyl), heteroaryl (e.g., pyridinyl), halogen, C$_1$-C$_4$ haloalkyl, C$_1$-C$_4$ alkyl (e.g., methyl), and —CO(C$_1$-C$_4$ alkyl) (e.g., —COCH$_3$), wherein said aryl and said heteroaryl are each optionally substituted with one or more groups (e.g., one, two or three groups) independently selected from halogen, C$_1$-C$_4$ haloalkyl, —CN, C$_1$-C$_4$ alkyl, —OH, —O(C$_1$-C$_4$ alkyl), —(C$_1$-C$_4$ alkylene)-OH, —(C$_1$-C$_4$ alkylene)-O(C$_1$-C$_4$ alkyl), —NH$_2$, —NH(C$_1$-C$_4$ alkyl), —N(C$_1$-C$_4$ alkyl)(C$_1$-C$_4$ alkyl), —CHO, —CO(C$_1$-C$_4$ alkyl), —COOH, tetrazolyl, —COO(C$_1$-C$_4$ alkyl), —OCO (C$_1$-C$_4$ alkyl), —CO—NH$_2$, —CO—NH(C$_1$-C$_4$ alkyl), —CO—N(C$_1$-C$_4$ alkyl)(C$_1$-C$_4$ alkyl), —NH—CO—(C$_1$-C$_4$ alkyl), —N(C$_1$-C$_4$ alkyl)-CO—(C$_1$-C$_4$ alkyl), —SO$_2$—NH (C$_1$-C$_4$ alkyl), —SO$_2$—N(C$_1$-C$_4$ alkyl)(C$_1$-C$_4$ alkyl), —NH—SO$_2$—(C$_1$-C$_4$ alkyl), —N(C$_1$-C$_4$ alkyl)-SO$_2$—(C$_1$-C$_4$ alkyl), cycloalkyl, heterocycloalkyl, aryl, and heteroaryl.

Each R$^{X12}$ is independently selected from hydrogen, C$_6$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and wherein if R$^{X12}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups (e.g., one, two, or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl.

Preferably, each R$^{X12}$ is independently selected from hydrogen, C$_1$-C$_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from C$_1$-C$_4$ alkyl, halogen, C$_1$-C$_4$ haloalkyl, —CN, —OH, —O(C$_1$-C$_4$ alkyl), —(C$_1$-C$_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and wherein said $C_1$-$C_{10}$ alkyl is optionally substituted with one or more groups (e.g., one, two, or three groups independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl. More preferably, each $R^{X12}$ is independently selected from hydrogen and $C_1$-$C_4$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl). For example, each $R^{X12}$ may be independently hydrogen or $C_1$-$C_4$ alkyl (e.g., methyl or ethyl).

Each $L^{X12}$ is independently selected from a bond, $C_1$-$C_{10}$ alkylene, $C_2$-$C_{10}$ alkenylene, and $C_2$-$C_{10}$ alkynylene, wherein one or more —$CH_2$— units (e.g., one, two or three —$CH_2$— units) comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Preferably, each $L^{X12}$ is independently selected from a bond and $C_1$-$C_{10}$ alkylene, wherein one or more —$CH_2$— units (e.g., one or two —$CH_2$— units) comprised in said alkylene are each optionally replaced by a group independently selected from —O—, —NH—, —N($C_1$-$C_4$ alkyl)-, —CO—, —S—, —SO—, and —$SO_2$—.

Each $R^{X13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, each $R^{X13}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —($C_1$-$C_4$ alkylene)-OH, —($C_1$-$C_4$ alkylene)-O($C_1$-$C_4$ alkyl), —SH, and —S($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two, or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl.

If $R^X$ is a group $R^{X1}$ and $R^Y$ is a group $R^{Y1}$, the atom X is preferably N or C (particularly N) and the atom Y is preferably C. In particular, in one embodiment, the atom X (which $R^{X1}$ is attached to) is N, and $R^{X1}$ is selected from hydrogen, phenyl, —($C_1$-$C_4$ alkylene)-phenyl (e.g., —$CH_2$-phenyl or —($CH_2$)$_2$-phenyl), pyridinyl, —($C_1$-$C_4$ alkylene)-pyridinyl, $C_1$-$C_4$ alkyl (e.g., methyl) and —CO—($C_1$-$C_4$ alkyl) (e.g., —CO-methyl). In a further embodiment, the atom Y (which $R^{Y1}$ is attached to) is C, and $R^{Y1}$ is hydrogen, in yet a further embodiment, X, Y, $R^{X1}$ and $R^{Y1}$ are as defined in the previous two sentences in this paragraph, and the bond ===== between X and Y is a single bond.

Z is O, S or N(—$R^Z$). Preferably, Z is O or S. More preferably, Z is O.

$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, $R^Z$ is selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl. More preferably, $R^Z$ is selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl. Even more preferably, $R^Z$ is hydrogen or $C_1$-$C_{10}$ alkyl. Yet even more preferably, $R^Z$ is hydrogen or $C_1$-$C_4$ alkyl (e.g., methyl or ethyl).

Each $R^1$ is independently a group -$L^1$-$R^1$.

Each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups (e.g., one, two, or three groups) independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —$CH_2$— units (e.g., one, two, or three —$CH_2$— units) comprised in said alkylene, said alkenylene or said alkynylene are each optionally replaced by a group independently selected from —O—, —$NR^{12}$—, —CO—, —S—, —SO—, and —$SO_2$—.

Preferably, each $L^1$ is independently selected from a bond, $C_1$-$C_{10}$ alkylene, and $C_2$-$C_{10}$ alkenylene, wherein said alkylene and said alkenylene are each optionally substituted with one or more groups (e.g., one, two, or three groups) independently selected from halogen, $C_1$-$C_4$ haloalkyl, —CN, —OR$^{12}$, —NR$^{12}$R$^{12}$, —COR$^{12}$, —COOR$^{12}$, —OCOR$^{12}$, —CONR$^{12}$R$^{12}$, —NR$^{12}$COR$^{12}$, —SR$^{12}$, —SOR$^{12}$, —SO$_2$R$^{12}$, —SO$_2$NR$^{12}$R$^{12}$, and —NR$^{12}$SO$_2$R$^{12}$, and further wherein one or more —CH$_2$— units (e.g., one, two, or three —OH$_2$— units) comprised in said alkenylene or said alkenylene are each optionally replaced by a group independently selected from —O—, —NR$^{12}$—, —CO—, —S—, —SO—, and —SO$_2$—. More preferably, each L$^1$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OR$^2$, —NR$^{12}$R$^{12}$, and —SR$^{12}$, and further wherein one or more —CH$_2$— units (e.g., one, two, or three —CH$_2$— units) comprised in said alkylene are each optionally replaced by a group independently selected from —O—, —NR$^{12}$—, —CO—, —S—, —SO—, and —SO$_2$—. Even more preferably, each L$^1$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OH, —O(C$_1$-C$_4$ alkyl), —NH$_2$, —NH(C$_1$-C$_4$ alkyl), —N(C$_1$-C$_4$ alkyl)(C$_1$-C$_4$ alkyl), —SH, and —S(C$_1$-C$_4$ alkyl), and further wherein one or two —CH$_2$— units comprised in said alkylene is/are each optionally replaced by a group independently selected from —O—, —NH—, —N(C$_1$-C$_4$ alkyl)-, —CO—, and —SO$_2$—. Yet even more preferably, each L$^1$ is independently selected from a bond and C$_1$-C$_6$ alkylene, wherein said alkylene is optionally substituted with one or more groups (e.g., one or two groups) independently selected from halogen, C$_1$-C$_4$ haloalkyl, —CN, —OH, —O(C$_1$-C$_4$ alkyl), —NH$_2$, —NH(C$_1$-C$_4$ alkyl), and —N(C$_1$-C$_4$ alkyl)(C$_1$-C$_4$ alkyl), and further wherein one or two —CH$_2$— units comprised in said alkylene is/are each optionally replaced by a group independently selected from —O—, —NH—, —N(C$_1$-C$_4$ alkyl)-, —CO—, and —SO$_2$—. Still more preferably, each L$^1$ is independently selected from a bond and C$_1$-C$_4$ alkylene (e.g., methylene or ethylene). Most preferably, L$^1$ is a bond.

Each R$^{11}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{12}$R$^{12}$, —OR$^{12}$, —SR$^{12}$, —SR$^{12}$, —SOR$^{12}$, —SO$_2$R$^{12}$, —COR$^{12}$, —COOR$^{12}$, —OCOR$^{12}$, —CONR$^{12}$, —NR$^{12}$COR$^{12}$, —SO$_2$NR$^{12}$R$^{12}$, —NR$^{12}$SO$_2$R$^{12}$, and —SO$_3$R$^{12}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_{1-1}$$_0$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$R$^{13}$, and further wherein, if R$^{11}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups (e.g., one, two or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—N H(C$_1$-C$_{10}$ alkyl), —CO—N (C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^1$-R$^{13}$.

Preferably, each R$^{11}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, —NR$^{12}$R$^{12}$, —OR$^{12}$, —SR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, and —NR$^{12}$SO$_2$R$^{12}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_{10}$ haloalkyl, —CN, C$_1$-C$_{10}$ alkyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH (C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^3$, and further wherein, if R$^{11}$ is C$_1$-C$_{10}$ alkyl, then said alkyl is optionally substituted with one or more groups (e.g., one, two or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N (C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$. More preferably, each R$^{11}$ is independently selected from aryl, heteroaryl, cycloalkyl, heterocycloalkyl, cycloalkenyl, heterocycloalkenyl, halogen, C$_1$-C$_4$ haloalkyl, —CN, C$_1$-C$_4$ alkyl, —NH$_2$, —NH (C$_1$-C$_4$ alkyl), —N(C$_1$-C$_4$ alkyl)(C$_1$-C$_4$ alkyl), —OH, and —O(C$_1$-C$_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_4$ haloalkyl, —CN, C$_1$-C$_4$ alkyl, —OH, —O(C$_1$-C$_4$ alkyl), —(C$_1$-C$_4$ alkylene)-OH, —(C$_1$-C$_4$ alkylene)-O(C$_1$-C$_4$ alkyl), —NH$_2$, —NH(C$_1$-C$_4$ alkyl), —N(C$_1$-C$_4$ alkyl)(C$_1$-C$_4$ alkyl), —CHO, —CO(C$_1$-C$_4$ alkyl), —COOH, tetrazolyl, —COO(C$_1$-C$_4$ alkyl), —OCO(C$_1$-C$_4$ alkyl), —CO—NH$_2$, —CO—NH(C$_1$-C$_4$ alkyl), —CO—N(C$_1$-C$_4$ alkyl)(C$_1$-C$_4$ alkyl), —NH—CO—(C$_1$-C$_4$ alkyl), —N(C$_1$-C$_4$ alkyl)-CO—(C$_1$-C$_4$ alkyl), —SO$_2$—NH(C$_1$-C$_4$ alkyl), —SO$_2$— (C$_1$-C$_4$ alkyl)(C$_1$-C$_4$ alkyl), —NH—SO$_2$—(C$_1$-C$_4$ alkyl), —N(C$_1$-C$_4$ alkyl)-SO$_2$—(C$_1$-C$_4$ alkyl), cycloalkyl, heterocycloalkyl, aryl, and heteroaryl, and further wherein, if R$^{11}$ is C$_1$-C$_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl. Even more preferably, each $R^{11}$ is independently selected from: phenyl; heteroaryl having 5 to 10 ring members, wherein 1, 2 or 3 ring members are heteroatoms selected independently from O, S and N, and the remaining ring members are carbon atoms (such as, e.g., pyridinyl (e.g., pyridin-2-yl, pyridin-3-yl, or pyridin-4-yl), pyrazolyl (e.g., pyrazol-4-yl or pyrazol-5-yl), oxazolyl (e.g., oxazol-5-yl), thiazolyl (e.g., thiazol-5-yl), pyrimidinyl (e.g., pyrimidin-5-yl), pyridazinyl (e.g., pyridazin-3-yl), pyrazinyl (e.g., pyrazin-2-yl), or imidazo[1,2-a]pyridinyl (e.g., imidazo[1,2-a]pyridin-6-yl)); $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms (such as, e.g., pyrrolidinyl (e.g., pyrrolidin-1-yl) or morpholinyl (e.g., morpholin-4-yl)); $C_5$-$C_7$ cycloalkenyl; heterocycloalkenyl having 5, 6 or 7 ring members, wherein 1, 2 or 3 ring members are heteroatoms selected independently from O, S and N, and the remaining ring members are carbon atoms (such as, e.g., 1,2,3,6-tetrahydropyridinyl (e.g., 1,2,3,6-tetrahydropyridin-4-yl)); and halogen; wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —CF$_3$), —CN, $C_1$-$C_4$ alkyl (e.g., methyl, ethyl, or n-propyl), —OH, —O($C_1$-$C_4$ alkyl) (e.g., —OCH$_3$), —($C_1$-$C_4$ alkylene)-OH, —($C_1$-$C_4$ alkylene)-O($C_1$-$C_4$ alkyl), —NH$_2$, —NH($C_1$-$C_4$ alkyl) (e.g., —NHCH$_3$), —N($C_1$-$C_4$ alkyl)($C_1$-$C_4$ alkyl) (e.g., —N(CH$_3$)$_2$), —CHO, —CO($C_1$-$C_4$ alkyl) (e.g., —COCH$_3$), —COOH, tetrazolyl (e.g., 1H-tetrazol-5-yl or 2H-tetrazol-5-yl), —COO($C_1$-$C_4$ alkyl) (e.g., —COOCH$_3$), —SO$_2$—NH($C_1$-$C_4$ alkyl) (e.g., —SO$_2$—NHCH$_3$), —SO$_2$—N($C_1$-$C_4$ alkyl)($C_1$-$C_4$ alkyl) (e.g., —SO$_2$—N(CH$_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl). Yet even more preferably, each $R^{11}$ is independently selected from phenyl, pyridinyl, imidazo[1,2-a]pyridinyl, and halogen (e.g., chloro), wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Yet even more preferably, each $R^{11}$ is independently selected from phenyl, pyridinyl, and imidazo[1,2-a]pyridinyl, wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Yet even more preferably, each $R^{11}$ is independently phenyl or pyridinyl (e.g., pyridin-2-yl, pyridin-3-yl, or pyridin-4-yl), wherein said phenyl or said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH; corresponding particularly preferred examples of $R^{11}$ are 3-cyanophenyl, 2-methylpyridin-3-yl, 2-fluoropyridin-3-yl, 6-fluoropyridin-3-yl, or 5-fluoropyridin-2-yl. Still more preferably, each $R^{11}$ is independently pyridinyl (e.g., pyridin-2-yl, pyridin-3-yl, or pyridin-4-yl), wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Most preferably, each $R^{11}$ is independently pyridinyl (e.g., pyridin-2-yl, pyridin-3-yl, or pyridin-4-yl; particularly pyridin-3-yl) which is substituted with one methyl or fluoro group (such as, e.g., 2-methylpyridin-3-yl, 2-fluoropyridin-3-yl, 6-fluoropyridin-3-yl, or 5-fluoropyridin-2-yl).

Each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

Preferably, each $R^{12}$ is independently selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl, wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to). More preferably, each $R^{12}$ is independently selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to). Even more preferably, each $R^{12}$ is independently selected from hydrogen and $C_1$-$C_4$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl), and further if two groups $R^{12}$ are attached to the same nitrogen atom, then these two groups $R^{12}$ may also together form a $C_4$-$C_6$ alkylene. Yet even more preferably, each $R^{12}$ is independently selected from hydrogen and $C_1$-$C_4$ alkyl, and if two groups $R^{12}$ are attached to the same nitrogen atom, then these two groups $R^{12}$ may also together form a $C_4$-$C_6$ alkylene. Most preferably, each $R^{12}$ is independently selected from hydrogen and $C_1$-$C_4$ alkyl (e.g., methyl or ethyl).

Each $L^{11}$ is independently selected from a bond, $C_1$-$C_{10}$ alkylene, $C_2$-$C_{10}$ alkenylene, and $C_2$-$C_{10}$ alkynylene, wherein one or more —CH$_2$— units (e.g., one, two or three —CH$_2$— units) comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—.

Preferably, each $L^{11}$ is independently selected from a bond and $C_1$-$C_{10}$ alkylene, wherein one or more —CH$_2$— units (e.g., one or two —CH$_2$— units) comprised in said alkylene are each optionally replaced by a group independently selected from —O—, —NH—, —N($C_1$-$C_4$ alkyl)-, —CO—, —S—, —SO—, and —SO$_2$—.

Each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, each $R^{13}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —NH$_2$, —NH($C_1$-$C_4$ alkyl), —N($C_1$-$C_4$ alkyl)($C_1$-$C_4$ alkyl), —OH, —O($C_1$-$C_4$ alkyl), —($C_1$-$C_4$ alkylene)-OH, —($C_1$-$C_4$ alkylene)-O($C_1$-$C_4$ alkyl), —SH, and —S($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl.

n is an integer of 0 to 4. For example, n may be 1, 2, 3 or 4. Preferably, n is 0, 1, 2 or 3. More preferably, n is 0, 1 or 2. Even more preferably, n is 1 or 2. Most preferably, n is 1.

It is to be understood that n indicates the number of substituents $R^1$ that are bound to the ring group A comprised in the compound of formula (I) or (Ia). If n is 0, then the ring group A is not substituted with any group $R^1$, i.e. is substituted with hydrogen instead of $R^1$.

If ring A in formula (I) or (Ia) is a 6-membered ring (e.g., phenyl or pyridinyl; including in particular any of the preferred 6-membered ring groups A described herein above), preferred points of attachment of the group(s) $R^1$, if present, on the corresponding ring A are the positions 8 and 9 (particularly position 9), as indicated in the following:

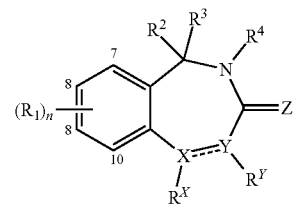

While the above-depicted illustration shows formula (I) with phenyl as ring A, it is to be understood that, for the purpose of defining preferred points of attachment of $R^1$, the same numbering of ring atoms as shown in this illustration also applies to any other 6-membered ring (such as, e.g., pyridinyl) that may be present as group A in formula (I) or (Ia).

Accordingly, if ring A is a 6-membered ring and if n is 1, it is preferred that the corresponding group $R^1$ is attached to the ring group A at position 8 or 9, most preferably at position 9 (as it is the case in the compounds of Examples 1 to 88). Moreover, if n is 1 or 2, it is preferred that the two groups $R^1$ are attached to the ring group A at positions 8 and 9, respectively.

In accordance with the above definitions of n, $L^1$ and $R^{11}$, it is particularly preferred that the compound of formula (I) or (Ia) comprises one group $R^1$ (i.e., n is 1), which is attached to position 9 of the ring group A (as described and depicted above), wherein said ring group A is phenyl or a monocyclic 6-membered heteroaryl, and wherein said group $R^1$ is selected from: phenyl; heteroaryl having 5 to 10 ring members, wherein 1, 2 or 3 ring members are heteroatoms selected independently from O, S and N, and the remaining ring members are carbon atoms (such as, e.g., pyridinyl (e.g., pyridin-2-yl, pyridin-3-yl, or pyridin-4-yl), pyrazolyl (e.g., pyrazol-4-yl or pyrazol-5-yl), oxazolyl (e.g., oxazol-5-yl), thiazolyl (e.g., thiazol-5-yl), pyrimidinyl (e.g., pyrimidin-5-yl), pyridazinyl (e.g., pyridazin-3-yl), pyrazinyl (e.g., pyrazin-2-yl), or imidazo[1,2-a]pyridinyl (e.g., imidazo[1,2-a]pyridin-6-yl)); $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms (such as, e.g., pyrrolidinyl (e.g., pyrrolidin-1-yl) or morpholinyl (e.g., morpholin-4-yl)); $C_5$-$C_7$ cycloalkenyl; heterocycloalkenyl having 5, 6 or 7 ring members, wherein 1, 2 or 3 ring members are heteroatoms selected independently from O, S and N, and the remaining ring members are carbon atoms (such as, e.g., 1,2,3,6-tetrahydropyridinyl (e.g., 1,2,3,6-tetrahydropyridin-4-yl)); and halogen; wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —CF$_3$), —CN, $C_1$-$C_4$ alkyl (e.g., methyl, ethyl, or n-propyl), —OH, —O($C_1$-$C_4$ alkyl) (e.g., —OCH$_3$), —($C_1$-$C_4$ alkylene)-OH, —($C_1$-$C_4$ alkylene)-O($C_1$-$C_4$ alkyl), —NH$_2$, —NH($C_1$-$C_4$ alkyl) (e.g., —NHCH$_3$), —N($C_1$-$C_4$ alkyl)($C_1$-$C_4$ alkyl) (e.g., —N(CH$_3$)$_2$), —CHO, —CO($C_1$-$C_4$ alkyl) (e.g., —COCH$_3$), —COOH, tetrazolyl (e.g., 1H-tetrazol-5-yl or 2H-tetrazol-5-yl), —COO($C_1$-$C_4$ alkyl) (e.g., —COOCH$_3$), —SO$_2$—NH($C_1$-$C_4$ alkyl) (e.g., —SO$_2$—NHCH$_3$), —SO$_2$—N($C_1$-$C_4$ alkyl)($C_1$-$C_4$ alkyl) (e.g., —SO$_2$—N(CH$_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl). Even more preferably, n is 1, the group $R^1$ is attached to position 9 of the ring group A comprised in the compound of formula (I) or (Ia), said ring group A is phenyl or a monocyclic 6-membered heteroaryl (including any of the corresponding exemplary heteroaryl groups described further above), and said group $R^1$ is selected from phenyl, pyridinyl, imidazo[1,2-a]pyridinyl, and halogen (e.g., chloro), wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Yet even more preferably, n is 1, the group $R^1$ is attached to position 9 of the ring group A comprised in the compound of formula (I) or (Ia), said ring group A is phenyl or a monocyclic 6-membered heteroaryl, and said group $R^1$ is selected from phenyl, pyridinyl, and imidazo[1,2-a]pyridinyl, wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Yet even more preferably, n is 1, the group $R^1$ is attached to position 9 of the ring group A comprised in the compound of formula (I) or (Ia), said ring group A is phenyl or a monocyclic 6-membered heteroaryl, and said group $R^1$ is phenyl or pyridinyl (e.g., pyridin-2-yl, pyridin-3-yl, or pyridin-4-yl), wherein said phenyl or said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH; corresponding particularly preferred examples of $R^1$ are 3-cyanophenyl, 2-methylpyridin-3-yl, 2-fluoropyridin-3-yl, 6-fluoropyridin-3-yl, or 5-fluoropyridin-2-yl. Still more preferably, n is 1, the group $R^1$ is attached to position 9 of the ring group A comprised in the compound of formula (I) or (Ia), said ring group A is phenyl or a monocyclic 6-membered heteroaryl, and said group $R^1$ is pyridinyl (e.g., pyridin-2-yl, pyridin-3-yl, or pyridin-4-yl), wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH. Most preferably, n is 1, the group $R^1$ is attached to position 9 of the ring group A comprised in the compound of formula (I) or (Ia), said ring group A is phenyl or a monocyclic 6-membered heteroaryl (including any of the corresponding exemplary heteroaryl groups described further above), and said group $R^1$ is pyridinyl (e.g., pyridin-2-yl, pyridin-3-yl, or pyridin-4-yl; particularly pyridin-3-yl) which is substituted with one methyl or fluoro group; corresponding particularly preferred examples of $R^1$ are 2-methylpyridin-3-yl, 6-fluoropyridin-3-yl, or 5-fluoropyridin-2-yl.

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —SO$_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups (e.g., one, two or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if one or both of $R^2$ and $R^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two or three groups) independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; or $R^2$ and $R^3$ together form a divalent group selected from =O, =S, =NH and =N($C_1$-$C_{10}$ alkyl).

If $R^2$ and $R^3$ are mutually linked, it is preferred that they form, together with the carbon atom that they are attached to, a $C_3$-$C_7$ cycloalkyl or a 3- to 7-membered heterocycloalkyl containing 1, 2 or 3 ring heteroatoms independently selected from O, S and N, more preferably a $C_3$-$C_7$ cycloalkyl, even more preferably a $C_3$-$C_5$ cycloalkyl (e.g., cyclopropyl, cyclobutyl, or cyclopentyl), even more preferably a cyclopropyl or cyclobutyl, and most preferably a cyclopropyl. It will be understood that any such cycloalkyl or heterocycloalkyl group, which is formed from $R^2$, $R^3$ and the carbon atom that they are attached to, is a spiro group since said carbon atom is also a ring member of the 7-membered ring comprised in the central ring system of the compound of formula (I) or (Ia).

If $R^2$ and $R^3$ are each independently selected from the above-defined groups, it is preferred that they are each independently selected from hydrogen, halogen, $C_1$-$C_4$ haloalkyl, $C_1$-$C_4$ alkyl, —OH, —O($C_1$-$C_4$ alkyl), —SH, —S($C_1$-$C_4$ alkyl), —SO—($C_1$-$C_4$ alkyl), —SO$_2$—($C_1$-$C_4$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups (e.g., one, two or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl, and further wherein, if one or both of $R^2$ and $R^3$ is/are $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl; more preferably, $R^2$ and $R^3$ are each independently selected from hydrogen, halogen, $C_1$-$C_4$ haloalkyl, $C_1$-$C_4$ alkyl, —OH, —O($C_1$-$C_4$ alkyl), —SH, —S($C_1$-$C_4$ alkyl), —SO—($C_1$-$C_4$ alkyl), —SO$_2$—($C_1$-$C_4$ alkyl), —CN, wherein said $C_1$-$C_4$ alkyl is optionally substituted with one or more groups (e.g., one, two or three groups) independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl); even more preferably, $R^2$ and $R^3$ are each independently selected from hydrogen, halogen, $C_1$-$C_4$ haloalkyl, $C_1$-$C_4$ alkyl, —OH, —O($C_1$-$C_4$ alkyl), and —CN; yet even more preferably, $R^2$ and $R^3$ are each independently selected from hydrogen, halogen, $C_1$-$C_4$ alkyl, —OH, and —O($C_1$-$C_4$ alkyl); still more preferably, $R^2$ and $R^3$ are each independently selected from hydrogen and $C_1$-$C_4$ alkyl (e.g., methyl or ethyl). For example, $R^2$ and $R^3$ may both be hydrogen, or may both independently be $C_1$-$C_4$ alkyl (e.g., they may both be methyl), or may be hydrogen and $C_1$-$C_4$ alkyl (e.g., $R^2$ may be hydrogen, and $R^3$ may be methyl or ethyl). Yet even more preferably, $R^2$ and $R^3$ are each hydrogen.

If $R^2$ and $R^3$ together form a divalent group, it is preferred that they form a group =O.

In accordance with the above definitions of $R^2$ and $R^3$, it is particularly preferred that $R^2$ and $R^3$ are mutually linked to form, together with the carbon atom that they are attached to, a $C_3$-$C_5$ cycloalkyl (e.g., a cyclopropyl, a cyclobutyl, or a cyclopentyl), or that $R^2$ and $R^3$ are each independently selected from hydrogen, halogen, $C_1$-$C_4$ alkyl, —OH, and —O($C_1$-$C_4$ alkyl). Even more preferably, $R^2$ and $R^3$ are mutually linked to form, together with the carbon atom that they are attached to, a $C_3$-$C_5$ cycloalkyl (e.g., cyclopropyl or cyclobutyl), or $R^2$ and $R^3$ are each independently selected from hydrogen and $C_1$-$C_4$ alkyl (e.g., methyl or ethyl). Yet even more preferably, $R^2$ and $R^3$ are mutually linked to form, together with the carbon atom that they are attached to, a cyclopropyl, or $R^2$ and $R^3$ are each hydrogen.

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups (e.g., one, two, or three groups) independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl.

Preferably, $R^4$ is $C_1$-$C_{10}$ alkyl, wherein said alkyl is optionally substituted with one or more groups (e.g., one, two, or three groups) independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl. For example, $R^4$ may be $C_1$-$C_{10}$ alkyl, wherein said alkyl is optionally substituted with one or more groups (e.g., one, two, or three groups) independently selected from halogen, $C_1$-$C_{10}$ haloalkyl, —O—($C_1$-$C_{10}$ haloalkyl), —CN, —OH, and —O($C_1$-$C_{10}$ alkyl). More preferably, $R^4$ is $C_1$-$C_4$ alkyl, wherein said alkyl is optionally substituted with one or more groups (e.g., one, two, or three groups) independently selected from halogen, $C_1$-$C_4$ haloalkyl, —O—($C_1$-$C_4$ haloalkyl), —CN, —OH and —O($C_1$-$C_4$ alkyl). Even more preferably, $R^4$ is $C_1$-$C_4$ alkyl, wherein said alkyl is optionally substituted with one or more groups (e.g., one or two groups) independently selected from —OH and —O($C_1$-$C_4$ alkyl) (e.g., —OCH$_3$). Yet even more preferably, $R^4$ is $C_1$-$C_4$ alkyl. Most preferably, $R^4$ is methyl.

Each $R^5$ is independently a group -$L^5$-$R^{51}$.

Each $L^5$ is independently selected from a bond, $C_1$-$C_{10}$ alkylene, $C_2$-$C_{10}$ alkenylene, and $C_2$-$C_{10}$ alkynylene (e.g., $C_3$-$C_{10}$ alkynylene), wherein said alkylene, said alkenylene and said alkynylene are each optionally substituted with one or more groups (e.g., one, two, or three groups) independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SR$^{52}$, —SO$_2$R$^{52}$, —SO$_2$NR$^{52}$R$^{52}$, and —NR$^{52}$SO$_2$R$^{52}$, and further wherein one or more —CH$_2$— units (e.g., one, two, or three —CH$_2$— units) comprised in said alkylene, said alkenylene or said alkynylene are each optionally replaced by a group independently selected from —O—, —NR$^{52}$—, —CO—, —S—, —SO—, and —SO$_2$—.

Preferably, each $L^5$ is independently selected from a bond and $C_1$-$C_{10}$ alkylene, wherein said alkylene is optionally substituted with one or more groups (e.g., one, two, or three groups) independently selected from halogen, $C_1$-$C_4$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —OH$_2$— units (e.g., one, two, or three —CH$_2$— units) comprised in said alkylene are each optionally replaced by a group independently selected from —O—, —NR$^{52}$—, —CO—, —S—, —SO—, and —SO$_2$—. More preferably, each $L^5$ is independently selected from a bond and $C_1$-$C_{10}$ alkylene, wherein said alkylene is optionally substituted with one or more groups (e.g., one, two, or three groups) independently selected from halogen, $C_1$-$C_4$ haloalkyl, —CN, —OR$^{52}$, —NR$^{52}$R$^{52}$, and —SR$^{52}$, and further wherein one or more —OH$_2$— units (e.g., one, two, or three —CH$_2$— units) comprised in said alkylene are each optionally replaced by a group independently selected from —O—, —NR$^{52}$—, —CO—, —S—, —SO—, and —SO$_2$—. Even more preferably, each $L^5$ is independently selected from a bond and $C_1$-$C_{10}$ alkylene, wherein said alkylene is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —OH$_2$— units comprised in said alkylene is/are each optionally replaced by a group independently selected from —O—, —NH—, —N($C_1$-$C_4$ alkyl)-, —CO—, and —SO$_2$—. Even more preferably, each $L^5$ is independently selected from a bond and $C_1$-$C_6$ alkylene, wherein said alkylene is optionally substituted with one or more groups (e.g., one or two groups) independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—. Yet even more preferably, each $L^5$ is independently selected from a bond and $C_1$-$C_4$ alkylene. Still more preferably, each $L^5$ is independently selected from a bond and methylene.

Each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl (e.g., $C_3$-$C_{10}$ alkynyl), —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{25}$, —NR$^{52}$OCOR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)

($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH ($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^5$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N ($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$.

Preferably, each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, —$NR^{52}R^{52}OR^{52}$, OR, —$SR^{52}$, —$SO_2R^{52}$, —$COR^{52}$, —$COOR^{52}$, —$OCOR^{52}$, —$CONR^{52}R^{52}$, —$NR^{52}COR^{52}$, —$SO_2NR^{52}R^{52}$, and —$NR^{52}SO_2R^{52}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH ($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, then said alkyl is optionally substituted with one or more groups (e.g., one, two or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N ($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^5$-$R^{53}$. More preferably, each $R^{51}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH ($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl, and further wherein, if $R^{51}$ is $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH ($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl. Even more preferably, each $R^{51}$ is independently selected from: phenyl; heteroaryl having 5 or 6 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; $C_5$-$C_7$ cycloalkenyl; heterocycloalkenyl having 5, 6 or 7 ring members, wherein 1, 2 or 3 ring members are heteroatoms selected independently from O, S and N, and the remaining ring members are carbon atoms; halogen; $C_1$-$C_4$ haloalkyl; —CN; $C_1$-$C_4$ alkyl; —$NH_2$; —NH($C_1$-$C_4$ alkyl); —N($C_1$-$C_4$ alkyl)($C_1$-$C_4$ alkyl); —OH; and —O($C_1$-$C_4$ alkyl); wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —$CF_3$), —CN, $C_1$-$C_4$ alkyl (e.g., methyl, ethyl, or n-propyl), —OH, —O($C_1$-$C_4$ alkyl) (e.g., —$OCH_3$), —($C_1$-$C_4$ alkylene)-OH, —($C_1$-$C_4$ alkylene)-O ($C_1$-$C_4$ alkyl), —$NH_2$, —NH($C_1$-$C_4$ alkyl) (e.g., —$NHCH_3$), —N($C_1$-$C_4$ alkyl)($C_1$-$C_4$ alkyl) (e.g., —N($CH_3$)$_2$), —CHO, —CO($C_1$-$C_4$ alkyl) (e.g., —$COCH_3$), —COOH, tetrazolyl (e.g., 1H-tetrazol-5-yl or 2H-tetrazol-5-yl), —COO($C_1$-$C_4$ alkyl) (e.g., —$COOCH_3$), —$SO_2$—$NH_2$, —$SO_2$—NH($C_1$-$C_4$ alkyl) (e.g., —$SO_2$—$NHCH_3$), —$SO_2$—N($C_1$-$C_4$ alkyl) ($C_1$-$C_4$ alkyl) (e.g., —$SO_2$—N($CH_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl); and further wherein, if $R^{51}$ is $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO ($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), cycloalkyl, heterocycloalkyl, aryl, and heteroaryl. Even more preferably, each $R^{51}$ is independently selected from: phenyl; heteroaryl having 5 or 6 ring members, wherein 1, 2 or 3 ring members are heteroatoms selected independently from O, S and N, and the remaining ring members are carbon atoms (such as, e.g., pyridinyl (e.g., pyridin-3-yl or pyridin-4-yl), thiazolyl (e.g., thiazol-2-yl), imidazolyl (e.g., 1H-imidazol-2-yl or 3H-imidazol-4-yl), pyrazolyl (e.g., 1H-pyrazol-3-yl or 2H-pyrazol-3-yl), oxazolyl (e.g., oxazol-5-yl), or oxadiazolyl (e.g., [1,3,4]oxadiazol-2-yl)); $C_1$-$C_4$ haloalkyl (e.g., —$CF_3$ or —$CHF_2$); $C_1$-$C_4$ alkyl (e.g., methyl or ethyl); —$NH_2$; —NH($C_1$-$C_4$ alkyl) (e.g., —$NHCH_3$); —N($C_1$-$C_4$ alkyl)($C_1$-$C_4$ alkyl) (e.g., —N($CH_3$)$_2$); —OH; and —O($C_1$-$C_4$ alkyl) (e.g., —$OCH_3$); wherein said phenyl and said heteroaryl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl) (e.g., methoxy), —$NH_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups (e.g., one or two groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl). Yet even more preferably, $R^{51}$ is oxadiazolyl (e.g., [1,3,4]oxadiazol-2-yl) or —O($C_1$-$C_4$ alkyl) (particularly methoxy), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl). Still more preferably, $R^{51}$ is oxadiazolyl (particularly [1,3,4]oxadiazol-2-yl) or —O($C_1$-$C_4$ alkyl) (particularly methoxy).

Each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to).

Preferably, each $R^{52}$ is independently selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to). More preferably, each $R^{52}$ is independently selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to). Even more preferably, each $R^{52}$ is independently selected from hydrogen and $C_1$-$C_4$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl), and further if two groups $R^{52}$ are attached to the same nitrogen atom, then these two groups $R^{52}$ may also together form a $C_4$-$C_6$ alkylene. Yet even more preferably, each $R^{52}$ is independently selected from hydrogen and $C_1$-$C_4$ alkyl, and if two groups $R^{52}$ are attached to the same nitrogen atom, then these two groups $R^{52}$ may also together form a $C_4$-$C_6$ alkylene. Most preferably, each $R^{52}$ is independently selected from hydrogen and $C_1$-$C_4$ alkyl (e.g., methyl or ethyl).

Each $L^{51}$ is independently selected from a bond, $C_1$-$C_{10}$ alkylene, $C_2$-$C_{10}$ alkenylene, and $C_2$-$C_{10}$ alkynylene, wherein one or more —$CH_2$— units (e.g., one, two or three —$CH_2$— units) comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Preferably, each $L^{51}$ is independently selected from a bond and $C_1$-$C_{10}$ alkylene, wherein one or more —$CH_2$— units (e.g., one or two —$CH_2$— units) comprised in said alkylene are each optionally replaced by a group independently selected from —O—, —NH—, —N($C_1$-$C_4$ alkyl)-, —CO—, —S—, —SO—, and —$SO_2$—.

Each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, each $R^{53}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —($C_1$-$C_4$ alkylene)-OH, —($C_1$-$C_4$ alkylene)-O($C_1$-$C_4$ alkyl), —SH, and —S($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl.

In accordance with the above definitions of $L^5$ and $R^{51}$, it is particularly preferred that each $L^5$ is independently a bond or $C_1$-$C_4$ alkylene (particularly methylene), and that each $R^{51}$ is independently selected from: phenyl; heteroaryl having 5 or 6 ring members, wherein 1, 2 or 3 ring members are heteroatoms selected independently from O, S and N, and the remaining ring members are carbon atoms (such as, e.g., pyridinyl (e.g., pyridin-3-yl or pyridin-4-yl), thiazolyl (e.g., thiazol-2-yl), imidazolyl (e.g., 1H-imidazol-2-yl or 3H-imidazol-4-yl), pyrazolyl (e.g., 1H-pyrazol-3-yl or 2H-pyrazol-3-yl), oxazolyl (e.g., oxazol-5-yl), or oxadiazolyl (e.g., [1,3,4]oxadiazol-2-yl)); $C_1$-$C_4$ haloalkyl (e.g., —$CF_3$ or —$CHF_2$); $C_1$-$C_4$ alkyl (e.g., methyl or ethyl); —$NH_2$; —NH($C_1$-$C_4$ alkyl) (e.g., —$NHCH_3$); —N($C_1$-$C_4$ alkyl)($C_1$-$C_4$ alkyl) (e.g., —N($CH_3$)$_2$); —OH; and —O($C_1$-$C_4$ alkyl); wherein said phenyl and said heteroaryl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl) (e.g., —$OCH_3$), —$NH_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups (e.g., one or two groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl). Even more preferably, $L^5$ is a bond and $R^{51}$ is oxadiazolyl (e.g., [1,3,4]oxadiazol-2-yl), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl), or $L^5$ is $C_1$-$C_4$ alkylene (particularly methylene) and $R^{51}$ is —O($C_1$-$C_4$ alkyl) (particularly —$OCH_3$). Accordingly, it is even more preferred that each $R^5$ (if present) is independently oxadiazolyl (e.g., [1,3,4]oxadiazol-2-yl) or —($C_1$-$C_4$ alkylene)-O—($C_1$-$C_4$ alkyl) (particularly —$CH_2$—O—$CH_3$), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl). Yet even more preferably, each $R^5$ (if present) is independently oxadiazolyl or —($C_1$-$C_4$ alkylene)-O—($C_1$-$C_4$ alkyl), particularly [1,3,4]oxadiazol-2-yl or —$CH_2$—O—$CH_3$.

As explained above, it is preferred that $R^X$ and $R^Y$ in formula (I) are mutually linked to form, together with the atoms X and Y that they are attached to, an aryl or heteroaryl group, wherein said aryl or heteroaryl group is optionally substituted with one or more groups $R^5$ (e.g., with one, two or three groups $R^5$). Preferably, said aryl or heteroaryl group is unsubstituted or is substituted with one or two groups $R^5$; more preferably, it is unsubstituted or is substituted with one group $R^5$; even more preferably, said aryl or heteroaryl group is unsubstituted. It will be understood that the substituent(s) $R^5$, if present, each replace a hydrogen atom attached to a ring atom (which may be a carbon ring atom or a nitrogen ring atom) of the aforementioned aryl or heteroaryl group.

m is an integer of 0 to 3. Preferably, m is 0, 1 or 2. More preferably, m is 0 or 1. Even more preferably, m is 0.

It is to be understood that m indicates the number of substituents $R^5$ that are bound to the ring group B (containing the ring atoms X and Y) which is comprised in the central ring system of the compound of formula (Ia). If m is 0, then ring B is unsubstituted, i.e. is not substituted with any group $R^5$. It will further be understood that the upper limit of m, i.e. the maximum number of substituents $R^5$, depends on the number of hydrogen atoms attached to the ring atoms of ring B (which hydrogen atoms are available for substitution/replacement with $R^5$) and may thus be lower than 3 (or may even be 0) in the case of specific rings B.

If ring B is a 5-membered (monocyclic) ring, then a preferred point of attachment of $R^5$ is the ring atom that is farthest away from the ring atoms X and Y, i.e. the same ring atom as the one that carries the methoxymethyl substituent in the compound of Example 65. Thus, if ring B is a 5-membered ring, it is preferred that at least one of the group(s) $R^5$, if present, is attached to this specific position. Accordingly, it is particularly preferred that m is 0 or 1, and that the one group $R^5$, if present (i.e., if m is 1), is attached to this specific position if ring B is a 5-membered ring.

In accordance with the present invention, if A in formula (I) is phenyl, X is N, Y is C, the bond ===== between X and Y is a single bond, and $R^X$ and $R^Y$ are mutually linked to form a heteroaryl group (which may be optionally substituted with one or more groups $R^5$), then said heteroaryl group is not (i.e., is different from) a 5-membered monocyclic heteroaryl group consisting of carbon and nitrogen ring atoms. It will be understood that the expression "heteroaryl group consisting of carbon and nitrogen ring atoms", as used in this context, refers to a heteroaryl group having only carbon and nitrogen ring atoms (but not having any other ring atoms, such as sulfur or oxygen ring atoms), and that the carbon and/or nitrogen ring atoms of a corresponding heteroaryl group may still carry hydrogen atoms and/or the substituent group(s) $R^5$.

This requirement can also be expressed as follows: If A in formula (I) is phenyl, X is N, Y is C, the bond ===== between X and Y is a single bond, and $R^X$ and $R^Y$ are mutually linked to form a heteroaryl group (which may be optionally substituted with one or more groups $R^5$)—i.e., if the aforementioned conditions are cumulatively fulfilled, then said heteroaryl group (which contains the ring atoms X and Y) must have more than 5 ring members. In particular, if A in formula (I) is phenyl, X is N, Y is C, the bond ===== between X and Y is a single bond, and $R^X$ and $R^Y$ are mutually linked to form a heteroaryl group (which may be optionally substituted with one or more groups $R^5$), then said heteroaryl group is preferably a 6-membered heteroaryl group.

Likewise, if A in formula (Ia) is phenyl, X is N, Y is C, the bond ===== between X and Y is a single bond, and B is a heteroaryl group, then said heteroaryl group is not (i.e., is different from) a 5-membered monocyclic heteroaryl group consisting of carbon and nitrogen ring atoms. It will be understood that the expression "heteroaryl group consisting of carbon and nitrogen ring atoms", as used in this context, refers to a heteroaryl group having only carbon and nitrogen ring atoms (but not having any other ring atoms, such as sulfur or oxygen ring atoms), and that the carbon and/or nitrogen ring atoms of a corresponding heteroaryl group may still carry hydrogen atoms and/or the substituent group(s) $R^5$.

In other words, if A in formula (Ia) is phenyl, X is N, Y is C, the bond ===== between X and Y is a single bond, and B is a heteroaryl group—i.e., if the aforementioned conditions are cumulatively fulfilled, then said heteroaryl group (which contains the ring atoms X and Y) must have more than 5 ring atoms. In particular, if A in formula (Ia) is phenyl, X is N, Y is C, the bond ===== between X and Y is a single bond, and B is a heteroaryl group, then said heteroaryl group is preferably a 6-membered heteroaryl group.

Furthermore, in accordance with the present invention, if A in formula (I) is phenyl, $R^2$ and $R^3$ are each hydrogen, $R^4$ is methyl, Z is O, X and Y are each C, and the bond ===== between X and Y is a double bond, then $R^X$ and $R^Y$ are not mutually linked to form a thiazolyl group that is substituted with one group -$L^5$-$R^{51}$, wherein $L^5$ is different from a bond and wherein $R^{51}$ is an optionally substituted aryl or an optionally substituted heteroaryl.

Likewise, if A in formula (Ia) is phenyl, $R^2$ and $R^3$ are each hydrogen, $R^4$ is methyl, Z is O, X and Y are each C, the bond ===== between X and Y is a double bond, m is 1, $L^5$ is different from a bond, and $R^{51}$ is an optionally substituted aryl or an optionally substituted heteroaryl, then B is not a thiazolyl group.

In accordance with the above requirement, it is preferred that, if A in formula (Ia) is phenyl, X and Y are each C, the bond ===== between X and Y is a double bond, m is 1, and $R^{51}$ is an optionally substituted aryl or an optionally substituted heteroaryl (i.e., if all the aforementioned conditions are cumulatively fulfilled), then B is not a thiazolyl group. More preferably, if A is phenyl, X and Y are each C, the bond ===== between X and Y is a double bond, and m is 1, then B is not a thiazolyl group. Even more preferably, if A is phenyl, X and Y are each C, and the bond ===== between X and Y is a double bond, then B is not a thiazolyl group.

In the second aspect, the invention relates to a compound of formula (I) or (Ia), or a pharmaceutically acceptable salt, solvate or prodrug thereof, wherein:
(i) the groups $R^2$ and $R^3$ are mutually linked to form, together with the carbon atom that they are attached to, a cycloalkyl or a heterocycloalkyl; or
(ii) the ring group A is heteroaryl, said heteroaryl being different from pyrimidinyl and from 1,3-benzodioxolyl, and wherein the following compounds are excluded from formula (I) or from formula (Ia):

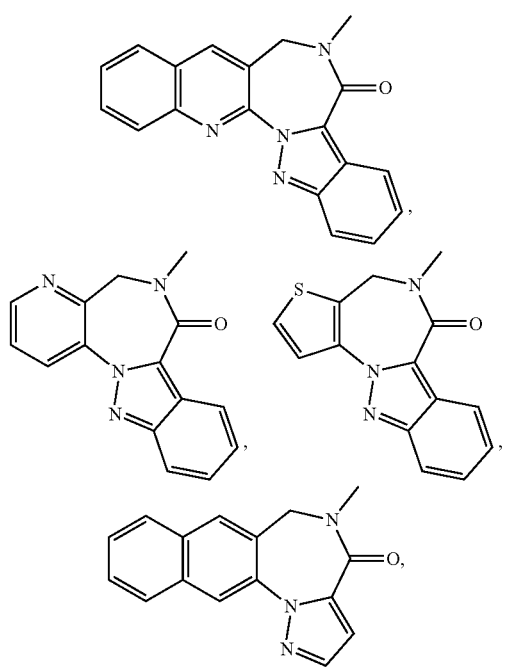

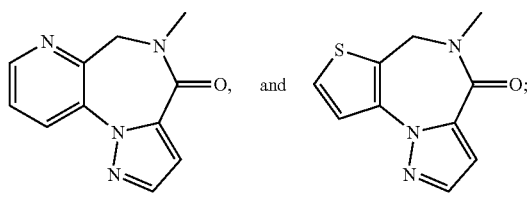

or
(iii) the ring group B in formula (Ia) is a heteroaryl group, said heteroaryl group being different from indolyl and from 1,3-benzodioxolyl,
wherein, if A is phenyl, X and Y are each C, Z is O, $R^2$ and $R^3$ are each hydrogen, $R^4$ is methyl or tert-butyl, n is 0 or 1, $R^1$ (if present) is methyl, m is 0 or 1, and $R^5$ (if present) is methyl, then B is not (i.e., is different from) pyridinyl,
and wherein, if A is phenyl, X and Y are each C, the bond ===== between X and Y is a double bond, Z is O, one of $R^2$ and $R^3$ is hydrogen and the other one of $R^2$ and $R^3$ is methyl, $R^4$ is isopropyl, and n is 0, then B is not (i.e., is different from) quinolinyl or 1,4-dihydroquinolinyl,
and further wherein the following compounds are excluded from formula (Ia):

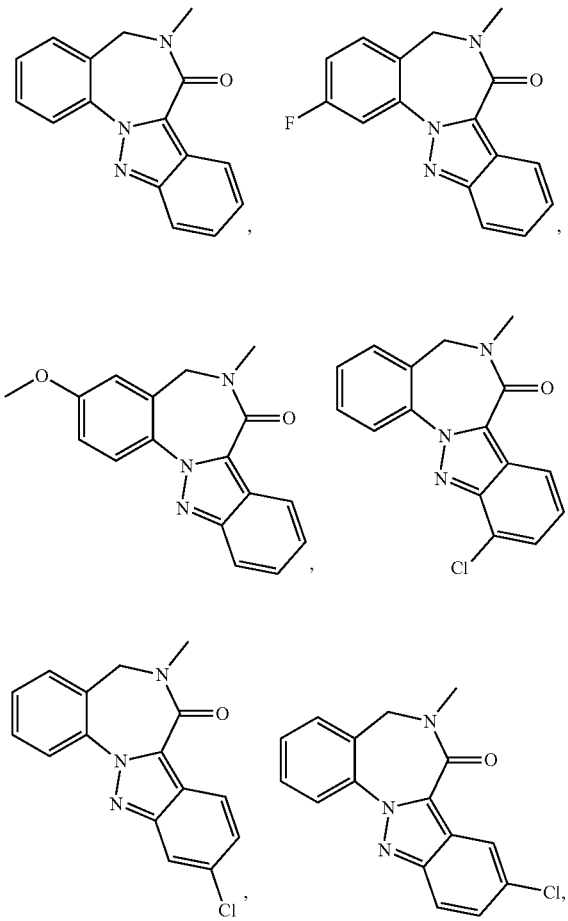

and wherein it is preferred that the following compound is also excluded from formula (Ia):

It is particularly preferred that the compound of formula (I) or (Ia) according to the first or second aspect of the invention is any one of the specific compounds of formula (I) or (Ia) as described in the examples section of this specification, including any one of the compounds of Examples 1 to 88 described further below, either in non-salt form or as a pharmaceutically acceptable salt, solvate or prodrug of the respective compound.

Accordingly, it is particularly preferred that the compound of formula (I) according to the first or the second aspect of the invention is selected from:

2'-Chloro-6'-methylspiro[cyclopropane-1,5'-pyrido[3,4-f]pyrrolo[1,2-a][1,4]diazepin]-7'(6'H)-one;

2',9'-Dichloro-6'-methylspiro[cyclopropane-1,5'-pyrido[3,4-f]pyrrolo[1,2-a][1,4]diazepin]-7'(6'H)-one;

2'-(2-Methyl-pyridin-3-yl)-6'-methylspiro[cyclopropane-1,5'-pyrido[3,4-f]pyrrolo[1,2-a][1,4]diazepin]-7'(6'H)-one;

9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;

9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;

5-Methyl-9-(2-methyl-pyridin-3-yl)-5,6-dihydro-5,7,10b-triaza-benzo[e]azulen-4-one;

5-M ethyl-9-(2-methyl-pyridin-3-yl)-5,6-dihydro-5,7,10,10b-tetraaza-benzo[e]azulen-4-one;

5-Methyl-9-(2-methyl-pyridin-3-yl)-5,6-dihydro-5,7,8,10b-tetraaza-benzo[e]azulen-4-one;

9-Chloro-5-methyl-5,6-dihydro-5,10,10b-triaza-benzo[e]azulen-4-one;

5-Methyl-9-(2-methyl-pyridin-3-yl)-5,6-dihydro-5,10,10b-triaza-benzo[e]azulen-4-one;

3-(5-Methyl-4-oxo-5,6-dihydro-4H-5,7,10b-triaza-benzo[e]azulen-9-yl)-benzonitrile;

9-Imidazo[1,2-a]pyridin-6-yl-5-methyl-5,6-dihydro-5,7,10b-triaza-benzo[e]azulen-4-one;

9-Chloro-5-methyl-5,6-dihydro-5,8,10,10b-tetraaza-benzo[e]azulen-4-one;

5-Methyl-9-(2-methyl-pyridin-3-yl)-5,6-dihydro-5,8,10,10b-tetraaza-benzo[e]azulen-4-one;

10-Chloro-6-methyl-6,7-dihydro-spiro[dibenzo[c,e]azepine-7,1'-cyclopropan]-5-one;

10-Bromo-3-chloro-6-methyl-6,7-dihydro-spiro[dibenzo[c,e]azepine-7,1'-cyclopropan]-5-one;

10-(2-Methyl-pyridin-3-yl)-6-methyl-6,7-dihydro-spiro[dibenzo[c,e]azepine-7,1'-cyclopropan]-5-one;

3-Chloro-10-(2-methyl-pyridin-3-yl)-6-methyl-6,7-dihydro-spiro[dibenzo[c,e]azepine-7,1'-cyclopropan]-5-one;

3-(2-Methyl-2H-pyrazol-3-yl)-10-(2-methyl-pyridin-3-yl)-6-methyl-6,7-dihydro-spiro[dibenzo[c,e]azepine-7,1'-cyclopropan]-5-one;

10-Chloro-6-methyl-6,7-dihydro-4,6-diaza-dibenzo[a,c]cyclohepten-5-one;

3-(6-Methyl-5-oxo-6,7-dihydro-5H-4,6-diaza-dibenzo[a,c]cyclohepten-10-yl)-benzonitrile;

6-Methyl-10-(2-methyl-pyridin-3-yl)-6,7-dihydro-4,6-diaza-dibenzo[a,c]cyclohepten-5-one;

10-(6-Fluoro-pyridin-3-yl)-6-methyl-6,7-dihydro-4,6-diaza-dibenzo[a,c]cyclohepten-5-one;

10-(5-Fluoro-pyridin-2-yl)-6-methyl-6,7-dihydro-4,6-diaza-dibenzo[a,c]cyclohepten-5-one;

10-Chloro-3-fluoro-6-methyl-6,7-dihydro-4,6-diaza-dihydro-4,6-diaza-dibenzo[a,c]cyclohepten-5-one;

3-Fluoro-6-methyl-10-(2-methyl-pyridin-3-yl)-6,7-dihydro-4,6-diaza-dibenzo[a,c]cyclohepten-5-one;

3-Fluoro-10-(6-fluoro-pyridin-3-yl)-6-methyl-6,7-dihydro-4,6-diaza-dibenzo[a,c]cyclohepten-5-one;

3-Fluoro-10-(5-fluoro-pyridin-2-yl)-6-methyl-6,7-dihydro-4,6-diaza-dibenzo[a,c]cyclohepten-5-one;

10-Chloro-3-methoxy-6-methyl-6,7-dihydro-4,6-diaza-dibenzo[a,c]cyclohepten-5-one;

10-(5-fluoro-pyridin-2-yl)-3-methoxy-6-methyl-6,7-dihydro-4,6-diaza-dibenzo[a,c]cyclohepten-5-one;

10-(6-Fluoro-pyridin-3-yl)-3-methoxy-6-methyl-6,7-dihydro-4,6-diaza-dibenzo[a,c]cyclohepten-5-one;

3-Methoxy-6-methyl-10-(2-methyl-pyridin-3-yl)-6,7-dihydro-4,6-diaza-dibenzo[a,c]cyclohepten-5-one;

3-Hydroxy-6-methyl-10-(2-methyl-pyridin-3-yl)-6,7-dihydro-4,6-diaza-dibenzo[a,c]cyclohepten-5-one;

10-Chloro-3,6-dimethyl-6,7-dihydro-4,6-diaza-dibenzo[a,c]cyclohepten-5-one;

10-(6-Fluoro-pyridin-3-yl)-3,6-dimethyl-6,7-dihydro-4,6-diaza-dibenzo[a,c]cyclohepten-5-one;

10-(5-Fluoro-pyridin-2-yl)-3,6-dimethyl-6,7-dihydro-4,6-diaza-dibenzo[a,c]cyclohepten-5-one;

3,6-Dimethyl-10-(2-methyl-pyridin-3-yl)-6,7-dihydro-4,6-diaza-dibenzo[a,c]cyclohepten-5-one;

10-Chloro-2,6-dimethyl-6,7-dihydro-4,6-diaza-dibenzo[a,c]cyclohepten-5-one;

2,6-Dimethyl-10-(2-methyl-pyridin-3-yl)-6,7-dihydro-4,6-diaza-dibenzo[a,c]cyclohepten-5-one;

10-(6-Fluoro-pyridin-3-yl)-2,6-dimethyl-6,7-dihydro-4,6-diaza-dibenzo[a,c]cyclohepten-5-one;

10-Chloro-2-fluoro-6-methyl-6,7-dihydro-4,6-diaza-dibenzo[a,c]cyclohepten-5-one;

2-Fluoro-6-methyl-10-(2-methyl-pyridin-3-yl)-6,7-dihydro-4,6-diaza-dibenzo[a,c]cyclohepten-5-one;

2-Fluoro-10-(6-fluoro-pyridin-3-yl)-6-methyl-6,7-dihydro-4,6-diaza-dibenzo[a,c]cyclohepten-5-one;

2-Methoxy-6-methyl-10-(2-methyl-pyridin-3-yl)-6,7-dihydro-4,6-diaza-dibenzo[a,c]cyclohepten-5-one;

10-Chloro-6-methylspiro[benzo[c]pyrido[3,2-e]azepine-7,1'-cyclopropan]-5(6H)-one;

10-(6-Fluoro-pyridin-3-yl)-6-methylspiro[benzo[c]pyrido[3,2-e]azepine-7,1'-cyclopropan]-5(6H)-one;

10-(5-Fluoro-pyridin-2-yl)-6-methylspiro[benzo[c]pyrido[3,2-e]azepine-7,1'-cyclopropan]-5(6H)-one;

10-chloro-3-methoxy-6-methylspiro[benzo[c]pyrido[3,2-e]azepine-7,1'-cyclopropan]-5(6H)-one;

10-(6-Fluoro-pyridin-3-yl)-3-methoxy-6-methylspiro[benzo[c]pyrido[3,2-e]azepine-7,1-cyclopropan]-5(6H)-one;

9-Chloro-5-methyl-5,6-dihydro-3-thia-5-aza-benzo[e]azulen-4-one;

5-Methyl-9-(2-methyl-pyridin-3-yl)-5,6-dihydro-3-thia-5-aza-benzo[e]azulen-4-one;

3-(5-Methyl-4-oxo-5,6-dihydro-4H-3-thia-5-aza-benzo[e]azulen-9-yl)-benzonitrile;

5-Methyl-9-(2-methyl-pyridin-3-yl)-5,6-dihydro-2H-2,3,5-triaza-benzo[e]azulen-4-one;

9-Chloro-5-methyl-5,6-dihydro-3H-3,5-diaza-benzo[e]azulen-4-one;

5-Methyl-9-(2-methyl-pyridin-3-yl)-5,6-dihydro-3H-3,5-diaza-benzo[e]azulen-4-one;

6-Methyl-10-(2-methyl-pyridin-3-yl)-6,7-dihydro-1,6-diaza-dibenzo[a,c]cyclohepten-5-one;

3-(6-Methyl-5-oxo-6,7-dihydro-5H-1,6-diaza-dibenzo[a,c]cyclohepten-10-yl)-benzonitrile;

6-Methyl-10-(2-methyl-pyridin-3-yl)-6,7-dihydro-3,6-diaza-dibenzo[a,c]cyclohepten-5-one;

6-Methyl-10-(2-methyl-pyridin-3-yl)-6,7-dihydro-2,6-diaza-dibenzo[a,c]cyclohepten-5-one;

9-Chloro-2-methoxymethyl-5-methyl-5,6-dihydro-2H-2,3,5-triaza-benzo[e]azulen-4-one;

2-Methoxymethyl-5-methyl-9-(2-methyl-pyridin-3-yl)-5,6-dihydro-2H-2,3,5-triaza-benzo[e]azulen-4-one;

2-Methoxymethyl-5-methyl-9-(6-fluoro-pyridin-3-yl)-5,6-dihydro-2H-2,3,5-triaza-benzo[e]azulen-4-one;

2-Methoxymethyl-5-methyl-9-(6-fluoro-pyridin-2-yl)-5,6-dihydro-2H-2,3,5-triaza-benzo[e]azulen-4-one;

2,5-Dimethyl-9-(2-methyl-pyridin-3-yl)-5,6-dihydro-2H-2,3,5-triaza-benzo[e]azulen-4-one;

3,5-Dimethyl-9-(2-methyl-pyridin-3-yl)-5,6-dihydro-2H-2,3,5-triaza-benzo[e]azulen-4-one;

2-Ethyl-5-methyl-9-(2-methyl-pyridin-3-yl)-5,6-dihydro-2H-2,3,5-triaza-benzo[e]azulen-4-one;

3-Ethyl-5-methyl-9-(2-methyl-pyridin-3-yl)-5,6-dihydro-2H-2,3,5-triaza-benzo[e]azulen-4-one;

2-(2-Methoxy-ethyl)-5-methyl-9-(2-methyl-pyridin-3-yl)-5,6-dihydro-2H-2,3,5-triaza-benzo[e]azulen-4-one;

3-(2-Methoxy-ethyl)-5-methyl-9-(2-methyl-pyridin-3-yl)-5,6-dihydro-2H-2,3,5-triaza-benzo[e]azulen-4-one;

9-Chloro-2-(methoxymethyl)-5-methyl-2H-spiro[benzo[c]pyrazolo[4,3-e]azepine-6,1'-cyclopropan]-4(5H)-one;

2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;

2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;

10-Chloro-6-methyl-6,7-dihydro-benzo[e]pyrrolo[1,2-c][1,3]diazepin-5-one;

10-(6-Fluoro-pyridin-3-yl)-6-methyl-6,7-dihydro-benzo[e]pyrrolo[1,2-c][1,3]diazepin-5-one;

6-Methyl-10-(2-methyl-pyridin-3-yl)-6,7-dihydro-benzo[e]pyrrolo[1,2-c][1,3]diazepin-5-one;

4-methyl-8-(2-methyl-pyridin-3-yl)-1,2,4,5-tetrahydro-benzo[e][1,4]diazepin-3-one;
4-methyl-8-(2-methyl-pyridin-3-yl)-1-phenethyl-1,2,4,5-tetrahydro-benzo[e][1,4]diazepin-3-one;
1-benzyl-4-methyl-8-(2-methyl-pyridin-3-yl)-1,2,4,5-tetrahydro-benzo[e][1,4]diazepin-3-one;
4-methyl-8-(2-methyl-pyridin-3-yl)-1-pyridin-4-yl-1,2,4,5-tetrahydro-benzo[e][1,4]diazepin-3-one;
4-methyl-8-(2-methyl-pyridin-3-yl)-1-phenyl-1,2,4,5-tetrahydro-benzo[e][1,4]diazepin-3-one;
8-(2-fluoro-pyridin-3-yl)-4-methyl-1,2,4,5-tetrahydro-benzo[e][1,4]diazepin-3-one;
8-(2-fluoro-pyridin-3-yl)-1,4-dimethyl-1,2,4,5-tetrahydro-benzo[e][1,4]diazepin-3-one;
8-(6-fluoro-pyridin-3-yl)-4-methyl-1,2,4,5-tetrahydro-benzo[e][1,4]diazepin-3-one;
1-acetyl-8-(6-fluoro-pyridin-3-yl)-4-methyl-1,2,4,5-tetrahydro-benzo[e][1,4]diazepin-3-one;
and pharmaceutically acceptable salts, solvates and prodrugs of any one of the aforementioned compounds.

Moreover, it is particularly preferred that the compound of formula (Ia) according to the first or the second aspect of the invention is selected from:
2'-Chloro-6'-methylspiro[cyclopropane-1,5'-pyrido[3,4-f]pyrrolo[1,2-a][1,4]diazepin]-7'(6'H)-one;
2',9'-Dichloro-6'-methylspiro[cyclopropane-1,5'-pyrido[3,4-f]pyrrolo[1,2-a][1,4]diazepin]-7'(6'H)-one;
2'-(2-Methyl-pyridin-3-yl)-6'-methylspiro[cyclopropane-1,5'-pyrido[3,4-f]pyrrolo[1,2-a][1,4]diazepin]-7'(6'H)-one;
9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;
9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;
5-Methyl-9-(2-methyl-pyridin-3-yl)-5,6-dihydro-5,7,10b-triaza-benzo[e]azulen-4-one;
5-Methyl-9-(2-methyl-pyridin-3-yl)-5,6-dihydro-5,7,10,10b-tetraaza-benzo[e]azulen-4-one;
5-Methyl-9-(2-methyl-pyridin-3-yl)-5,6-dihydro-5,7,8,10b-tetraaza-benzo[e]azulen-4-one;
9-Chloro-5-methyl-5,6-dihydro-5,10,10b-triaza-benzo[e]azulen-4-one;
5-Methyl-9-(2-methyl-pyridin-3-yl)-5,6-dihydro-5,10,10b-triaza-benzo[e]azulen-4-one;
3-(5-Methyl-4-oxo-5,6-dihydro-4H-5,7,10b-triaza-benzo[e]azulen-9-yl)-benzonitrile;
9-imidazo[1,2-a]pyridin-6-yl-5-methyl-5,6-dihydro-5,7,10b-triaza-benzo[e]azulen-4-one;
9-Chloro-5-methyl-5,6-dihydro-5,8,10,10b-tetraaza-benzo[e]azulen-4-one;
5-Methyl-9-(2-methyl-pyridin-3-yl)-5,6-dihydro-5,8,10,10b-tetraaza-benzo[e]azulen-4-one;
10-Chloro-6-methyl-6,7-dihydro-spiro[dibenzo[c,e]azepine-7,1'-cyclopropan]-5-one;
10-Bromo-3-chloro-6-methyl-6,7-dihydro-spiro[dibenzo[c,e]azepine-7,1'-cyclopropan]-5-one;
10-(2-Methyl-pyridin-3-yl)-6-methyl-6,7-dihydro-spiro[dibenzo[c,e]azepine-7,1'-cyclopropan]-5-one;
3-Chloro-10-(2-methyl-pyridin-3-yl)-6-methyl-6,7-dihydro-spiro[dibenzo[c,e]azepine-7,1'-cyclopropan]-5-one;
3-(2-Methyl-2H-pyrazol-3-yl)-10-(2-methyl-pyridin-3-yl)-6-methyl-6,7-dihydro-spiro[dibenzo[c,e]azepine-7,1'-cyclopropan]-5-one;
10-Chloro-6-methyl-6,7-dihydro-4,6-diaza-dibenzo[a,c]cyclohepten-5-one;
3-(6-Methyl-5-oxo-6,7-dihydro-5H-4,6-diaza-dibenzo[a,c]cyclohepten-1-10-yl)-benzonitrile;
6-Methyl-10-(2-methyl-pyridin-3-yl)-6,7-dihydro-4,6-diaza-dibenzo[a,c]cyclohepten-5-one;
10-(6-Fluoro-pyridin-3-yl)-6-methyl-6,7-dihydro-4,6-diaza-dibenzo[a,c]cyclohepten-5-one;
10-(5-Fluoro-pyridin-2-yl)-6-methyl-6,7-dihydro-4,6-diaza-dibenzo[a,c]cyclohepten-5-one;
10-Chloro-3-fluoro-6-methyl-6,7-dihydro-4,6-diaza-dibenzo[a,c]cyclohepten-5-one;
3-Fluoro-6-methyl-10-(2-methyl-pyridin-3-yl)-6,7-dihydro-4,6-diaza-dibenzo[a,c]cyclohepten-5-one;
3-Fluoro-10-(6-fluoro-pyridin-3-yl)-6-methyl-6,7-dihydro-4,6-diaza-dibenzo[a,c]cyclohepten-5-one;
3-Fluoro-10-(5-fluoro-pyridin-2-yl)-6-methyl-6,7-dihydro-4,6-diaza-dibenzo[a,c]cyclohepten-5-one;
10-Chloro-3-methoxy-6-methyl-6,7-dihydro-4,6-diaza-dibenzo[a,c]cycohepten-5-one;
10-(5-Fluoro-pyridin-2-yl)-3-methoxy-6-methy-6,7-dihydro-4,6-diaza-dibenzo[a,c]cyclohepten-5-one;
10-(6-fluoro-pyridine-3-yl)-3-methoxy-6-methyl-6,7-dihydro-4,6-diaza-dibenzo[a,c]cyclohepten-5-one;
3-Methoxy-6-methyl-10-(2-methyl-pyridin-3-yl)-6,7-dihydro-4,6-diaza-dibenzo[a,c]cyclohepten-5-one;
3-Hydroxy-6-methyl-10-(2-methyl-pyridin-3-yl)-6,7-dihydro-4,6-diaza-dibenzo[a,c]cyclohepten-5-one;
10-Chloro-3,6-dimethyl-6,7-dihydro-4,6-diaza-dibenzo[a,c]cyclohepten-5-one;
10-(6-Fluoro-pyridin-3-yl)-3,6-dimethyl-6,7-dihydro-4,6-diaza-dibenzo[a,c]cyclohepten-5-one;
10-(5-Fluoro-pyridin-2-yl)-3,6-dimethyl-6,7-dihydro-4,6-diaza-dibenzo[a,c]cyclohepten-5-one;
3,6-Dimethyl-10-(2-methyl-pyridin-3-yl)-6,7-dihydro-4,6-diaza-dibenzo[a,c]cyclohepten-5-one;
10-Chloro-2,6-dimethyl-6,7-dihydro-4,6-diaza-dibenzo[a,c]cyclohepten-5-one;
2,6-Dimethyl-10-(2-methyl-pyridin-3-yl)-6,7-dihydro-4,6-diaza-dibenzo[a,c]cyclohepten-5-one;
10-(6-Fluoro-pyridin-3-yl)-2,6-dimethyl-6,7-dihydro-4,6-diaza-dibenzo[a,c]cyclohepten-5-one;
10-Chloro-2-fluoro-6-methyl-6,7-dihydro-4,6-diaza-dibenzo[a,c]cycohepten-5-one;
2-Fluoro-6-methyl-10-(2-methyl-pyridin-3-yl)-6,7-dihydro-4,6-diaza-dibenzo[a,c]cyclohepten-5-one;
2-Fluoro-10-(6-fluoro-pyridin-3-yl)-6-methyl-6,7-dihydro-4,6-diaza-dibenzo[a,c]cyclohepten-5-one;
2-Methoxy-6-methyl-10-(2-methyl-pyridin-3-yl)-6,7-dihydro-4,6-diaza-dibenzo[a,c]cyclohepten-5-one;
10-Chloro-6-methylspiro[benzo[c]pyrido[3,2-e]azepine-7,1'-cyclopropan]-5(6H)-one;
10-(6-Fluoro-pyridin-3-yl)-6-methylspiro[benzo[c]pyrido[3,2-e]azepine-7,1'-cyclopropan]-5(6H)-one;
10-(5-Fluoro-pyridin-2-yl)-6-methylspiro[benzo[c]pyrido[3,2-e]azepine-7,1'-cyclopropan]-5(6H)-one;
10-Chloro-3-methoxy-6-methylspiro[benzo[c]pyrido[3,2-e]azepine-7,1'-cyclopropan]-5(6H)-one;
10-(6-Fluoro-pyridin-3-yl)-3-methoxy-6-methylspiro[benzo[c]pyrido[3,2-e]azepine-7,1'-cyclopropan]-5(6H)-one;
9-Chloro-5-methyl-5,6-dihydro-3-thia-5-aza-benzo[e]azulen-4-one;
5-Methyl-9-(2-methyl-pyridin-3-yl)-5,6-dihydro-3-thia-5-aza-benzo[e]azulen-4-one;
3-(5-Methyl-4-oxo-5,6-dihydro-4H-3-thia-5-aza-benzo[e]azulen-9-yl)-benzonitrile;
5-Methyl-9-(2-methyl-pyridin-3-yl)-5,6-dihydro-2H-2,3,5-triaza-benzo[e]azulen-4-one;

9-Chloro-5-methyl-5,6-dihydro-3H-3,5-diaza-benzo[e]azulen-4-one;
5-Methyl-9-(2-methyl-pyridin-3-yl)-5,6-dihydro-3H-3,5-diaza-benzo[e]azulen-4-one;
6-Methyl-10-(2-methyl-pyridin-3-yl)-6,7-dihydro-1,6-diaza-dibenzo[a,c]cyclohepten-5-one;
3-(6-Methyl-5-oxo-6,7-dihydro-5H-1,6-diaza-dibenzo[a,c]cyclohepten-10-yl)-benzonitrile;
6-Methyl-10-(2-methyl-pyridin-3-yl)-6,7-dihydro-3,6-diaza-dibenzo[a,c]cyclohepten-5-one;
6-Methyl-10-(2-methyl-pyridin-3-yl)-6,7-dihydro-2,6-diaza-dibenzo[a,c]cyclohepten-5-one;
9-Chloro-2-methoxymethyl-5-methyl-5,6-dihydro-2H-2,3,5-triaza-benzo[e]azulen-4-one;
2-Methoxymethyl-5-methyl-9-(2-methyl-pyridin-3-yl)-5,6-dihydro-2H-2,3,5-triaza-benzo[e]azulen-4-one;
2-Methoxymethyl-5-methyl-9-(6-fluoro-pyridin-3-yl)-5,6-dihydro-2H-2,3,5-triaza-benzo[e]azulen-4-one;
2-Methoxymethyl-5-methyl-9-(6-fluoro-pyridin-2-yl)-5,6-dihydro-2H-2,3,5-triaza-benzo[e]azulen-4-one;
2,5-Dimethyl-9-(2-methyl-pyridin-3-yl)-5,6-dihydro-2H-2,3,5-triaza-benzo[e]azulen-4-one;
3,5-Dimethyl-9-(2-methyl-pyridin-3-yl)-5,6-dihydro-2H-2,3,5-triaza-benzo[e]azulen-4-one;
2-Ethyl-5-methyl-9-(2-methyl-pyridin-3-yl)-5,6-dihydro-2H-2,3,5-triaza-benzo[e]azulen-4-one;
3-Ethyl-5-methyl-9-(2-methyl-pyridin-3-yl)-5,6-dihydro-2H-2,3,5-triaza-benzo[e]azulen-4-one;
2-(2-Methoxy-ethyl)-5-methyl-9-(2-methyl-pyridin-3-yl)-5,6-dihydro-2H-2,3,5-triaza-benzo[e]azulen-4-one;
3-(2-Methoxy-ethyl)-5-methyl-9-(2-methyl-pyridin-3-yl)-5,6-dihydro-2H-2,3,5-triaza-benzo[e]azulen-4-one;
9-Chloro-2-(methoxymethyl)-5-methyl-2H-spiro[benzo[c]pyrazolo[4,3-e]azepine-6,1'-cyclopropan]-4(5H)-one;
2-(Methoxymethyl)-5-methyl-9-(6-fluoro-pyridin-3-yl)-2H-spiro[benzo[o]pyrazolo[4,3-e]azepine-6,1'-cyclopropan]-4(5H)-one;
2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;
10-Chloro-6-methyl-6,7-dihydro-benzo[e]pyrrolo[1,2-c][1,3]diazepin-5-one;
10-(6-Fluoro-pyridin-3-yl)-6-methyl-6,7-dihydro-benzo[e]pyrrolo[1,2-c][1,3]diazepin-5-one;
6-Methyl-10-(2-methyl-pyridin-3-yl)-6,7-dihydro-benzo[e]pyrrolo[1,2-c][1,3]diazepin-5-one;
and pharmaceutically acceptable salts, solvates and prodrugs of any one of the aforementioned compounds.

In a first specific embodiment, the compound of formula (Ia) according to the first or the second aspect of the invention is a compound of the following formula:

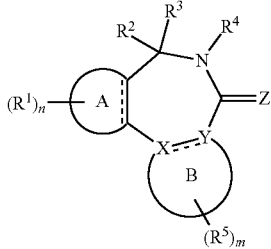

or a pharmaceutically acceptable salt, solvate or prodrug thereof;

wherein A is phenyl;

and wherein the further groups/variables in the above-depicted formula, including in particular =====, B, X, Y, Z, $R^1$, $R^2$, $R^3$, $R^4$, $R^5$, n and m, have the same meanings, including the same preferred meanings, as described and defined herein for the corresponding groups/variables in formula (Ia).

In a second specific embodiment, the compound of formula (Ia) according to the first or the second aspect of the invention is a compound of the following formula:

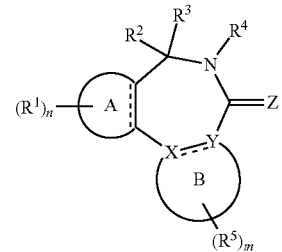

or a pharmaceutically acceptable salt, solvate or prodrug thereof;

wherein A is a monocyclic 5- or 6-membered heteroaryl, wherein 1, 2 or 3 ring atoms of said 5-membered heteroaryl are nitrogen atoms and the remaining ring atoms are carbon atoms, and wherein 1, 2, 3 or 4 ring atoms of said 6-membered heteroaryl are nitrogen atoms and the remaining ring atoms are carbon atoms;

and wherein the further groups/variables in the above-depicted formula, including in particular =====, B, X, Y, Z, $R^1$, $R^2$, $R^3$, $R^4$, $R^5$, n and m, have the same meanings, including the same preferred meanings, as described and defined herein for the corresponding groups/variables in formula (Ia).

In this second embodiment, A is preferably a monocyclic 6-membered heteroaryl, wherein 1, 2, 3 or 4 ring atoms (particularly 1 or 2 ring atoms) of said heteroaryl are nitrogen atoms and the remaining ring atoms are carbon atoms. More preferably, A is a monocyclic 6-membered heteroaryl, wherein 1 or 2 ring atoms of said heteroaryl are nitrogen atoms and the remaining ring atoms are carbon atoms (such as, e.g., pyridinyl, pyrimidinyl, pyrazinyl, or pyridazinyl).

Corresponding examples of preferred groups A are shown in the following (where the substituent(s) $R^1$ that may be attached to ring A are also depicted):

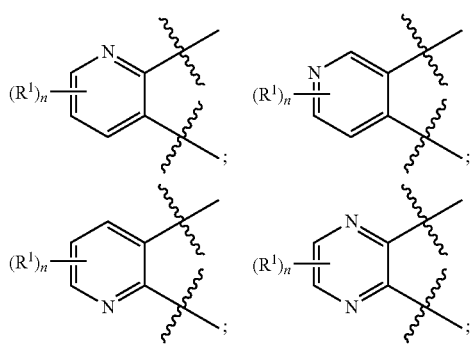

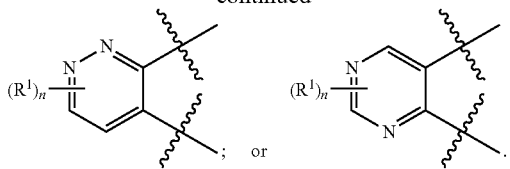

Examples of particularly preferred ring groups A are shown in the following

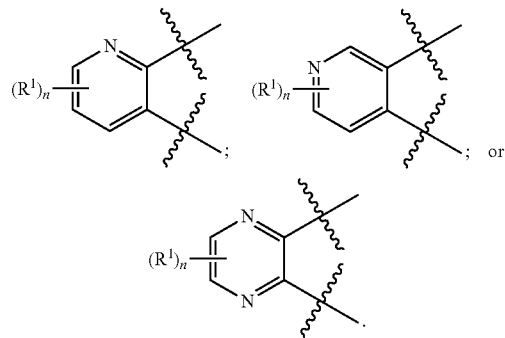

In a third specific embodiment, the compound of formula (Ia) according to the first or the second aspect of the invention is a compound of the following formula:

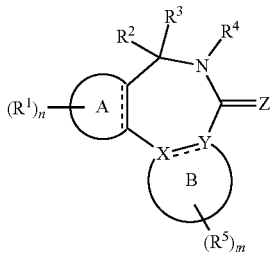

or a pharmaceutically acceptable salt, solvate or prodrug thereof;

wherein A is a group

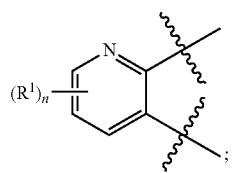

and wherein the further groups/variables in the above-depicted formula, including in particular ====, B, X, Y, Z, $R^1$, $R^2$, $R^3$, $R^4$, $R^5$, n and m, have the same meanings, including the same preferred meanings, as described and defined herein for the corresponding groups/variables in formula (Ia).

In a fourth specific embodiment, the compound of formula (Ia) according to the first or the second aspect of the invention is a compound of the following formula:

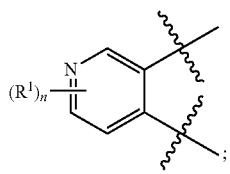

or a pharmaceutically acceptable salt, solvate or prodrug thereof;

wherein A is a group

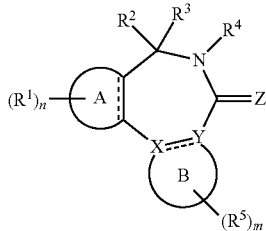

and wherein the further groups/variables in the above-depicted formula, including in particular ====, B, X, Y, Z, $R^1$, $R^2$, $R^3$, $R^4$, $R^5$, n and m, have the same meanings, including the same preferred meanings, as described and defined herein for the corresponding groups/variables in formula (Ia).

In a fifth specific embodiment, the compound of formula (Ia) according to the first or the second aspect of the invention is a compound of the following formula:

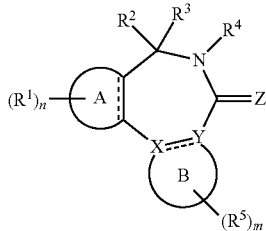

or a pharmaceutically acceptable salt, solvate or prodrug thereof;

wherein A is a group

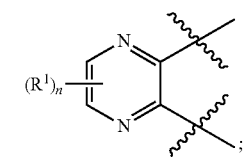

and wherein the further groups/variables in the above-depicted formula, including in particular ====, B, X, Y, Z, $R^1$, $R^2$, $R^3$, $R^4$, $R^5$, n and m, have the same meanings, including the same preferred meanings, as described and defined herein for the corresponding groups/variables in formula (Ia).

In a sixth specific embodiment, the compound of formula (Ia) according to the first or the second aspect of the invention is a compound of the following formula:

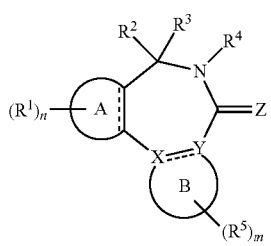

or a pharmaceutically acceptable salt, solvate or prodrug thereof;

wherein B is phenyl (and, accordingly, both ring atoms X and Y are carbon atoms);

and wherein the further groups/variables in the above-depicted formula, including in particular =====, A, Z, R¹, R², R³, R⁴, R⁵, n and m, have the same meanings, including the same preferred meanings, as described and defined herein for the corresponding groups/variables in formula (Ia).

In a seventh specific embodiment, the compound of formula (Ia) according to the first or the second aspect of the invention is a compound of the following formula:

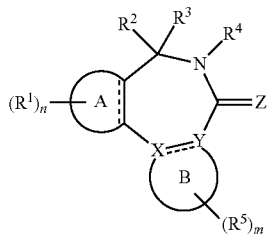

or a pharmaceutically acceptable salt, solvate or prodrug thereof;

wherein B is a monocyclic 5- or 6-membered heteroaryl;

and wherein the further groups/variables in the above-depicted formula, including in particular =====, A, X, Y, Z, R¹, R², R³, R⁴, R⁵, n and m, have the same meanings, including the same preferred meanings, as described and defined herein for the corresponding groups/variables in formula (Ia).

In this seventh embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

Corresponding examples of preferred ring groups B are shown in the following (where the substituent(s) R⁵ that may be attached to ring B are also depicted):

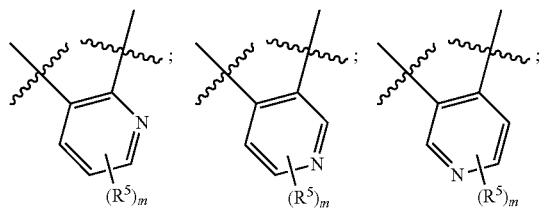

-continued

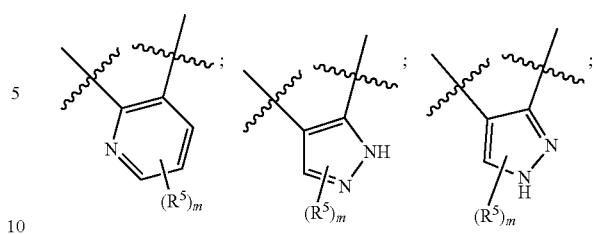

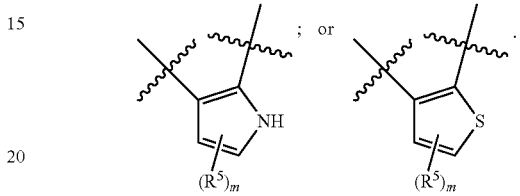

Particularly preferred examples of ring B are shown in the following:

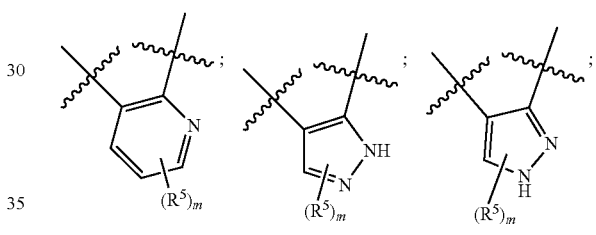

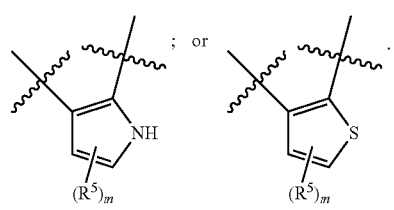

Even more preferred examples of ring B are shown in the following:

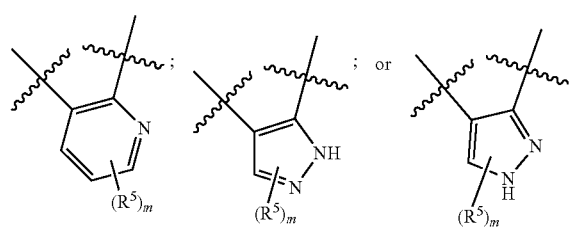

In an eighth specific embodiment, the compound of formula (Ia) according to the first or the second aspect of the invention is a compound of the following formula:

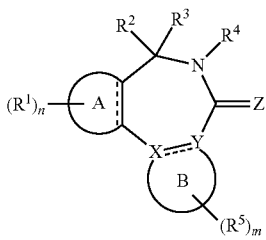

or a pharmaceutically acceptable salt, solvate or prodrug thereof;

wherein B is a group

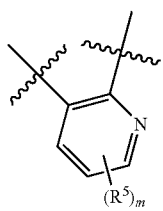

(and, accordingly, both ring atoms X and Y are carbon atoms);

and wherein the further groups/variables in the above-depicted formula, including in particular ====, A, Z, R$^1$, R$^2$, R$^3$, R$^4$, R$^5$, n and m, have the same meanings, including the same preferred meanings, as described and defined herein for the corresponding groups/variables in formula (Ia).

In a ninth specific embodiment, the compound of formula (Ia) according to the first or the second aspect of the invention is a compound of the following formula:

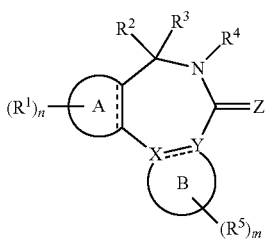

or a pharmaceutically acceptable salt, solvate or prodrug thereof;

wherein B is a group

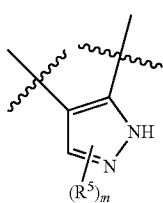

(and, accordingly, both ring atoms X and Y are carbon atoms); and wherein the further groups/variables in the above-depicted formula, including in particular ====, A, Z, R$^1$, R$^2$, R$^3$, R$^4$, R$^5$, n and m, have the same meanings, including the same preferred meanings, as described and defined herein for the corresponding groups/variables in formula (Ia).

In a tenth specific embodiment, the compound of formula (Ia) according to the first or the second aspect of the invention is a compound of the following formula:

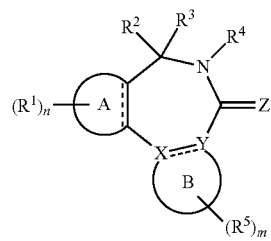

or a pharmaceutically acceptable salt, solvate or prodrug thereof;

wherein B is a group

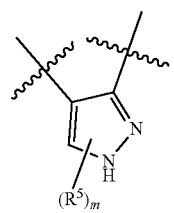

(and, accordingly, both ring atoms X and Y are carbon atoms);

and wherein the further groups/variables in the above-depicted formula, including in particular ====, A, Z, R$^1$, R$^2$, R$^3$, R$^4$, R$^5$, n and m, have the same meanings, including the same preferred meanings, as described and defined herein for the corresponding groups/variables in formula (Ia).

In an 11$^{th}$ specific embodiment, the compound of formula (Ia) according to the first or the second aspect of the invention is a compound of the following formula:

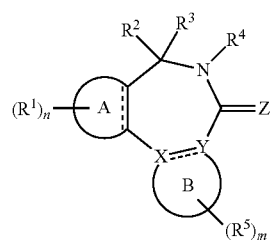

or a pharmaceutically acceptable salt, solvate or prodrug thereof;

wherein B is a group

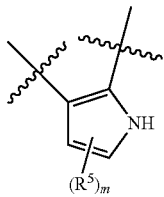

(and, accordingly, both ring atoms X and Y are carbon atoms); and wherein the further groups/variables in the above-depicted formula, including in particular =====, A, Z, $R^1$, $R^2$, $R^3$, $R^4$, $R^5$, n and m, have the same meanings, including the same preferred meanings, as described and defined herein for the corresponding groups/variables in formula (Ia).

In a 12th specific embodiment, the compound of formula (Ia) according to the first or the second aspect of the invention is a compound of the following formula:

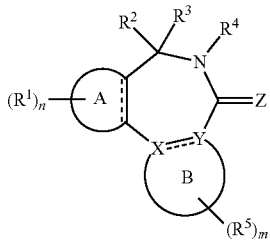

or a pharmaceutically acceptable salt, solvate or prodrug thereof;
wherein B is a group

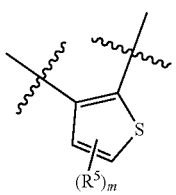

(and, accordingly, both ring atoms X and Y are carbon atoms); and wherein the further groups/variables in the above-depicted formula, including in particular =====, A, Z, $R^1$, $R^2$, $R^3$, $R^4$, $R^5$, n and m, have the same meanings, including the same preferred meanings, as described and defined herein for the corresponding groups/variables in formula (Ia).

In a 13th specific embodiment, the compound of formula (Ia) according to the first or the second aspect of the invention is a compound of the following formula:

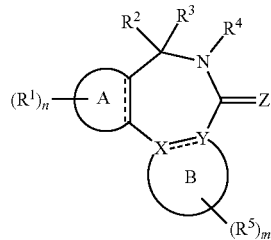

or a pharmaceutically acceptable salt, solvate or prodrug thereof;
wherein A is phenyl;
wherein B is phenyl (and, accordingly, both ring atoms X and Y are carbon atoms);
and wherein the further groups/variables in the above-depicted formula, including in particular =====, Z, $R^1$, $R^2$, $R^3$, $R^4$, $R^5$, n and m, have the same meanings, including the same preferred meanings, as described and defined herein for the corresponding groups/variables in formula (Ia).

In a 14th specific embodiment, the compound of formula (Ia) according to the first or the second aspect of the invention is a compound of the following formula:

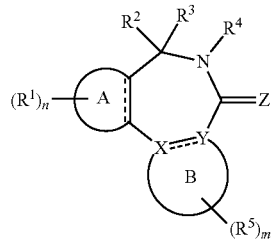

or a pharmaceutically acceptable salt, solvate or prodrug thereof;
wherein A is phenyl;
wherein B is a monocyclic 5- or 6-membered heteroaryl;
and wherein the further groups/variables in the above-depicted formula, including in particular =====, X, Y, Z, $R^1$, $R^2$, $R^3$, $R^4$, $R^5$, n and m, have the same meanings, including the same preferred meanings, as described and defined herein for the corresponding groups/variables in formula (Ia).

In this 14th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 15th specific embodiment, the compound of formula (Ia) according to the first or the second aspect of the invention is a compound of the following formula:

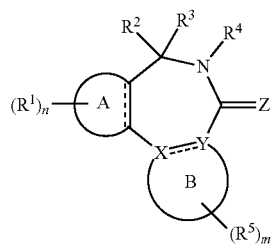

or a pharmaceutically acceptable salt, solvate or prodrug thereof;

wherein A is phenyl;

wherein B is a group

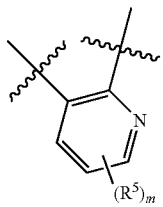

(and, accordingly, both ring atoms X and Y are carbon atoms);

and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 16$^{th}$ specific embodiment, the compound of formula (Ia) according to the first or the second aspect of the invention is a compound of the following formula:

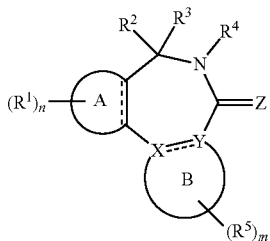

or a pharmaceutically acceptable salt, solvate or prodrug thereof;

wherein A is phenyl;

wherein B is a group

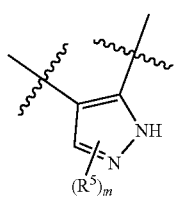

(and, accordingly, both ring atoms X and Y are carbon atoms); and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 17$^{th}$ specific embodiment, the compound of formula (Ia) according to the first or the second aspect of the invention is a compound of the following formula:

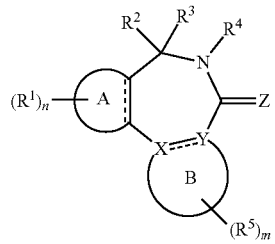

or a pharmaceutically acceptable salt, solvate or prodrug thereof;

wherein A is phenyl;

wherein B is a group

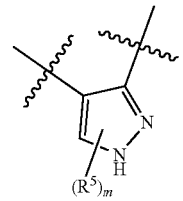

(and, accordingly, both ring atoms X and Y are carbon atoms); and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In an 18$^{th}$ specific embodiment, the compound of formula (Ia) according to the first or the second aspect of the invention is a compound of the following formula:

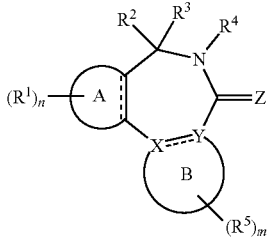

or a pharmaceutically acceptable salt, solvate or prodrug thereof;

wherein A is phenyl;

wherein B is a group

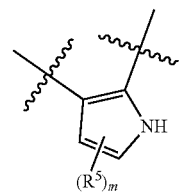

(and, accordingly, both ring atoms X and Y are carbon atoms); and wherein the further groups/variables in the above-depicted formula, including in particular =====, Z, R$^1$, $R^2$, $R^3$, $R^4$, $R^5$, n and m, have the same meanings, including the same preferred meanings, as described and defined herein for the corresponding groups/variables in formula (Ia).

In a 19th specific embodiment, the compound of formula (Ia) according to the first or the second aspect of the invention is a compound of the following formula:

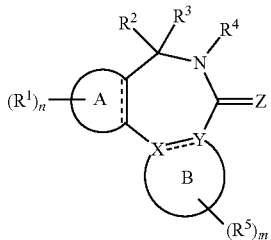

or a pharmaceutically acceptable salt, solvate or prodrug thereof;

wherein A is phenyl;

wherein B is a group

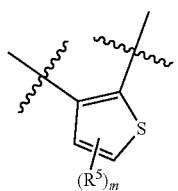

(and, accordingly, both ring atoms X and Y are carbon atoms); and wherein the further groups/variables in the above-depicted formula, including in particular =====, Z, $R^1$, $R^2$, $R^3$, $R^4$, $R^5$, n and m, have the same meanings, including the same preferred meanings, as described and defined herein for the corresponding groups/variables in formula (Ia).

In a 20th specific embodiment, the compound of formula (Ia) according to the first or the second aspect of the invention is a compound of the following formula:

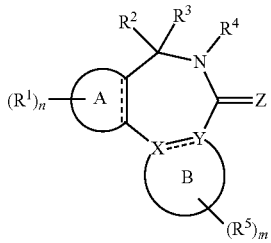

or a pharmaceutically acceptable salt, solvate or prodrug thereof;

wherein A is a group

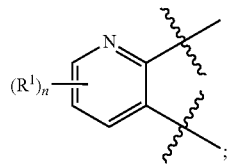

wherein B is phenyl (and, accordingly, both ring atoms X and Y are carbon atoms); and wherein the further groups/variables in the above-depicted formula, including in particular =====, Z, $R^1$, $R^2$, $R^3$, $R^4$, $R^5$, n and m, have the same meanings, including the same preferred meanings, as described and defined herein for the corresponding groups/variables in formula (Ia).

In a 21st specific embodiment, the compound of formula (Ia) according to the first or the second aspect of the invention is a compound of the following formula:

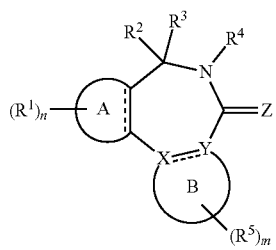

or a pharmaceutically acceptable salt, solvate or prodrug thereof;

wherein A is a group

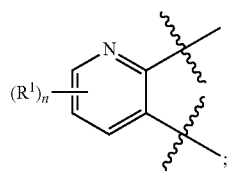

wherein B is a monocyclic 5- or 6-membered heteroaryl;

and wherein the further groups/variables in the above-depicted formula, including in particular =====, X, Y, Z, $R^1$, $R^2$, $R^3$, $R^4$, $R^5$, n and m, have the same meanings, including the same preferred meanings, as described and defined herein for the corresponding groups/variables in formula (Ia).

In this 21st embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 22nd specific embodiment, the compound of formula (Ia) according to the first or the second aspect of the invention is a compound of the following formula:

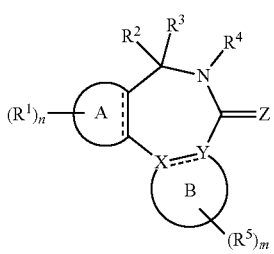

or a pharmaceutically acceptable salt, solvate or prodrug thereof;

wherein A is a group

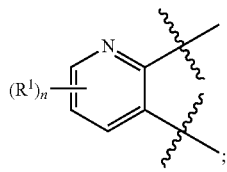

wherein B is a group

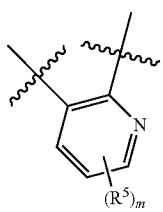

(and, accordingly, both ring atoms X and Y are carbon atoms);

and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 23$^{rd}$ specific embodiment, the compound of formula (Ia) according to the first or the second aspect of the invention is a compound of the following formula:

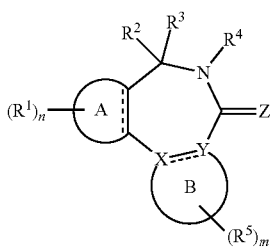

or a pharmaceutically acceptable salt, solvate or prodrug thereof;

wherein A is a group

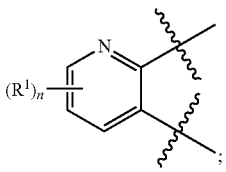

wherein B is a group

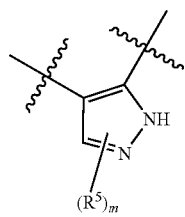

(and, accordingly, both ring atoms X and Y are carbon atoms); and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 24$^{th}$ specific embodiment, the compound of formula (Ia) according to the first or the second aspect of the invention is a compound of the following formula:

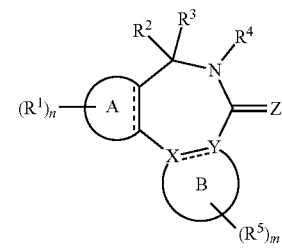

or a pharmaceutically acceptable salt, solvate or prodrug thereof;

wherein A is a group,

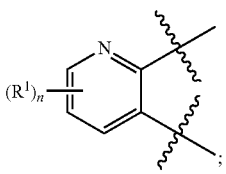

wherein B is a group

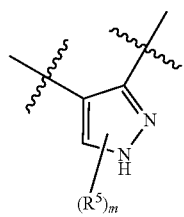

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 25$^{th}$ specific embodiment, the compound of formula (Ia) according to the first or the second aspect of the invention is a compound of the following formula:

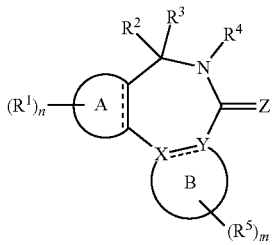

or a pharmaceutically acceptable salt, solvate or prodrug thereof;
wherein A is a group

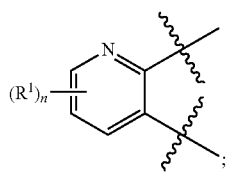

wherein B is a group

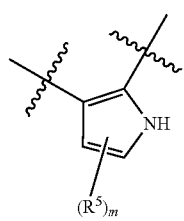

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 26$^{th}$ specific embodiment, the compound of formula (Ia) according to the first or the second aspect of the invention is a compound of the following formula:

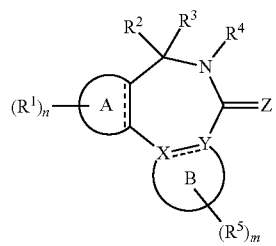

or a pharmaceutically acceptable salt, solvate or prodrug thereof;
wherein A is a group

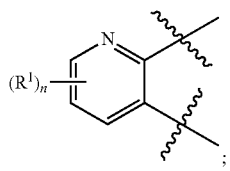

wherein B is a group

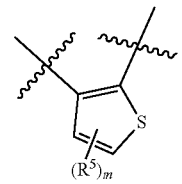

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 27$^{th}$ specific embodiment, the compound of formula (Ia) according to the first or the second aspect of the invention is a compound of the following formula:

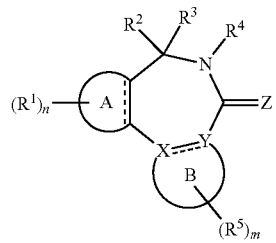

or a pharmaceutically acceptable salt, solvate or prodrug thereof;

wherein A is a group

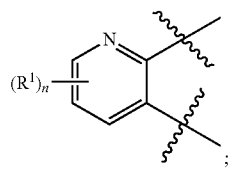

wherein B is a group

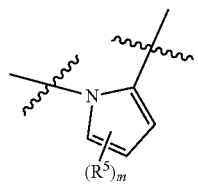

(and, accordingly, X is N, and Y is C);

and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 28$^{th}$ specific embodiment, the compound of formula (Ia) according to the first or the second aspect of the invention is a compound of the following formula:

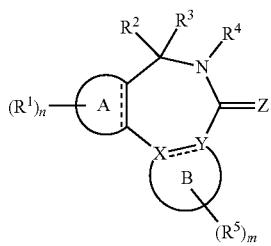

or a pharmaceutically acceptable salt, solvate or prodrug thereof;
wherein A is a group

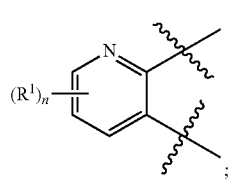

wherein B is a group

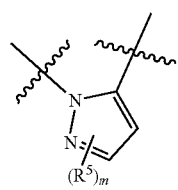

(and, accordingly, X is N, and Y is C);

and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 29$^{th}$ specific embodiment, the compound of formula (Ia) according to the first or the second aspect of the invention is a compound of the following formula:

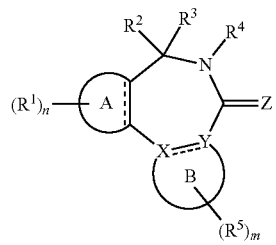

or a pharmaceutically acceptable salt, solvate or prodrug thereof;
wherein A is a group

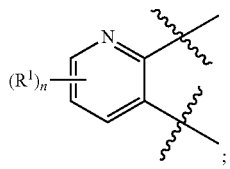

wherein B is phenyl (and, accordingly, both ring atoms X and Y are carbon atoms);

and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 30$^{th}$ specific embodiment, the compound of formula (Ia) according to the first or the second aspect of the invention is a compound of the following formula:

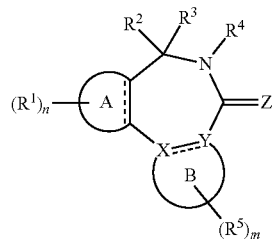

or a pharmaceutically acceptable salt, solvate or prodrug thereof;

wherein A is a group

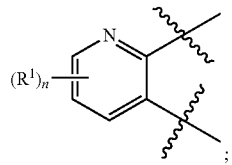

wherein B is a monocyclic 5- or 6-membered heteroaryl;

and wherein the further groups/variables in the above-depicted formula, including in particular =====, Y, Z, R$^1$, R$^2$, R$^3$, R$^4$, R$^5$, n and m, have the same meanings, including the same preferred meanings, as described and defined herein for the corresponding groups/variables in formula (Ia).

In this 30$^{th}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 31$^{st}$ specific embodiment, the compound of formula (Ia) according to the first or the second aspect of the invention is a compound of the following formula:

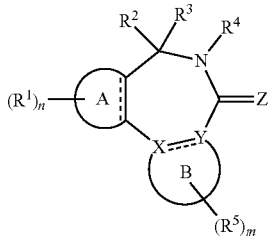

or a pharmaceutically acceptable salt, solvate or prodrug thereof;

wherein A is a group

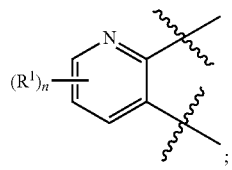

wherein B is a group

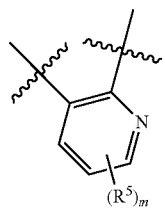

(and, accordingly, both ring atoms X and Y are carbon atoms);

and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 32$^{nd}$ specific embodiment, the compound of formula (Ia) according to the first or the second aspect of the invention is a compound of the following formula:

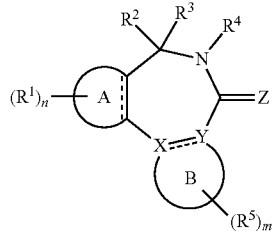

or a pharmaceutically acceptable salt, solvate or prodrug thereof;

wherein A is a group,

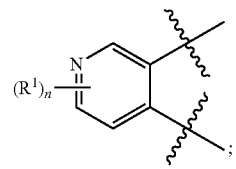

wherein B is a group

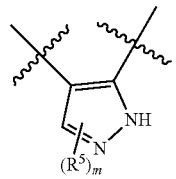

(and, accordingly, both ring atoms X and Y are carbon atoms); and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 33$^{rd}$ specific embodiment, the compound of formula (Ia) according to the first or the second aspect of the invention is a compound of the following formula:

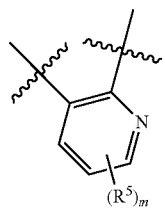

or a pharmaceutically acceptable salt, solvate or prodrug thereof;

wherein A is a group

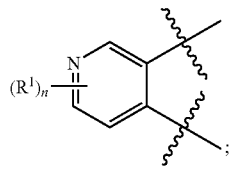

wherein B is a group

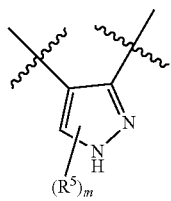

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 34$^{th}$ specific embodiment, the compound of formula (Ia) according to the first or the second aspect of the invention is a compound of the following formula:

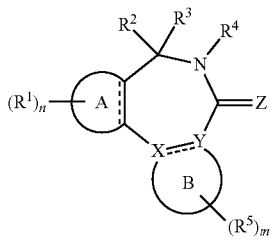

or a pharmaceutically acceptable salt, solvate or prodrug thereof;
wherein A is a group

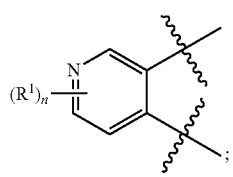

wherein B is a group

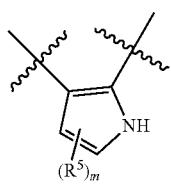

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 35$^{th}$ specific embodiment, the compound of formula (Ia) according to the first or the second aspect of the invention is a compound of the following formula:

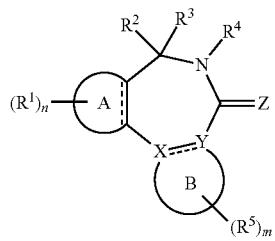

or a pharmaceutically acceptable salt, solvate or prodrug thereof;
wherein A is a group

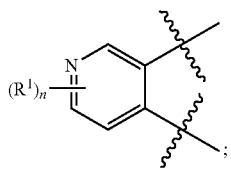

wherein B is a group

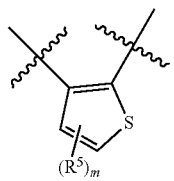

(and, accordingly, both ring atoms X and Y are carbon atoms); and wherein the further groups/variables in the above-depicted formula, including in particular ====, Z, R$^1$, R$^2$, R$^3$, R$^4$, R$^5$, n and m, have the same meanings, including the same preferred meanings, as described and defined herein for the corresponding groups/variables in formula (Ia).

In a 36$^{th}$ specific embodiment, the compound of formula (Ia) according to the first or the second aspect of the invention is a compound of the following formula:

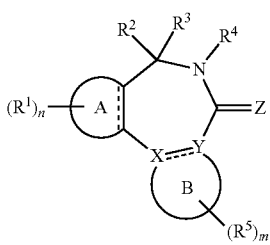

or a pharmaceutically acceptable salt, solvate or prodrug thereof;

wherein A is a group

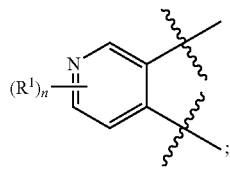

wherein B is a group

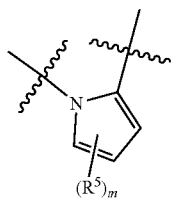

(and, accordingly, X is N, and Y is C);

and wherein the further groups/variables in the above-depicted formula, including in particular =====, Z, R¹, R², R³, R⁴, R⁵, n and m, have the same meanings, including the same preferred meanings, as described and defined herein for the corresponding groups/variables in formula (Ia).

In a 37$^{th}$ specific embodiment, the compound of formula (Ia) according to the first or the second aspect of the invention is a compound of the following formula:

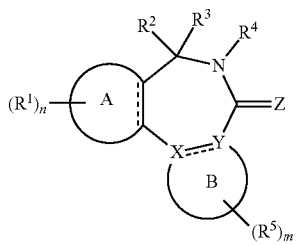

or a pharmaceutically acceptable salt, solvate or prodrug thereof;

wherein A is a group

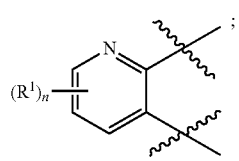

wherein B is a group

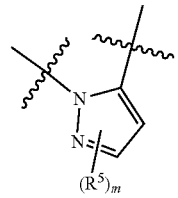

(and, accordingly, X is N, and Y is C);

and wherein the further groups/variables in the above-depicted formula, including in particular =====, Z, R¹, R², R³, R⁴, R⁵, n and m, have the same meanings, including the same preferred meanings, as described and defined herein for the corresponding groups/variables in formula (Ia).

In a 38$^{th}$ specific embodiment, the compound of formula (Ia) according to the first or the second aspect of the invention is a compound of the following formula:

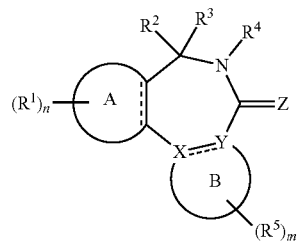

or a pharmaceutically acceptable salt, solvate or prodrug thereof;

wherein A is a group

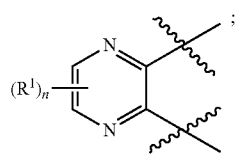

wherein B is phenyl (and, accordingly, both ring atoms X and Y are carbon atoms);

and wherein the further groups/variables in the above-depicted formula, including in particular =====, Z, R¹, R², R³, R⁴, R⁵, n and m, have the same meanings, including the same preferred meanings, as described and defined herein for the corresponding groups/variables in formula (Ia).

In a 39$^{th}$ specific embodiment, the compound of formula (Ia) according to the first or the second aspect of the invention is a compound of the following formula:

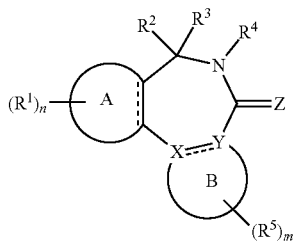

or a pharmaceutically acceptable salt, solvate or prodrug thereof;

wherein A is a group

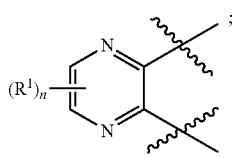

wherein B is a monocyclic 5- or 6-membered heteroaryl;

and wherein the further groups/variables in the above-depicted formula, including in particular =====, X, Y, Z, R$^1$, R$^2$, R$^3$, R$^4$, R$^5$, n and m, have the same meanings, including the same preferred meanings, as described and defined herein for the corresponding groups/variables in formula (Ia).

In this 39$^{th}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 40$^{th}$ specific embodiment, the compound of formula (Ia) according to the first or the second aspect of the invention is a compound of the following formula:

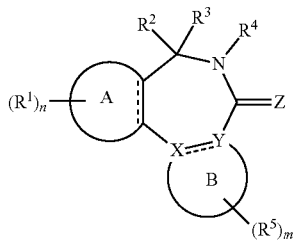

or a pharmaceutically acceptable salt, solvate or prodrug thereof;

wherein A is a group

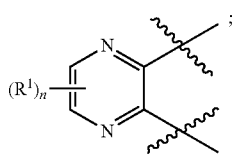

wherein B is a group

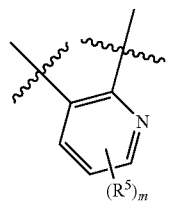

(and, accordingly, both ring atoms X and Y are carbon atoms);

and wherein the further groups/variables in the above-depicted formula, including in particular =====, Z, R$^1$, R$^2$, R$^3$, R$^4$, R$^5$, n and m, have the same meanings, including the same preferred meanings, as described and defined herein for the corresponding groups/variables in formula (Ia).

In a 41$^{st}$ specific embodiment, the compound of formula (Ia) according to the first or the second aspect of the invention is a compound of the following formula:

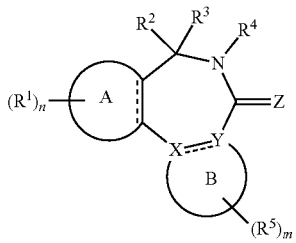

or a pharmaceutically acceptable salt, solvate or prodrug thereof;

wherein A is a group

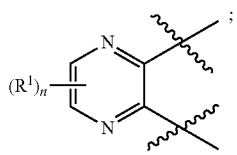

wherein B is a group

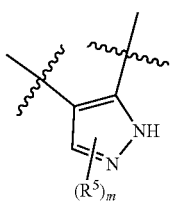

(and, accordingly, both ring atoms X and Y are carbon atoms);

and wherein the further groups/variables in the above-depicted formula, including in particular =====, Z, R$^1$, R$^2$, R$^3$, R$^4$, R$^5$, n and m, have the same meanings, including the same preferred as described and defined herein for the corresponding groups/variables in formula (Ia).

In a 42$^{nd}$ specific embodiment, the compound of formula (Ia) according to the first or the second aspect of the invention is a compound of the following formula:

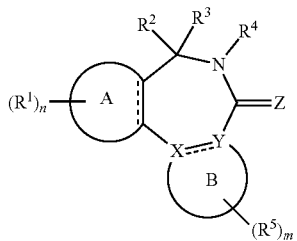

or a pharmaceutically acceptable salt, solvate or prodrug thereof;

wherein A is a group

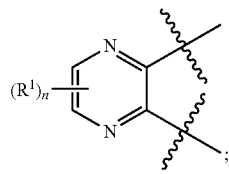

wherein B is a group

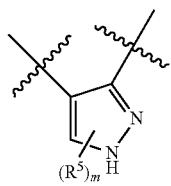

(and, accordingly, both ring atoms X and Y are carbon atoms);

and wherein the further groups/variables in the above-depicted formula, including in particular =====, Z, R¹, R², R³, R⁴, R⁵, n and m, have the same meanings, including the same preferred meanings, as described and defined herein for the corresponding groups/variables in formula (Ia).

In a 43$^{rd}$ specific embodiment, the compound of formula (Ia) according to the first or the second aspect of the invention is a compound of the following formula:

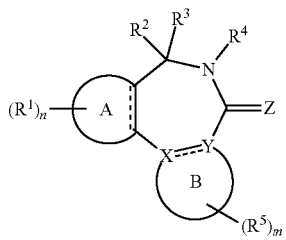

or a pharmaceutically acceptable salt, solvate or prodrug thereof;

wherein A is a group

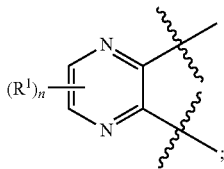

wherein B is a group

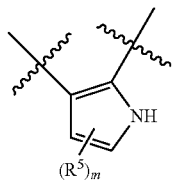

(and, accordingly, both ring atoms X and Y are carbon atoms); and wherein the further groups/variables in the above-depicted formula, including in particular =====, Z, R¹, R², R³, R⁴, R⁵, n and m, have the same meanings, including the same preferred meanings, as described and defined herein for the corresponding groups/variables in formula (Ia).

In a 44$^{th}$ specific embodiment, the compound of formula (Ia) according to the first or the second aspect of the invention is a compound of the following formula:

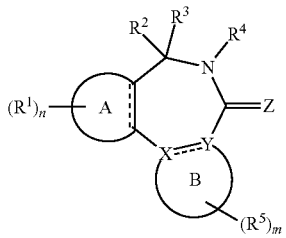

or a pharmaceutically acceptable salt, solvate or prodrug thereof;

wherein A is a group

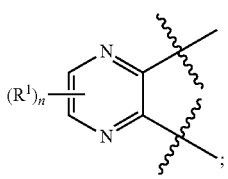

wherein B is a group

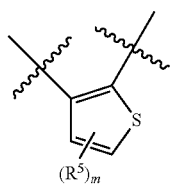

(and, accordingly, both ring atoms X and Y are carbon atoms);

and wherein the further groups/variables in the above-depicted formula, including in particular ====, Z, R¹, R², R³, R⁴, R⁵, n and m, have the same meanings, including the same preferred meanings, as described and defined herein for the corresponding groups/variables in formula (Ia).

In a 45th specific embodiment, the compound of formula (Ia) according to the first or the second aspect of the invention is a compound of the following formula:

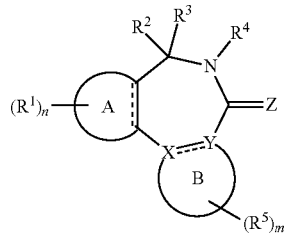

or a pharmaceutically acceptable salt, solvate or prodrug thereof;

wherein A is a group

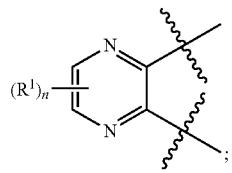

wherein B is a group

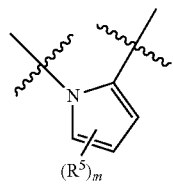

(and, accordingly, X is N, and Y is C);

and wherein the further groups/variables in the above-depicted formula, including in particular ====, Z, R¹, R², R³, R⁴, R⁵, n and m, have the same meanings, including the same preferred meanings, as described and defined herein for the corresponding groups/variables in formula (Ia).

In a 46th specific embodiment, the compound of formula (Ia) according to the first or the second aspect of the invention is a compound of the following formula:

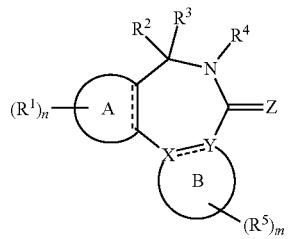

or a pharmaceutically acceptable salt, solvate or prodrug thereof;

wherein A is a group

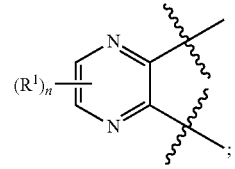

wherein B is a group

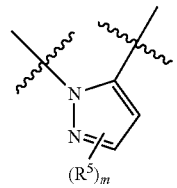

(and, accordingly, X is N, and Y is C);

and wherein the further groups/variables in the above-depicted formula, including in particular ====, Z, R¹, R², R³, R⁴, R⁵, n and m, have the same meanings, including the same preferred meanings, as described and defined herein for the corresponding groups/variables in formula (Ia).

In a 47th specific embodiment, the compound of formula (Ia) according to the first or the second aspect of the invention is a compound of the following formula:

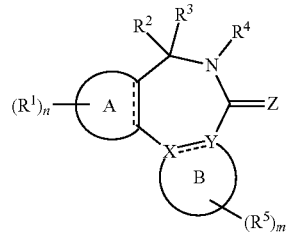

or a pharmaceutically acceptable salt, solvate or prodrug thereof;

wherein A is phenyl;

wherein Z is O;

wherein R² and R³ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, B, X, Y, R¹, R⁴, R⁵, n and m, have the same meanings, including the same preferred meanings, as described and defined herein for the corresponding groups/variables in formula (Ia).

In a 48th specific embodiment, the compound of formula (Ia) according to the first or the second aspect of the invention is a compound of the following formula:

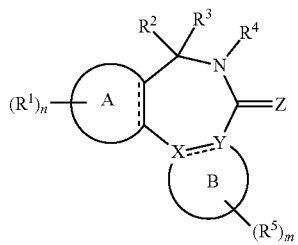

or a pharmaceutically acceptable salt, solvate or prodrug thereof;

wherein A is a monocyclic 5- or 6-membered heteroaryl, wherein 1, 2 or 3 ring atoms of said 5-membered heteroaryl are nitrogen atoms and the remaining ring atoms are carbon atoms, and wherein 1, 2, 3 or 4 ring atoms of said 6-membered heteroaryl are nitrogen atoms and the remaining ring atoms are carbon atoms;

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In this 48$^{th}$ embodiment, A is preferably a monocyclic 6-membered heteroaryl, wherein 1, 2, 3 or 4 ring atoms (particularly 1 or 2 ring atoms) of said heteroaryl are nitrogen atoms and the remaining ring atoms are carbon atoms. More preferably, A is a monocyclic 6-membered heteroaryl, wherein 1 or 2 ring atoms of said heteroaryl are nitrogen atoms and the remaining ring atoms are carbon atoms (such as, e.g., pyridinyl, pyrimidinyl, pyrazinyl, or pyridazinyl).

Corresponding examples of preferred groups A are shown in the following (where the substituent(s) $R^1$ that may be attached to ring A are also depicted):

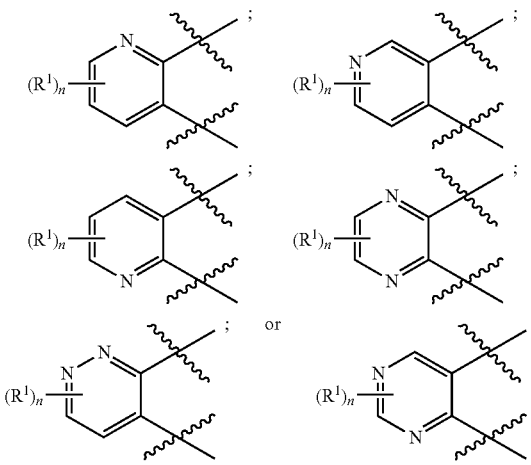

Examples of particularly preferred ring groups A are shown in the following:

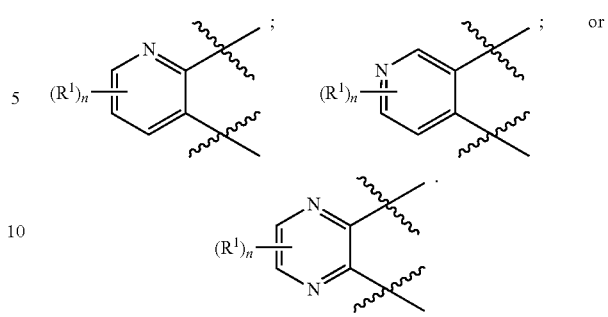

In a 49$^{th}$ specific embodiment, the compound of formula (Ia) according to the first or the second aspect of the invention is a compound of the following formula:

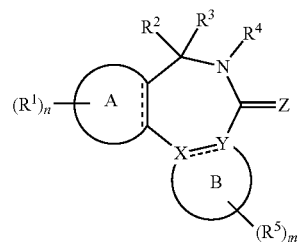

or a pharmaceutically acceptable salt, solvate or prodrug thereof;

wherein A is a group

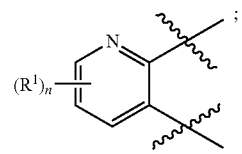

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In a 50$^{th}$ specific embodiment, the compound of formula (Ia) according to the first or the second aspect of the invention is a compound of the following formula:

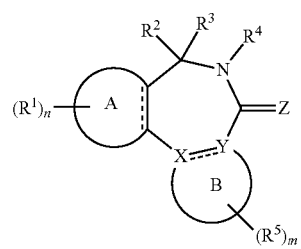

or a pharmaceutically acceptable salt, solvate or prodrug thereof;

wherein A is a group

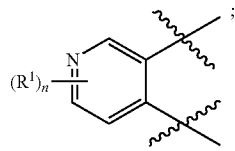

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular -----, B, X, Y, $R^1$, $R^4$, $R^5$, n and m, have the same meanings, including the same preferred meanings, as described and defined herein for the corresponding groups/variables in formula (Ia).

In a 51st specific embodiment, the compound of formula (Ia) according to the first or the second aspect of the invention is a compound of the following formula:

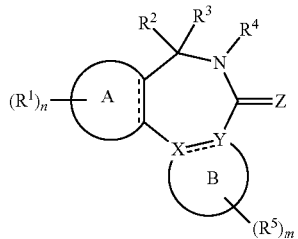

or a pharmaceutically acceptable salt, solvate or prodrug thereof;

wherein A is a group

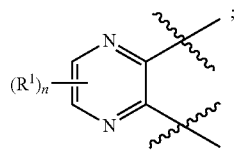

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular -----, B, X, Y, $R^1$, $R^4$, $R^5$, n and m, have the same meanings, including the same preferred meanings, as described and defined herein for the corresponding groups/variables in formula (Ia).

In a 52nd specific embodiment, the compound of formula (Ia) according to the first or the second aspect of the invention is a compound of the following formula:

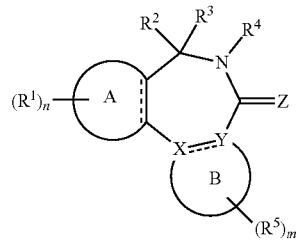

or a pharmaceutically acceptable salt, solvate or prodrug thereof;

wherein B is phenyl (and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular -----, A, $R^1$, $R^4$, $R^5$, n and m, have the same meanings, including the same preferred meanings, as described and defined herein for the corresponding groups/variables in formula (Ia).

In a 53rd specific embodiment, the compound of formula (Ia) according to the first or the second aspect of the invention is a compound of the following formula:

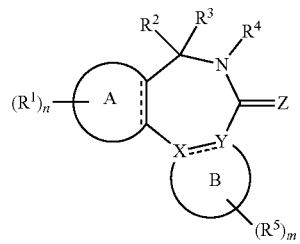

or a pharmaceutically acceptable salt, solvate or prodrug thereof;

wherein B is a monocyclic 5- or 6-membered heteroaryl;

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular -----, A, X, Y, $R^1$, $R^4$, $R^5$, n and m, have the same meanings, including the same preferred meanings, as described and defined herein for the corresponding groups/variables in formula (Ia).

In this 53rd embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

Corresponding examples of preferred ring groups B are shown in the following (where the substituent(s) $R^5$ that may be attached to ring B are also depicted):

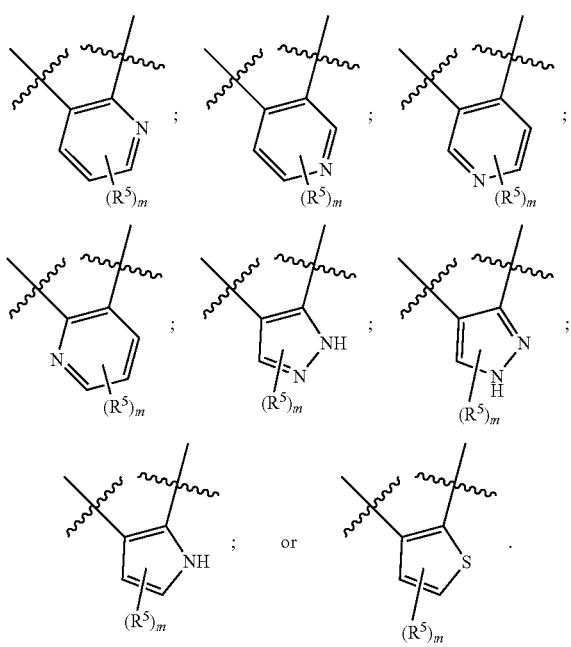

Particularly preferred examples of ring B are shown in the following:

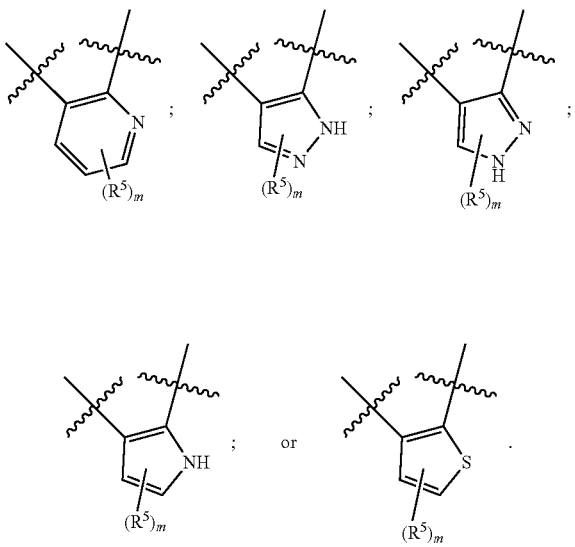

Even more preferred examples of ring B are shown in the following:

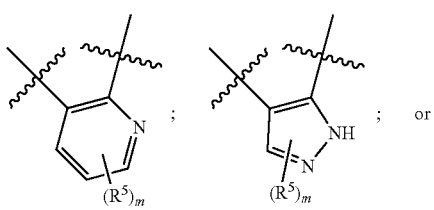

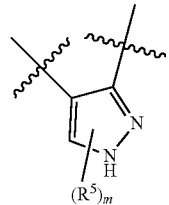

In a 54$^{th}$ specific embodiment, the compound of formula (Ia) according to the first or the second aspect of the invention is a compound of the following formula:

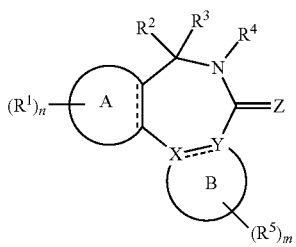

or a pharmaceutically acceptable salt, solvate or prodrug thereof;
wherein B is a group

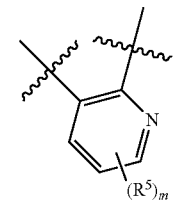

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, A, $R^1$, $R^4$, $R^5$, n and m, have the same meanings, including the same preferred meanings, as described and defined herein for the corresponding groups/variables in formula (Ia).

In a 55$^{th}$ specific embodiment, the compound of formula (Ia) according to the first or the second aspect of the invention is a compound of the following formula:

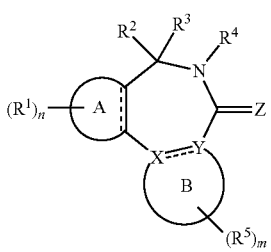

or a pharmaceutically acceptable salt, solvate or prodrug thereof;
wherein B is a group

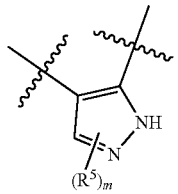

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 56$^{th}$ specific embodiment, the compound of formula (Ia) according to the first or the second aspect of the invention is a compound of the following formula:

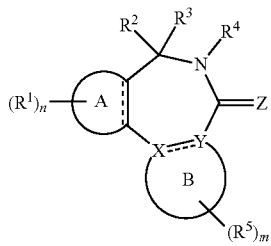

or a pharmaceutically acceptable salt, solvate or prodrug thereof;
wherein B is a group

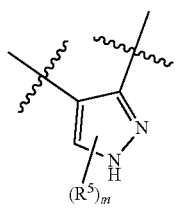

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 57$^{th}$ specific embodiment, the compound of formula (Ia) according to the first or the second aspect of the invention is a compound of the following formula:

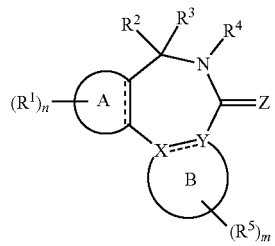

or a pharmaceutically acceptable salt, solvate or prodrug thereof;
wherein B is a group

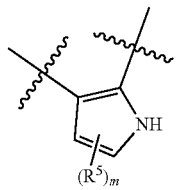

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 58$^{th}$ specific embodiment, the compound of formula (Ia) according to the first or the second aspect of the invention is a compound of the following formula:

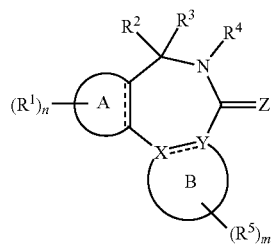

or a pharmaceutically acceptable salt, solvate or prodrug thereof;

wherein B is a group

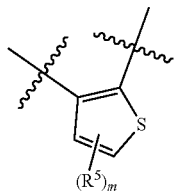

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 59th specific embodiment, the compound of formula (Ia) according to the first or the second aspect of the invention is a compound of the following formula:

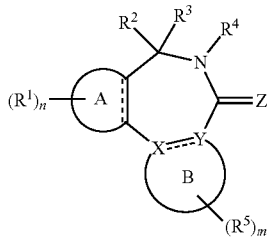

or a pharmaceutically acceptable salt, solvate or prodrug thereof;
wherein A is phenyl;
wherein B is phenyl (and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 60th specific embodiment, the compound of formula (Ia) according to the first or the second aspect of the invention is a compound of the following formula:

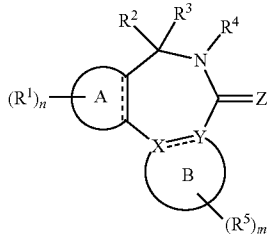

or a pharmaceutically acceptable salt, solvate or prodrug thereof;
wherein A is phenyl;
wherein B is a monocyclic 5- or 6-membered heteroaryl;
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, X, Y, R, $R^4$, $R^5$, n and m, have the same meanings, including the same preferred meanings, as described and defined herein for the corresponding groups/variables in formula (Ia).

In this 60th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 61st specific embodiment, the compound of formula (Ia) according to the first or the second aspect of the invention is a compound of the following formula:

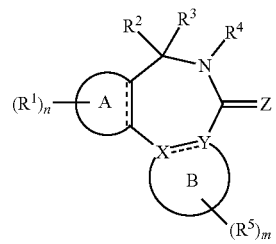

or a pharmaceutically acceptable salt, solvate or prodrug thereof;
wherein A is phenyl;
wherein B is a group

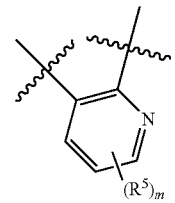

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 62nd specific embodiment, the compound of formula (Ia) according to the first or the second aspect of the invention is a compound of the following formula:

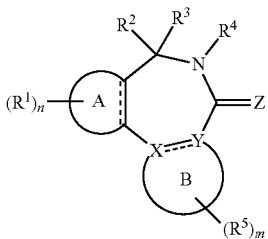

or a pharmaceutically acceptable salt, solvate or prodrug thereof;
wherein A is phenyl;
wherein B is a group

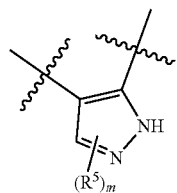

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 63$^{rd}$ specific embodiment, the compound of formula (Ia) according to the first or the second aspect of the invention is a compound of the following formula:

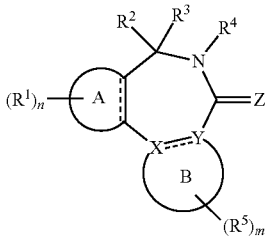

or a pharmaceutically acceptable salt, solvate or prodrug thereof;
wherein A is phenyl;
wherein B is a group

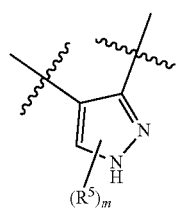

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 64$^{th}$ specific embodiment, the compound of formula (Ia) according to the first or the second aspect of the invention is a compound of the following formula:

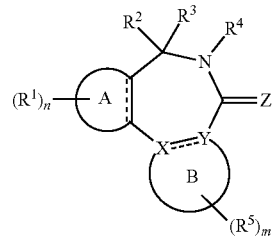

or a pharmaceutically acceptable salt, solvate or prodrug thereof;
wherein A is phenyl;
wherein B is a group

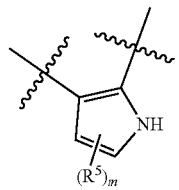

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 65$^{th}$ specific embodiment, the compound of formula (Ia) according to the first or the second aspect of the invention is a compound of the following formula:

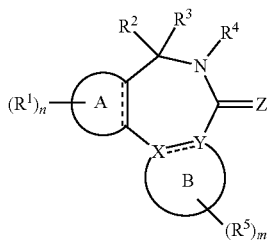

or a pharmaceutically acceptable salt, solvate or prodrug thereof;
wherein A is phenyl;
wherein B is a group

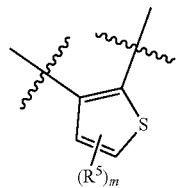

(and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 66th specific embodiment, the compound of formula (Ia) according to the first or the second aspect of the invention is a compound of the following formula:

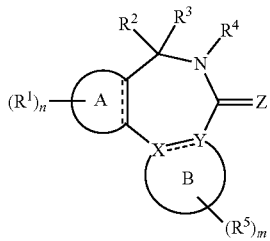

or a pharmaceutically acceptable salt, solvate or prodrug thereof;
wherein A is a group

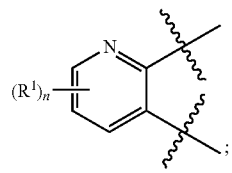

wherein B is phenyl (and, accordingly, both ring atoms X and Y are carbon atoms);
wherein Z is O;
wherein $R^2$ and $R^3$ are mutually linked to form, together with the carbon atom that they are attached to, a $C_3$—C cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 67st specific embodiment, the compound of formula (Ia) according to the first or the second aspect of the invention is a compound of the following formula:

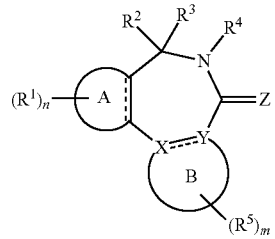

or a pharmaceutically acceptable salt, solvate or prodrug thereof;
wherein A is a group

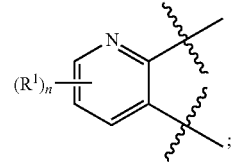

wherein B is a monocyclic 5- or 6-membered heteroaryl;
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, X, Y, $R^1$, $R^4$, $R^5$, n and m, have the same meanings, including the same preferred meanings, as described and defined herein for the corresponding groups/variables in formula (Ia).

In this 67th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 68th specific embodiment, the compound of formula (Ia) according to the first or the second aspect of the invention is a compound of the following formula:

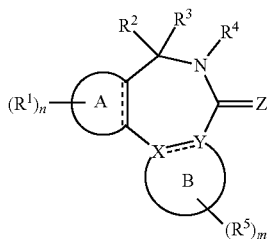

or a pharmaceutically acceptable salt, solvate or prodrug thereof;

wherein A is a group

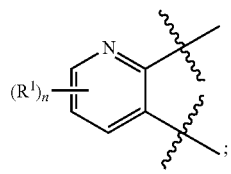

wherein B is a group

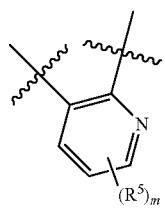

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ═══, $R^1$, $R^4$, $R^5$, n and m, have the same meanings, including the same preferred meanings, as described and defined herein for the corresponding groups/variables in formula (Ia).

In a 69$^{th}$ specific embodiment, the compound of formula (Ia) according to the first or the second aspect of the invention is a compound of the following formula:

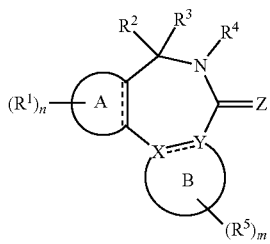

or a pharmaceutically acceptable salt, solvate or prodrug thereof;

wherein A is a group

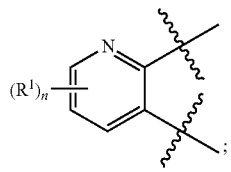

wherein B is a group

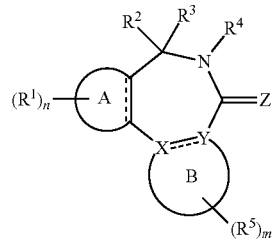

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ═══, $R^1$, $R^4$, $R^5$, n and m, have the same meanings, including the same preferred meanings, as described and defined herein for the corresponding groups/variables in formula (Ia).

In a 70$^{th}$ specific embodiment, the compound of formula (Ia) according to the first or the second aspect of the invention is a compound of the following formula:

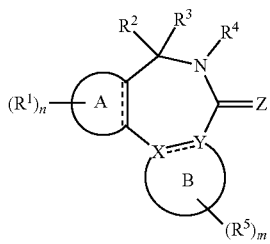

or a pharmaceutically acceptable salt, solvate or prodrug thereof;

wherein A is a group

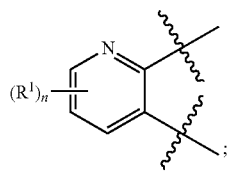

wherein B is a group

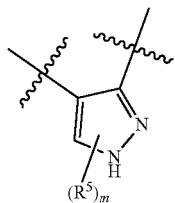

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 71$^{st}$ specific embodiment, the compound of formula (Ia) according to the first or the second aspect of the invention is a compound of the following formula:

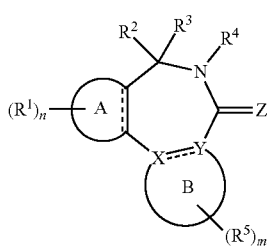

or a pharmaceutically acceptable salt, solvate or prodrug thereof;

wherein A is a group;

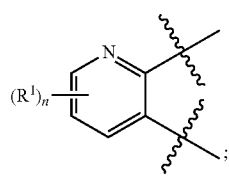

wherein B is a group

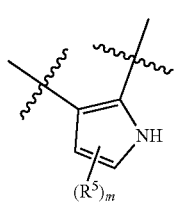

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 72$^{nd}$ specific embodiment, the compound of formula (Ia) according to the first or the second aspect of the invention is a compound of the following formula:

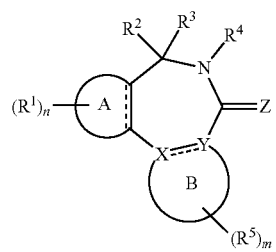

or a pharmaceutically acceptable salt, solvate or prodrug thereof;

wherein A is a group

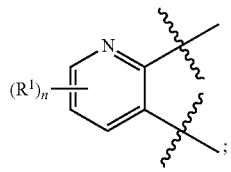

wherein B is a group

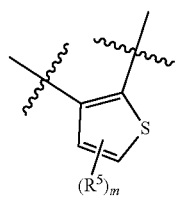

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 73$^{rd}$ specific embodiment, the compound of formula (Ia) according to the first or the second aspect of the invention is a compound of the following formula:

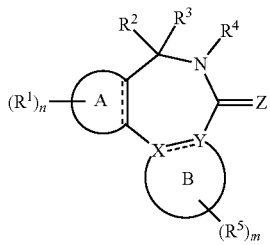

or a pharmaceutically acceptable salt, solvate or prodrug thereof;
wherein A is a group

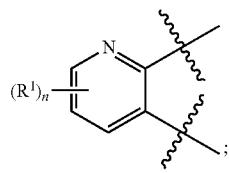

wherein B is a group

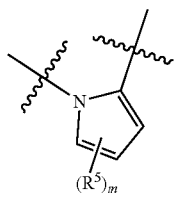

(and, accordingly, X is N, and Y is C);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 74th specific embodiment, the compound of formula (Ia) according to the first or the second aspect of the invention is a compound of the following formula:

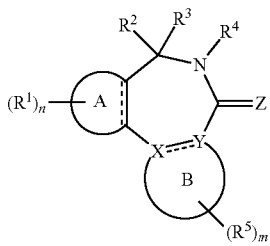

or a pharmaceutically acceptable salt, solvate or prodrug thereof;
wherein A is a group;
wherein B is a group

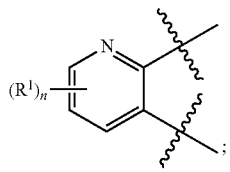

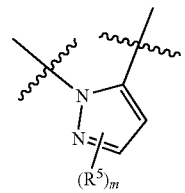

(and, accordingly, X is N, and Y is C);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 75th specific embodiment, the compound of formula (Ia) according to the first or the second aspect of the invention is a compound of the following formula:

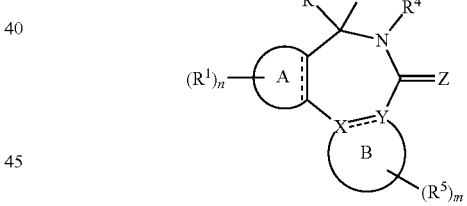

or a pharmaceutically acceptable salt, solvate or prodrug thereof;
wherein A is a group

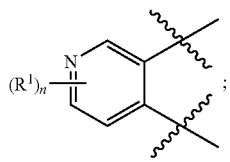

wherein B is phenyl (and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 76th specific embodiment, the compound of formula (Ia) according to the first or the second aspect of the invention is a compound of the following formula:

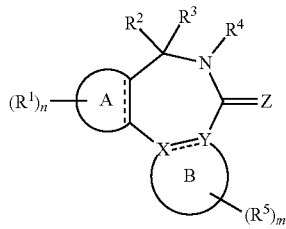

or a pharmaceutically acceptable salt, solvate or prodrug thereof;

wherein A is a group;

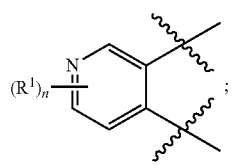

wherein B is a monocyclic 5- or 6-membered heteroaryl;

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, X, Y, $R^1$, $R^4$, $R^5$, n and m, have the same meanings, including the same preferred meanings, as described and defined herein for the corresponding groups/variables in formula (Ia).

In this 76th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 77th specific embodiment, the compound of formula (Ia) according to the first or the second aspect of the invention is a compound of the following formula:

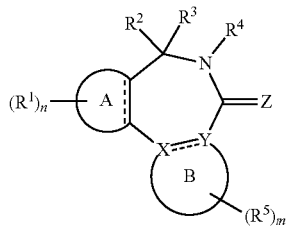

or a pharmaceutically acceptable salt, solvate or prodrug thereof;

wherein A is a group

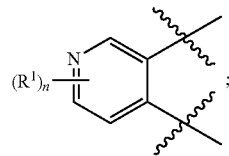

wherein B is a group

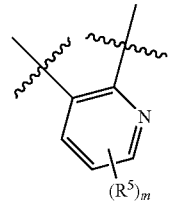

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 78th specific embodiment, the compound of formula (Ia) according to the first or the second aspect of the invention is a compound of the following formula:

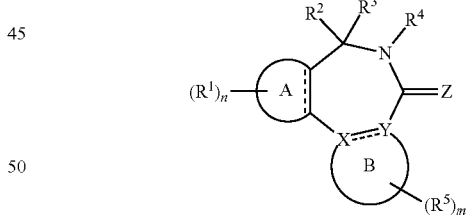

or a pharmaceutically acceptable salt, solvate or prodrug thereof;

wherein A is a group

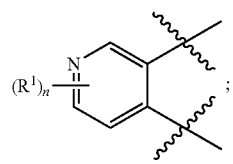

wherein B is a group

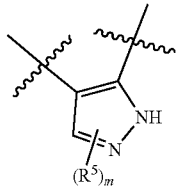

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 79$^{th}$ specific embodiment, the compound of formula (Ia) according to the first or the second aspect of the invention is a compound of the following formula:

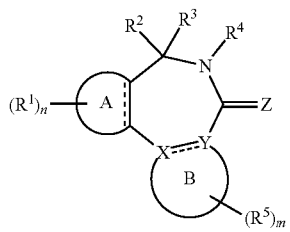

or a pharmaceutically acceptable salt, solvate or prodrug thereof;

wherein A is a group

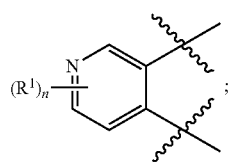

wherein B is a group

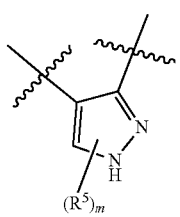

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 80$^{th}$ specific embodiment, the compound of formula (Ia) according to the first or the second aspect of the invention is a compound of the following formula:

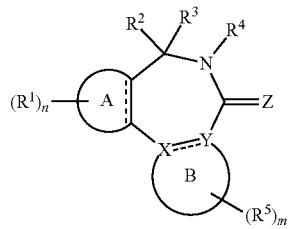

or a pharmaceutically acceptable salt, solvate or prodrug thereof;

wherein A is a group

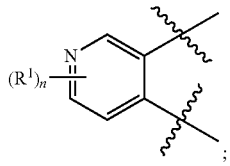

wherein B is a group

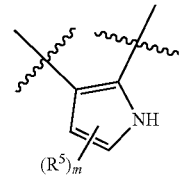

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ===== $R^1$, $R^4$, $R^5$, n and m, have the same meanings, including the same preferred meanings, as described and defined herein for the corresponding groups/variables in formula (Ia).

In a 81$^{st}$ specific embodiment, the compound of formula (Ia) according to the first or the second aspect of the invention is a compound of the following formula:

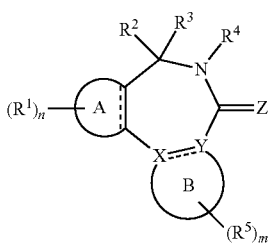

or a pharmaceutically acceptable salt, solvate or prodrug thereof;

wherein A is a group

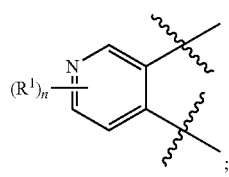

wherein B is a group

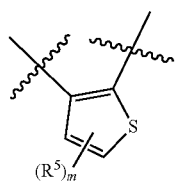

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 82$^{nd}$ specific embodiment, the compound of formula (Ia) according to the first or the second aspect of the invention is a compound of the following formula:

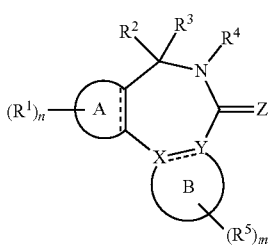

or a pharmaceutically acceptable salt, solvate or prodrug thereof;

wherein A is a group

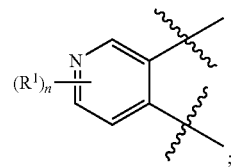

wherein B is a group

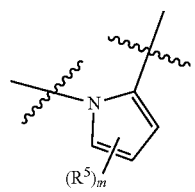

(and, accordingly, X is N, and Y is C);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 83$^{rd}$ specific embodiment, the compound of formula (Ia) according to the first or the second aspect of the invention is a compound of the following formula:

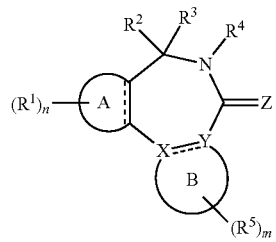

or a pharmaceutically acceptable salt, solvate or prodrug thereof;

wherein A is a group

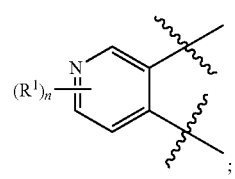

wherein B is a group

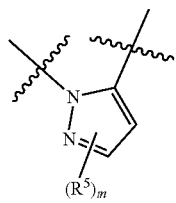

(and, accordingly, X is N, and Y is C);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 84$^{th}$ specific embodiment, the compound of formula (Ia) according to the first or the second aspect of the invention is a compound of the following formula:

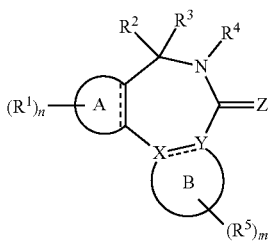

or a pharmaceutically acceptable salt, solvate or prodrug thereof;
wherein A is a group

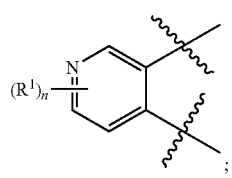

wherein B is phenyl (and, accordingly, both ring atoms X and Y are carbon atoms);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 85$^{th}$ specific embodiment, the compound of formula (Ia) according to the first or the second aspect of the invention is a compound of the following formula:

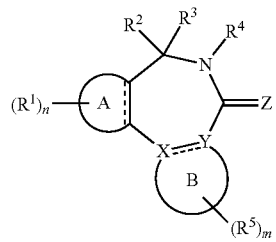

or a pharmaceutically acceptable salt, solvate or prodrug thereof;
wherein A is a group

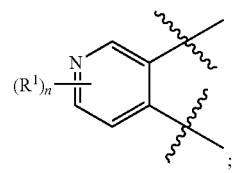

wherein B is a monocyclic 5- or 6-membered heteroaryl;
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, X, Y, $R^1$, $R^4$, $R^5$, n and m, have the same meanings, including the same preferred meanings, as described and defined herein for the corresponding groups/variables in formula (Ia).

In this 85$^{th}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 86$^{th}$ specific embodiment, the compound of formula (Ia) according to the first or the second aspect of the invention is a compound of the following formula:

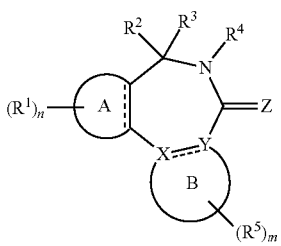

or a pharmaceutically acceptable salt, solvate or prodrug thereof;
wherein A is a group

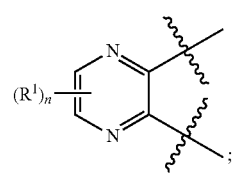

wherein B is a group

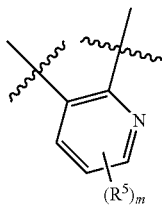

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular $=\!=\!=\!=$, $R^1$, $R^4$, $R^5$, n and m, have the same meanings, including the same preferred meanings, as described and defined herein for the corresponding groups/variables in formula (Ia).

In a 87$^{th}$ specific embodiment, the compound of formula (Ia) according to the first or the second aspect of the invention is a compound of the following formula:

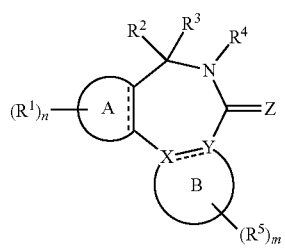

or a pharmaceutically acceptable salt, solvate or prodrug thereof;

wherein A is a group

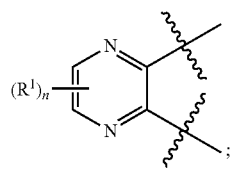

wherein B is a group

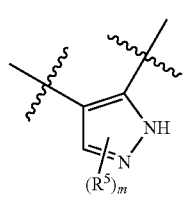

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular $=\!=\!=\!=$, $R^1$, $R^4$, $R^5$, n and m, have the same meanings, including the same preferred meanings, as described and defined herein for the corresponding groups/variables in formula (Ia).

In a 88$^{th}$ specific embodiment, the compound of formula (Ia) according to the first or the second aspect of the invention is a compound of the following formula:

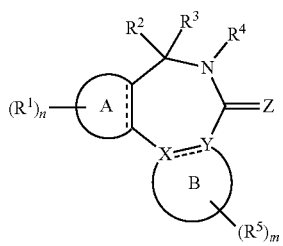

or a pharmaceutically acceptable salt, solvate or prodrug thereof;

wherein A is a group

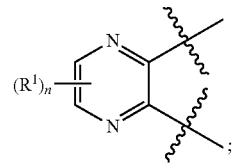

wherein B is a group

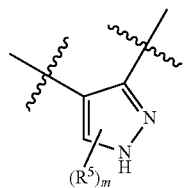

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular $=\!=\!=\!=$, $R^1$, $R^4$, $R^5$, n and m, have the same meanings, including the same preferred meanings, as described and defined herein for the corresponding groups/variables in formula (Ia).

In a 89$^{th}$ specific embodiment, the compound of formula (Ia) according to the first or the second aspect of the invention is a compound of the following formula:

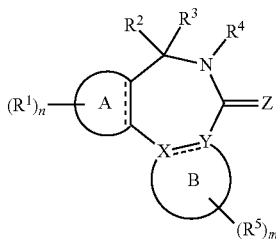

or a pharmaceutically acceptable salt, solvate or prodrug thereof;

wherein A is a group

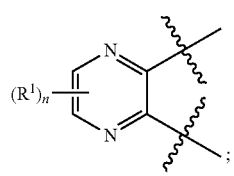

wherein B is a group

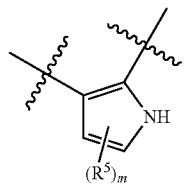

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 90$^{th}$ specific embodiment, the compound of formula (Ia) according to the first or the second aspect of the invention is a compound of the following formula:

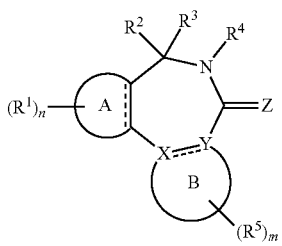

or a pharmaceutically acceptable salt, solvate or prodrug thereof;

wherein A is a group

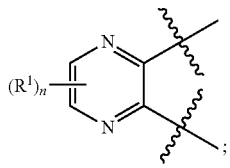

wherein B is a group

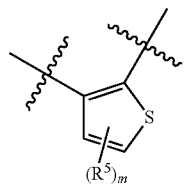

(and, accordingly, both ring atoms X and Y are carbon atoms);

wherein Z is O;

wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl); and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 91$^{st}$ specific embodiment, the compound of formula (Ia) according to the first or the second aspect of the invention is a compound of the following formula:

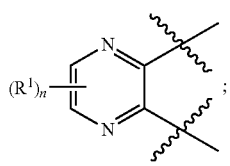

or a pharmaceutically acceptable salt, solvate or prodrug thereof;

wherein A is a group wherein B is a group

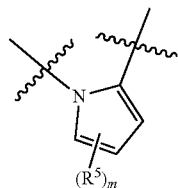

(and, accordingly, X is N, and Y is C);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);
and wherein the further groups/variables in the above-depicted formula, including in particular =====, $R^1$, $R^4$, $R^5$, n and m, have the same meanings, including the same preferred meanings, ===== as described and defined herein for the corresponding groups/variables in formula (Ia).

In a 92$^{nd}$ specific embodiment, the compound of formula (Ia) according to the first or the second aspect of the invention is a compound of the following formula:

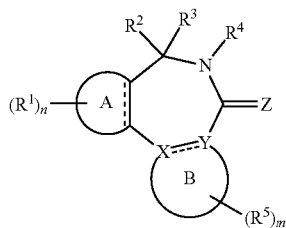

or a pharmaceutically acceptable salt, solvate or prodrug thereof;
wherein A is a group

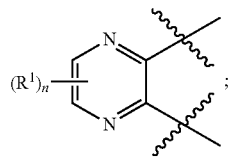

wherein B is a group

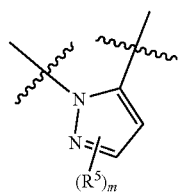

(and, accordingly, X is N, and Y is C);
wherein Z is O;
wherein $R^2$ and $R^3$ are mutually linked to form, together with the carbon atom that they are attached to, a $C_3$-$C_5$ cycloalkyl (e.g., a cyclopropyl or a cyclobutyl; preferably a cyclopropyl);

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 93$^{rd}$ specific embodiment, the compound of formula (Ia) according to the first or the second aspect of the invention is a compound of the following formula:

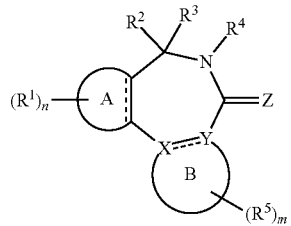

or a pharmaceutically acceptable salt, solvate or prodrug thereof;
wherein A is phenyl;
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In a 94$^{th}$ specific embodiment, the compound of formula (Ia) according to the first or the second aspect of the invention is a compound of the following formula:

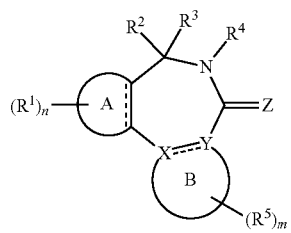

or a pharmaceutically acceptable salt, solvate or prodrug thereof;
wherein A is a monocyclic 5- or 6-membered heteroaryl, wherein 1, 2 or 3 ring atoms of said 5-membered heteroaryl are nitrogen atoms and the remaining ring atoms are carbon atoms, and
wherein 1, 2, 3 or 4 ring atoms of said 6-membered heteroaryl are nitrogen atoms and the remaining ring atoms are carbon atoms;
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In this 94th embodiment, A is preferably a monocyclic 6-membered heteroaryl, wherein 1, 2, 3 or 4 ring atoms (particularly 1 or 2 ring atoms) of said heteroaryl are nitrogen atoms and the remaining ring atoms are carbon atoms. More preferably, A is a monocyclic 6-membered heteroaryl, wherein 1 or 2 ring atoms of said heteroaryl are nitrogen atoms and the remaining ring atoms are carbon atoms (such as, e.g., pyridinyl, pyrimidinyl, pyrazinyl, or pyridazinyl).

Corresponding examples of preferred groups A are shown in the following (where the substituent(s) $R^1$ that may be attached to ring A are also depicted):

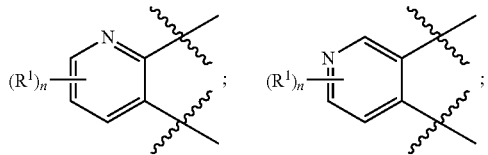

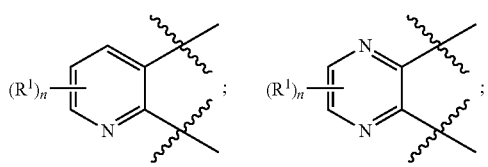

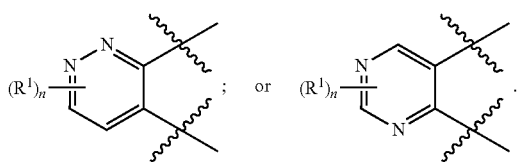

Examples of particularly preferred ring groups A are shown in the following:

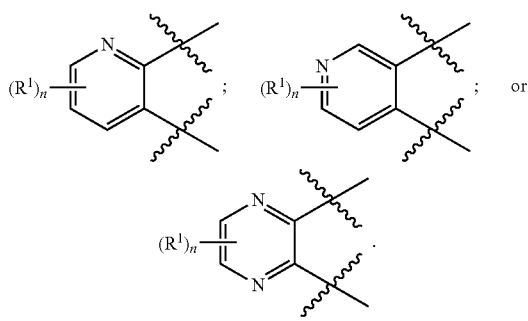

In a 95th specific embodiment, the compound of formula (Ia) according to the first or the second aspect of the invention is a compound of the following formula:

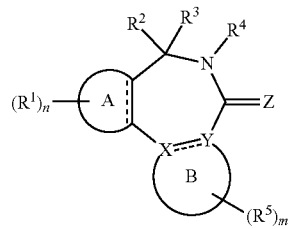

or a pharmaceutically acceptable salt, solvate or prodrug thereof;

wherein A is a group

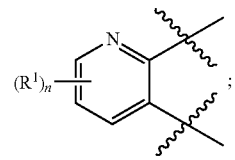

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In a 96th specific embodiment, the compound of formula (Ia) according to the first or the second aspect of the invention is a compound of the following formula:

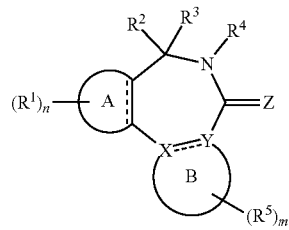

or a pharmaceutically acceptable salt, solvate or prodrug thereof;

wherein A is a group

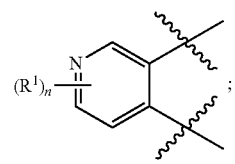

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In a 97th specific embodiment, the compound of formula (Ia) according to the first or the second aspect of the invention is a compound of the following formula:

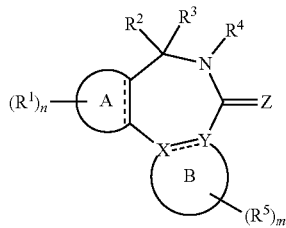

or a pharmaceutically acceptable salt, solvate or prodrug thereof;

wherein A is a group

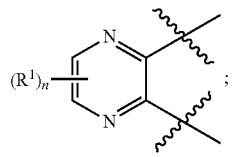

wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, B, X, Y, $R^1$, $R^4$, $R^5$, n and m, have the same meanings, including the same preferred meanings, as described and defined herein for the corresponding groups/variables in formula (Ia).

In a 98th specific embodiment, the compound of formula (Ia) according to the first or the second aspect of the invention is a compound of the following formula:

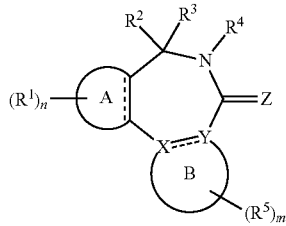

or a pharmaceutically acceptable salt, solvate or prodrug thereof;

wherein B is phenyl (and, accordingly, both ring atoms X and Y are carbon atoms);

wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 99th specific embodiment, the compound of formula (Ia) according to the first or the second aspect of the invention is a compound of the following formula:

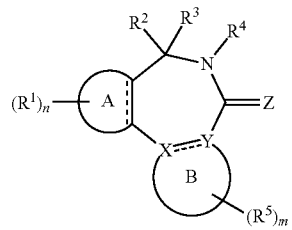

or a pharmaceutically acceptable salt, solvate or prodrug thereof;

wherein B is a monocyclic 5- or 6-membered heteroaryl;
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, A, X, Y, $R^1$, $R^4$, $R^5$, n and m, have the same meanings, including the same preferred meanings, as described and defined herein for the corresponding groups/variables in formula (Ia).

In this 99th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

Corresponding examples of preferred ring groups B are shown in the following (where the substituent(s) $R^5$ that may be attached to ring B are also depicted):

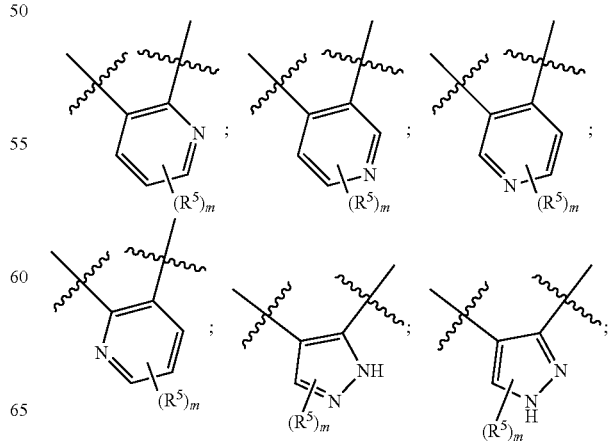

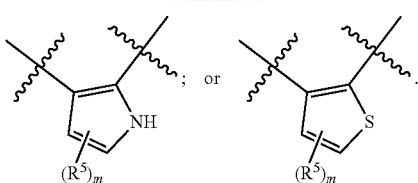

Particularly preferred examples of ring B are shown in the following:

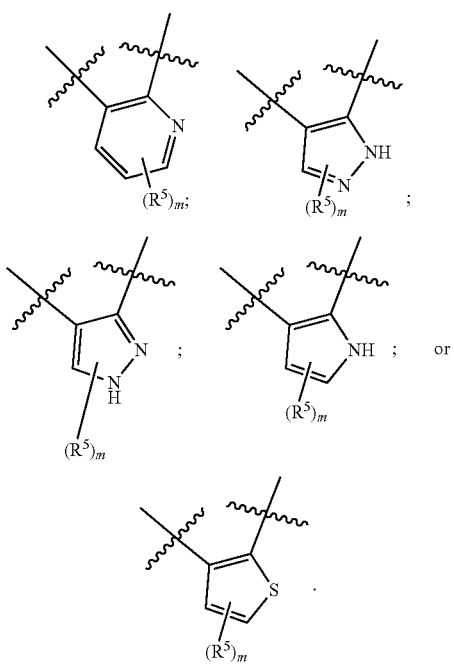

Even more preferred examples of ring B are shown in the following:

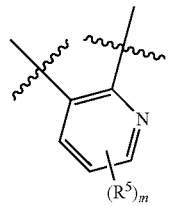

In a 100<sup>th</sup> specific embodiment, the compound of formula (Ia) according to the first or the second aspect of the invention is a compound of the following formula:

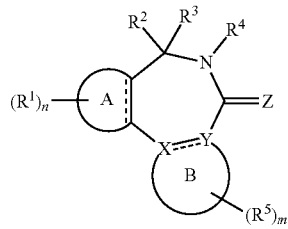

or a pharmaceutically acceptable salt, solvate or prodrug thereof;
wherein B is a group

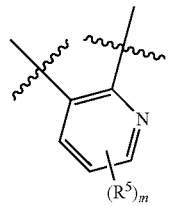

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, A, $R^1$, $R^4$, $R^5$, n and m, have the same meanings, including the same preferred meanings, as described and defined herein for the corresponding groups/variables in formula (Ia).

In a 101<sup>st</sup> specific embodiment, the compound of formula (Ia) according to the first or the second aspect of the invention is a compound of the following formula:

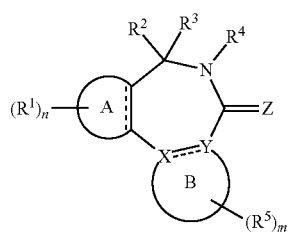

or a pharmaceutically acceptable salt, solvate or prodrug thereof;
wherein B is a group

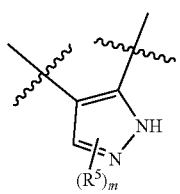

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ≡≡≡, A, $R^1$, $R^4$, $R^5$, n and m, have the same meanings, including the same preferred meanings, as described and defined herein for the corresponding groups/variables in formula (Ia).

In a 102$^{nd}$ specific embodiment, the compound of formula (Ia) according to the first or the second aspect of the invention is a compound of the following formula:

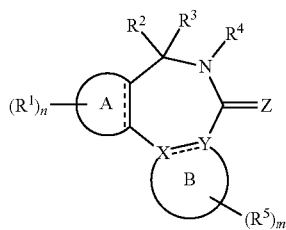

or a pharmaceutically acceptable salt, solvate or prodrug thereof;

wherein B is a group

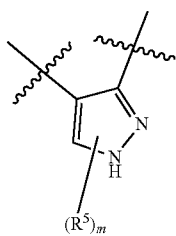

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ≡≡≡, A, $R^1$, $R^4$, $R^5$, n and m, have the same meanings, including the same preferred meanings, as described and defined herein for the corresponding groups/variables in formula (Ia).

In a 103$^{rd}$ specific embodiment, the compound of formula (Ia) according to the first or the second aspect of the invention is a compound of the following formula:

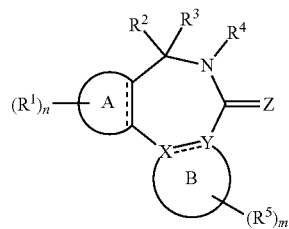

or a pharmaceutically acceptable salt, solvate or prodrug thereof;

wherein B is a group

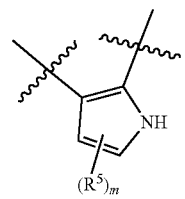

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ≡≡≡, A, $R^1$, $R^4$, $R^5$, n and m, have the same meanings, including the same preferred meanings, as described and defined herein for the corresponding groups/variables in formula (Ia).

In a 104$^{th}$ specific embodiment, the compound of formula (Ia) according to the first or the second aspect of the invention is a compound of the following formula:

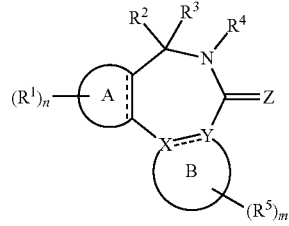

or a pharmaceutically acceptable salt, solvate or prodrug thereof;

wherein B is a group

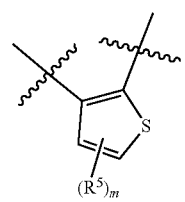

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, A, $R^1$, $R^4$, $R^5$, n and m, have the same meanings, including the same preferred meanings, as described and defined herein for the corresponding groups/variables in formula (Ia).

In a 105$^{th}$ specific embodiment, the compound of formula (Ia) according to the first or the second aspect of the invention is a compound of the following formula:

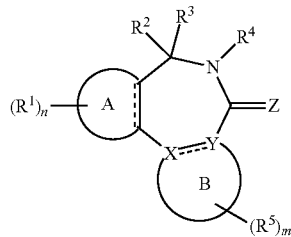

or a pharmaceutically acceptable salt, solvate or prodrug thereof;

wherein A is phenyl;

wherein B is phenyl (and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 106$^{th}$ specific embodiment, the compound of formula (Ia) according to the first or the second aspect of the invention is a compound of the following formula:

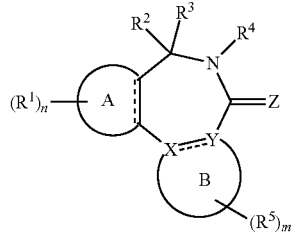

or a pharmaceutically acceptable salt, solvate or prodrug thereof;

wherein A is phenyl;

wherein B is a monocyclic 5- or 6-membered heteroaryl;

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, X, Y, $R^1$, $R^4$, $R^5$, n and m, have the same meanings, including the same preferred meanings, as described and defined herein for the corresponding groups/variables in formula (Ia).

In this 106$^{th}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 107$^{th}$ specific embodiment, the compound of formula (Ia) according to the first or the second aspect of the invention is a compound of the following formula:

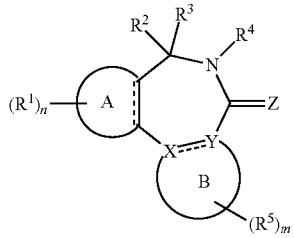

or a pharmaceutically acceptable salt, solvate or prodrug thereof;

wherein A is phenyl;

wherein B is a group

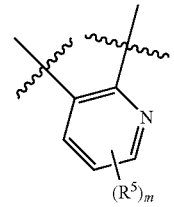

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 108$^{th}$ specific embodiment, the compound of formula (Ia) according to the first or the second aspect of the invention is a compound of the following formula:

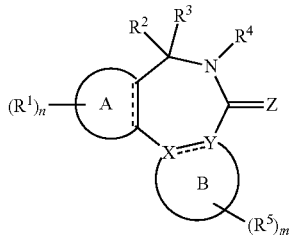

or a pharmaceutically acceptable salt, solvate or prodrug thereof;

wherein A is phenyl;
wherein B is a group

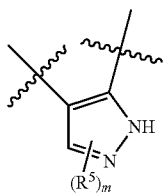

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 109th specific embodiment, the compound of formula (Ia) according to the first or the second aspect of the invention is a compound of the following formula:

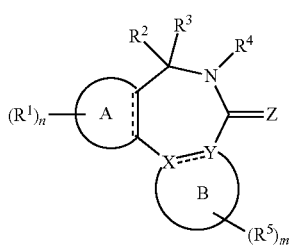

or a pharmaceutically acceptable salt, solvate or prodrug thereof;

wherein A is phenyl;
wherein B is a group

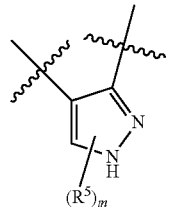

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 110th specific embodiment, the compound of formula (Ia) according to the first or the second aspect of the invention is a compound of the following formula:

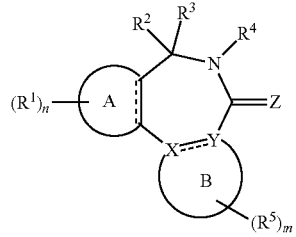

or a pharmaceutically acceptable salt, solvate or prodrug thereof;

wherein A is phenyl;
wherein B is a group

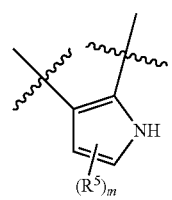

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 111th specific embodiment, the compound of formula (Ia) according to the first or the second aspect of the invention is a compound of the following formula:

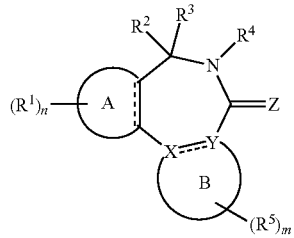

or a pharmaceutically acceptable salt, solvate or prodrug thereof;

wherein A is phenyl;

wherein B is a group

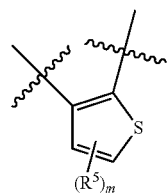

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 112th specific embodiment, the compound of formula (Ia) according to the first or the second aspect of the invention is a compound of the following formula:

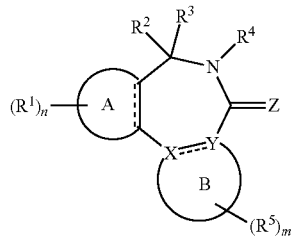

or a pharmaceutically acceptable salt, solvate or prodrug thereof;

wherein A is a group

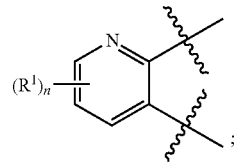

wherein B is phenyl (and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 113th specific embodiment, the compound of formula (Ia) according to the first or the second aspect of the invention is a compound of the following formula:

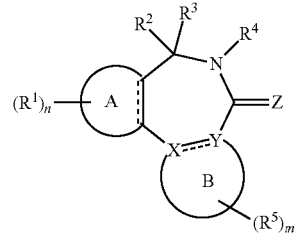

or a pharmaceutically acceptable salt, solvate or prodrug thereof;

wherein A is a group

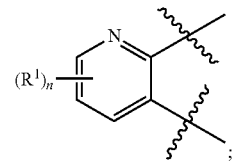

wherein B is a monocyclic 5- or 6-membered heteroaryl;

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, X, Y, $R^1$, $R^4$, $R^5$, n and m, have the same meanings, including the same preferred meanings, as described and defined herein for the corresponding groups/variables in formula (Ia).

In this 113th embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 114th specific embodiment, the compound of formula (Ia) according to the first or the second aspect of the invention is a compound of the following formula:

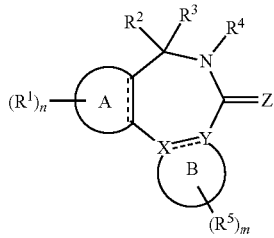

or a pharmaceutically acceptable salt, solvate or prodrug thereof;

wherein A is a group

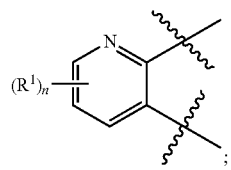

wherein B is a group

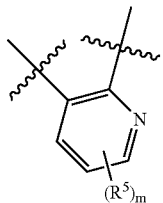

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 115th specific embodiment, the compound of formula (Ia) according to the first or the second aspect of the invention is a compound of the following formula:

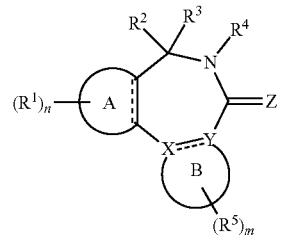

or a pharmaceutically acceptable salt, solvate or prodrug thereof;

wherein A is a group

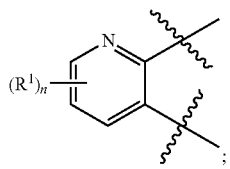

wherein B is a group

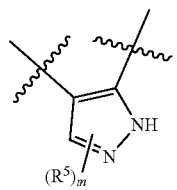

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular =====, $R^1$, $R^4$, $R^5$, n and m, have the same meanings, including the same preferred meanings, described and defined herein for the corresponding groups/variables in formula (Ia).

In a 116th specific embodiment, the compound of formula (Ia) according to the first or the second aspect of the invention is a compound of the following formula:

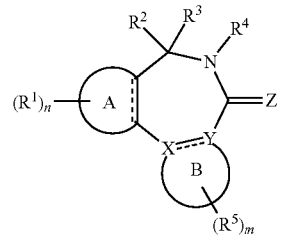

or a pharmaceutically acceptable salt, solvate or prodrug thereof;

wherein A is a group

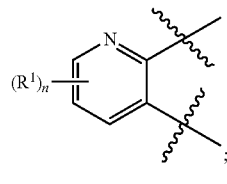

wherein B is a group

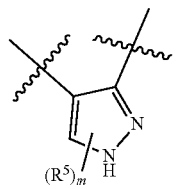

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 117$^{th}$ specific embodiment, the compound of formula (Ia) according to the first or the second aspect of the invention is a compound of the following formula:

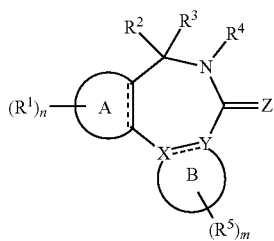

or a pharmaceutically acceptable salt, solvate or prodrug thereof;

wherein A is a group

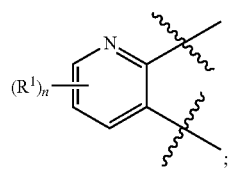

wherein B is a group

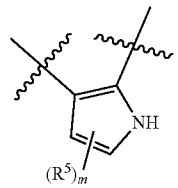

(and, accordingly, both ring atoms X and Y are carbon atoms);

wherein Z is O;

wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;

and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 118$^{th}$ specific embodiment, the compound of formula (Ia) according to the first or the second aspect of the invention is a compound of the following formula:

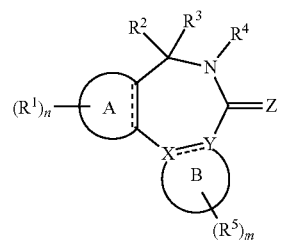

or a pharmaceutically acceptable salt, solvate or prodrug thereof;

wherein A is a group

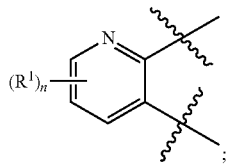

wherein B is a group

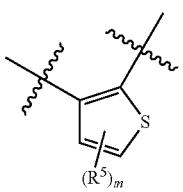

(and, accordingly, both ring atoms X and Y are carbon atoms);

wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;

and wherein the further groups/variables in the above-depicted formula, including in particular =====, R¹, R⁴, R⁵, n and m, have the same meanings, including the same preferred meanings, as described and defined herein for the corresponding groups/variables in formula (Ia).

In a 119$^{th}$ specific embodiment, the compound of formula (Ia) according to the first or the second aspect of the invention is a compound of the following formula:

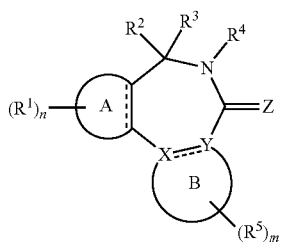

or a pharmaceutically acceptable salt, solvate or prodrug thereof;
wherein A is a group

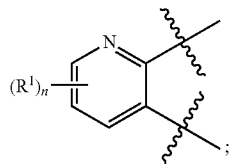

wherein B is a group

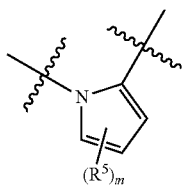

(and, accordingly, X is N, and Y is C);
wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;

and wherein the further groups/variables in the above-depicted formula, including in particular =====, R¹, R⁴, R⁵, n and m, have the same meanings, including the same preferred meanings, as described and defined herein for the corresponding groups/variables in formula (Ia).

In a 120$^{th}$ specific embodiment, the compound of formula (Ia) according to the first or the second aspect of the invention is a compound of the following formula:

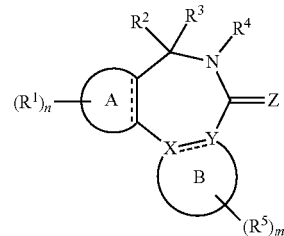

or a pharmaceutically acceptable salt, solvate or prodrug thereof;
wherein A is a group

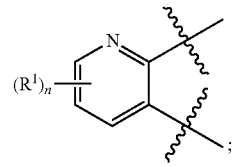

wherein B is a group

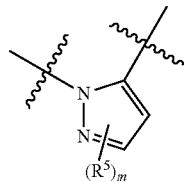

(and, accordingly, X is N, and Y is C);
wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;

and wherein the further groups/variables in the above-depicted formula, including in particular =====, R¹, R⁴, R⁵, n and m, have the same meanings, including the same preferred meanings, as described and defined herein for the corresponding groups/variables in formula (Ia).

In a 121$^{st}$ specific embodiment, the compound of formula (Ia) according to the first or the second aspect of the invention is a compound of the following formula:

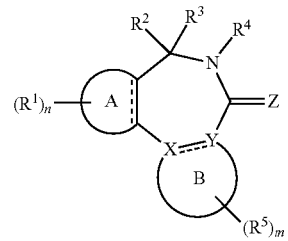

or a pharmaceutically acceptable salt, solvate or prodrug thereof;

wherein A is a group

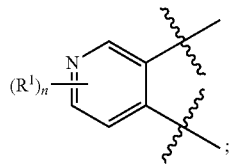

wherein B is phenyl (and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 122$^{nd}$ specific embodiment, the compound of formula (Ia) according to the first or the second aspect of the invention is a compound of the following formula:

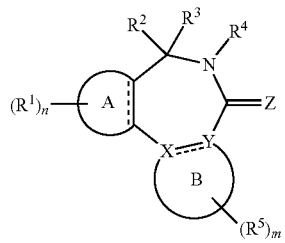

or a pharmaceutically acceptable salt, solvate or prodrug thereof;
wherein A is a group

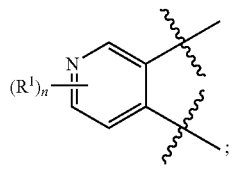

wherein B is a monocyclic 5- or 6-membered heteroaryl;
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, X, Y, $R^1$, $R^4$, $R^5$, n and m, have the same meanings, including the same preferred meanings, as described and defined herein for the corresponding groups/variables in formula (Ia).

In this 122$^{nd}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 123$^{rd}$ specific embodiment, the compound of formula (Ia) according to the first or the second aspect of the invention is a compound of the following formula:

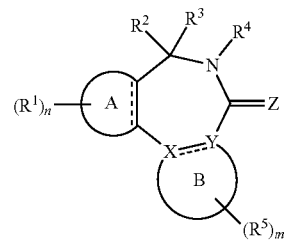

or a pharmaceutically acceptable salt, solvate or prodrug thereof;
wherein A is a group

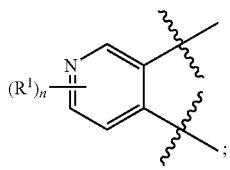

wherein B is a group

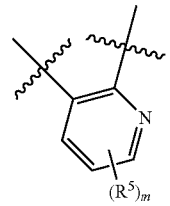

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 124$^{th}$ specific embodiment, the compound of formula (Ia) according to the first or the second aspect of the invention is a compound of the following formula:

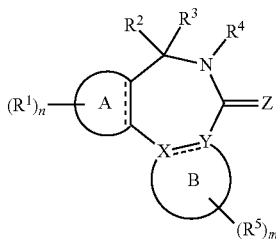

or a pharmaceutically acceptable salt, solvate or prodrug thereof;
wherein A is a group

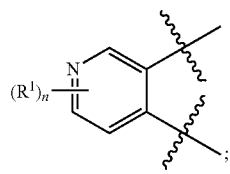

wherein B is a group

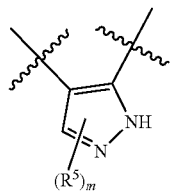

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 125th specific embodiment, the compound of formula (Ia) according to the first or the second aspect of the invention is a compound of the following formula:

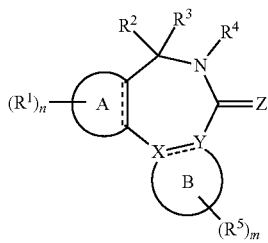

or a pharmaceutically acceptable salt, solvate or prodrug thereof;
wherein A is a group

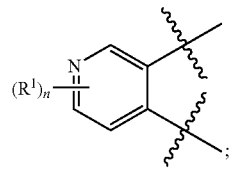

wherein B is a group

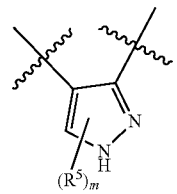

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 126th specific embodiment, the compound of formula (Ia) according to the first or the second aspect of the invention is a compound of the following formula:

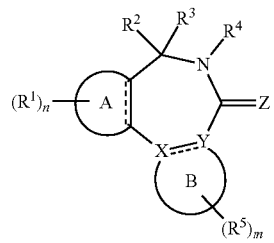

or a pharmaceutically acceptable salt, solvate or prodrug thereof;
wherein A is a group

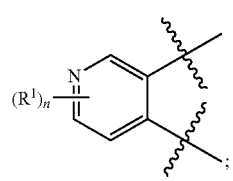

wherein B is a group

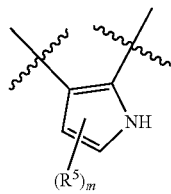

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 127$^{th}$ specific embodiment, the compound of formula (Ia) according to the first or the second aspect of the invention is a compound of the following formula:

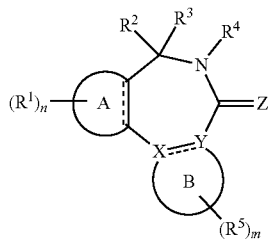

or a pharmaceutically acceptable salt, solvate or prodrug thereof;
wherein A is a group

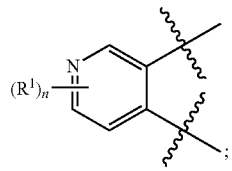

wherein B is a group

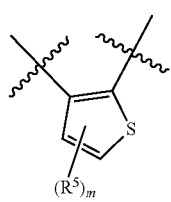

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 128$^{th}$ specific embodiment, the compound of formula (Ia) according to the first or the second aspect of the invention is a compound of the following formula:

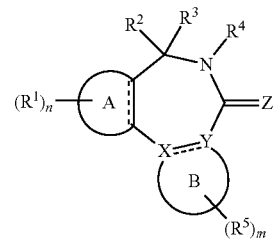

or a pharmaceutically acceptable salt, solvate or prodrug thereof;
wherein A is a group

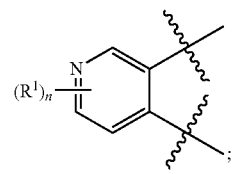

wherein B is a group

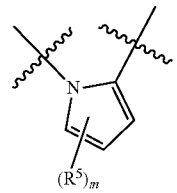

(and, accordingly, X is N, and Y is C);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular =====, $R^1$, $R^4$, $R^5$, n and m, have the same meanings, including the same preferred meanings, as described and defined herein for the corresponding groups/variables in formula (Ia).

In a 129$^{th}$ specific embodiment, the compound of formula (Ia) according to the first or the second aspect of the invention is a compound of the following formula:

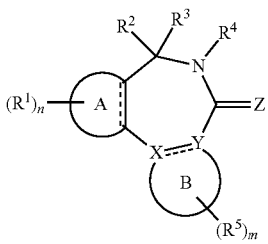

or a pharmaceutically acceptable salt, solvate or prodrug thereof;
wherein A is a group

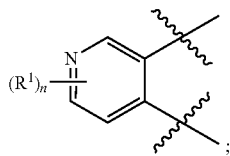

wherein B is a group

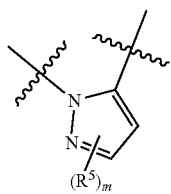

(and, accordingly, X is N, and Y is C);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 130$^{th}$ specific embodiment, the compound of formula (Ia) according to the first or the second aspect of the invention is a compound of the following formula:

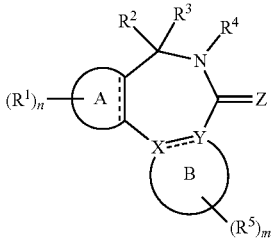

or a pharmaceutically acceptable salt, solvate or prodrug thereof;

wherein A is a group

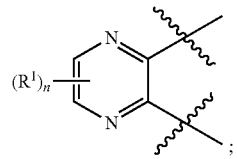

wherein B is phenyl (and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 131$^{st}$ specific embodiment, the compound of formula (Ia) according to the first or the second aspect of the invention is a compound of the following formula:

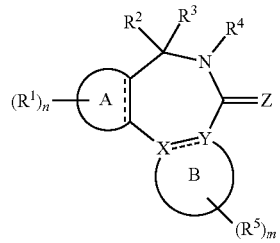

or a pharmaceutically acceptable salt, solvate or prodrug thereof;
wherein A is a group

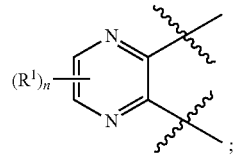

wherein B is a monocyclic 5- or 6-membered heteroaryl;
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====X, Y, $R^1$, $R^4$, $R^5$, n and m, have the same meanings, including the same preferred meanings, as described and defined herein for the corresponding groups/variables in formula (Ia).

In this 131$^{st}$ embodiment, B is preferably a monocyclic 5- or 6-membered heteroaryl (such as, e.g., pyrrolyl, pyrazolyl, thiophenyl, or pyridinyl), in which both ring atoms X and Y are carbon atoms.

In a 132$^{nd}$ specific embodiment, the compound of formula (Ia) according to the first or the second aspect of the invention is a compound of the following formula:

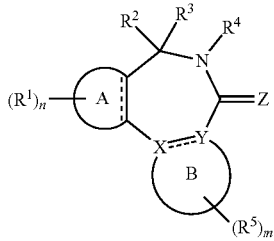

or a pharmaceutically acceptable salt, solvate or prodrug thereof;

wherein A is a group

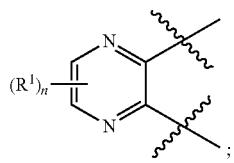

wherein B is a group

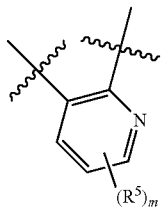

(and, accordingly, both ring atoms X and Y are carbon atoms);

wherein Z is O;

wherein R$^2$ and R$^3$ are each independently selected from hydrogen, halogen, C$_1$-C$_4$ alkyl, —OH, and —O(C$_1$-C$_4$ alkyl), wherein it is preferred that R$^2$ and R$^3$ are each independently selected from hydrogen and C$_1$-C$_4$ alkyl (e.g., methyl or ethyl), and wherein it is more preferred that R$^2$ and R$^3$ are each hydrogen;

and wherein the further groups/variables in the above-depicted formula, including in particular =====, R$^1$, R$^4$, R$^5$, n and m, have the same meanings, including the same preferred meanings, as described and defined herein for the corresponding groups/variables in formula (Ia).

In a 133$^{rd}$ specific embodiment, the compound of formula (Ia) according to the first or the second aspect of the invention is a compound of the following formula:

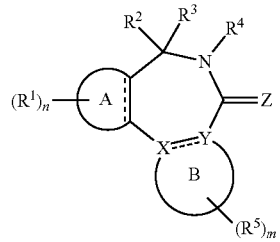

or a pharmaceutically acceptable salt, solvate or prodrug thereof;

wherein A is a group

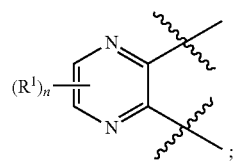

wherein B is a group

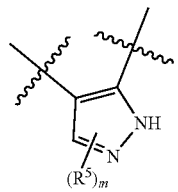

(and, accordingly, both ring atoms X and Y are carbon atoms);

wherein Z is O;

wherein R$^2$ and R$^3$ are each independently selected from hydrogen, halogen, C$_1$-C$_4$ alkyl, —OH, and —O(C$_1$-C$_4$ alkyl), wherein it is preferred that R$^2$ and R$^3$ are each independently selected from hydrogen and C$_1$-C$_4$ alkyl (e.g., methyl or ethyl), and wherein it is more preferred that R$^2$ and R$^3$ are each hydrogen;

and wherein the further groups/variables in the above-depicted formula, including in particular =====, R$^1$, R$^4$, R$^5$, n and m, have the same meanings, including the same preferred meanings, as described and defined herein for the corresponding groups/variables in formula (Ia).

In a 134$^{th}$ specific embodiment, the compound of formula (Ia) according to the first or the second aspect of the invention is a compound of the following formula:

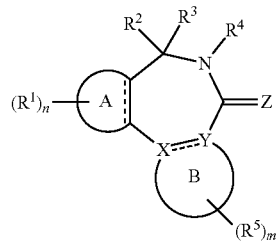

or a pharmaceutically acceptable salt, solvate or prodrug thereof;

wherein A is a group

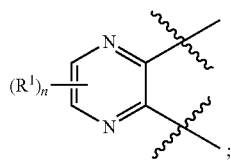

wherein B is a group

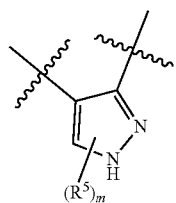

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 135$^{th}$ specific embodiment, the compound of formula (Ia) according to the first or the second aspect of the invention is a compound of the following formula:

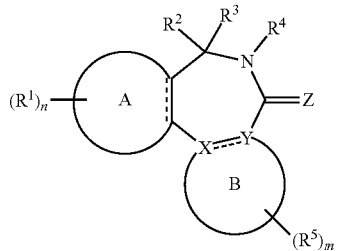

or a pharmaceutically acceptable salt, solvate or prodrug thereof;
wherein A is a group

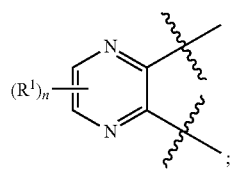

wherein B is a group

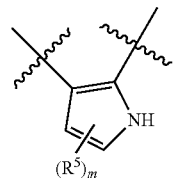

(and, accordingly, both ring atoms X and Y are carbon atoms);
wherein Z is O;
wherein $R^2$ and $R^3$ are each independently selected from hydrogen, halogen, $C_1$-$C_4$ alkyl, —OH, and —O($C_1$-$C_4$ alkyl), wherein it is preferred that $R^2$ and $R^3$ are each independently selected from hydrogen and $C_1$-$C_4$ alkyl (e.g., methyl or ethyl), and wherein it is more preferred that $R^2$ and $R^3$ are each hydrogen;
and wherein the further groups/variables in the above-depicted formula, including in particular ====, $R^1$, $R^4$, $R^5$, n and m, have the same meanings, including the same preferred meanings, as described and defined herein for the corresponding groups/variables in formula (Ia).

In a 136$^{th}$ specific embodiment, the compound of formula (Ia) according to the first or the second aspect of the invention is a compound of the following formula:

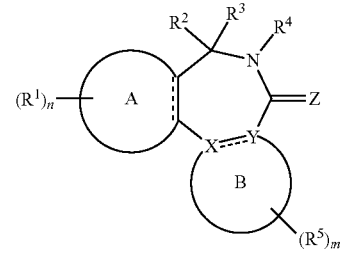

or a pharmaceutically acceptable salt, solvate or prodrug thereof;
wherein A is a group

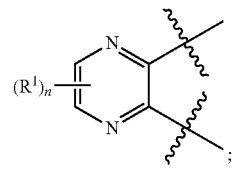

wherein B is a group

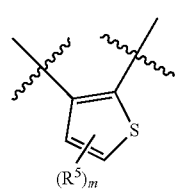

(and, accordingly, both ring atoms X and Y are carbon atoms);

wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;
and wherein the further groups/variables in the above-depicted formula, including in particular ====, R¹, R⁴, R⁵, n and m, have the same meanings, including the same preferred meanings, as described and defined herein for the corresponding groups/variables in formula (Ia).

In a 137th specific embodiment, the compound of formula (Ia) according to the first or the second aspect of the invention is a compound of the following formula:

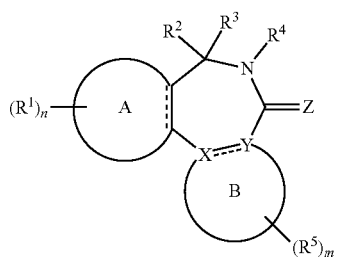

or a pharmaceutically acceptable salt, solvate or prodrug thereof; wherein A is a group

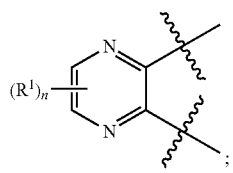

wherein B is a group

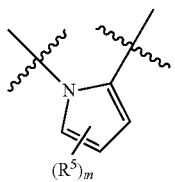

(and, accordingly, X is N, and Y is C);
wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;
and wherein the further groups/variables in the above-depicted formula, including in particular ====, R¹, R⁴, R⁵, n and m, have the same meanings, including the same preferred meanings, as described and defined herein for the corresponding groups/variables in formula (Ia).

In a 138th specific embodiment, the compound of formula (Ia) according to the first or the second aspect of the invention is a compound of the following formula:

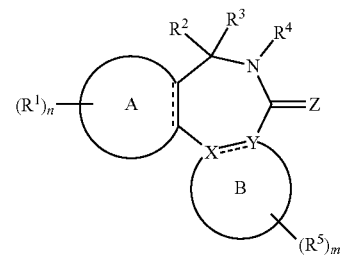

or a pharmaceutically acceptable salt, solvate or prodrug thereof;
wherein A is a group

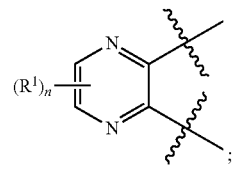

wherein B is a group

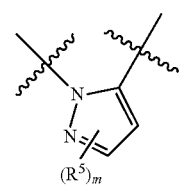

(and, accordingly, X is N, and Y is C);
wherein Z is O;
wherein R² and R³ are each independently selected from hydrogen, halogen, C₁-C₄ alkyl, —OH, and —O(C₁-C₄ alkyl), wherein it is preferred that R² and R³ are each independently selected from hydrogen and C₁-C₄ alkyl (e.g., methyl or ethyl), and wherein it is more preferred that R² and R³ are each hydrogen;
and wherein the further groups/variables in the above-depicted formula, including in particular ====, R¹, R⁴, R⁵, n and m, have the same meanings, including the same preferred meanings, as described and defined herein for the corresponding groups/variables in formula (Ia).

In a 139th specific embodiment, the compound of formula (I) according to the first or the second aspect of the invention is a compound of the following formula:

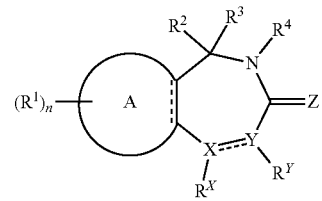

or a pharmaceutically acceptable salt, solvate or prodrug thereof;
wherein $R^X$ is a group $R^{X1}$, and $R^Y$ is a group $R^{Y1}$;
and wherein the further groups/variables in the above-depicted formula, including in particular ====, A, X, Y, Z, $R^1$, $R^2$, $R^3$, $R^4$, $R^{X1}$, $R^{X2}$ and n, have the same meanings, including the same preferred meanings, as described and defined herein for the corresponding groups/variables in formula (I).

The present invention furthermore relates to the following novel compounds:

9-Bromo-5-methyl-5,6-dihydro-spiro[benzo[f]pyrrolo[1,2-a][1,4]diazepine-6,1'-cyclobutan]-4-one;

9-(6-Fluoro-pyridin-3-yl)-5-methyl-5,6-dihydro-spiro[benzo[f]pyrrolo[1,2-a][1,4]diazepine-6,1'-cyclobutan]-4-one;

9-(2-Methyl-pyridin-3-yl)-5-methyl-5,6-dihydro-spiro[benzo[f]pyrrolo[1,2-a][1,4]diazepine-6,1'-cyclobutan]-4-one;

9-(6-Fluoro-pyridin-2-yl)-5-methyl-5,6-dihydro-spiro[benzo[f]pyrrolo[1,2-a][1,4]diazepine-6,1'-cyclobutan]-4-one;

and pharmaceutically acceptable salts, solvates and prodrugs of any one of these compounds.

The above-mentioned novel compounds can each be used as a medicament, particularly for use in the treatment and/or prophylaxis of a condition associated with altered glutamatergic signalling and/or functions, and/or a condition which can be affected by alteration of glutamate level or signalling, such as Parkinson's disease, as described herein with reference to the compounds of formula (I) or (Ia). The detailed description provided herein with respect to the compounds of formula (I) or (Ia), including in particular any of the therapeutic uses described for the compounds of formula (I) or (Ia), thus also applies to the above-mentioned novel compounds.

For a person skilled in the field of synthetic chemistry, various ways for the preparation of the compounds of general formula (I) or (Ia) will be readily apparent. For example, the compounds of the present invention can be prepared in accordance with or in analogy to the synthetic routes described in detail in the examples section. In particular, compounds of the general formula (I) or (Ia) and their pharmaceutically acceptable salts can be synthesized according to (or in analogy to) the methods described in the following schemes, where $X_1$ and $X_2$ independently represent a halogen, M a metallic species and R any group at the corresponding position of the general formula (I) or (Ia). It will be understood that these schemes explain the preparation of compounds of formula (I) or (Ia) and, thus, that these groups R are defined in accordance with the corresponding groups at the same positions of attachment in the general formula (I) or (Ia). Furthermore, where the following schemes depict a substituent $R_1$ and/or a substituent $R_5$, it will be understood that one or more (or none) of the corresponding substituent(s) $R_1$ and/or $R_5$ may be present, in accordance with the definition of formula (I) or (Ia), including in particular the definition of the variables n and m, which have been omitted from these schemes for simplicity.

Intermediate C can be obtained by an aromatic nucleophilic substitution between heteroaromatic A and ring B. A subsequent tandem Kulinkovich-Szymoniak cyclopropanation-lactamization of C allows the formation of the core structure D. Alkylation of intermediate D gives examples of the present invention (F). Examples can be further modified by methods well known in the art. For example, the $R_1$ group can be introduced by a cross-coupling reaction with metallic species G, thus giving access to different examples H (scheme 1).

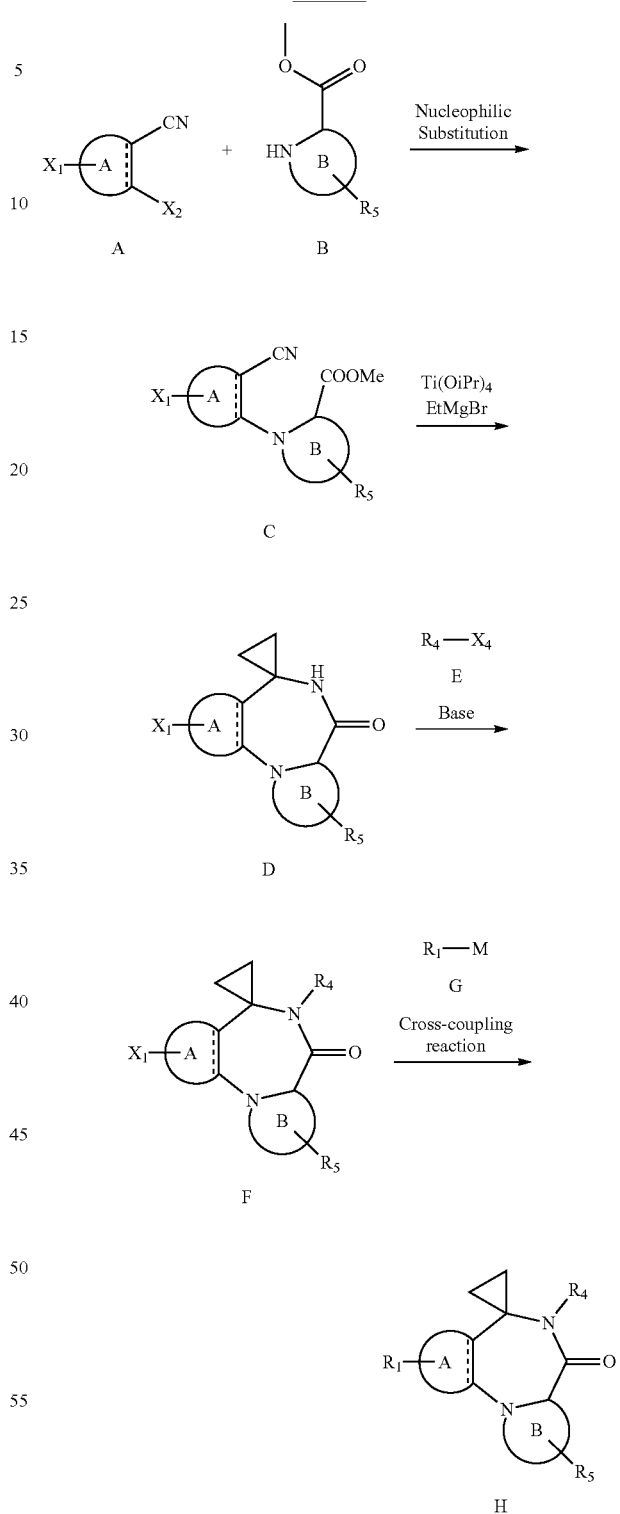

Scheme 1

Starting from any heteroaromatic benzylamine I, the 7-membered diazepinone ring can be obtained by forming the amide junction at first, giving intermediate K. A subsequent intramolecular aromatic nucleophilic substitution can be used to close the ring, thus giving access to examples F and H (scheme 2).

Scheme 2

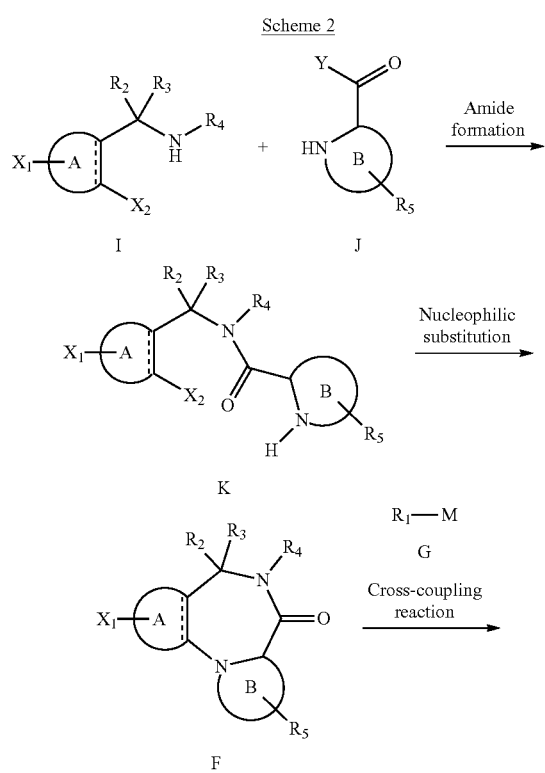

Y = OH or Cl

Any aromatic or heteroaromatic ring, bearing a boronic acid or ester, can be substituted to A via a C—C cross-coupling reaction. Then, H1 can be obtained in a similar 3-steps sequence as the one depicted in scheme 1 (scheme 3):

Scheme 3

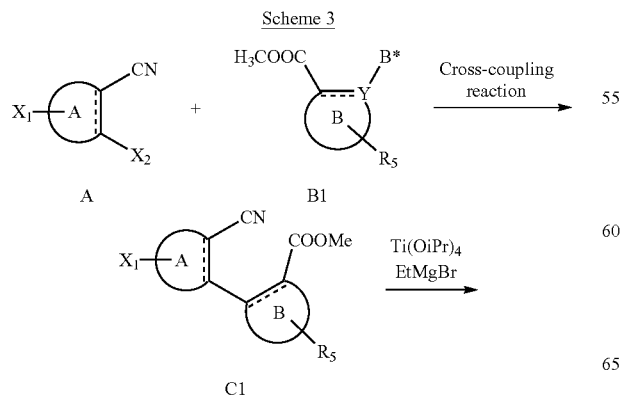

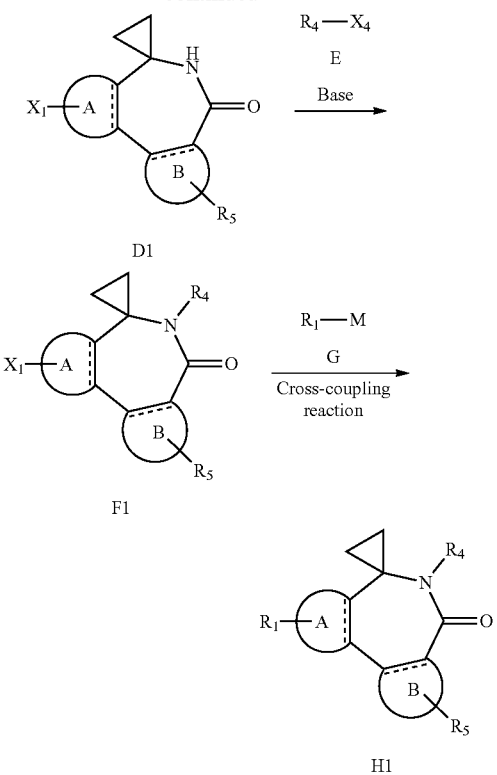

B* = any boronic acid or ester

Partners of the C—C cross coupling reaction can be reversed, thus offering a broader diversity of (hetero)aromatic compounds: A2, bearing the boronic acid or ester, is coupled to B2 to generate C2. A subsequent reductive amination using E2 with in situ cyclization can give examples F2 (scheme 4):

Scheme 4

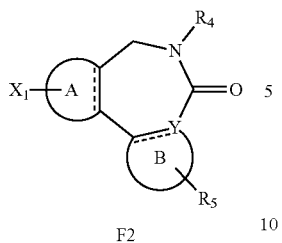

F2

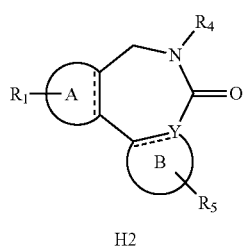

H2

B* = any boronic acid or ester
R = Methyl or ethyl or terbutyl
Y = C or N

In an alternative sequence, the same example F2 can be obtained starting from protected benzylic amine A3. C—C cross-coupling reaction with B2 can afford intermediate C3, which then undergoes protecting group removal and cyclization to provide example F2 (scheme 5). A cross-coupling reaction of example F2 with metallic species G (not illustrated in scheme 5) can be used to afford example H2 (in the same manner as shown in scheme 4).

Scheme 5

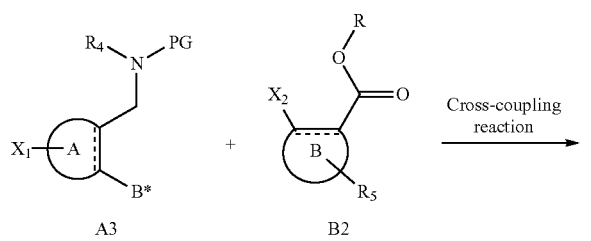

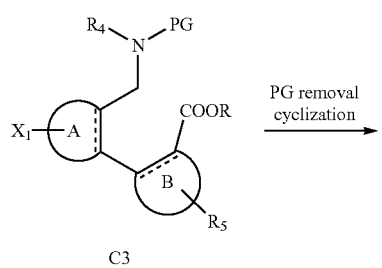

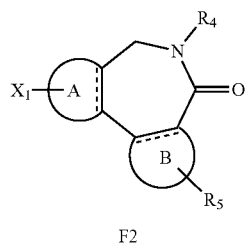

F2

B* = any boronic acid or ester
R = Methyl or ethyl
PG = protecting group

In addition to scheme 5, similar intermediates C3 and F2 can be obtained when N-protected benzylamine I1 is coupled to boronic acid or ester B1. This method was employed when R2 and/or R3 were different from hydrogen atom (scheme 6).

Scheme 6

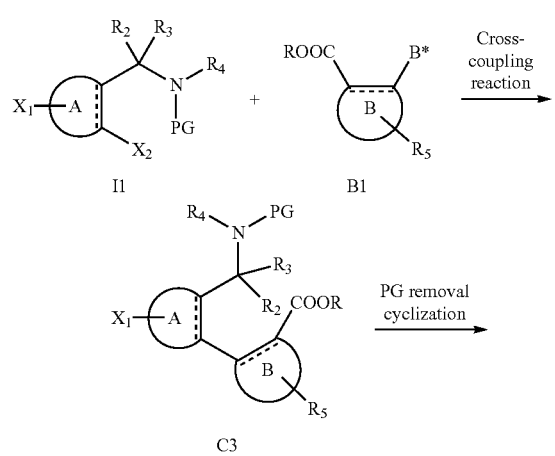

B* = any boronic acid or ester
R = Methyl or ethyl
PG = protecting group

Intermediate B3, heteroaromatic boronic acid or ester, bearing an N in meta position and substituted by an halogen X3 in orhto position can be coupled to benzylamine I1 to form intermediate C4. Then, halogen X3 can undergo nucleophilic or catalytic cyanation, followed by smooth nitrile hydrolysis to provide the intermediate amide D4.

Finally, protecting group removal with in situ cyclization can be realized to obtain intermediate F2 bearing an N in meta position (scheme 7).

Scheme 7

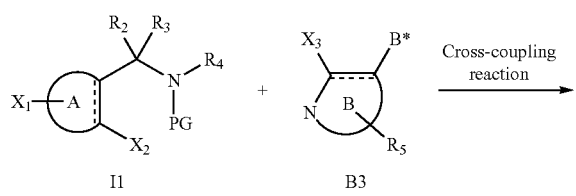

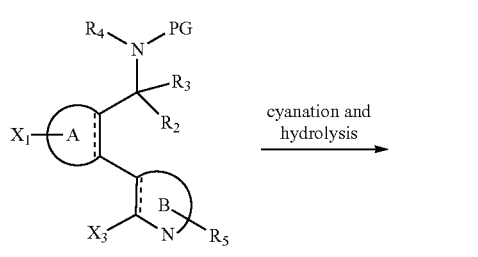

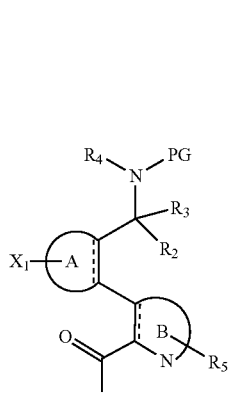

B* = any boronic acid or ester
PG = protecting group

When intermediate B3 did not bear any halogen X3 (X3=H), a cross-coupling reaction was realized to form intermediate C4 and the nitrogen atom was oxidized to provide the N-oxyde intermediate C4'. Then, nucleophilic cyanation followed by smooth nitrile hydrolysis can be realized to give intermediate D4 (scheme 8).

Scheme 8

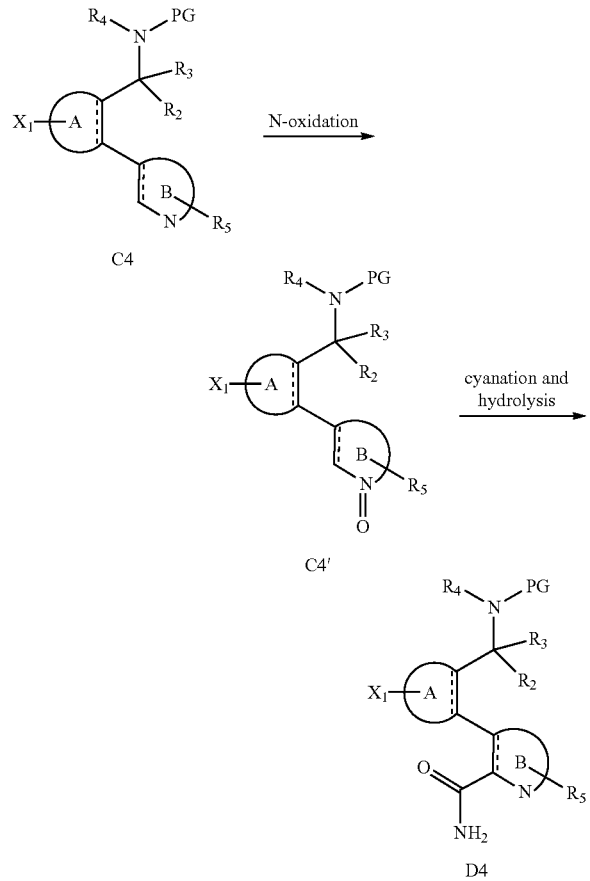

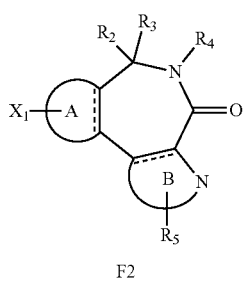

Other Z groups than Z=O can be introduced using methods known in the art. For example, Z=S can be introduced in a late stage by reacting example F or H with Lawesson's reagent, and Z=N(—$R_Z$) can be introduced from the Z=S using a corresponding primary amine $H_2N$—$R_Z$ and a desulfurization reagent such as mercury dioxide.

The following definitions apply throughout the present specification, unless specifically indicated otherwise.

As used herein, the term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_1$-$C_{10}$ alkyl" denotes an alkyl group having 1 to 10 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_1$-$C_6$ alkyl, more preferably to $C_1$-$C_4$ alkyl, even more preferably to methyl or ethyl, and most preferably to methyl.

As used herein, the term "alkenyl" refers to a monovalent unsaturated acyclic hydrocarbon group which may be linear or branched and comprises one or more (e.g., one, two or three) carbon-to-carbon double bonds while it does not comprise any carbon-to-carbon triple bond. The term "$C_2$-

$C_{10}$ alkenyl" denotes an alkenyl group having 2 to 10 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_2$-$C_6$ alkenyl, and more preferably to $C_2$-$C_4$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_2$-$C_{10}$ alkynyl" denotes an alkynyl group having 2 to 10 carbon atoms. Preferred exemplary alkynyl groups are ethynyl, propynyl (e.g., propargyl), or butynyl. Unless defined otherwise, the term "alkynyl" preferably refers to $C_2$-$C_6$ alkynyl, and more preferably to $C_2$-$C_4$ alkynyl.

As used herein, the term "alkylene" refers to an alkanediyl group, i.e. a divalent saturated acyclic hydrocarbon group which may be linear or branched. A "$C_1$-$C_{10}$ alkylene" denotes an alkylene group having 1 to 10 carbon atoms. Preferred exemplary alkylene groups are methylene (—$CH_2$—), ethylene (e.g., —$CH_2$—$CH_2$— or —CH(—$CH_3$)—), propylene (e.g., —$CH_2$—$CH_2$—$CH_2$—, —CH(—$CH_2$—$CH_3$)—, —$CH_2$—(—$CH_3$)—, or —CH(—$CH_3$)—$CH_2$—), or butylene (e.g., —$CH_2$—$CH_2$—$CH_2$—$CH_2$—). Unless defined otherwise, the term "alkylene" preferably refers to $C_1$-$C_6$ alkylene, more preferably to $C_1$-$C_4$ alkylene (including, in particular, linear $C_1$-$C_4$ alkylene), even more preferably to methylene or ethylene, and most preferably to methylene.

As used herein, the term "alkenylene" refers to an alkenediyl group, i.e. a divalent unsaturated acyclic hydrocarbon group which may be linear or branched and comprises one or more (e.g., one or two) carbon-to-carbon double bonds while it does not comprise any carbon-to-carbon triple bond. A "$C_2$-$C_{10}$ alkenylene" denotes an alkenylene group having 2 to 10 carbon atoms. Unless defined otherwise, the term "alkenylene" preferably refers to $C_2$-$C_6$ alkenylene, and more preferably to $C_2$-$C_4$ alkenylene (including, in particular, linear $C_1$-$C_4$ alkenylene).

As used herein, the term "alkynylene" refers to an alkynediyl group, i.e. a divalent unsaturated acyclic hydrocarbon group which may be linear or branched and comprises one or more (e.g., one or two) carbon-to-carbon triple bonds and optionally one or more carbon-to-carbon double bonds. A "$C_2$-$C_{10}$ alkynylene" denotes an alkynylene group having 2 to 10 carbon atoms. Unless defined otherwise, the term "alkynylene" preferably refers to $C_2$-$C_6$ alkynylene, and more preferably to $C_2$-$C_4$ alkynylene (including, in particular, linear $C_1$-$C_4$ alkynylene).

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_3$-$C_{11}$ cycloalkyl, and more preferably refers to a $C_3$-$C_7$ cycloalkyl. A particularly preferred "cycloalkyl" is a monocyclic saturated hydrocarbon ring having 3 to 7 ring members (e.g., cyclopropyl or cyclohexyl).

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_3$-$C_{11}$ cycloalkenyl, and more preferably refers to a $C_3$-$C_7$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from 0, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), pyranyl (e.g., 2H-pyranyl or 4H-pyranyl), thiopyranyl (e.g., 2H-thiopyranyl or 4H-thiopyranyl), octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —$CF_3$, —$CHF_2$, —$CH_2F$, —$CF_2$—$CH_3$, —$CH_2$—$CF_3$, —$CH_2$—$CHF_2$, —$CH_2$—$CF_2$—$CH_3$, —$CH_2$—$CF_2$—$CF_3$, or —$CH(CF_3)_2$. A particularly preferred "haloalkyl" group is —$CF_3$.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

A skilled person will appreciate that the substituent groups comprised in the compounds of formula (I) or (Ia) may be attached to the remainder of the respective compound via a number of different positions of the corresponding specific substituent group. Unless defined otherwise, the preferred attachment positions for the various specific substituent groups are as illustrated in the examples.

As used herein, the term "about" preferably refers to ±10% of the indicated numerical value, more preferably to ±5% of the indicated numerical value, and in particular to the exact numerical value indicated.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

In the following, where reference is made to the compounds of the general formula (I), this is intended to refer to the compounds of formula (I) according to the first and/or the second aspect of the invention. Likewise, any reference to the compounds of formula (Ia) is intended to refer to the compounds of formula (Ia) according to the first and/or the second aspect of the invention.

Compounds of the general formula (I) or (Ia) may exist in the form of different isomers, in particular stereoisomers (including geometric isomers (or cis-trans isomers), enantiomers, atropisomers and diastereomers) or tautomers. All such isomers of the compounds according to the invention are contemplated as being part of the present invention, either in admixture or in pure or substantially pure form. As for stereoisomers, the invention embraces mixtures (such as racemic forms) and the isolated optical isomers of the compounds according to the invention. The racemic forms can be resolved by physical methods, such as, e.g., fractional crystallization, separation or crystallization of diastereomeric derivatives or separation by chiral column chromatography.

The scope of the invention also embraces compounds of the general formula (I) or (Ia), in which one or more atoms are replaced by a specific isotope of the corresponding atom. For example, the invention encompasses compounds of formula (I) or (Ia), in which one or more hydrogen atoms (or, e.g., all hydrogen atoms) are replaced by deuterium atoms (i.e., $^2H$; also referred to as "D"). Accordingly, the invention also embraces compounds of formula (I) or (Ia) which are enriched in deuterium. Naturally occurring hydrogen is an isotopic mixture comprising about 99.98 mol-% hydrogen-1 ($^1H$) and about 0.0156 mol-% deuterium ($^2H$ or D). The content of deuterium in one or more hydrogen positions in the compounds of formula (I) or (Ia) can be increased using deuteration techniques known in the art. For example, a compound of formula (I) or (Ia) or a reactant or precursor to be used in the synthesis of the compound of formula (I) or (Ia) can be subjected to an H/D exchange reaction using, e.g., heavy water ($D_2O$). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) or (Ia) is not enriched in deuterium. Accordingly, the presence of naturally occurring hydrogen atoms or $^1H$ hydrogen atoms in the compounds of formula (I) or (Ia) is preferred. The present invention also embraces compounds of formula (I) or (Ia), in which one or more atoms are replaced by a positron-emitting isotope of the corresponding atom, such as, e.g., $^{18}F$, $^{11}C$, $^{13}N$, $^{15}O$, $^{76}Br$, $^{77}Br$, $^{120}I$ and/or $^{124}I$. Such compounds can be used as tracers or imaging probes in positron emission tomography (PET). The invention thus includes (i) compounds of formula (I) or (Ia), in which one or more fluorine atoms (or, e.g., all fluorine atoms) are replaced by $^{18}F$ atoms, (ii) compounds of formula (I) or (Ia), in which one or more carbon atoms (or, e.g., all carbon atoms) are replaced by $^{11}C$ atoms, (iii) compounds of formula (I) or (Ia), in which one or more nitrogen atoms (or, e.g., all nitrogen atoms) are replaced by $^{13}N$ atoms, (iv) compounds of formula (I) or (Ia), in which one or more oxygen atoms (or, e.g., all oxygen atoms) are replaced by $^{15}O$ atoms, (v) compounds of formula (I) or (Ia), in which one or more bromine atoms (or, e.g., all bromine atoms) are replaced by $^{76}Br$ atoms, (vi) compounds of formula (I) or (Ia), in which one or more bromine atoms (or, e.g., all bromine atoms) are replaced by $^{77}Br$ atoms, (vii) compounds of formula (I) or (Ia), in which one or more iodine atoms (or, e.g., all iodine atoms) are replaced by $^{120}I$ atoms, and (viii) compounds of formula (I) or (Ia), in which one or more iodine atoms (or, e.g., all iodine atoms) are replaced by $^{124}I$ atoms. In general, it is preferred that none of the atoms in the compounds of formula (I) or (Ia) are replaced by specific isotopes.

The scope of the invention embraces all pharmaceutically acceptable salt forms of the compounds of the general formula (I) or (Ia) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts. A preferred pharmaceutically acceptable salt of the compound of formula (I) or (Ia) is a hydrochloride salt.

Moreover, the scope of the invention embraces solid forms of the compounds of the general formula (I) or (Ia) in any solvated form, including e.g. solvates with water, for example hydrates, or with organic solvents such as, e.g., methanol, ethanol or acetonitrile, i.e. as a methanolate, ethanolate or acetonitrilate, respectively; or in any crystalline form (i.e., as any polymorph), or in amorphous form. It is to be understood that such solvates of the compounds of the formula (I) or (Ia) also include solvates of pharmaceutically acceptable salts of the compounds of the formula (I) or (Ia).

Pharmaceutically acceptable prodrugs of compounds of the general formula (I) or (Ia) are derivatives which have chemically or metabolically cleavable groups and become, by solvolysis or under physiological conditions, the compounds of formula (I) or (Ia) which are pharmaceutically active in vivo. Prodrugs of compounds of formula (I) or (Ia) may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the general formula (I) or (Ia) has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester. When a compound of formula (I) or (Ia) has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. When a compound of formula (I) or (Ia) has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds of general formula (I) or (Ia) or pharmaceutically acceptable salts, solvates or prodrugs thereof, may be administered as compounds per se or may be formulated as medicaments. Within the scope of the present invention are pharmaceutical compositions comprising as an active ingredient one or more compounds of the general formula (I) or (Ia), or pharmaceutically acceptable salts, solvates or prodrugs thereof. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions may also comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of the general formula (I) or (Ia) or pharmaceutically acceptable salts, solvates or prodrugs thereof, or the above described pharmaceutical compositions, may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. It is preferred that the compound of formula (I) or (Ia) or the corresponding pharmaceutical composition is to be administered orally (particularly via peroral ingestion or swallowing).

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; Japanese Pat. Appl. 83-118008; U.S. Pat. Nos. 4,485,045 and 4,544,545; and EP0102324.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the general formula (I) or (Ia) for administration, particularly for oral administration, to a human (of approximately 70 kg body weight) may be 0.05 to 2000 mg, preferably 0.1 mg to 1000 mg, of the active ingredient per unit dose. The unit dose may be administered, for example, 1 to 4 times per day. The unit dose may also be administered 1 to 7 times per week, e.g., with not more than one administration per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The compound of formula (I) or (Ia) or a corresponding pharmaceutical composition according to the invention can be administered in monotherapy (e.g., without concomitantly administering any further therapeutic agents, or without concomitantly administering any further therapeutic agents against the same disease that is to be treated or prevented with the compound of formula (I) or (Ia)). However, the compound of formula (I) or (Ia) or the pharmaceutical composition comprising the respective compound can also be administered in combination with one or more further therapeutic agents. If the compound of formula (I) or (Ia) is used in combination with a second therapeutic agent active against the same disease or condition, the dose of each compound may differ from that when the corresponding compound is used alone, in particular, a lower dose of each compound may be used. The combination of the compound of formula (I) or (Ia) with one or more further therapeutic agents may comprise the simultaneous/concomitant administration of the compound of formula (I) or (Ia) and the further therapeutic agent(s) (either in a single pharmaceutical formulation or in separate pharmaceutical formulations), or the sequential/separate administration of the compound of formula (I) or (Ia) and the further therapeutic agent(s). If administration is sequential, either the compound of formula (I) or (Ia) according to the invention or the one or more further therapeutic agents may be administered first. If administration is simultaneous, the one or more further therapeutic agents may be included in the same pharmaceutical formulation as the compound of formula (I) or (Ia), or they may be administered in one or more different (separate) pharmaceutical formulations.

For the treatment or prophylaxis of Parkinson's disease, the compound of formula (I) or (Ia) or a pharmaceutical composition comprising the compound of formula (I) or (Ia) can also be administered in combination with one or more further antiparkinson agents. Such further antiparkinson agents may, for example, be selected from levodopa, melevodopa, etilevodopa, droxidopa, aplindore, apomorphine, bromocriptine, cabergoline, ciladopa, dihydroergocryptine, lisuride, pardoprunox, pergolide, piribedil, pramipexole, ropinirole, rotigotine, ladostigil, lazabemide, mofegiline, pargyline, rasagiline, selegiline, entacapone, nitecapone, tolcapone, benserazide, carbidopa, methyldopa, benzatropine, biperiden, bornaprine, chlorphenoxamine, cycrimine, dexetimide, dimenhydrinate, diphenhydramine, etanautine, etybenzatropine, mazaticol, metixene, orphenadrine, phenglutarimide, piroheptine, procyclidine, profenamine, trihexyphenidyl, tropatepine, amantadine, budipine, memantine, methylxanthines, rimantadine, UWA-101, and pharmaceutically acceptable salts and solvates of any of these agents.

The present invention thus relates to a compound of formula (I) or (Ia) or a pharmaceutically acceptable salt, solvate, or prodrug thereof, or a pharmaceutical composition comprising any of the aforementioned entities in combination with a pharmaceutically acceptable excipient, for use in the treatment or prevention of Parkinson's disease, wherein the compound or the pharmaceutical composition is to be administered in combination with one or more further antiparkinson agents (e.g., one or more of the specific antiparkinson agents described above). The combined administration of the compound or the pharmaceutical composition of the present invention with one or more further antiparkinson agents may be effected, e.g., by simultaneous/concomitant administration (either in a single pharmaceutical formulation or in separate pharmaceutical formulations) or by sequential/separate administration.

The subject or patient, such as the subject in need of treatment or prophylaxis, may be an animal (e.g., a non-human animal), a vertebrate animal, a mammal (e.g., a non-human mammal), a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig). Most preferably, the subject/patient is a human.

The term "treatment" of a condition, disorder or disease as used herein is well known in the art. "Treatment" of a condition, disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

The treatment of a condition, disorder or disease may, for example, lead to a halt in the progression of the condition, disorder or disease (e.g. no deterioration of symptoms) or a delay in the progression of the disorder or disease (in case the halt in progression is of a transient nature only). Treatment may also lead to a partial response (e.g. amelioration of symptoms) or complete response (e.g. disappearance of symptoms) of the subject/patient suffering from the condition, disorder or disease. Amelioration of a condition, disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g. the exemplary responses as described herein above).

Treatment of a condition, disorder or disease may, inter alia, comprise curative treatment (preferably leading to a complete response and eventually to healing of the disorder or disease) and palliative treatment (including symptomatic relief).

Also the term "prophylaxis" or "prevention" of a condition, disorder or disease as used herein is well known in the art. For example, a patient/subject suspected of being prone to suffer from a condition, disorder or disease as defined herein may, in particular, benefit from a prophylaxis of the disorder or disease. Said subject/patient may have a susceptibility or predisposition for a condition, disorder or disease, including but not limited to hereditary predisposition. Such a predisposition can be determined by standard assays, using, for example, genetic markers or phenotypic indicators. It is to be understood that a condition, disorder or disease to be prevented in accordance with the present invention has not been diagnosed or cannot be diagnosed in said patient/subject (for example, said patient/subject does not show any clinical or pathological symptoms). Thus, the term "prophylaxis" comprises the use of compounds of the present invention before any clinical and/or pathological symptoms are diagnosed or determined or can be diagnosed or determined by the attending physician. The terms "prophylaxis" and "prevention" are used herein interchangeably.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in the general formula (I) or (Ia).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention particularly relates to the following items:

1. A compound of the general formula (Ia):

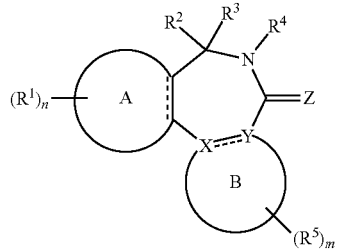

(Ia)

wherein:
A is aryl or heteroaryl;
B is an aryl or heteroaryl group;
X and Y are each independently N or C;
Z is O, S or N(—$R^Z$);
each ==== is independently a single bond or a double bond, wherein the bond ==== between X and Y is a single bond if one or both of X and Y is/are N;
$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —N($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;
each $R^1$ is independently a group -$L^1$-$R^{11}$;
each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}$, and —$NR^{12}R^{12}$, and —$NR^{12}SO_2R^{12}$, and further wherein one or more —$CH_2$— units comprised in said alkylene, said alkenylene or said alkynylene are each optionally replaced by a group independently selected from —O—, —$NR^{12}$—, —CO—, —S—, —SO—, and —$SO_2$—;
each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{12}R^{12}$, —$OR^{12}$, —$SR^{12}$, —$SOR^{12}$, —$SO_2R^{12}$, —$COR^{12}$, —$COOR^{12}$, —$OCOR^{12}$, —$CONR^{12}$, —$NR^{12}COR^{12}$, —$SO_2NR^{12}R^{12}$, —$NR^{12}SO_2R^{12}$, and —$SO_3R_2$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{11}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{11}R^{13}$;

each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene;

each $L^{11}$ is independently selected from a bond, $C_1$-$C_{10}$ alkylene, $C_{2-10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—;

each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_{2-10}$ alkynyl, —OH, —O($C_1$-$C_{10}$ alkyl), —SH, —S($C_1$-$C_{10}$ alkyl), —SO—($C_1$-$C_{10}$ alkyl), —SO$_2$—($C_1$-$C_{10}$ alkyl), —CON, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkyene)-O($C_1$-$C_{10}$ alkyl), —NH$_2$, —N($C_1$-$C_{10}$ alkyl), —N($C_1$-$C_{10}$ alkyl)($C_1$-$C_{10}$ alkyl), cycloalkyl, and heterocycloalkyl, and further wherein, if one or both of $R^2$ and $R^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$—$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; or $R^2$ and $R^3$ together form a divalent group selected from =O, =S, =NH and =N($C_1$-$C_{10}$ alkyl);

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each $R^5$ is independently a group -$L^5$-$R^{51}$;

each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—;

each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-

$C_{10}$ alkyl), $-SO_2-N(C_1-C_{10}$ alkyl)($C_1-C_{10}$ alkyl), $-NH-SO_2-(C_1-C_{10}$ alkyl), $-N(C_1-C_{10}$ alkyl)-$SO_2-(C_1-C_{10}$alkyl), cycloalkyl, heterocycloalkyl, aryl, heteroaryl, and $-L^5-R^{53}$, and further wherein, if $R^{51}$ is $C_1-C_{10}$ alkyl, $C_2-C_{10}$ alkenyl or $C_2-C_{10}$ alkynyl, then said alkyl, said alkenyl or said alkynyl is optionally substituted with one or more groups independently selected from halogen, $C_1-C_{10}$ haloalkyl, $-CN$, $-OH$, $-O(C_1-C_{10}$ alkyl), $-NH_2$, $-NH(C_1-C_{10}$ alkyl), $-N(C_1-C_{10}$ alkyl)($C_1-C_{10}$ alkyl), $-CHO$, $-CO(C_1-C_{10}$ alkyl), $-COOH$, tetrazolyl, $-COO(C_1-C_{10}$ alkyl), $-OCO(C_1-C_{10}$ alkyl), $-CO-NH_2$, $-CO-NH(C_1-C_{10}$ alkyl), $-CO-N(C_1-C_{10}$ alkyl)($C_1-C_{10}$ alkyl), $-NH-CO-(C_1-C_{10}$ alkyl), $-N(C_1-C_{10}$ alkyl)-$CO-(C_1-C_{10}$ alkyl), $-SO_2-NH_2$, $-SO_2-NH(C_1-C_{10}$ alkyl), $-SO_2-N(C_1-C_{10}$ alkyl)($C_1-C_{10}$ alkyl), $-NH-SO_2-(C_1-C_{10}$ alkyl), $-N(C_1-C_{10}$ alkyl)-$SO_2-(C_1-C_{10}$ alkyl), cycloalkyl, heterocycloalkyl, aryl, heteroaryl, and $-L^{51}-R^{53}$;

each $R^{52}$ is independently selected from hydrogen, $C_1-C_{10}$ alkyl, $C_2-C_{10}$ alkenyl, $C_2-C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1-C_{10}$ alkyl, $C_2-C_{10}$ alkenyl, $C_2-C_{10}$ alkynyl, halogen, $C_1-C_{10}$ haloalkyl, $-CN$, $-OH$, $-O(C_1-C_{10}$ alkyl), $-(C_1-C_{10}$ alkylene)-OH, $-(C_1-C_{10}$ alkylene)-O($C_1-C_{10}$ alkyl), $-NH_2$, $-NH(C_1-C_{10}$ alkyl), $-N(C_1-C_{10}$ alkyl)($C_1-C_{10}$ alkyl), cycloalkyl, and heterocycloalkyl, wherein if $R^{52}$ is $C_1-C_{10}$ alkyl, $C_2-C_{10}$ alkenyl or $C_2-C_{10}$ alkynyl, then said alkyl, said alkenyl or said alkynyl is optionally substituted with one or more groups independently selected from halogen, $C_1-C_{10}$ haloalkyl, $-CN$, $-OH$, $-O(C_1-C_{10}$ alkyl), $-NH_2$, $-NH(C_1-C_{10}$ alkyl), $-N(C_1-C_{10}$ alkyl)($C_1-C_{10}$ alkyl), cycloalkyl, and heterocycloalkyl, and further if two groups $R^{52}$ are attached to the same nitrogen atom, then these two groups $R^{52}$ may also together form a $C_2-C_8$ alkylene;

each $L^{51}$ is independently selected from a bond, $C_1-C_{10}$ alkylene, $C_2-C_{10}$ alkenylene, and $C_2-C_{10}$ alkynylene, wherein one or more $-CH_2-$ units comprised in said alkylene, said alkenylene or said alkynylene are each optionally replaced by a group independently selected from $-O-$, $-NH-$, $-N(C_1-C_{10}$ alkyl)-, $-CO-$, $-S-$, $-SO-$, and $-SO_2-$;

each $R^{53}$ is independently selected from aryl, heteroaryl, cycloalkyl, heterocycloalkyl, cycloalkenyl, heterocycloalkenyl, halogen, $C_1-C_{10}$ haloalkyl, $-CN$, $C_1-C_{10}$ alkyl, $C_2-C_{10}$ alkenyl, $C_2-C_{10}$ alkynyl, $-NH_2$, $-NH(C_1-C_{10}$ alkyl), $-N(C_1-C_{10}$ alkyl)($C_1-C_{10}$ alkyl), $-OH$, $-O(C_1-C_{10}$ alkyl), $-(C_1-C_{10}$ alkylene)-OH, $-(C_1-C_{10}$ alkylene)-O($C_1-C_{10}$ alkyl), $-SH$, and $-S(C_1-C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1-C_{10}$ haloalkyl, $-CN$, $C_1-C_{10}$ alkyl, $C_2-C_{10}$ alkenyl, $C_2-C_{10}$ alkynyl, $-OH$, $-O(C_1-C_{10}$ alkyl), $-(C_1-C_{10}$ alkylene)-OH, $-(C_1-C_{10}$ alkylene)-O($C_1-C_{10}$ alkyl), $-NH_2$, $-NH(C_1-C_{10}$ alkyl), $-N(C_1-C_{10}$ alkyl)($C_1-C_{10}$ alkyl), cycloalkyl, and heterocycloalkyl; and m is an integer of 0 to 3;

provided that, if A is phenyl, X is N, Y is C, the bond ==== between X and Y is a single bond, and B is a heteroaryl group, then said heteroaryl group is not a 5-membered monocyclic heteroaryl group consisting of carbon and nitrogen ring atoms;

and further provided that, if A is phenyl, $R^2$ and $R^3$ are each hydrogen, $R^4$ is methyl, Z is O, X and Y are each C, the bond ==== between X and Y is a double bond, m is 1, $L^5$ is different from a bond, and $R^{51}$ is an optionally substituted aryl or an optionally substituted heteroaryl, then B is not a thiazolyl group;

or a pharmaceutically acceptable salt, solvate or prodrug thereof;

for use in the treatment and/or prevention of a condition associated with altered glutamatergic signalling and/or functions, and/or a condition which can be affected by alteration of glutamate level or signalling;

wherein the condition to be treated or prevented is selected from: epilepsy; dementias; parkinsonism and movement disorders; motor neuron disease; amyotrophic lateral sclerosis; neurodegenerative and/or hereditary disorders of the nervous system; disorders of the peripheral nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; acute and chronic pain; nausea and vomiting; and irritable bowel syndrome.

2. A compound of formula (Ia) as defined in item 1 or a pharmaceutically acceptable salt, solvate or prodrug thereof, for use in the treatment and/or prophylaxis of Parkinson's disease.

3. A compound of formula (Ia) as defined in item 1 or a pharmaceutically acceptable salt, solvate or prodrug thereof; wherein $R^2$ and $R^3$ are mutually linked to form, together with the carbon atom that they are attached to, a cycloalkyl or a heterocycloalkyl.

4. The compound of item 3 for use as a medicament.

5. A compound of formula (Ia) as defined in item 1 or a pharmaceutically acceptable salt, solvate or prodrug thereof; wherein A is heteroaryl, said heteroaryl being different from pyrimidinyl and from 1,3-benzodioxolyl; for use as a medicament.

6. A compound of formula (Ia) as defined in item 5 or a pharmaceutically acceptable salt, solvate or prodrug thereof, wherein the following compounds are excluded from formula (Ia):

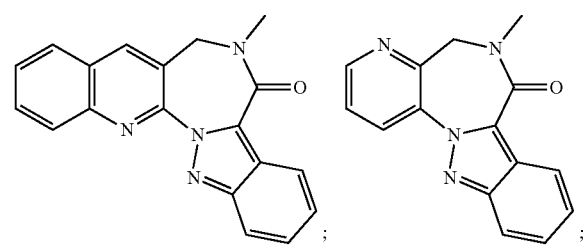

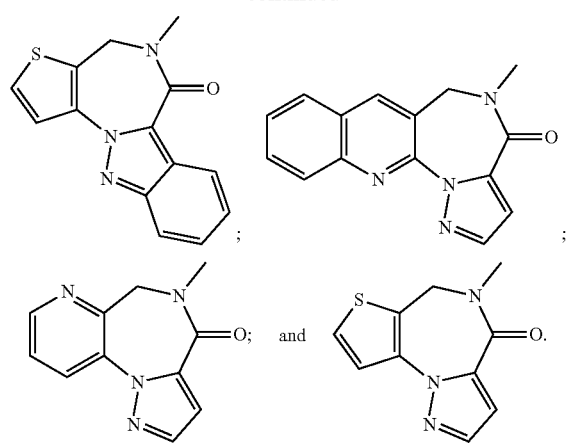

7. A compound of formula (Ia) as defined in item 1 or a pharmaceutically acceptable salt, solvate or prodrug thereof; wherein B is a heteroaryl group, said heteroaryl group being different from indolyl and from 1,3-benzodioxolyl; for use as a medicament.

8. A compound of formula (Ia) as defined in item 7 or a pharmaceutically acceptable salt, solvate or prodrug thereof;

wherein, if A is phenyl, X and Y are each C, Z is O, $R^2$ and $R^3$ are each hydrogen, $R^4$ is methyl or tert-butyl, n is 0 or 1, $R^1$ (if present) is methyl, m is 0 or 1, and $R^5$ (if present) is methyl, then B is not pyridinyl;

and wherein, if A is phenyl, X and Y are each C, the bond ==== between X and Y is a double bond, Z is O, one of $R^2$ and $R^3$ is hydrogen and the other one of $R^2$ and $R^3$ is methyl, $R^4$ is isopropyl, and n is 0, then B is not quinolinyl or 1,4-dihydroquinolinyl; and further wherein the following compounds are excluded from formula (Ia):

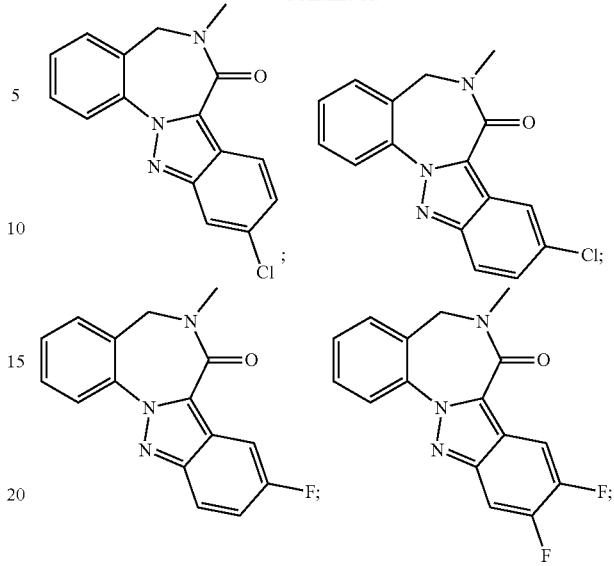

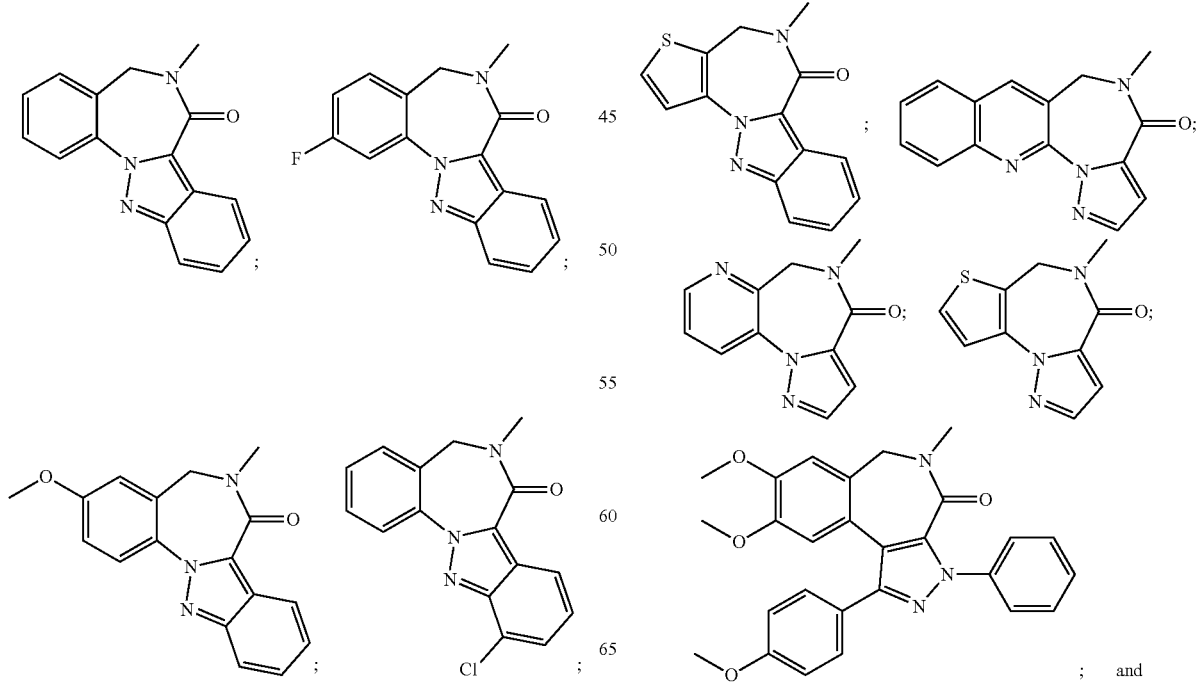

-continued

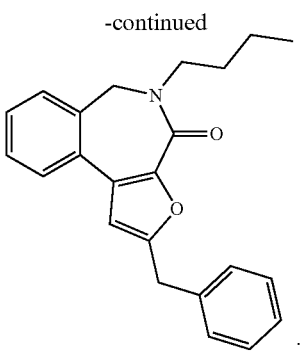

9. The compound for use according to any one of items 1, 2, 4 or 7 or the compound of item 3 or 8, wherein A is phenyl or a monocyclic 5- or 6-membered heteroaryl, wherein 1, 2 or 3 ring atoms of said 5-membered heteroaryl are nitrogen atoms and the remaining ring atoms are carbon atoms, and wherein 1, 2, 3 or 4 ring atoms of said 6-membered heteroaryl are nitrogen atoms and the remaining ring atoms are carbon atoms.

10. The compound for use according to any one of items 1, 2, 4 or 7 or the compound of item 3 or 8, wherein A is phenyl.

11. The compound for use according to any one of items 1, 2, 4, 5 or 7 or the compound of any one of items 3, 6 or 8, wherein A is a monocyclic 5- or 6-membered heteroaryl, wherein 1, 2 or 3 ring atoms of said 5-membered heteroaryl are nitrogen atoms and the remaining ring atoms are carbon atoms, and wherein 1, 2, 3 or 4 ring atoms of said 6-membered heteroaryl are nitrogen atoms and the remaining ring atoms are carbon atoms.

12. The compound for use according to any one of items 1, 2, 4 or 5 or any one of their dependent items 9 to 11 or the compound of item 3 or 6 or any one of their dependent items 9 to 11, wherein B is phenyl or a monocyclic 5- or 6-membered heteroaryl.

13. The compound for use according to any one of items 1, 2, 4, 5 or 7 or any one of their dependent items 9 to 11 or the compound of item 3, 6 or 8 or any one of their dependent items 9 to 11, wherein B is a monocyclic 5- or 6-membered heteroaryl.

14. The compound for use according to any one of items 1, 2, 4, 5, 7 or 9 to 13 or the compound of any one of items 3, 6 or 8 to 13, wherein X and Y are each C.

15. The compound for use according to any one of items 1, 2, 4, 5, 7 or 9 to 14 or the compound of any one of items 3, 6 or 8 to 14, wherein Z is O.

16. The compound for use according to any one of items 1, 2, 4, 5, 7 or 9 to 15 or the compound of any one of items 3, 6 or 8 to 15, wherein each $L^1$ is independently selected from a bond and $C_1$-$C_{10}$ alkylene, wherein said alkylene is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—.

17. The compound for use according to any one of items 1, 2, 4, 5, 7 or 9 to 16 or the compound of any one of items 3, 6 or 8 to 16, wherein each $R^{11}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —NH$_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl, and further wherein, if $R^{11}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl.

18. The compound for use according to any one of items 1, 2, 4, 5, 7 or 9 to 17 or the compound of any one of items 3, 6 or 8 to 17, wherein n is 1 or 2.

19. The compound for use according to any one of items 1, 2, 5 or 7 or any one of their dependent items 9 to 18 or the compound of item 6 or 8 or any one of their dependent items 9 to 18, wherein $R^2$ and $R^3$ are mutually linked to form, together with the carbon atom that they are attached to, a $C_3$-$C_5$ cycloalkyl, or $R^2$ and $R^3$ are each independently selected from hydrogen, halogen, $C_1$-$C_4$ alkyl, —OH, and —O($C_1$-$C_4$ alkyl).

20. The compound for use according to any one of items 1, 2, 4, 5, 7 or 9 to 18 or the compound of any one of items 3, 6 or 8 to 18, wherein $R^2$ and $R^3$ are mutually linked to form, together with the carbon atom that they are attached to, a $C_3$-$C_5$ cycloalkyl.

21. The compound for use according to item 20 or the compound of item 20, wherein $R^2$ and $R^3$ are mutually linked to form, together with the carbon atom that they are attached to, a cyclopropyl.

22. The compound for use according to any one of items 1, 2, 5 or 7 or any one of their dependent items 9 to 19 or the compound of item 6 or 8 or any one of their dependent items 9 to 19, wherein $R^2$ and $R^3$ are each hydrogen.

23. The compound for use according to any one of items 1, 2, 4, 5, 7 or 9 to 22 or the compound of any one of items 3, 6 or 8 to 22, wherein $R^4$ is $C_1$-$C_4$ alkyl, wherein said alkyl is optionally substituted with one or more groups independently selected from halogen, $C_1$-$C_4$ haloalkyl, —O—($C_1$-$C_4$ haloalkyl), —CN, —OH and —O($C_1$-$C_4$ alkyl).

24. The compound for use according to item 23 or the compound of item 23, wherein $R^4$ is methyl.

25. The compound for use according to any one of items 1, 2, 4, 5, 7 or 9 to 24 or the compound of any one of items 3, 6 or 8 to 24, wherein each $L^5$ is independently selected from a bond and $C_1$-$C_{10}$ alkylene, wherein said alkylene is optionally substituted with one or more groups independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —$CH_2$— units comprised in said alkylene is/are each optionally replaced by a group independently selected from —O—, —NH—, —N($C_1$-$C_4$ alkyl)-, —CO—, and —$SO_2$—.

26. The compound for use according to any one of items 1, 2, 4, 5, 7 or 9 to 25 or the compound of any one of items 3, 6 or 8 to 25, wherein each $R^{51}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl, and further wherein, if $R^{51}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl.

27. The compound for use according to any one of items 1, 2, 4, 5, 7 or 9 to 24 or the compound of any one of items 3, 6 or 8 to 24, wherein m is 0.

28. The compound for use according to item 1 or 2, wherein said compound is selected from:

2'-Chloro-6'-methylspiro[cyclopropane-1,5'-pyrido[3,4-f]pyrrolo[1,2-a][1,4]diazepin]-7'(6'H)-one;
2',9'-Dichloro-6'-methylspiro[cyclopropane-1,5'-pyrido[3,4-f]pyrrolo[1,2-a][1,4]diazepin]-7'(6'H)-one;
2'-(2-Methyl-pyridin-3-yl)-6'-methylspiro[cyclopropane-1,5'-pyrido[3,4-f]pyrrolo[1,2-a][1,4]diazepin]-7'(6'H)-one;
9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;
9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;
5-Methyl-9-(2-methyl-pyridin-3-yl)-5,6-dihydro-5,7,10b-triaza-benzo[e]azulen-4-one;
5-Methyl-9-(2-methyl-pyridin-3-yl)-5,6-dihydro-5,7,10,10b-tetraaza-benzo[e]azulen-4-one;
5-Methyl-9-(2-methyl-pyridin-3-yl)-5,6-dihydro-5,7,8,10b-tetraaza-benzo[e]azulen-4-one;
9-Chloro-5-methyl-5,6-dihydro-5,10,10b-triaza-benzo[e]azulen-4-one;
5-Methyl-9-(2-methyl-pyridin-3-yl)-5,6-dihydro-5,10,10b-triaza-benzo[e]azulen-4-one;
3-(5-Methyl-4-oxo-5,6-dihydro-4H-5,7,10b-triaza-benzo[e]azulen-9-yl)-benzonitrile;
9-imidazo[1,2-a]pyridin-6-yl-5-methyl-5,6-dihydro-5,7,10b-triaza-benzo[e]azulen-4-one;
9-Chloro-5-methyl-5,6-dihydro-5,8,10,10b-tetraaza-benzo[e]azulen-4-one;
5-Methyl-9-(2-methyl-pyridin-3-yl)-5,6-dihydro-5,8,10,10b-tetraaza-benzo[e]azulen-4-one;
10-Chloro-6-methyl-6,7-dihydro-spiro[dibenzo[c,e]azepine-7,1'-cyclopropan]-5-one;
10-Bromo-3-chloro-6-methyl-6,7-dihydro-spiro[dibenzo[c,e]azepine-7,1'-cyclopropan]-5-one;
10-(2-Methyl-pyridin-3-yl)-6-methyl-6,7-dihydro-spiro[dibenzo[c,e]azepine-7,1'-cyclopropan]-5-one;
3-Chloro-10-(2-methyl-pyridin-3-yl)-6-methyl-6,7-dihydro-spiro[dibenzo[c,e]azepine-7,1'-cyclopropan]-5-one;
3-(2-Methyl-2H-pyrazol-3-yl)-10-(2-methyl-pyridin-3-yl)-6-methyl-6,7-dihydro-spiro[dibenzo[c,e]azepine-7,1'-cyclopropan]-5-one;
10-Chloro-6-methyl-6,7-dihydro-4,6-diaza-dibenzo[a,c]cyclohepten-5-one;
3-(6-Methyl-5-oxo-6,7-dihydro-5H-4,6-diaza-dibenzo[a,c]cyclohepten-10-yl)-benzonitrile;
6-Methyl-10-(2-methy-pyridin-3-yl)-6,7-dihydro-4,6-diaza-dibenzo[a,c]cyclohepten-5-one;
10-(6-Fluoro-pyridin-3-yl)-6-methyl-6,7-dihydro-4,6-diaza-dibenzo[a,c]cyclohepten-5-one;
10-(5-Fluoro-pyridin-2-yl)-6-methyl-6,7-dihydro-4,6-diaza-dibenzo[a,c]cyclohepten-5-one;
10-Chloro-3-fluoro-6-methyl-6,7-dihydro-4,6-diaza-dibenzo[a,c]cyclohepten-5-one;
3-Fluoro-6-methyl-10-(2-methyl-pyridin-3-yl)-6,7-dihydro-4,6-diaza-dibenzo[a,c]cyclohepten-5-one;
3-Fluoro-10-(6-fluoro-pyridin-3-yl)-6-methyl-6,7-dihydro-4,6-diaza-dibenzo[a,c]cyclohepten-5-one;
3-Fluoro-10-(5-fluoro-pyridin-2-yl)-6-methyl-6,7-dihydro-4,6-diaza-dibenzo[a,c]cyclohepten-5-one;
10-Chloro-3-methoxy-6-methyl-6,7-dihydro-4,6-diaza-dibenzo[a,c]cyclohepten-5-one;
10-(5-fluoro-pyridin-2-yl)-3-methoxy-6-methyl-6,7-dihydro-4,6-diaza-dibenzo[a,c]cyclohepten-5-one;
10-(6-Fluoro-pyridin-3-yl)-3-methoxy-6-methyl-6,7-dihydro-4,6-diaza-dibenzo[a,c]cyclohepten-5-one;
3-Methoxy-6-methyl-10-(2-methyl-pyridin-3-yl)-6,7-dihydro-4,6-diaza-dibenzo[a,c]cyclohepten-5-one;
3-Hydroxy-6-methyl-10-(2-methyl-pyridin-3-yl)-6,7-dihydro-4,6-diaza-dibenzo[a,c]cyclohepten-5-one;
10-Chloro-3,6-dimethyl-6,7-dihydro-4,6-diaza-dibenzo[a,c]cyclohepten-5-one;
10-(6-Fluoro-pyridin-3-yl)-3,6-di methyl-6,7-dihydro-4,6-diaza-dibenzo[a,c]cyclohepten-5-one;
10-(5-Fluoro-pyridin-2-yl)-3,6-dimethyl-6,7-dihydro-4,6-diaza-dibenzo[a,c]cyclohepten-5-one;
3,6-Dimethyl-10-(2-methyl-pyridin-3-yl)-6,7-dihydro-4,6-diaza-dibenzo[a,c]cyclohepten-5-one;
10-Chloro-2,6-dimethyl-6,7-dihydro-4,6-diaza-dibenzo[a,c]cyclohepten-5-one;
2,6-Dimethyl-10-(2-methyl-pyridin-3-yl)-6,7-dihydro-4,6-diaza-dibenzo[a,c]cyclohepten-5-one;
10-(6-Fluoro-pyridin-3-yl)-2,6-dimethyl-6,7-dihydro-4,6-diaza-dibenzo[a,c]cyclohepten-5-one;

10-Chloro-2-fluoro-6-methyl-6,7-dihydro-4,6-diaza-dibenzo[a,c]cyclohepten-5-one;
2-Fluoro-6-methyl-10-(2-methyl-pyridin-3-yl)-6,7-dihydro-4,6-diaza-dibenzo[a,c]cyclohepten-5-one;
2-Fluoro-10-(6-fluoro-pyridin-3-yl)-6-methyl-6,7-dihydro-4,6-diaza-dibenzo[a,c]cyclohepten-5-one;
2-Methoxy-6-methyl-10-(2-methyl-pyridin-3-yl)-6,7-dihydro-4,6-diaza-dibenzo[a,c]cyclohepten-5-one;
10-Chloro-6-methylspiro[benzo[c]pyrido[3,2-e]azepine-7,1'-cyclopropan]-5(6H)-one;
10-(6-Fluoro-pyridin-3-yl)-6-methylspiro[benzo[c]pyrido[3,2-e]azepine-7,1'-cyclopropan]-5(6H)-one;
10-(5-Fluoro-pyridin-2-yl)-6-methylspiro[benzo[c]pyrido[3,2-e]azepine-7,1'-cyclopropan]-5(6H)-one;
10-chloro-3-methoxy-6-methylspiro[benzo[c]pyrido[3,2-e]azepine-7,1'-cyclopropan]-5(6H)-one;
10-(6-Fluoro-pyridin-3-yl)-3-methoxy-6-methylspiro[benzo[c]pyrido[3,2-e]azepine-7,1'-cyclopropan]-5(6H)-one;
9-Chloro-5-methyl-5,6-dihydro-3-thia-5-aza-benzo[e]azulen-4-one;
5-Methyl-9-(2-methyl-pyridin-3-yl)-5,6-dihydro-3-thia-5-aza-benzo[e]azulen-4-one;
3-(5-Methyl-4-oxo-5,6-dihydro-4H-3-thia-5-aza-benzo[e]azulen-9-yl)-benzonitrile;
5-Methyl-9-(2-methyl-pyridin-3-yl)-5,6-dihydro-2H-2,3,5-triaza-benzo[e]azulen-4-one;
9-Chloro-5-methyl-5,6-dihydro-3H-3,5-diaza-benzo[e]azulen-4-one;
5-Methyl-9-(2-methyl-pyridin-3-yl)-5,6-dihydro-3H-3,5-diaza-benzo[e]azulen-4-one;
6-Methyl-10-(2-methyl-pyridin-3-yl)-6,7-dihydro-1,6-diaza-dibenzo[a,c]cyclohepten-5-one;
3-(6-Methyl-5-oxo-6,7-dihydro-5H-1,6-diaza-dibenzo[a,c]cyclohepten-10-yl)-benzonitrile;
6-Methyl-10-(2-methyl-pyridin-3-yl)-6,7-dihydro-3,6-diaza-dibenzo[a,c]cyclohepten-5-one;
6-Methyl-10-(2-methyl-pyridin-3-yl)-6,7-dihydro-2,6-diaza-dibenzo[a,c]cyclohepten-5-one;
9-Chloro-2-methoxymethyl-5-methyl-5,6-dihydro-2H-2,3,5-triaza-benzo[e]azulen-4-one;
2-Methoxymethyl-5-methyl-9-(2-methyl-pyridin-3-yl)-5,6-dihydro-2H-2,3,5-triaza-benzo[e]azulen-4-one;
2-Methoxymethyl-5-methyl-9-(6-fluoro-pyridin-3-yl)-5,6-dihydro-2H-2,3,5-triaza-benzo[e]azulen-4-one;
2-Methoxymethyl-5-methyl-9-(6-fluoro-pyridin-2-yl)-5,6-dihydro-2H-2,3,5-triaza-benzo[e]azulen-4-one;
2,5-Dimethyl-9-(2-methyl-pyridin-3-yl)-5,6-dihydro-2H-2,3,5-triaza-benzo[e]azulen-4-one;
3,5-Dimethyl-9-(2-methyl-pyridin-3-yl)-5,6-dihydro-2H-2,3,5-triaza-benzo[e]azulen-4-one;
2-Ethyl-5-methyl-9-(2-methyl-pyridin-3-yl)-5,6-dihydro-2H-2,3,5-triaza-benzo[e]azulen-4-one;
3-Ethyl-5-methyl-9-(2-methyl-pyridin-3-yl)-5,6-dihydro-2H-2,3,5-triaza-benzo[e]azulen-4-one;
2-(2-Methoxy-ethyl)-5-methyl-9-(2-methyl-pyridin-3-yl)-5,6-dihydro-2H-2,3,5-triaza-benzo[e]azulen-4-one;
3-(2-Methoxy-ethyl)-5-methyl-9-(2-methyl-pyridin-3-yl)-56-dihydro-2H-2,3,5-triaza-benzo[e]azulen-4-one;
9-Chloro-2-(methoxymethyl)-5-methyl-2H-spiro[benzo[c]pyrazolo[4,3-e]azepine-6,1'-cyclopropan]-4(5H)-one;
2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;
2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;
10-Chloro-6-methyl-6,7-dihydro-benzo[e]pyrrolo[1,2-c][1,3]diazepin-5-one;
10-(6-Fluoro-pyridin-3-yl)-6-methyl-6,7-dihydro-benzo[e]pyrrolo[1,2-c][1,3]diazepin-5-one;
6-Methyl-10-(2-methyl-pyridin-3-yl)-6,7-dihydro-benzo[e]pyrrolo[1,2-c][1,3]diazepin-5-one;
and pharmaceutically acceptable salts, solvates and prodrugs thereof.

29. The compound of item 3 or the compound for use according to item 4, wherein said compound is selected from:
2'-Chloro-6'-methylspiro[cyclopropane-1,5'-pyrido[3,4-f]pyrrolo[1,2-a][1,4]diazepin]-7'(6'H)-one;
2',9'-Dichloro-6'-methylspiro[cyclopropane-1,5'-pyrido[3,4-f]pyrrolo[1,2-a][1,4]diazepin]-7'(6'H)-one;
2'-(2-Methyl-pyridin-3-yl)-6'-methylspiro[cyclopropane-1,5'-pyrido[3,4-f]pyrrolo[1,2-a][1,4]diazepin]-7'(6'H)-one;
9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;
9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;
10-Chloro-6-methyl-6,7-dihydro-spiro[dibenzo[c,e]azepine-7,1'-cyclopropan]-5-one;
10-Bromo-3-chloro-6-methyl-6,7-dihydro-spiro[dibenzo[c,e]azepine-7,1'-cyclopropan]-5-one;
10-(2-Methyl-pyridin-3-yl)-6-methyl-6,7-dihydro-spiro[dibenzo[c,e]azepine-7,1'-cyclopropan]-5-one;
3-Chloro-10-(2-methyl-pyridin-3-yl)-6-methyl-6,7-dihydro-spiro[dibenzo[c,e]azepine-7,1'-cyclopropan]-5-one;
3-(2-Methyl-2H-pyrazol-3-yl)-10-(2-methyl-pyridin-3-yl)-6-methyl-6,7-dihydro-spiro[dibenzo[c,e]azepine-7,1'-cyclopropan]-5-one;
10-chloro-6-methylspiro[benzo[c]pyrido[3,2-e]azepine-7,1'-cyclopropan]-5(6H)-one;
10-(6-Fluoro-pyridin-3-yl)-6-methylspiro[benzo[c]pyrido[3,2-e]azepine-7,1'-cyclopropan]-5(6H)-one;
10-(5-Fluoro-pyridin-2-yl)-6-methylspiro[benzo[c]pyrido[3,2-e]azepine-7,1'-cyclopropan]-5(6H)-one;
10-chloro-3-methoxy-6-methylspiro[benzo[c]pyrido[3,2-e]azepine-7,1'-cyclopropan]-5(6H)-one;
10-(6-Fluoro-pyridin-3-yl)-3-methoxy-6-methylspiro[benzo[c]pyrido[3,2-e]azepine-7,1'-cyclopropan]-5(6H)-one;
9-Chloro-2-(methoxymethyl)-5-methyl-2H-spiro[benzo[c]pyrazolo[4,3-e]azepine-6,1'-cyclopropan]-4(5H)-one;
2-(Methoxymethyl)-5-methy-9-(6-fluoro-pyridin-3-yl)-2H-spiro[benzo[c]pyrazolo[4,3-e]azepine-6,1'-cyclopropan]-4(5H)-one;
2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;
and pharmaceutically acceptable salts, solvates and prodrugs thereof.

30. The compound for use according to item 5 or the compound of item 6, wherein said compound is selected from:
2'-Chloro-6'-methylspiro[cyclopropane-1,5'-pyrido[3,4-f]pyrrolo[1,2-a][1,4]diazepin]-7'(6'H)-one;
2',9'-Dichloro-6'-methylspiro[cyclopropane-1,5'-pyrido[3,4-f]pyrrolo[1,2-a][1,4]diazepin]-7'(6'H)-one;
2'-(2-Methyl-pyridin-3-yl)-6'-methylspiro[cyclopropane-1,5'-pyrido[3,4-f]pyrrolo[1,2-a][1,4]diazepin]-7'(6'H)-one;
9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;

9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;

5-Methyl-9-(2-methyl-pyridin-3-yl)-5,6-dihydro-5,7,10b-triaza-benzo[e]azulen-4-one;

5-Methyl-9-(2-methyl-pyridin-3-yl)-5,6-dihydro-5,7,10,10b-tetraaza-benzo[e]azulen-4-one;

5-Methyl-9-(2-methyl-pyridin-3-yl)-5,6-dihydro-5,7,8,10b-tetraaza-benzo[e]azulen-4-one;

9-Chloro-5-methyl-5,6-dihydro-5,10,10b-triaza-benzo[e]azulen-4-one;

5-Methyl-9-(2-methyl-pyridin-3-yl)-5,6-dihydro-5,10,10b-triaza-benzo[e]azulen-4-one;

3-(5-Methyl-4-oxo-5,6-dihydro-4H-5,7,10b-triaza-benzo[e]azulen-9-yl)-benzonitrile;

9-Imidazo[1,2-a]pyridin-6-yl-5-methyl-5,6-dihydro-5,7,10b-triaza-benzo[e]azulen-4-one;

and pharmaceutically acceptable salts, solvates and prodrugs thereof.

31. The compound for use according to item 7 or the compound of item 8, wherein said compound is selected from:

2'-Chloro-6'-methylspiro[cyclopropane-1,5'-pyrido[3,4-f]pyrrolo[1,2-a][1,4]diazepin]-7'(6'H)-one;

2',9'-Dichloro-6'-methylspiro[cyclopropane-1,5'-pyrido[3,4-f]pyrrolo[1,2-a][1,4]diazepin]-7'(6'H)-one;

2'-(2-Methyl-pyridin-3-yl)-6'-methylspiro[cyclopropane-1,5'-pyrido[3,4-f]pyrrolo[1,2-a][1,4]diazepin]-7'(6'H)-one;

9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one;

9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6'H)-one;

5-Methyl-9-(2-methyl-pyridin-3-yl)-5,6-dihydro-5,7,10b-triaza-benzo[e]azulen-4-one;

5-Methyl-9-(2-methyl-pyridin-3-yl)-5,6-dihydro-5,7,10,10b-tetraaza-benzo[e]azulen-4-one;

5-Methyl-9-(2-methyl-pyridin-3-yl)-5,6-dihydro-5,7,8,10b-tetraaza-benzo[e]azulen-4-one;

9-Chloro-5-methyl-5,6-dihydro-5,10,10-triaza-benzo[e]azulen-4-one;

5-Methyl-9-(2-methyl-pyridin-3-yl)-5,6-dihydro-5,10,10b-triaza-benzo[e]azulen-4-one;

3-(5-Methyl-4-oxo-5,6-dihydro-4H-5,7,10b-triaza-benzo[e]azulen-9-yl)-benzonitrile;

9-Imidazo[1,2-a]pyridin-6-yl-5-methyl-5,6-dihydro-5,7,10-triaza-benzo[e]azulen-4-one;

9-Chloro-5-methyl-5,6-dihydro-5,8,10,10b-tetraaza-benzo[e]azulen-4-one;

5-Methyl-9-(2-methyl-pyridin-3-yl)-5,6-dihydro-5,8,10,10b-tetraaza-benzo[e]azulen-4-one;

10-Chloro-6-methyl-6,7-dihydro-4,6-diaza-dibenzo[a,c]cyclohepten-5-one;

3-(6-Methyl-5-oxo-6,7-dihydro-5H-4,6-diaza-dibenzo[a,c]cyclohepten-10-yl)-benzonitrile;

6-Methyl-10-(2-methyl-pyridin-3-yl)-6,7-dihydro-4,6-diaza-dibenzo[a,c]cyclohepten-5-one;

10-(6-Fluoro-pyridin-3-yl)-6-methyl-6,7-dihydro-4,6-diaza-dibenzo[a,c]cyclohepten-5-one;

10-(5-Fluoro-pyridin-2-yl)-6-methyl-6,7-dihydro-4,6-diaza-dibenzo[a,c]cyclohepten-5-one;

10-Chloro-3-fluoro-6-methyl-6,7-dihydro-4,6-diaza-dibenzo[a,c]cyclohepten-5-one;

3-Fluoro-6-methyl-10-(2-methyl-pyridin-3-yl)-6,7-dihydro-4,6-diaza-dibenzo[a,c]cyclohepten-5-one;

3-Fluoro-10-(6-fluoro-pyridin-3-yl)-6-methyl-6,7-dihydro-4,6-diaza-dibenzo[a,c]cyclohepten-5-one;

3-Fluoro-10-(5-fluoro-pyridin-2-yl)-6-methyl-6,7-dihydro-4,6-diaza-dibenzo[a,c]cyclohepten-5-one;

10-Chloro-3-methoxy-6-methyl-6,7-dihydro-4,6-diaza-dibenzo[a,c]cyclohepten-5-one;

10-(5-Fluoro-pyridin-2-yl)-3-methoxy-6-methyl-6,7-dihydro-4,6-diaza-dibenzo[a,c]cyclohepten-5-one;

10-(6-Fluoro-pyridin-3-yl)-3-methoxy-6-methyl-6,7-dihydro-4,6-diaza-dibenzo[a,c]cyclohepten-5-one;

3-Methoxy-6-methyl-10-(2-methyl-pyridin-3-yl)-6,7-dihydro-4,6-diaza-dibenzo[a,c]cyclohepten-5-one;

3-Hydroxy-6-methyl-10-(2-methyl-pyridin-3-yl)-6,7-dihydro-4,6-diaza-dibenzo[a,c]cyclohepten-5-one;

10-Chloro-3,6-dimethyl-6,7-dihydro-4,6-diaza-dibenzo[a,c]cyclohepten-5-one;

10-(6-Fluoro-pyridin-3-yl)-3,6-dimethyl-6,7-dihydro-4,6-diaza-dibenzo[a,c]cyclohepten-5-one;

10-(5-Fluoro-pyridin-2-yl)-3,6-dimethyl-6,7-dihydro-4,6-diaza-dibenzo[a,c]cyclohepten-5-one;

3,6-Dimethyl-10-(2-methyl-pyridin-3-yl)-6,7-dihydro-4,6-diaza-dibenzo[a,c]cyclohepten-5-one;

10-Chloro-2,6-dimethyl-6,7-dihydro-4,6-diaza-dibenzo[a,c]cyclohepten-5-one;

2,6-Dimethyl-10-(2-methyl-pyridin-3-yl)-6,7-dihydro-4,6-diaza-dibenzo[a,c]cyclohepten-5-one;

10-(6-Fluoro-pyridin-3-yl)-2,6-dimethyl-6,7-dihydro-4,6-diaza-dibenzo[a,c]cyclohepten-5-one;

10-Chloro-2-fluoro-6-methyl-6,7-dihydro-4,6-diaza-dibenzo[a,c]cyclohepten-5-one;

2-Fluoro-6-methyl-10-(2-methyl-pyridin-3-yl)-6,7-dihydro-4,6-diaza-dibenzo[a,c]cyclohepten-5-one;

2-Fluoro-10-(6-fluoro-pyridin-3-yl)-6-methyl-6,7-dihydro-4,6-diaza-dibenzo[a,c]cyclohepten-5-one;

2-Methoxy-6-methy-10-(2-methyl-pyridin-3-yl)-6,7-dihydro-4,6-diaza-dibenzo[a,c]cyclohepten-5-one;

10-chloro-6-methylspiro[benzo[c]pyrido[3,2-e]azepine-7,1'-cyclopropan]-5(6H)-one;

10-(6-Fluoro-pyridin-3-yl)-6-methylspiro[benzo[c]pyrido[3,2-e]azepine-7,1'-cyclopropan]-5(6H)-one;

10-(5-Fluoro-pyridin-2-yl)-6-methylspiro[benzo[c]pyrido[3,2-e]azepine-7,1'-cyclopropan]-5(6H)-one;

10-chloro-3-methoxy-6-methylspiro[benzo[c]pyrido[3,2-e]azepine-7,1'-cyclopropan]-5(6H)-one;

10-(6-Fluoro-pyridin-3-yl)-3-methoxy-6-methylspiro[benzo[c]pyrido[3,2-e]azepine-7,1'-cyclopropan]-5(6H)-one;

9-Chloro-5-methyl-5,6-dihydro-3-thia-5-aza-benzo[e]azulen-4-one;

5-Methyl-9-(2-methy-pyridin-3-yl)-5,6-dihydro-3-thia-5-aza-benzo[e]azulen-4-one;

3-(5-Methyl-4-oxo-56-dihydro-4H-3-thia-5-aza-benzo[e]azulen-9-yl)-benzonitrile;

5-Methyl-9-(2-methy-pyridin-3-yl)-5,6-dihydro-2H-2,3,5-triaza-benzo[e]azulen-4-one;

9-Chloro-5-methyl-5,6-dihydro-3H-3,5-diaza-benzo[e]azulen-4-one;

5-Methyl-9-(2-methyl-pyridin-3-yl)-5,6-dihydro-3H-3,5-diaza-benzo[e]azulen-4-one;

6-Methyl-10-(2-methyl-pyridin-3-yl)-6,7-dihydro-1,6-diaza-dibenzo[a,c]cyclohepten-5-one;

3-(6-Methyl-5-oxo-6,7-dihydro-5H-1,6-diaza-dibenzo[a,c]cyclohepten-10-yl)-benzonitrile;

6-Methyl-10-(2-methyl-pyridin-3-yl)-6,7-dihydro-3,6-diaza-dibenzo[a,c]cyclohepten-5-one;

6-Methyl-10-(2-methyl-pyridin-3-yl)-6,7-dihydro-2,6-diaza-dibenzo[a,c]cyclohepten-5-one;

9-Chloro-2-methoxymethyl-5-methyl-5,6-dihydro-2H-2,3,5-triaza-benzo[e]azulen-4-one;
2-Methoxymethyl-5-methyl-9-(2-methyl-pyridin-3-yl)-5,6-dihydro-2H-2,3,5-triaza-benzo[e]azulen-4-one;
2-Methoxymethyl-5-methyl-9-(6-fluoro-pyridin-3-yl)-5,6-dihydro-2H-2,3,5-triaza-benzo[e]azulen-4-one;
2-Methoxymethyl-5-methyl-9-(6-fluoro-pyridin-2-yl)-5,6-dihydro-2H-2,3,5-triaza-benzo[e]azulen-4-one;
2,5-Dimethyl-9-(2-methyl-pyridin-3-yl)-5,6-dihydro-2H-2,3,5-triaza-benzo[e]azulen-4-one;
3,5-Dimethyl-9-(2-methyl-pyridin-3-yl)-5,6-dihydro-2H-2,3,5-triaza-benzo[e]azulen-4-one;
2-Ethyl-5-methyl-9-(2-methyl-pyridin-3-yl)-5,6-dihydro-2H-2,3,5-triaza-benzo[e]azulen-4-one;
3-Ethyl-5-methyl-9-(2-methyl-pyridin-3-yl)-5,6-dihydro-2H-2,3,5-triaza-benzo[e]azulen-4-one;
2-(2-Methoxy-ethyl)-5-methyl-9-(2-methyl-pyridin-3-yl)-5,6-dihydro-2-2,3,5-triaza-benzo[e]azulen-4-one;
3-(2-Methoxy-ethyl)-5-methyl-9-(2-methyl-pyridin-3-yl)-5,6-dihydro-2H-2,3,5-triaza-benzo[e]azulen-4-one;
9-Chloro-2-(methoxymethyl)-5-methyl-2H-spiro[benzo[c]pyrazolo[4,3-e]azepine-6,1'-cyclopropan]-4(5H)-one;
2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;
2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;
10-Chloro-6-methyl-6,7-dihydro-benzo[e]pyrrolo[1,2-c][1,3]diazepin-5-one;
10-(6-Fluoro-pyridin-3-yl)-6-methyl-6,7-dihydro-benzo[e]pyrrolo[1,2-c][1,3]diazepin-5-one;
6-Methyl-10-(2-methyl-pyridin-3-yl)-6,7-dihydro-benzo[e]pyrrolo[1,2-c][1,3]diazepin-5-one;
and pharmaceutically acceptable salts, solvates and prodrugs thereof.

32. A pharmaceutical composition comprising a compound as defined in any one of items 3 to 8 or any one of their dependent items 9 to 27 or 29 to 31 and optionally a pharmaceutically acceptable excipient.

33. A compound as defined in any one of items 3 to 8 or any one of their dependent items 9 to 27 or 29 to 31 or the pharmaceutical composition of item 32 for use in the treatment and/or prophylaxis of a condition associated with altered glutamatergic signalling and/or functions, and/or a condition which can be affected by alteration of glutamate level or signalling.

34. Use of a compound as defined in any one of items 3 to 8 or any one of their dependent items 9 to 27 or 29 to 31 for the preparation of a medicament for the treatment and/or prophylaxis of a condition associated with altered glutamatergic signalling and/or functions, and/or a condition which can be affected by alteration of glutamate level or signalling.

35. A method of treating and/or preventing a condition associated with altered glutamatergic signalling and/or functions, and/or a condition which can be affected by alteration of glutamate level or signalling, the method comprising the administration of a compound as defined in any one of items 3 to 8 or any one of their dependent items 9 to 27 or 29 to 31 or the pharmaceutical composition of item 32 to a subject in need of such treatment or prevention.

36. The compound for use according to item 33 or the pharmaceutical composition for use according to item 33 or the use of item 34 or the method of item 35, wherein the condition to be treated or prevented is selected from: epilepsy; dementias; parkinsonism and movement disorders; motor neuron disease; amyotrophic lateral sclerosis; neurodegenerative and/or hereditary disorders of the nervous system; disorders of the peripheral nervous system; multiple sclerosis and other demyelinating diseases of the nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; endocrine and metabolic diseases; acute and chronic pain; nausea and vomiting; irritable bowel syndrome; and cancers.

37. A compound as defined in any one of items 1 to 31 or a pharmaceutical composition comprising said compound and optionally a pharmaceutically acceptable excipient, for use in the treatment and/or prophylaxis of a condition selected from: epilepsy; dementias; parkinsonism and movement disorders; motor neuron disease; amyotrophic lateral sclerosis; neurodegenerative and/or hereditary disorders of the nervous system; disorders of the peripheral nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; acute and chronic pain; nausea and vomiting; and irritable bowel syndrome.

38. Use of a compound as defined in any one of items 1 to 31 for the preparation of a medicament for the treatment and/or prophylaxis of a condition selected from: epilepsy; dementias; parkinsonism and movement disorders; motor neuron disease; amyotrophic lateral sclerosis; neurodegenerative and/or hereditary disorders of the nervous system; disorders of the peripheral nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; acute and chronic pain; nausea and vomiting; and irritable bowel syndrome.

39. A method of treating and/or preventing a condition in a subject, the method comprising the administration of a compound as defined in any one of items 1 to 31 or a pharmaceutical composition comprising said compound and optionally a pharmaceutically acceptable excipient, to a subject in need thereof, wherein said condition is selected from: epilepsy; dementias; parkinsonism and movement disorders; motor neuron disease; amyotrophic lateral sclerosis; neurodegenerative and/or hereditary disorders of the nervous system; disorders of the peripheral nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; acute and chronic pain; nausea and vomiting; and irritable bowel syndrome.

40. A compound as defined in any one of items 1 to 31 or a pharmaceutical composition comprising said compound and optionally a pharmaceutically acceptable excipient, for use in the treatment and/or prophylaxis of Parkinson's disease.

41. Use of a compound as defined in any one of items 1 to 31 for the preparation of a medicament for the treatment and/or prophylaxis of Parkinson's disease.

42. A method of treating and/or preventing Parkinson's disease in a subject, the method comprising the administration of a compound as defined in any one of items 1 to 31 or a pharmaceutical composition comprising said compound and optionally a pharmaceutically acceptable excipient, to a subject in need thereof.

43. The compound for use according to any one of items 1, 2, 4, 5, 7, 9 to 24, 28 to 31, 33, 36, 37 or 40 or the pharmaceutical composition for use according to any one of items 33, 36, 37 or 40 or the use of any one of items 34, 36, 38 or 41 or the method of any one of items 35, 36, 39 or 42, wherein the subject to be treated is a human.

44. The compound for use according to any one of items 1, 2, 4, 5, 7, 9 to 24, 28 to 31, 33, 36, 37, 40 or 43 or the pharmaceutical composition for use according to any one of items 33, 36, 37, 40 or 43 or the use of any one of items 34, 36, 38, 41 or 43 or the method of any one of items 35, 36, 39, 42 or 43, wherein the compound or the pharmaceutical composition or the medicament is to be administered orally.

45. In vitro use of a compound as defined in any one of items 1 to 31 as a positive allosteric modulator of mGluR3.

46. An in vitro method of modulating mGluR3, the method comprising the application of a compound as defined in any one of items 1 to 31.

47. A method for identifying an agent that binds to metabotropic glutamate receptor 3 (mGluR3), comprising the following steps:
   (a) contacting mGluR3 with a compound as defined in any one of items 1 to 31, wherein said compound is radio-labeled or fluorescence-labeled, under conditions that permit binding of the compound to mGluR3, thereby generating bound, labeled compound;
   (b) detecting a signal that corresponds to the amount of bound, labeled compound in the absence of test agent;
   (c) contacting the bound, labeled compound with a test agent;
   (d) detecting a signal that corresponds to the amount of bound labeled compound in the presence of test agent; and
   (e) comparing the signal detected in step (d) to the signal detected in step (b) to determine whether the test agent binds to mGluR3.

The invention will now be described by reference to the following examples which are merely illustrative and are not to be construed as a limitation of the scope of the present invention.

EXAMPLES

In this section, the term "compound" refers to a synthesis intermediate, and the term "example" refers to a compound of the general formula (I) according to the invention.

The compounds/examples described in this section are defined by their chemical formulae and their corresponding chemical names. In case of conflict between any chemical formula and the corresponding chemical name indicated herein, the present invention relates to both the compound/example defined by the chemical formula and the compound/example defined by the chemical name, and particularly relates to the compound/example defined by the chemical formula.

EXPERIMENTAL

Experimental Section

All reagents were commercial grade and used without further purification. Commercially available anhydrous solvents were used for reactions conducted under inert atmosphere. Silica gel generally used for column chromatography was SDS silica gel (60AAC 40-63 µM). Thin layer chromatography was carried out using pre-coated silica gel F-254plate. $^1$H NMR spectra were recorded on a Bruker AMX-400 spectrometer. Proton chemical shifts are listed relative to residual $CDCl_3$ (7.27 ppm), DMSO-D6 (2.51 ppm) or $D_2O$ (4.60 ppm). Splitting patterns are designated as s (singlet), d (doublet), dd (double-doublet), t (triplet), tt (triplet-triplet), dt (doublet-triplet), q (quartet), quint (quintuplet), sex (sextuplet), sept (septuplet), m (multiplet), b (broad).

Electrospray MS spectra were obtained on a Waters micromass platform LCMS spectrometer. All mass spectra were full-scan experiments (mass range 100-800 amu). Mass spectra were obtained using electro spray ionization. The HPLC system was a Waters platform with a 2767 sample manager, a 2525 pump, a photodiode array detector (190-400 nM). The column used was an XBridge $C_{18}$ 3.5 µM (4.6×50 mm) in analytical mode and an XBridge C18 OBD 5 μM (30×100 mm) in preparative mode. The mobile phase in both cases consisted in an appropriate gradient of A and B. A was water with 0.05% of TFA and B was MeOH with 0.05% of TFA. Flow rate was 1 mL per min in analytical mode and 25 mL min in preparative mode. All LCMS were performed at room temperature. At the end of each preparative HPLC, the tubes were collected and TFA was neutralized with potassium carbonate before extraction or filtration of the product. Microwave experiments were performed on a Biotage Initiator. The microwave modulates the power in order to reach the selected temperature as fast as possible. The time of each experiment is the time at the selected temperature.

Melting Points are measure on a Barnstead Electrothermal 9100 and are not corrected.

General Procedure I: Formation of Intermediate C from the Corresponding Nitrile a and Methyl Ester B (Scheme 1)

Method (i): Under Oil Bath Heating:

At 0° C., to a suspension of sodium hydride (60% dispersion in oil, 1.5 equiv.) in DMF or DMA (0.80 mol·L$^{-1}$), a solution of methyl ester B (1.0 equiv.) in DMF or DMA (0.65 mol·L$^{-1}$) was slowly added, followed after 15 minutes by a solution of nitrile A (1.1 equiv.) in DMF or DMA (0.65 mol·L$^{-1}$). The reaction mixture was stirred at 70° C. (oil bath) for 3 hours, before being poured into an ice cold saturated aqueous solution of NH$_4$Cl and extracted twice with CH$_2$Cl$_2$. The organic layers were combined, washed with brine, dried over MgSO$_4$, concentrated under vacuum and purified by flash column chromatography on silica gel (using a gradient of EtOAc in cyclohexane as eluent) to afford the product.

Method (ii): Under Microwave Irradiation:

Under inert atmosphere, a mixture of nitrile A (1.0 equiv.), methyl ester B (1.0 equiv.) and cesium carbonate (2.5 equiv.) in DMF or DMA (0.20 mol·L$^{-1}$) was submitted to microwave irradiation at 130° C. for 10 minutes. The reaction mixture was neutralized with aqueous HCl (1N) and extracted twice with EtOAc. The organic layers were combined, washed with brine, dried over MgSO$_4$, concentrated and purified by flash column chromatography on silica gel (using a gradient of EtOAc in cyclohexane as eluent) to afford the product.

Compound 1: 1-(5-Bromo-2-cyano-pyridin-3-yl)-1H-pyrrole-2-carboxylic acid methyl ester Compound 1 was obtained according to general procedure I(ii), starting from 5-bromo-3-fluoropyridine-2-carbonitrile and pyrrole-2-carboxylic acid methyl ester. It was isolated as a yellow solid in 53% yield. M/Z (M[$^{79}$Br]+H)$^+$=306.

Compound 2: 1-(2-Chloro-5-cyano-pyridin-4-yl)-1H-pyrrole-2-carboxylic acid methyl ester Compound 2 was obtained according to general procedure I (i), starting from 4,6-dichloro-nicotinonitrile and pyrrole-2-carboxylic acid methyl ester, from 0° C. to 25° C. over 1 hour. Purification by column chromatography on silica gel: 25 μm particle size (using 0% to 10% ethyl acetate in cyclohexane as eluent) afforded the product as a white solid in 22% yield. $^1$H-NMR (400 MHz, DMSO-D6): 9.06 (s, 1H, Ar); 8.06 (s, 1H, Ar); 7.47 (dd, J 2.8, 1.8 Hz, 1H, Ar); 7.19 (dd, J 3.8, 1.8 Hz, 1H, Ar); 6.51 (dd, J 3.8, 2.8 Hz, 1H, Ar); 3.70 (s, 3H, CH$_3$). M/Z (M[$^{35}$Cl]+H)$^+$=261.9.

Compound 3: 3-Chloro-5-(2-methyl-pyridin-3-yl)-pyrazine-2-carbonitrile

Under inert atmosphere, a mixture of 3,5-dichloropyrazine-2-carbonitrile (1 equiv.), 2-methylpyridine-3-boronic acid pinacol ester (1 equiv.), cesium carbonate (3 equiv.) and PdCl$_2$(dppf).CH$_2$Cl$_2$ (0.1 equiv.) in dioxane (0.10 mol·L$^{-1}$) and water (0.80 mol·L$^{-1}$) was heated at 80° C. for 1 hour. The reaction mixture was hydrolysed and extracted twice with ethyl acetate. The organic layers were combined, washed with brine, dried over MgSO$_4$, concentrated under vacuum and purified by flash column chromatography on silica gel (using 20% to 100% ethyl acetate (EtOAc) in cyclohexane as eluent) to afford the product as a brown solid in 57% yield. $^1$H-NMR (400 MHz, DMSO-D6): 9.17 (s, 1H, Ar); 8.65 (dd, J 4.8, 1.7 Hz, 1H, Ar); 8.02 (dd, J 7.8, 1.7 Hz, 1H, Ar); 7.46 (dd, J 7.8, 4.8 Hz, 1H, Ar); 2.62 (s, 3H, CH$_3$). M/Z (M[$^{35}$Cl]+H)$^+$=230.9.

Compound 4: 1-[3-Cyano-6-(2-methyl-pyridin-3-yl)-pyrazin-2-yl]-1H-pyrrole-2-carboxylic acid methyl ester Compound 4 was obtained according to general procedure I(i), starting from compound 3 and pyrrole-2-carboxylic acid methyl ester, from 0° C. to 25° C. over 3 hours. Purification by column chromatography on silica gel (using 90% to 100% ethyl acetate in cyclohexane as eluent) afforded the product as a brown oil in 49% yield. $^1$H-NMR (400 MHz, DMSO-D6): 9.28 (s, 1H, Ar); 8.64 (dd, J 4.8, 1.6 Hz, 1H, Ar); 8.10 (dd, J 7.7, 1.6 Hz, 1H, Ar); 7.61 (dd, J 2.8, 1.7 Hz, 1H, Ar); 7.46 (dd, 7.7, 4.8 Hz, 1H, Ar); 7.21 (dd, J 3.8, 1.7 Hz, 1H, Ar); 6.54 (dd, J 3.8, 2.8 Hz, 1H, Ar); 3.71 (s, 3H, CH$_3$); 2.61 (s, 3H, CH$_3$). M/Z (M+H)$^+$=320.0.

Compound 5: 4-Chloro-1-(2-chloro-5-cyano-pyridin-4-yl)-1H-pyrrole-2-carboxylic acid methyl ester Compound 5 was obtained according to general procedure I(i), starting from 4,6-dichloro-nicotinonitrile and 4-chloro-1H-pyrrole-2-carboxylic acid methyl ester, from 0° C. to 25° C. over 1 hour. Purification by column chromatography on silica gel: 25 μm particle size (using 0% to 20% ethyl acetate in cyclohexane as eluent) afforded the product as a yellow solid in 38% yield. $^1$H-NMR (400 MHz, DMSO-D6): 9.10 (s, 1H, Ar); 8.15 (s, 1H, Ar); 7.72 (d, J 1.4 Hz, 1H, Ar); 7.24 (d, J 1.4 Hz, 1H, Ar); 3.71 (s, 3H, CH$_3$). M/Z (M[$^{35}$Cl][$^{35}$Cl]+H)+=296.1.

General Procedure II: Formation of Azepinone D or D1 from Intermediate C or C1 (Schemes 1 and 3)

Under anhydrous conditions, at room temperature, ethylmagnesium bromide (1M solution in THF, 2.0 equiv.) was added dropwise to a solution of intermediate C or C1 (1.0 equiv.) and titanium isopropoxide (1.0 equiv.) in THF (0.20 mol·L$^{-1}$). The reaction mixture was stirred at room temperature for 3 hours to give a dark brown solution. When the reaction was not complete, 1.0-2.0 equiv. of ethylmagnesium bromide (1M solution in THF) was added again and the reaction mixture further stirred for 1 hour at room temperature. After cooling at 0° C., the reaction mixture was hydrolyzed with aqueous HCl (1N) and extracted twice with CH$_2$Cl$_2$. The organic layers were combined, washed with brine, dried over MgSO₄, concentrated under vacuum and purified by flash column chromatography on silica gel (using a gradient of ethyl acetate in cyclohexane) to afford the product.

Compound 6: 2'-Chlorospiro[cyclopropane-1,5'-pyrido[3,4-f]pyrrolo[1,2-a][1,4]diazepin]-7'(6'H)-one Compound 6 (which can also be referred to as 9-chloro-spiro[6,1'-cyclopropan]-5,8,10b-triaza-benzo[e]azulen-4-one) was obtained according to general procedure II, starting from compound 2. The reaction was completed by addition of more ethylmagnesium bromide (1M solution in THF, 1 equiv.) and titanium isopropoxide (1 equiv.). Purification by column chromatography on silica gel (using 0% to 5% MeOH in dichloromethane as eluent) afforded compound 6 as a beige solid in 42% yield. M/Z (M[$^{35}$Cl]+H)⁺=260.5.

Compound 7: 2',9'-Dichlorospiro[cyclopropane-1,5'-pyrido[3,4-f]pyrrolo[1,2-a][1,4]diazepin]-7'(6'H)-one Compound 7 was obtained according to general procedure II, starting from compound 5. The reaction was completed by addition of more ethylmagnesium bromide (1M solution in THF, 1 equiv.) and titanium isopropoxide (1 equiv.). Purification by column chromatography on silica gel (using 0% to 5% MeOH in dichloromethane as eluent) afforded compound 7 as a beige solid in 72% yield. M/Z (M[$^{35}$Cl][$^{35}$Cl]+H)⁺=294.5.

General Procedure III: Formation of N-Substituted Azepinone F or F1 from Azepinone D or D1 with Electrophile E (Schemes 1 and 3)

Under anhydrous conditions, to a solution of azepinone D or D1 (1.0 equiv.) in DMF (0.10 mol·L⁻¹) cooled by an ice bath, NaH (60% dispersion in mineral oil, 1.7 equiv.) was added in 3 portions. The mixture was stirred for 15 minutes, then electrophile E (2.0 equiv.) was added and the reaction mixture was stirred at room temperature. When the reaction was complete, the mixture was hydrolysed with an aqueous HCl solution (1N) and extracted with EtOAc. The organic layers were combined, washed with brine, dried over MgSO₄, concentrated under vacuum and purified by flash column chromatography on silica gel.

Example 1: 2'-Chloro-6'-methylspiro[cyclopropane-1,5'-pyrido[3,4-f]pyrrolo[1,2-a][1,4]diazepin]-7'(6'H)-one

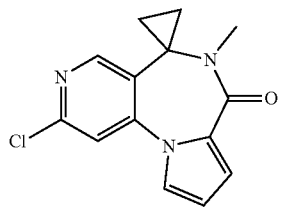 [SMILES: CN1C(=O)c2cccn2-c2cc(Cl)ncc2C12CC2]

Example 1 (which can also be referred to as 9-chloro-5-methyl-spiro[6,1'-cyclopropan]-5,8,10b-triaza-benzo[e]azulen-4-one) was obtained according to general procedure III, starting from compound 6 in presence of iodomethane. The reaction mixture was stirred at room temperature for 3 hours. Purification by flash column chromatography on silica gel (using 50% ethyl acetate in cycloheaxane as eluent) afforded the product as a white solid in 95% yield. ¹H-NMR (400 MHz, DMSO-D6): 8.51 (s, 1H, Ar); 7.80 (s, 1H, Ar); 7.67 (dd, J 2.8, 1.8 Hz, 1H, Ar); 6.96 (dd, J 3.8, 1.8 Hz, 1H, Ar); 6.50 (dd, J 3.8, 2.8 Hz, 1H, Ar); 2.92 (s, 3H, CH₃); 1.61 (m, 1H, cyclopropyl); 1.48 (m, 1H, cyclopropyl); 0.94 (m, 1H, cyclopropyl); 0.55 (m, 1H, cyclopropyl). M/Z (M[$^{35}$Cl]+H)⁺=273.9.

Example 2: 2,9'-Dichloro-6'-methylspiro[cyclopropane-1,5'-pyrido[3,4-f]pyrrolo[1,2-a][1,4]diazepin]-7'(6'H)-one

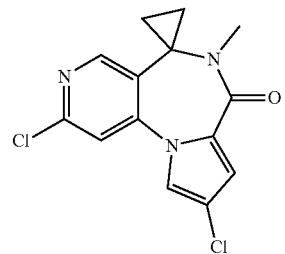 [SMILES: CN1C(=O)c2cc(Cl)cn2-c2cc(Cl)ncc2C12CC2]

Example 2 was obtained according to general procedure II, starting from compound 7 in presence of iodomethane. The reaction mixture was stirred at room temperature for 1 hour. Purification by flash column chromatography on silica gel (using 0% to 10% methanol in dichloromethane as eluent) and trituration in diisopropylether afforded the product as a brown solid in 56% yield. ¹H-NMR (400 MHz, DMSO-D6): 8.53 (s, 1H, Ar); 7.87 (d, J 1.9 Hz, 1H, Ar); 7.83 (s, 1H, Ar); 6.96 (d, J 1.9 Hz, 1H, Ar); 2.94 (s, 3H, CH₃); 1.64 (m, 1H, cyclopropyl); 1.52 (m, 1H, cyclopropyl); 1.00 (m, 1H, cyclopropyl); 0.63 (m, 1H, cyclopropyl). M/Z (M[$^{35}$Cl][$^{35}$Cl]+H)⁺=308.5.

General Procedure IV: Formation of Azepinone H, H1 or H2 from Azepinone F, F1 or F2 and Boronic Acid Derivatives G (Schemes 1, 2, 3 and 4)

Method (i):
Under inert atmosphere, a mixture of halide F, F1- or F2 (1.0 equiv.), boronic acid derivative G (1.5 equiv.) and PdCl₂(dppf).CH₂Cl₂ (0.10 equiv.) in a mixture of DMF or DMA (0.10 mol·L⁻¹) and aqueous K₂CO₃ (1.2 mol·L⁻¹) was heated at 110° C. for 16 hours. After cooling, the reaction mixture was hydrolysed and extracted twice with EtOAc. The organic layers were combined, washed with brine, dried over MgSO₄, concentrated and purified to afford the product.

Method (ii):
Under inert atmosphere, XPhos precatalyst (0.05 equiv.) was added to a mixture of halide F, F1 or F2 (1.0 equiv.), boronic acid derivative G (1.5 equiv.) and tripotassium phosphate (2.0 equiv.) in dioxane (0.15 mol·L⁻¹) and water (1.0 mol·L⁻¹). The reaction mixture was heated at 80° C. for 2 hours. After cooling, the reaction mixture was hydrolysed and extracted twice with EtOAc. The organic layers were combined, washed with brine, dried over MgSO₄, concentrated and purified to afford the product.

General Procedure V: Formation of HCl Salt
Method (i): in DCM:
To a solution of the free base in dichloromethane, HCl (2N solution in Et₂O, 5 equiv.) was added. The resulting precipitate was collected, washed with Et₂O and dried at 50° C. under reduced pressure with P₂O₅.

Method (ii): Concentration from MeOH:

To a solution or suspension of the free base in methanol, HCl (1.25N solution in MeOH, 5 equiv.) was added. The mixture was vigorously stirred, then concentrated. The residue was taken in Et₂O. The resulting solid was collected, washed with Et₂O and dried at 50° C. under reduced pressure with P₂O₅.

Example 3: 2'-(2-Methyl-pyridin-3-yl)-6'-methyl-spiro[cyclopropane-1,5'-pyrido[3,4-f]pyrrolo[1,2-a][1,4]diazepin]-7'(6 ¹H)-one

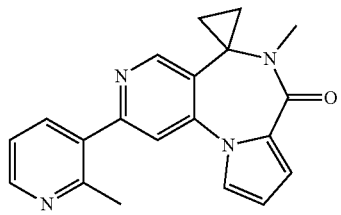 [SMILES: Cc1ncccc1-c1cc2c(cn1)C1(CC1)N(C)C(=O)c1cccn1-2]

Example 3 (which can also be referred to as 9-(2-methyl-pyridin-3-yl)-5-methyl-spiro[6,1'-cyclopropan]-5,8,10b-tri-aza-benzo[e]azulen-4-one) was obtained according to general procedure IV(i), starting from example 1 and 2-methylpyridine-3-boronic acid pinacol ester, using dioxane as solvent at 100° C. for 3 hours. Purification by flash column chromatography on silica gel (0% to 5% MeOH in dichloromethane) afforded example 3 as a beige solid in 63% yield. ¹H-NMR (400 MHz, DMSO-D6): 8.78 (s, 1H, Ar); 8.53 (dd, J 4.8, 1.8 Hz, 1H, Ar); 7.93 (dd, J 7.7, 1.8 Hz, 1H, Ar); 7.82 (s, 1H, Ar); 7.73 (dd, J 2.8, 1.8 Hz, 1H, Ar); 7.36 (dd, J 7.7, 4.8 Hz, 1H, Ar); 6.97 (dd, J 3.8, 1.8 Hz, 1H, Ar); 6.50 (dd, J 3.8, 2.8 Hz, 1H, Ar); 2.97 (s, 3H, CH₃); 2.57 (s, 3H, CH₃); 1.59 (m, 1H, cyclopropyl); 1.53 (m, 1H, cyclopropyl); 0.98 (m, 1H, cyclopropyl); 0.60 (m, 1H, cyclopropyl). M/Z (M+H)⁺=331.0. MP=250° C.

Example 4: 9'-Chloro-2'-(2-methyl-pyridin-3-yl)-6'-methylspiro[cyclopropane-1,5'-pyrido[3,4-f]pyrrolo[1,2-a][1,4]diazepin]-7'(6'H)-one

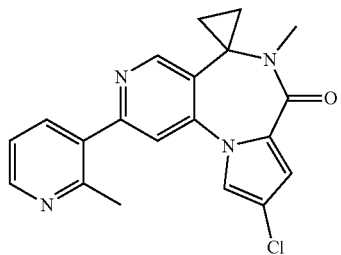 [SMILES: Cc1ncccc1-c1cc2c(cn1)C1(CC1)N(C)C(=O)c1cc(Cl)cn1-2]

Example 4 was obtained according to general procedure IV(i), starting from example 2 and 2-methylpyridine-3-boronic acid pinacol ester, using dioxane as solvent at 100° C. for 1 hour. Purification by flash column chromatography on silica gel (0% to 10% MeOH in dichloromethane) afforded example 4 as a white solid in 25% yield. ¹H-NMR (400 MHz, DMSO-D6): 8.81 (s, 1H, Ar); 8.52 (dd, J 4.8, 1.8 Hz, 1H, Ar); 7.95-7.92 (m, 2H, Ar); 7.85 (s, 1H, Ar); 7.36 (dd, J 7.7, 4.8 Hz, 1H, Ar); 6.96 (d, J 1.9 Hz, 1H, Ar); 2.96 (s, 3H, CH₃); 2.57 (s, 3H, CH₃); 1.69 (m, 1H, cyclopropyl); 1.56 (m, 1H, cyclopropyl); 1.05 (m, 1H, cyclopropyl); 0.96 (m, 1H, cyclopropyl). M/Z (M[³⁵Cl]+H)⁺=365.4.

Example 5: 9'-(1-Methyl-1H-pyrazol-5-yl)-2'-(2-methyl-pyridin-3-yl)-6'-methylspiro[cyclopropane-1,5'-pyrido[3,4-f]pyrrolo[1,2-a][1,4]diazepin]-7'(6H)-one

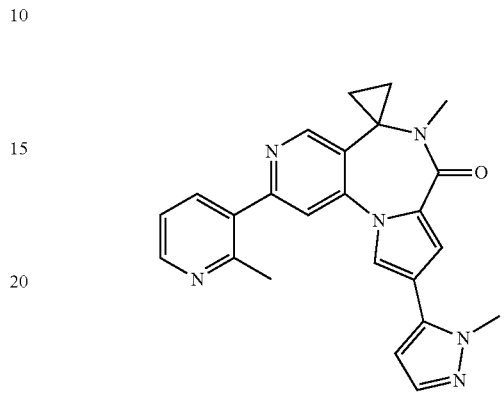

Example 5 was obtained according to general procedure IV(ii), starting from example 4 and 1-methyl-5-(4,4,5,5-tetramethyl-[1,3,2]dioxaborolan-2-yl)-1H-pyrazole, using tBuXPhos precatalyst, at 100° C. for 1 hour. Purification by flash column chromatography on silica gel (0% to 10% MeOH in dichloromethane) afforded example 5 as a white solid in 38% yield. ¹H-NMR (400 MHz, DMSO-D6): 8.81 (s, 1H, Ar); 8.55 (dd, J 4.8, 1.8 Hz, 1H, Ar); 8.04 (d, J 1.9 Hz, 1H, Ar); 7.99 (s, 1H, Ar); 7.92 (dd, J 7.7, 1.8 Hz, 1H, Ar); 7.41 (d, J 1.9 Hz, 1H, Ar); 7.37 (dd, J 7.7, 4.8 Hz, 1H, Ar); 7.27 (d, J 1.9 Hz, 1H, Ar); 6.56 (d, J 1.9 Hz, 1H, Ar); 4.00 (s, 3H, CH₃); 2.99 (s, 3H, COH₃); 2.57 (s, 3H, CH₃); 1.73 (m, 1H, cyclopropyl); 1.57 (m, 1H, cyclopropyl); 1.06 (m, 1H, cyclopropyl); 0.70 (m, 1H, cyclopropyl). M/Z (M+H)⁺=411.6.

Compound 8: 1-(6-Cyano-2'-methyl-[3,3']bipyridi-nyl-5-yl)-1H-pyrrole-2-carboxylic acid methyl ester Under inert atmosphere, a mixture of compound 1 (1.0 equiv.), 2-methylpyridine-3-boronic acid pinacol ester (1.3 equiv.), cesium fluoride (3.0 equiv.) and Pd(PPh₃)₄ (0.1 equiv.) in anhydrous THF (0.15 mol·L⁻¹) was heated at 70° C. for 16 hours. After cooling to room temperature, the reaction mixture was neutralized with aqueous NaHCO₃ and extracted twice with EtOAc. The combined organic layers were dried with brine, over MgSO₄, concentrated and purified by flash column chromatography on silica gel (using 0% to 80% EtOAc in cyclohexane as eluent) to afford the product as a white solid in 77% yield. 1H-NMR (400 MHz, DMSO-D6): 8.90 (d, J 2.0 Hz, 1H, Ar); 8.57 (dd, J 4.8, 1.8 Hz, 1H, Ar); 8.33 (d, J 2.0 Hz, 1H, Ar); 7.81 (dd, J 7.7, 1.8 Hz, 1H, Ar); 7.51 (dd, J 2.8, 1.8 Hz, 1H, Ar); 7.40 (dd, J 7.7, 4.8 Hz, 1H, Ar); 7.18 (d, J 3.8, 1.8 Hz, 1H, Ar); 6.50 (d, J 3.8, 2.8 Hz, 1H, Ar); 3.68 (s, 3H, CH₃); 2.49 (s, 3H, CH₃). M/Z (M+H)⁺=319.3.

Compound 9: 9-(2-Methyl-pyridin-3-yl)-5,6-di-hydro-5,7,10b-triaza-benzo[e]azulen-4-one At 0° C., sodium borohydrate (10 equiv.) was slowly added to a mixture of compound 8 (1.0 equiv.) and cobalt chloride hexahydrate (2.0 equiv.) in methanol (0.15 mol·L$^{-1}$). The reaction mixture was subjected to microwave irradiation at 120° C. for 20 minutes. After cooling to room temperature, the reaction mixture was neutralized with an aqueous solution of ammonium chloride (NH$_4$Cl) and extracted twice with dichloromethane. The organic layers were combined, washed with brine, dried over MgSO$_4$, concentrated and purified by flash column chromatography on silica gel (using 0% to 10% MeOH in dichloromethane as eluent) to afford the product as a beige solid in 40% yield. $^1$H-NMR (400 MHz, DMSO-D6): 8.54-8.47 (m, 3H, Ar+NH); 8.07 (d, J 1.8 Hz, 1H, Ar); 7.80 (dd, J 7.7, 1.7 Hz, 1H, Ar); 7.66 (d, J 2.9, 1.9 Hz, 1H, Ar); 7.37 (dd, J 7.7, 4.9 Hz, 1H, Ar); 6.96 (d, J 3.8, 1.9 Hz, 1H, Ar); 6.47 (dd, J 3.8, 2.9 Hz, 1H, Ar); 4.30 (d, J 5.6 Hz, 2H, CH$_2$); 2.25 (s, 3H, CH$_3$). M/Z (M+H)$^+$=291.3.

Example 6: 5-Methyl-9-(2-methyl-pyridin-3-yl)-5,6-dihydro-5,7,10b-triaza-benzo[e]azulen-4-one, dihydrochloride

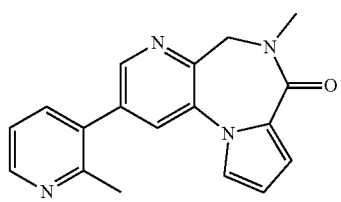 [SMILES: Cc1ncccc1-c1cnc2c(c1)-n1cccc1C(=O)N(C)C2]

Example 6 was prepared according to general procedure III, starting from compound 9 in presence of iodomethane. The reaction mixture was stirred at room temperature for 1.5 hour. Purification by flash column chromatography on silica gel (0% to 5% MeOH in dichloromethane) afforded the product as a white solid in 48% yield. Salt formation was performed by method V(ii). $^1$H-NMR (400 MHz, DMSO-D6): 8.85 (dd, J 5.8, 1.4 Hz, 1H, Ar); 8.64 (d, J 1.8 Hz, 1H, Ar); 8.55 (dd, J 7.7, 1.4 Hz, 1H, Ar); 8.24 (d, J 1.8 Hz, 1H, Ar); 7.99 (d, J 7.7, 5.8 Hz, 1H, Ar); 7.62 (dd, J 2.9, 1.8 Hz, 1H, Ar); 6.97 (d, J 3.8, 1.8 Hz, 1H, Ar); 6.51 (dd, J 3.8, 2.9 Hz, 1H, Ar); 4.57 (s, 2H, CH$_2$); 3.14 (s, 3H, CH$_3$); 2.77 (s, 3H, CH$_3$). M/Z (M+H)$^+$=305.2. MP>250° C.

Compound 10: 9-(2-Methyl-pyridin-3-yl)-5,6-dihydro-5,7,10,10b-tetraaza-benzo[e]azulen-4-one Under hydrogen atmosphere (P=1 atm), a suspension of compound 4 (1 equiv.), palladium 10% on charcoal (0.1 equiv.) and concentrated aqueous HCl (12%, 5 equiv.) in methanol (0.10 mol·L$^{-1}$) was stirred at room temperature for 2 hours. Pd/C was filtered off on celite and the filtrate was concentrated under vacuum. The resulting brown oil was dissolved in dioxane (0.20 mol·L$^{-1}$) and aqueous sodium bicarbonate (0.40 mol·L$^{-1}$) was added. The reaction mixture was stirred at room temperature for 2 days. The organic phase was extracted twice with EtOAc. The combined organic extracts were washed with brine, dried over MgSO$_4$ and concentrated under vacuum. Purification by trituration in small quantities of EtOAc and Et$_2$O afforded the product as a yellow powder in 68% yield. $^1$H-NMR (400 MHz, DMSO-D6): 8.82 (s, 1H, Ar); 8.59 (dd, J 4.8, 1.7 Hz, 1H, Ar); 8.52 (t, J 5.2 Hz, 1H, NH); 8.03 (dd, J 7.8, 1.7 Hz, 1H, Ar); 7.83 (dd, J 2.9, 1.8 Hz, 1H, Ar); 7.42 (d, J 7.8, 4.8 Hz, 1H, Ar); 7.06 (d, J 3.8, 1.8 Hz, 1H, Ar); 6.52 (dd, J 3.8, 2.9 Hz, 1H, Ar); 4.38 (d, J 5.2 Hz, 2H, CH$_2$); 2.63 (s, 3H, CH$_3$). M/Z (M+H)$^+$=292.0.

Example 7: 5-Methyl-9-(2-methyl-pyridin-3-yl)-5,6-dihydro-5,7,10,10b-tetraaza-benzo[e]azulen-4-one, dihydrochloride

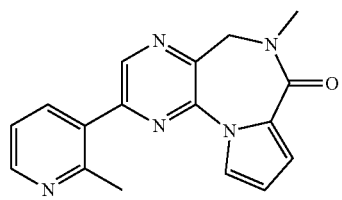 [SMILES: Cc1ncccc1-c1cnc2c(n1)-n1cccc1C(=O)N(C)C2]

Example 7 was prepared according to general procedure III, starting from compound 10 in presence of iodomethane. The reaction mixture was stirred at room temperature for 2 hours. Purification by flash column chromatography on silica gel (0% to 5% MeOH in dichloromethane) afforded the product as a beige solid in 31% yield. Salt formation was performed by method V(ii). $^1$H-NMR (400 MHz, DMSO-D6): 8.91 (s, 1H, Ar); 8.79 (dd, J 5.1, 1.5 Hz, 1H, Ar); 8.51 (d, J 7.7 Hz, 1H, Ar); 7.82 (dd, J 7.7, 5.1 Hz, 1H, Ar); 7.80 (dd, J 2.9, 1.9 Hz, 1H, Ar); 7.05 (d, J 3.7, 1.9 Hz, 1H, Ar); 6.53 (dd, J 3.7, 2.9 Hz, 1H, Ar); 4.64 (s, 2H, CH$_2$); 3.15 (s, 3H, CH$_3$); 2.80 (s, 3H, CH$_3$). M/Z (M+H)$^+$=306.0. MP>250° C.

Compound 11: 1-(3,6-Dichloro-pyridazin-4-yl)-1H-pyrrole-2-carboxylic acid methyl ester Under dry atmosphere, in a sealed vial, a mixture of 3,4,6-trichloropyridazine (1.2 equiv.), methyl 2-pyrrole carboxylate (1.0 equiv.) and cesium carbonate (1.7 equiv.) in anhydrous DMA (0.10 mol·L$^{-1}$) was heated at 80° C. for 2 hours. After cooling to room temperature, the reaction mixture was neutralized with aqueous NH$_4$Cl and extracted twice with EtOAc. The combined organic layers were washed with water, dried with brine and over MgSO$_4$, filtered off and concentrated under vacuum. Purification by flash column chromatography on silica gel (using 0% to 15% EtOAc in cyclohexane as eluent) afforded the product as a white solid in 43% yield. $^1$H-NMR (400 MHz, DMSO-D6): 8.46 (s, 1H, Ar); 7.39 (dd, J 2.7, 1.8 Hz, 1H, Ar); 7.16 (dd, J 3.8, 1.8 Hz, 1H, Ar); 6.50 (dd, J 3.8, 2.7 Hz, 1H, Ar); 3.68 (s, 3H, CH$_3$). M/Z (M[$^{35}$Cl][$^{35}$Cl]+H)$^+$=272.4.

Compound 12: 1-[3-Chloro-6-(2-methyl-pyridin-3-yl)-pyridazin-4-yl]-1H-pyrrole-2-carboxylic acid methyl ester Compound 12 was prepared according to procedure IV(ii), starting from compound 11 and 2-methylpyridine-3-boronic acid pinacol ester, and using PdCl$_2$(dppf).CH$_2$Cl$_2$ instead of XPhos precatalyst. Purification by flash column chromatography on silica gel (using 0% to 60% EtOAc in cyclohexane as eluent) afforded the product as a white solid in 63% yield. $^1$H-NMR (400 MHz, DMSO-D6): 8.63 (d, J 4.3 Hz, 1H, Ar); 8.36 (s, 1H, Ar); 7.98 (d, J 7.6 Hz, 1H, Ar); 7.46-7.42 (m, 2H, Ar); 7.16 (d, J 3.4 Hz, 1H, Ar); 6.50 (t, J 3.3 Hz, 1H, Ar); 3.68 (s, 3H, CH$_3$); 2.58 (s, 3H, CH$_3$). M/Z (M[$^{35}$Cl]+H)$^+$=329.4.

Compound 13: 1-[3-Cyano-6-(2-methyl-pyridin-3-yl)-pyridazin-4-yl]-1H-pyrrole-2-carboxylic acid methyl ester Under inert atmosphere, a mixture of compound 12 (1.0 equiv.), zinc cyanide (2.0 equiv.) and bis(tri-tert-butylphosphine)palladium (0.10 equiv.) in anhydrous DMA (0.20 mol·L$^{-1}$) was heated at 130° C. for 1 hour. After cooling to room temperature, the reaction mixture was taken in aqueous NaHCO$_3$ and extracted twice with EtOAc. The combined organic layers were washed with water, dried with brine and over MgSO$_4$, filtered off and concentrated under vacuum. Purification by flash column chromatography on silica gel (using 0% to 60% EtOAc in cyclohexane as eluent) afforded the product as a colorless oil in 73% yield. M/Z (M+H)$^+$=320.5.

Example 8: 5-Methyl-9-(2-methyl-pyridin-3-yl)-5,6-dihydro-5,7,8,10b-tetraaza-benzo[e]azulen-4-one, dihydrochloride

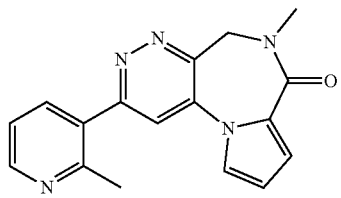 [SMILES: Cc1ncccc1-c1cc2c(nn1)CN(C)C(=O)c1cccn1-2]

Example 8 was prepared according to a similar sequence as example 7, starting from compound 13. Purification by flash column chromatography on silica gel (0% to 10% MeOH in dichloromethane) afforded the product as a white solid in 34% yield. $^1$H-NMR (400 MHz, DMSO-D6): 8.55 (dd, J 4.7, 1.8 Hz, 1H, Ar); 8.09 (s, 1H, Ar); 7.92 (d, J 7.7, 1.8 Hz, 1H, Ar); 7.74 (dd, J 2.9, 1.8 Hz, 1H, Ar); 7.37 (dd, J 7.7, 4.7 Hz, 1H, Ar); 6.97 (d, J 3.7, 1.8 Hz, 1H, Ar); 6.51 (dd, J 3.7, 2.9 Hz, 1H, Ar); 4.73 (s, 2H, CH$_2$); 3.10 (s, 3H, CH$_3$); 2.51 (s, 3H, CH$_3$). M/Z (M+H)$^+$=306.5. MP>250° C.

Compound 14: (2,6-Dichloro-pyridin-3-ylmethyl)-methyl-amine

A solution of 2,6-dichloropyridine-3-carboxaldehyde (1.0 equiv.) and methylamine (2M solution in THF, 2.0 equiv.) in MeOH (0.2 mol·L$^{-1}$) was stirred at room temperature for 1 hour. Sodium borohydride (8.0 equiv.) was slowly added and the reaction mixture was stirred for 1 hour at room temperature before being hydrolysed and extracted twice with dichloromethane. The combined extracts were dried with brine and MgSO$_4$, filtered off and concentrated under vacuum. Purification by column chromatography on silica gel (using 0% to 10% MeOH in dichloromethane as eluent) afforded the product as a colorless oil in 84% yield. $^1$H-NMR (400 MHz, DMSO-D6): 7.97 (d, J 8.0 Hz, 1H, Ar); 7.57 (d, J 8.0 Hz, 1H, Ar); 3.68 (s, 2H, CH$_2$); 2.29 (s, 3H, CH$_3$). Proton for NH not observed.

Compound 15: 1H-Pyrrole-2-carboxylic acid (2,6-dichloro-pyridin-3-ylmethyl)-methyl-amide At 0° C., to a solution of compound 14 (1.0 equiv.) and triethylamine (5.0 equiv.) in dichloromethane (0.15 mol·L$^{-1}$), 1H-pyrrole-2-carbonyl chloride (1.3 equiv.) was slowly added. The reaction mixture was stirred at room temperature for 1 hour before being hydrolyzed with NaHCO$_3$ and extracted twice with dichloromethane. The combined organic layers were dried with brine and over MgSO$_4$, filtered off and concentrated under vacuum. Purification by column chromatography on silica gel (using 0% to 10% MeOH in dichloromethane as eluent) afforded the product as a beige solid in 79% yield. $^1$H-NMR (400 MHz, DMSO-D6): 11.65 (bs, 1H, NH); 7.77 (d, J 8.0 Hz, 1H, Ar); 7.64 (d, J 8.0 Hz, 1H, Ar); 6.99 (m, 1H, Ar); 6.59 (bs, 1H, Ar); 6.20 (m, 1H, Ar); 4.81 (m, 2H, Ar); 3.37 (s, 3H, CH$_3$). M/Z (M[$^{35}$Cl][$^{35}$Cl]+H)$^+$=284.5.

Example 9: 9-Chloro-5-methyl-5,6-dihydro-5,10,10b-triaza-benzo[e]azulen-4-one

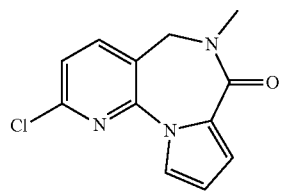 [SMILES: CN1Cc2ccc(Cl)nc2-n2cccc2C1=O]

At room temperature, sodium hydride (60% dispersion in oil, 1.2 equiv.) was added to a solution of compound 15 in dry DMA (0.15 mol·L−1). After 10 minutes stirring, the reaction mixture was heated at 100° C. for 1 hour before being hydrolyzed with NH$_4$Cl and extracted twice with EtOAc. The combined organic layers were dried with brine and over MgSO$_4$, filtered off and concentrated under vacuum. Purification by column chromatography on silica gel (using 0% to 10% MeOH in dichloromethane as eluent) afforded example 9 as a beige solid in 71% yield. $^1$H-NMR (400 MHz, DMSO-D6): 8.19 (d, J 7.8 Hz, 1H, Ar); 7.71 (dd, J 2.9, 1.9 Hz, 1H, Ar); 7.60 (d, J 7.8 Hz, 1H, Ar); 7.03 (dd, J 3.7, 1.9 Hz, 1H, Ar); 6.51 (dd, J 3.7, 2.9 Hz, 1H, Ar); 4.46 (s, 2H, CH$_2$); 3.13 (s, 3H, CH$_3$). M/Z (M[$^{35}$Cl]+H)+=248.5.

Example 10: 5-Methyl-9-(2-methyl-pyridin-3-yl)-5,6-dihydro-5,10,10 b-triaza-benzo[e]azulen-4-one

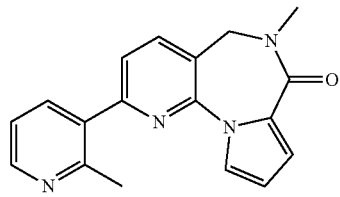 [SMILES: Cc1ncccc1-c1ccc2c(n1)-n1cccc1C(=O)N(C)C2]

Example 10 was prepared according to general procedure IV(i), starting from example 9 and 2-methylpyridine-3-boronic acid pinacol ester. Purification by column chromatography on silica gel (using 0% to 10% MeOH in dichloromethane as eluent) afforded the product as a beige solid in 50% yield. $^1$H-NMR (400 MHz, DMSO-D6): 8.52 (dd, J 4.8, 1.8 Hz, 1H, Ar); 8.17 (d, J 7.7 Hz, 1H, Ar); 7.91 (dd, J 7.7, 1.8 Hz, 1H, Ar); 7.74 (dd, J 2.8, 1.9 Hz, 1H, Ar); 7.64 (d, J 7.7 Hz, 1H, Ar); 7.36 (dd, J 7.7, 4.8 Hz, 1H, Ar); 6.95 (dd, J 3.8, 1.9 Hz, 1H, Ar); 6.42 (dd, J 3.8, 2.8 Hz, 1H, Ar); 4.45 (s, 2H, CH$_2$); 3.10 (s, 3H, CH$_3$); 2.59 (s, 3H, CH$_3$). M/Z (M+H)$^+$=305.6.

Compound 16: (5-Chloro-3-fluoro-pyridin-2-ylmethyl)-methyl-amine

Compound 16 was prepared according to procedure of compound 14, starting from 5-chloro-3-fluoropyridine-2-carbaldehyde. Purification by column chromatography on silica gel (using 0% to 10% MeOH in dichloromethane as eluent) afforded the product as a yellow oil in 68% yield. $^1$H-NMR (400 MHz, DMSO-D6): 8.48 (d, J 2.1 Hz, 1H, Ar); 8.03 (dd, J 9.5, 2.1 Hz, 1H, Ar); 3.77 (d, J 2.3 Hz, 2H, CH$_2$); 2.27 (s, 3H, OH$_3$); 2.15 (bs, 1H, NH).

Example 11: 3-(5-Methyl-4-oxo-5,6-dihydro-4H-5,7,1 b-triaza-benzo[e]azulen-9-yl)-benzonitrile

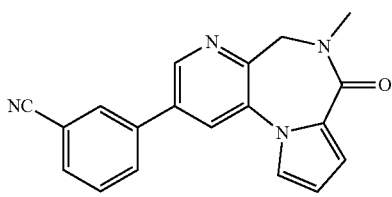 [SMILES: CN1Cc2ncc(-c3cccc(C#N)c3)cc2-n2cccc2C1=O]

Example 11 was prepared according to synthetic route of scheme 2, in a similar sequence as for example 10, and starting from compound 16. 3-benzonitrile boronic acid was used in the last step with general procedure IV(i). Purification by column chromatography on silica gel (using 0% to 10% MeOH in dichloromethane as eluent) and trituration in Et$_2$O afforded example 11 as a white solid in 25% yield. $^1$H-NMR (400 MHz, DMSO-D6): 8.88 (d, J 1.9, Hz, 1H, Ar); 8.45 (s, 1H, Ar); 8.36 (d, J 1.9 Hz, 1H, Ar); 8.25 (d, J 7.9 Hz, 1H, Ar); 7.94 (d, J 7.9 Hz, 1H, Ar); 7.79 (dd, J 2.8, 1.9 Hz, 1H, Ar); 7.75 (t, J 7.9 Hz, 1H, Ar); 6.95 (dd, J 3.8, 1.9 Hz, 1H, Ar); 6.51 (dd, J 3.8, 2.8 Hz, 1H, Ar); 4.53 (s, 2H, CH$_2$); 3.11 (s, 3H, CH$_3$). M/Z (M+H)$^+$=315.5.

Example 12: 9-Imidazo[1,2-a]pyridin-6-yl-5-methyl-5,6-dihydro-5,7,10b-triaza-benzo[e]azulen-4-one

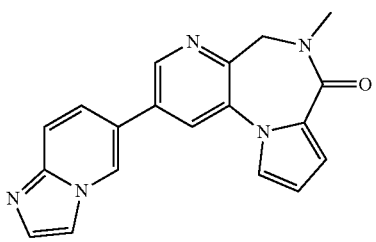 [SMILES: CN1Cc2ncc(-c3ccc4nccn4c3)cc2-n2cccc2C1=O]

Example 12 was prepared according to procedure of example 11 and using imidazo[1,2-a]pyridine-6-boronic acid in the last step with general procedure IV(i). Purification by column chromatography on silica gel (using 0% to 10% MeOH in dichloromethane as eluent) and trituration in Et$_2$O afforded example 12 as a white solid in 26% yield. $^1$H-NMR (400 MHz, DMSO-D6): 9.22 (d, J 1.8 Hz, 1H, Ar); 8.91 (d, J 1.9, Hz, 1H, Ar); 8.38 (d, J 1.9 Hz, 1H, Ar); 8.04 (s, 1H, Ar); 7.85 (d, J 9.5, 1.8 Hz, 1H, Ar); 7.82 (dd, J 2.8, 1.9 Hz, 1H, Ar); 7.78 (d, J 9.5 Hz, 1H, Ar); 7.72 (d, J 1.2 Hz, 1H, Ar); 7.02 (dd, J 3.8, 1.9 Hz, 1H, Ar); 6.57 (dd, J 3.8, 2.8 Hz, 1H, Ar); 4.59 (s, 2H, CH$_2$); 3.18 (s, 3H, CH$_3$). M/Z (M+H)$^+$=330.5.

Compound 17: 1H-Pyrrole-2-carboxylic acid (2,4-dichloro-pyrimidin-5-ylmethyl)-methyl-amide Under dry atmosphere, at –78° C., a solution of 2,4-dichloro-5-iodomethylpyridine (1.0 equiv.) in anhydrous THF (0.30 mol·L$^{-1}$) was added dropwise to a solution of methylamine (3.0 equiv.) in anhydrous THF (0.30 mol·L$^{-1}$). After 30 minutes, always at –78° C., a solution of 1H-pyrrole-2-carbonyl chloride (1.0 equiv.) in anhydrous THF (0.30 mol·L$^{-1}$) was added dropwise and the reaction mixture was allowed to reach room temperature over 1 hour. At 0° C., the reaction mixture was neutralized by addition of aqueous HCl (1N) and extracted twice with dichloromethane. The combined extracts were dried with brine and MgSO$_4$, filtered off and concentrated under vacuum. Purification by column chromatography on silica gel (using 0% to 40% ethyl acetate in cyclohexane as eluent) afforded the product as a white solid in 32% yield. $^1$H-NMR (400 MHz, DMSO-D6): 11.50 (bs, 1H, NH); 8.63 (s, 1H, Ar); 6.93 (m, 1H, Ar); 6.59 (m, 1H, Ar); 6.14 (m, 1H, Ar); 4.74 (s, 2H, CH$_2$); 3.27 (s, 3H, CH$_3$). M/Z (M[$^{35}$Cl][$^{35}$Cl]+H)$^+$=285.4.

Example 13: 9-Chloro-5-methyl-5,6-dihydro-5,8,10,10b-tetraaza-benzo[e]azulen-4-one

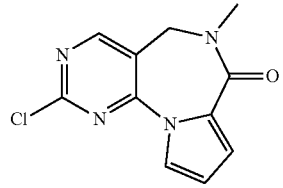 [SMILES: CN1Cc2cnc(Cl)nc2-n2cccc2C1=O]

At 0° C., to a solution of compound 17 (1.0 equiv.) in anhydrous DMA (0.10 mol·L$^{-1}$), sodium hydride (1.1 equiv.) was slowly added and the reaction mixture was stirred at room temperature for 2 hours. At 0° C., the reaction mixture was neutralized by addition of aqueous HCl (1N) and extracted twice with EtOAc. The combined extracts were washed with water, dried with brine and over MgSO$_4$, filtered off and concentrated under vacuum. Purification by trituration in iPr$_2$O afforded example 13 as a yellow solid in 87% yield. $^1$H-NMR (400 MHz, DMSO-D6): 8.90 (s, 1H, Ar); 7.76 (dd, J 3.1, 1.9 Hz, 1H, Ar); 7.09 (dd, J 3.7, 1.9 Hz, 1H, Ar); 6.54 (t, J 3.3 Hz, 1H, Ar); 4.44 (s, 2H, CH$_2$); 3.08 (s, 3H, CH$_3$). M/Z (M[$^{35}$Cl]+H)$^+$=249.5.

Example 14: 5-Methyl-9-(2-methyl-pyridin-3-yl)-5,6-dihydro-5,8,10,10 b-tetraaza-benzo[e]azulen-4-one

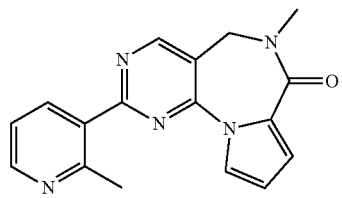 [SMILES: Cc1ncccc1-c1ncc2c(n1)-n1cccc1C(=O)N(C)C2]

Example 14 was prepared according to general procedure IV(i) starting from example 13 in presence of 2-methylpyridine-3-boronic acid pinacol ester and heating at 80° C. for 1 hour. Purification by flash column chromatography on silica gel (using 0% to 6% MeOH in dichloromethane as eluent) and tritutation in iPr$_2$O afforded example 14 as a beige solid in 29% yield. $^1$H-NMR (400 MHz, DMSO-D6): 9.10 (s, 1H, Ar); 8.59 (dd, J 4.8, 1.7 Hz, 1H, Ar); 8.32 (dd, J 7.8, 1.7 Hz, 1H, Ar); 7.93 (dd, J 3.0, 1.9 Hz, 1H, Ar); 7.41 (dd, J 7.8, 4.8 Hz, 1H, Ar); 7.09 (dd, J 3.6, 1.9 Hz, 1H, Ar); 6.54 (t, J 3.3 Hz, 1H, Ar); 4.51 (s, 2H, CH$_2$); 3.14 (s, 3H, CH$_3$); 2.79 (s, 3H, CH$_3$). M/Z (M[$^{35}$Cl]+H)$^+$=306.6.

Compound 18: 1-(4-Bromo-2-fluoro-phenyl)-cyclobutanecarbonitrile

Under dry atmosphere, at 0° C., a solution of 4-bromo-2-fluorobenzylcyanide (1.0 equiv.) and 1,3-dibromopropane (1.1 equiv.) in diethylether (3.0 mol·L$^{-1}$) was added dropwise to a suspension of sodium hydride (2.2 equiv.) in anhydrous DMA (0.10 mol·L$^{-1}$). The resulting yellow mixture was stirred at room temperature for 1 hour. At 0° C., the reaction mixture was neutralized by addition of aqueous ammonium chloride and extracted twice with ethyl acetate. The combined extracts were dried with brine and MgSO$_4$, filtered off and concentrated under vacuum. Purification by column chromatography on silica gel (using 0% to 10% ethyl acetate in cyclohexane as eluent) afforded the product as a colorless oil in 63% yield. $^1$H-NMR (400 MHz, DMSO-D6): 7.66 (dd, J 10.3, 1.9 Hz, 1H, Ar); 7.52-7.49 (m, 1H, Ar); 7.40 (t, J 8.4 Hz, 1H, Ar); 2.77-2.61 (m, 4H, cyclobutyl); 2.31 (m, 1H, cyclobutyl); 1.97 (m, 1H, cyclobutyl). Product not observed in mass spectrum ES+.

Compound 19: 1-(4-Bromo-2-fluoro-phenyl)-cyclobutanecarboxylic acid

Aqueous hydrogen peroxide (2.0 equiv.) was added to a suspension of compound 18 (1.0 equiv.) and potassium carbonate (0.2 equiv.) in DMSO (0.10 mol·L$^{-1}$). The reaction mixture was stirred at room temperature for 16 hours before being partitioned between water and ethyl acetate and extracted twice with ethyl acetate. The combined extracts were dried with brine and MgSO$_4$, filtered off and concentrated under vacuum. Purification by column chromatography on silica gel (using 0% to 20% ethyl acetate in cyclohexane as eluent) afforded the intermediate carboxamide as a colorless oil in quantitative yield. M/Z (M[$^{79}$Br]+H)$^+$=272.5.

The carboxamide (1.0 equiv.) was dissolved in dioxane (0.20 mol·L$^{-1}$) and an aqueous 3N solution of HCl (0.20 mol·L$^{-1}$) was added. The resulting solution was heated at 100° C. for 16 hours. After cooling to room temperature, the mixture was extracted twice with ethyl ecetate. The combined extracts were dried with brine and MgSO$_4$, filtered off and concentrated under vacuum to give compound 19 as a white solid in 99% yield. $^1$H-NMR (400 MHz, DMSO-D6): 12.52 (bs, 1H, COOH); 7.46 (dd, J 10.3, 1.9 Hz, 1H, Ar); 7.40 (dd, J 8.1, 1.9 Hz, 1H, Ar); 7.30 (t, J 8.4 Hz, 1H, Ar); 2.66 (m, 2H, cyclobutyl); 2.42 (m, 2H, cyclobutyl); 2.10 (m, 1H, cyclobutyl); 1.84 (m, 1H, cyclobutyl). M/Z (M[$^{79}$Br]+H)+=273.5.

Compound 20: 1-(4-Bromo-2-fluoro-phenyl)-cyclobutylamine

Diphenylphosphonyl azide (1.3 equiv.) was added to a solution of compound 19 (1.0 equiv.) and triethylamine (1.3 equiv.) in dioxane (0.30 mol·L$^{-1}$). The reaction mixture was stirred at room temperature for 2 hours before being treated with water and extracted twice with dichloromethane. The crude isocyanate was dissolved in aqueous HCl (2N, 0.10 mol·L$^{-1}$) and the resulting solution was heated at 60° C. for 16 hours. After cooling to room temperature, the mixture was neutralized with potassium carbonate and extracted twice with ethyl ecetate. The combined extracts were dried with brine and MgSO$_4$, filtered and concentrated under vacuum. Purification by column chromatography on silica gel (using 0% to 4% MeOH in dichloromethane as eluent) afforded compound 20 as a colorless residue in 80% yield. $^1$H-NMR (400 MHz, DMSO-D6): 7.43 (dd, J 10.3, 1.9 Hz, 1H, Ar); 7.35 (dd, J 8.1, 1.9 Hz, 1H, Ar); 7.24 (t, J 8.4 Hz, 1H, Ar); 2.39 (m, 2H, cyclobutyl); 2.09 (m, 5H, 3H cyclobutyl+NH$_2$); 1.67 (m, 1H, cyclobutyl). M/Z (M[$^{79}$Br]+H—NH$_2$)$^+$=229.4.

Compound 21: 1H-Pyrrole-2-carboxylic acid [1-(4-bromo-2-fluoro-phenyl)-cyclobutyl]-amide Benzotriazol-1-yloxytris(dimethylamino)phosphonium hexafluorophosphate (1.3 equiv.) was added to a solution of compound 20 (1.0 equiv.) and diisopropylethylamine (3.0 equiv.) in THF (0.20 mol·L$^{-1}$). The reaction mixture was stirred at room temperature for 16 hours before being treated with water and extracted twice with ethyl acetate. The combined extracts were dried with brine and MgSO$_4$, filtered off and concentrated under vacuum. Purification by column chromatography on silica gel (using 0% to 20% ethyl acetate in cyclohexane as eluent) afforded compound 21 as a white solid in 98% yield. $^1$H-NMR (400 MHz, DMSO-D6): 11.25 (bs, 1H, NH); 8.46 (s, 1H, NH); 7.46 (t, J 8.5 Hz, 1H, Ar); 7.40 (dd, J 10.8, 1.9 Hz, 1H, Ar); 7.34 (dd, J 8.3, 1.9 Hz, 1H, Ar); 6.86 (m, 1H, Ar); 6.81 (m, 1H, Ar); 6.05 (m, 1H, Ar); 2.59 (m, 4H, cyclobutyl); 2.06 (m, 1H, cyclobutyl); 1.80 (m, 1H, cyclobutyl). M/Z (M[79Br]+H)$^+$=337.4.

Compound 22: 9-Bromo-5,6-dihydro-spiro[benzo[f]pyrrolo[1,2-a][1,4]diazepine-6,1'-cyclobutan]-4-one A suspension of compound 21 (1.0 equiv.) and potassium carbonate (2.0 equiv.) in anhydrous DMA (0.15 mol·L$^{-1}$) was subjected to microwave irradiation at 190° C. for 1 hour and again at 210° C. for 1 hour to complete the conversion. After cooling to room temperature, the reaction mixture was treated with water and extracted twice with ethyl acetate. The combined extracts were dried with brine and MgSO$_4$, filtered off and concentrated under vacuum. Purification by column chromatography on silica gel (using 0% to 80% ethyl acetate in cyclohexane as eluent) afforded compound 22 as a beige solid in 57% yield. $^1$H-NMR (400 MHz, DMSO-D6): 8.68 (s, 1H, NH); 7.68 (d, J 1.9 Hz, 1H, Ar); 7.57 (dd, J 8.2, 1.9 Hz, 1H, Ar); 7.53 (dd, J 2.8, 1.8 Hz, 1H, Ar); 7.46 (d, J 8.2 Hz, 1H, Ar); 6.85 (dd, J 3.6, 1.8 Hz, 1H, Ar); 6.39 (dd, J 3.6, 2.8 Hz, 1H, Ar); 2.85 (m, 1H, cyclobutyl); 2.42 (m, 1H, cyclobutyl); 1.97 (m, 1H, cyclobutyl); 1.84 (m, 1H, cyclobutyl); 1.67 (m, 2H, cyclobutyl). M/Z (M[$^{79}$Br]+H)$^+$=317.4.

Example 15: 9-Bromo-5-methyl-5,6-dihydro-spiro[benzo[f]pyrrolo[1,2-a][1,4]diazepine-6,1'-cyclobutan]-4-one

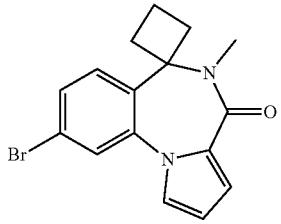 [SMILES: CN1C(=O)c2cccn2-c2cc(Br)ccc2C12CCC2]

Example 15 was obtained according to general procedure III, starting from compound 22 in presence of iodomethane. The reaction mixture was stirred at room temperature for 1 hour. Purification by column chromatography on silica gel (using 0% to 70% EtOAc in cyclohexane as eluent) afforded the product as a white solid in quantitative yield. $^1$H-NMR (400 MHz, DMSO-D6): 7.77 (d, J 1.9 Hz, 1H, Ar); 7.67 (d, J 8.3 Hz, 1H, Ar); 7.60 (dd, J 8.3, 1.9 Hz, 1H, Ar); 7.50 (dd, J 2.8, 1.8 Hz, 1H, Ar); 6.79 (dd, J 3.6, 1.8 Hz, 1H, Ar); 6.39 (dd, J 3.6, 2.8 Hz, 1H, Ar); 2.85 (m, 1H, cyclobutyl); 2.81 (s, 3H, CH$_3$); 2.64 (m, 1H, cyclobutyl); 2.07 (m, 1H, cyclobutyl); 1.69 (m, 1H, cyclobutyl); 1.39 (m, 2H, cyclobutyl). M/Z (M[$^{79}$Br]+H)$^+$=331.4.

Example 16: 9-(6-Fluoro-pyridin-3-yl)-5-methyl-5,6-dihydro-spiro[benzo[f]pyrrolo[1,2-a][1,4]diazepine-6,1'-cyclobutan]-4-one

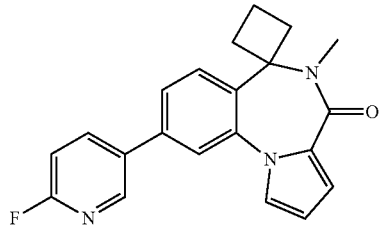 [SMILES: CN1C(=O)c2cccn2-c2cc(-c3ccc(F)nc3)ccc2C12CCC2]

Example 16 was prepared according to general procedure IV(i) starting from example 15 in presence of 6-fluoro-3-pyridinylboronic acid, at 100° C. for 2 hours. Purification by flash column chromatography on silica gel (using 0% to 100% EtOAc in cyclohexane as eluent) afforded example 16 as a beige solid in 93% yield. $^1$H-NMR (400 MHz, DMSO-D6): 8.70 (d, J 2.0 Hz, 1H, Ar); 8.44 (dt, J 8.3, 2.6 Hz, 1H, Ar); 7.86-7.83 (m, 2H, Ar); 7.75 (dd, J 8.0, 1.9 Hz, 1H, Ar); 7.65 (dd, J 2.8, 1.8 Hz, 1H, Ar); 7.33 (dd, J 8.5, 2.6 Hz, 1H, Ar); 6.81 (dd, J 3.6, 1.8 Hz, 1H, Ar); 6.41 (dd, J 3.6, 2.8 Hz, 1H, Ar); 2.94 (m, 1H, cyclobutyl); 2.85 (s, 3H, CH$_3$); 2.68 (m, 1H, cyclobutyl); 2.12 (m, 1H, cyclobutyl); 1.73 (m, 1H, cyclobutyl); 1.43 (m, 2H, cyclobutyl). M/Z (M+H)$^+$=348.6.

Example 17: 9-(2-Methyl-pyridin-3-yl)-5-methyl-5,6-dihydro-spiro[benzo[f]pyrrolo[, 2-a][1,4]diazepine-6,1'-cyclobutan]-4-one

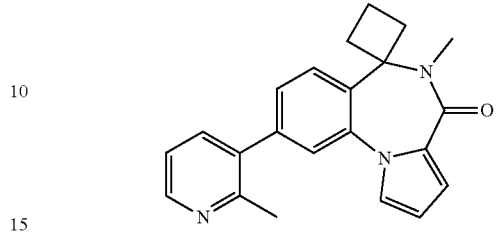

Example 17 was prepared according to general procedure IV(i), starting from example 15 and heating at 100° C. for 2 hours. Purification by flash column chromatography on silica gel (using 0% to 5% MeOH in dichloromethane as eluent) and trituration in Et$_2$O afforded example 17 as a beige solid in 92% yield. $^1$H-NMR (400 MHz, DMSO-D6): 8.49 (dd, J 4.8, 1.6 Hz, 1H, Ar); 7.80 (d, J 8.0 Hz, 1H, Ar); 7.76 (dd, J 7.7, 1.6 Hz, 1H, Ar); 7.57 (d, J 1.7 Hz, 1H, Ar); 7.52 (dd, J 2.8, 1.8 Hz, 1H, Ar); 7.46 (dd, J 8.0, 1.7 Hz, 1H, Ar); 7.33 (dd, J 7.7, 4.8 Hz, 1H, Ar); 6.80 (dd, J 3.7, 1.8 Hz, 1H, Ar); 6.38 (dd, J 3.7, 2.8 Hz, 1H, Ar); 2.97-2.90 (m, 1H, cyclobutyl); 2.86 (s, 3H, CH$_3$); 2.74-2.66 (m, 1H, cyclobutyl); 2.52 (s, 3H, CH$_3$); 2.17-2.07 (m, 1H, cyclobutyl); 1.77-1.70 (m, 1H, cyclobutyl); 1.50-1.42 (m, 2H, cyclobutyl). M/Z (M+H)$^+$=344.5.

Example 18: 9-(6-Fluoro-pyridin-2-yl)-5-methyl-5,6-dihydro-spiro[benzo[f]pyrrolo[1,2-a][1,4]diazepine-6,1'-cyclobutan]-4-one

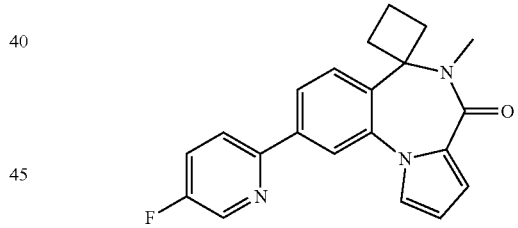

Under inert atmosphere, PdCl$_2$(dppf).CH$_2$Cl$_2$ (0.10 equiv.) was added to a suspension of example 15 (1.0 equiv.), bispinacolatodiboron (1.2 equiv.) and potassium acetate (2.7 equiv.) in dioxane (0.15 mol·L$^{-1}$). The reaction mixture was heated at 100° C. for 3 hours. After cooling to room temperature, potassium carbonate (3.0 equiv.) and a solution of 2-bromo-5-fluoropyridine (2.0 equiv.) in dioxane (0.90 mol·L$^{-1}$) were successively added. The reaction mixture was heated at 100° C. for 2 hours. After cooling to room temperature, the reaction mixture was treated with water and extracted twice with ethyl acetate. The combined extracts were dried with brine and MgSO$_4$, filtered off and concentrated under vacuum. Purification by column chromatography on silica gel (using 0% to 100% ethyl acetate in cyclohexane as eluent) and trituration in diethyl ether afforded example 18 as a white solid in 84% yield. $^1$H-NMR (400 MHz, DMSO-D6): 8.70 (d, J 3.0 Hz, 1H, Ar); 8.22 (dd, J 8.8, 4.4 Hz, 1H, Ar); 8.13 (d, J 1.7 Hz, 1H, Ar); 8.09 (dd, J 8.1, 1.7 Hz, 1H, Ar); 7.88 (dt, J 8.8, 3.0 Hz, 1H, Ar); 7.84

(d, J 8.1 Hz, 1H, Ar); 7.59 (dd, J 2.8, 1.8 Hz, 1H, Ar); 6.81 (dd, J 3.6, 1.8 Hz, 1H, Ar); 6.41 (dd, J 3.6, 2.8 Hz, 1H, Ar); 2.93 (m, 1H, cyclobutyl); 2.85 (s, 3H, CH$_3$); 2.68 (m, 1H, cyclobutyl); 2.12 (m, 1H, cyclobutyl); 1.72 (m, 1H, cyclobutyl); 1.44 (m, 2H, cyclobutyl). M/Z (M+H)$^+$=348.5.

General Procedure VI: Preparation of Intermediate C1 from Halogeno-Benzonitrile A and (Hetero)Aromatic Boronic Acid or Ester B1 (Scheme 3)

Under inert atmosphere, a mixture of halogeno-benzonitrile A (1.0 equiv.), boronic acid derivative B1 (1.1 equiv.) and PdCl$_2$(dppf).CH$_2$Cl$_2$ (0.10 equiv.) in a mixture of dioxane (0.10 mol·L) and aqueous K$_2$CO$_3$ (1.2 mol·L) was heated at 80° C. for 1 hour. After cooling to room temperature, the reaction mixture was hydrolyzed and extracted twice with EtOAc. The organic layers were combined, washed with brine, dried over MgSO$_4$, concentrated and purified to afford the product.

Compound 23: 4-Chloro-2-iodo-benzonitrile

Under inert atmosphere, a mixture of 4-chlorobenzonitrile (1 equiv.), N-iodosuccinimide (1.1 equiv.), p-toluenesulfonic acid (0.5 equiv.), palladium acetate (0.05 equiv.) in 1,2-dichloroethane (0.2 mol·L$^{-1}$) was heated at 70° C. for 16 hours. The mixture was concentrated under vacuum and purified by column chromatography on silica gel (using 0% to 50% EtOAc in cyclohexane as eluent) to afford the product as a white solid in 44% yield. $^1$H-NMR (400 MHz, DMSO-D6): 8.21 (d, J 2.0 Hz, 1H, Ar); 7.88 (d, J 8.3 Hz, 1H, Ar); 7.69 (dd, J 8.3, 2.0 Hz, 1H, Ar). Product not observed in mass spectrum ES+.

Compound 24: 4-Bromo-2-iodo-benzonitrile

Compound 24 was prepared according to procedure of compound 23, starting from 4-bromobenzonitrile. Purification by column chromatography on silica gel (using 0% to 10% EtOAc in cyclohexane as eluent) afforded compound 24 as a white solid in 41% yield. $^1$H-NMR (400 MHz, DMSO-D6): 8.33 (d, J 1.8 Hz, 1H, Ar); 7.84-7.70 (m, 2H, Ar). Product not observed in mass spectrum ES+.

Compound 25: 5'-Chloro-2'-cyano-biphenyl-2-carboxylic acid methyl ester

Compound 25 was prepared according to general procedure VI, starting from compound 23 and 2-methoxycarbonyl-phenylboronic acid. Purification by column chromatography on silica gel (using 0% to 20% EtOAc in cyclohexane as eluent) afforded the product as a white solid in 60% yield. $^1$H-NMR (400 MHz, DMSO-D6): 8.06 (dd, J 7.8, 1.2 Hz, 1H, Ar); 7.94 (d, J 8.3 Hz, 1H, Ar); 7.78-7.74 (m, 1H, Ar); 7.69-7.64 (m, 2H, Ar); 7.59 (d, J 1.9 Hz, 1H, Ar); 7.45 (dd, J 7.7, 1.2 Hz, 1H, Ar); 3.67 (s, 3H, CH$_3$). M/Z (M[$^{35}$Cl]+H)$^+$=239.8.

Compound 26: 5'-Bromo-4-chloro-2'-cyano-biphenyl-2-carboxylic acid methyl ester

Compound 26 was prepared according to general procedure VI, starting from compound 24 and 5-Chloro-2-(4,4,5,5-tetramethyl-[1,3,2]dioxaborolan-2-yl)-benzoic acid methyl ester. Purification by column chromatography on silica gel (using 0% to 10% EtOAc in cyclohexane as eluent) afforded the product as a white solid in 36% yield. $^1$H-NMR (400 MHz, DMSO-D6): 8.04 (d, J 8.2 Hz, 1H, Ar); 7.87-7.81 (m, 3H, Ar); 7.75 (d, J 1.8 Hz, 1H, Ar); 7.51 (d, J 8.2 Hz, 1H, Ar); 3.68 (s, 3H, CH$_3$). M/Z (M[$^{35}$Cl][$^{80}$Br]+H)$^+$=319.9.

Compound 27: 10-Chloro-6,7-dihydro-spiro[dibenzo[c, e]azepine-7,1'-cyclopropan]-5-one Compound 27 was obtained according to general procedure II, starting from compound 25. The reaction was completed by addition of ethylmagnesium bromide (1M solution in THF, 1 equiv.) and titanium isopropoxide (1 equiv.). Purification by column chromatography on silica gel (using 10% to 60% EtOAc in cyclohexane as eluent) afforded the product as a white solid in 72% yield. M/Z (M[$^{35}$Cl]+H)$^+$=269.9.

Compound 28: 10-Bromo-3-chloro-6,7-dihydro-spiro[dibenzo[c,e]azepine-7,1'-cyclopropan]-5-one Compound 28 was obtained according to general procedure II, starting from compound 26. The reaction was completed by addition of ethylmagnesium bromide (1M solution in THF, 2.5 equiv.) and titanium isopropoxide (1 equiv.). Purification by column chromatography on silica gel (using 10% to 60% EtOAc in cyclohexane as eluent) afforded the product as a white solid in 60% yield. $^1$H-NMR (400 MHz, DMSO-D6): 9.08 (s, 1H, NH); 7.83 (s, 1H, Ar); 7.75-7.70 (m, 3H, Ar); 7.60 (d, J 8.0 Hz, 1H, Ar); 7.33 (d, J 8.0 Hz, 1H, Ar); 1.47 (m, 1H, cyclopropyl); 1.13 (m, 1H, cyclopropyl); 0.77 (m, 1H, cyclopropyl); 0.32 (m, 1H, cyclopropyl). M/Z (M[$^{35}$Cl][$^{80}$Br]+H)$^+$=349.9.

Example 19: 10-Chloro-6-methyl-6,7-dihydro-spiro[dibenzo[c,e]azepine-7,1'-cyclopropan]-5-one

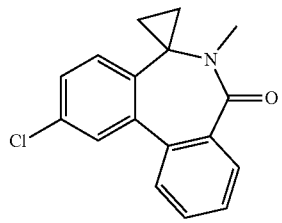

Example 19 was obtained according to general procedure III, starting from compound 27 in presence of iodomethane. The reaction mixture was stirred at room temperature for 1 hour. Purification by column chromatography on silica gel (using 0% to 50% EtOAc in cyclohexane as eluent) afforded the product as a white solid in 58% yield. $^1$H-NMR (400 MHz, DMSO-D6): 7.75-7.73 (m, 2H, Ar); 7.67-7.61 (m, 2H, Ar); 7.57-7.53 (m, 1H, Ar); 7.47 (m, 2H, Ar); 2.94 (s, 3H, CH$_3$); 1.39 (m, 2H, cyclopropyl); 0.81 (m, 1H, cyclopropyl); 0.32 (m, 1H, cyclopropyl). M/Z (M[$^{35}$Cl]+H)$^+$=239.8.

Example 20: 10-Bromo-3-chloro-6-methyl-6,7-dihydro-spiro[dibenzo[c,e]azepine-7,1'-cyclopropan]-5-one

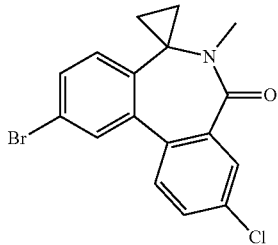 [SMILES: CN1C(=O)c2cc(Cl)ccc2-c2cc(Br)ccc2C12CC2]

Example 20 was obtained according to general procedure III, starting from compound 26 in presence of iodomethane. The reaction mixture was stirred at room temperature for 1 hour. Purification by column chromatography on silica gel (using 0% to 2% MeOH in dichloromethane as eluent) afforded the product as a white solid in 90% yield. $^1$H-NMR (400 MHz, DMSO-D6): 7.89 (s, 1H, Ar); 7.71-7.67 (m, 3H, Ar); 7.69 (d, J 8.0 Hz, 1H, Ar); 7.42 (d, J 8.0 Hz, 1H, Ar); 2.93 (s, 3H, CH$_3$); 1.42 (m, 2H, cyclopropyl); 0.90 (m, 1H, cyclopropyl); 0.35 (m, 1H, cyclopropyl). M/Z (M[$^{35}$Cl][$^{80}$Br]+H)$^+$=364.2.

Example 21: 10-(2-Methyl-pyridin-3-yl)-6-methyl-6,7-dihydro-spiro[dibenzo[c,e]azepine-7,1'-cyclopropan]-5-one, hydrochloride

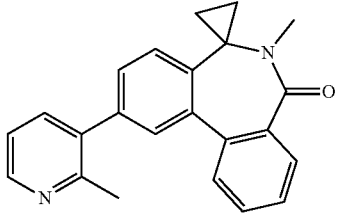 [SMILES: Cc1ncccc1-c1ccc2c(c1)-c1ccccc1C(=O)N(C)C21CC1]

Example 21 was prepared according to general procedure IV(ii), starting from example 19 and heating at 100° C. for 1 hour. Purification by column chromatography on silica gel (using 20% to 100% EtOAc in cyclohexane as eluent) afforded the product as a white solid in 67% yield. Salt formation was performed according to method V(i). $^1$H-NMR (400 MHz, DMSO-D6): 8.75 (dd, J 5.5, 1.3 Hz, 1H, Ar); 8.40 (d, J 7.9 Hz, 1H, Ar); 7.85 (dd, J 7.9, 5.5 Hz, 1H, Ar); 7.82 (d, J 1.6 Hz, 1H, Ar); 7.77 (dd, J 7.7, 1.3 Hz, 1H, Ar); 7.71 (dd, J 7.7, 1.0 Hz, 1H, Ar); 7.66-7.61 (m, 2H, Ar); 7.57-7.53 (m, 2H, Ar); 2.99 (s, 3H, CH$_3$); 2.70 (s, 3H, CH$_3$); 1.47 (m, 2H, cyclopropyl); 0.87 (m, 1H, cyclopropyl); 0.39 (m, 1H, cyclopropyl). M/Z (M+H)$^+$=340.9. MP>250° C.

Example 22: 3-Chloro-10-(2-methyl-pyridin-3-yl)-6-methyl-6,7-dihydro-spiro[dibenzo[c, e]azepine-7,1'-cyclopropan]-5-one

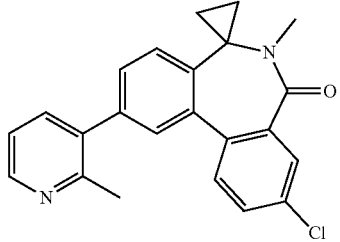 [SMILES: Cc1ncccc1-c1ccc2c(c1)-c1ccc(Cl)cc1C(=O)N(C)C21CC1]

Example 22 was prepared according to general procedure IV(i), starting from example 20 and heating at 100° C. for 1 hour. Purification by column chromatography on silica gel (using 0% to 4% MeOH in dichloromethane as eluent) afforded the product as a white solid in 61% yield. $^1$H-NMR (400 MHz, DMSO-D6): 8.47 (dd, J 4.9, 1.4 Hz, 1H, Ar); 7.76-7.69 (m, 4H, Ar); 7.67 (dd, J 8.5, 2.2 Hz, 1H, Ar); 7.55 (d, J 7.9 Hz, 1H, Ar); 7.47 (dd, J 7.7, 1.4 Hz, 1H, Ar); 7.31 (dd, J 7.7, 4.9 Hz, 1H, Ar); 2.98 (s, 3H, CH$_3$); 2.47 (s, 3H, CH$_3$); 1.46 (m, 2H, cyclopropyl); 0.93 (m, 1H, cyclopropyl); 0.40 (m, 1H, cyclopropyl). M/Z (M[$^{35}$Cl]+H)$^+$=375.3.

Example 23: 3-(2-Methyl-2H-pyrazol-3-yl)-10-(2-methyl-pyridin-3-yl)-6-methyl-6,7-dihydro-spiro[dibenzo[c, e]azepine-7,1'-cyclopropan]-5-one

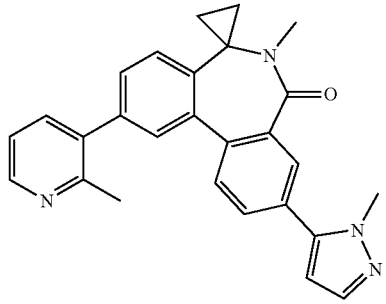 [SMILES: Cc1ncccc1-c1ccc2c(c1)-c1ccc(-c3ccnn3C)cc1C(=O)N(C)C21CC1]

Example 23 was obtained according to general procedure IV(ii), starting from example 22 and 1-methyl-5-(4,4,5,5-tetramethyl-[1,3,2]dioxaborolan-2-yl)-1H-pyrazole and heating at 100° C. for 1 hour. Purification by flash column chromatography on silica gel (0% to 5% MeOH in dichloromethane) afforded example 23 as a yellow solid in 18% yield. $^1$H-NMR (400 MHz, DMSO-D6): 8.46 (dd, J 4.8, 1.7 Hz, 1H, Ar); 7.85 (d, J 1.7 Hz, 1H, Ar); 7.82 (d, J 8.0 Hz, 1H, Ar); 7.78 (dd, J 8.3, 1.7 Hz, 1H, Ar); 7.74-7.71 (m, 2H, Ar); 7.57 (d, J 7.8 Hz, 1H, Ar); 7.51 (d, J 1.9 Hz, 1H, Ar); 7.48 (dd, J 7.7, 1.7 Hz, 1H, Ar); 7.33 (dd, J 7.7, 4.8 Hz, 1H, Ar); 6.54 (d, J 1.9 Hz, 1H, Ar); 3.92 (s, 3H, CH$_3$); 2.99 (s, 3H, CH$_3$); 2.49 (s, 3H, CH$_3$); 1.47 (m, 2H, cyclopropyl); 0.96 (m, 1H, cyclopropyl); 0.42 (m, 1H, cyclopropyl). M/Z (M+H)$^+$=421.6.

Compound 29: 4-Chloro-2-(4,4,5,5-tetramethyl-[1,3,2]dioxaborolan-2-yl)-benzaldehyde Under inert atmosphere, a mixture of 2-bromo-4-chlorobenzaldehyde (1.0 equiv.), bispinacolatodiboron (2.0 equiv.), potassium acetate (2.0 equiv.) and PdCl$_2$(dppf).CH$_2$Cl$_2$ (0.1 equiv.) in dioxane (0.10 mol·L$^{-1}$) was heated at 80° C. for 3 hours. After cooling, the reaction mixture was hydrolyzed and extracted twice with EtOAc. The combined organic layers were dried with brine and over MgSO$_4$, filtered off and concentrated under vacuum. Purification by flash column chromatography on silica gel (using dichloromethane as eluent) afforded the product as a beige solid in 55% yield. $^1$H-NMR (400 MHz, DMSO-D6): 10.27 (s, 1H, CHO); 7.93 (d, J 8.2 Hz, 1H, Ar); 7.74 (dd, J 8.2, 2.1 Hz, 1H, Ar); 7.69 (d, J 2.1 Hz, 1H, Ar); 1.35 (s, 12H, 4CH$_3$).

Compound 30:
3-(5-Chloro-2-formyl-phenyl)-pyridine-2-carboxylic acid methyl ester Under inert atmosphere, a mixture of compound 29 (1.0 equiv.), methyl 3-bromopicolinate (1.0 equiv.), cesium fluoride (3.0 equiv.) and PdCl$_2$(dppf).CH$_2$Cl$_2$ (0.10 equiv.) in anhydrous THF (0.20 mol·L$^{-1}$) was heated at 70° C. for 3 hours. After cooling, the reaction mixture was hydrolyzed and extracted twice with EtOAc. The combined organic layers were dried with brine and over MgSO$_4$, filtered off and concentrated under vacuum. Purification by flash column chromatography on silica gel (using 0% to 60% ethyl acetate in cyclohexane as eluent) afforded the product as a yellow oil in 33% yield. M/Z (M[$^{35}$Cl]+H)$^+$=276.5.

Compound 31:
3-(5-Chloro-2-formyl-phenyl)-pyridine-2-carboxylic acid methylamide A solution of compound 30 (1.0 equiv.) and methylamine (10 equiv.) in THF (0.2 mol·L$^{-1}$) was heated at 80° C. for 4 days before being concentrated under vacuum. Purification by flash column chromatography on silica gel (using 0% to 7% MeOH in dichloromethane as eluent) afforded the product as a colorless oil in 82% yield. M/Z (M[$^{35}$Cl]+H)$^+$=275.5.

Example 24: 10-Chloro-6-methyl-6,7-dihydro-4,6-diaza-dibenzo[a,c]cyclohepten-5-one

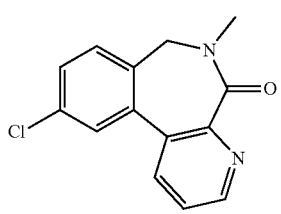 [SMILES: CN1Cc2ccc(Cl)cc2-c2cccnc2C1=O]

A mixture of compound 31 (1.0 equiv.), trifluoroacetic acid (2.0 equiv.) and triethylsilane (3.0 equiv.) in anhydrous acetonitrile (0.1 mol·L$^{-1}$) was refluxed for 16 hours. After cooling, the reaction mixture was neutralized with aqueous sodium bicarbonate and extracted twice with EtOAc. The combined organic layers were dried with brine and over MgSO$_4$, filtered off and concentrated under vacuum. Purification by flash column chromatography on silica gel (using 0% to 4% MeOH in dichloromethane as eluent) afforded example 24 as a beige solid in 59% yield. $^1$H-NMR (400 MHz, DMSO-D6): 8.75 (dd, J 4.7, 1.6 Hz, 1H, Ar); 8.16 (d, J 8.1, 1.6 Hz, 1H, Ar); 7.86 (d, J 2.1 Hz, 1H, Ar); 7.66-7.61 (m, 2H, Ar); 7.55 (dd, J 8.1, 2.1 Hz, 1H, Ar); 4.29 (d, J 15.2 Hz, 1H, CHaHb); 4.24 (d, J 15.2 Hz, 1H, CHaHb); 3.04 (s, 3H, OH$_3$); M/Z (M[$^{35}$Cl]+H)$^+$=259.5.

Example 25: 3-(6-Methyl-5-oxo-6,7-dihydro-5H-4,6-diaza-dibenzo[a,c]cyclohepten-10-yl)-benzonitrile

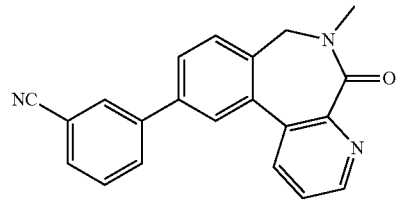 [SMILES: CN1Cc2ccc(-c3cccc(C#N)c3)cc2-c2cccnc2C1=O]

Example 25 was prepared according to general procedure IV(ii), starting from example 24 and 3-cyanophenylboronic acid. Purification by column chromatography on silica gel (using 0% to 5% MeOH in dichloromethane as eluent) afforded example 25 as a beige solid in 66% yield. $^1$H-NMR (400 MHz, DMSO-D6): 8.75 (dd, J 4.6, 1.5 Hz, 1H, Ar); 8.36-8.34 (m, 2H, Ar); 8.18-8.13 (m, 2H, Ar); 7.87-7.84 (m, 2H, Ar); 7.72-7.65 (m, 3H, Ar); 4.37 (d, J 15.0 Hz, 1H, CHaHb); 4.28 (d, J 15.0 Hz, 1H, CHaHb); 3.07 (s, 3H, CH$_3$); M/Z (M+H)$^+$=326.4.

Compound 32:
(2-Bromo-4-chloro-benzyl)-methyl-carbamic acid tert-butyl ester

To a solution of 2-bromo-4-chlorobenzaldehyde (1.0 equiv.) in MeOH (0.20 mol·L$^{-1}$), methylamine (2M solution in THF, 1.1 equiv.) was added and the reaction mixture was stirred at room temperature for 2 hours. Sodium borohydride (1.2 equiv.) was slowly added and the resulting yellow mixture was stirred at room temperature for 1 hour. MeOH was removed under vacuum and the residue was dissolved in a mixture of THF (0.30 mol·L$^{-1}$) and saturated aqueous sodium bicarbonate (0.30 mol·L$^{-1}$). Di-tert-butyl-dicarbonate (1.0 equiv.) was added and the reaction mixture was stirred at room temperature for 2 hours, before being hydrolyzed and extracted twice with EtOAc. The organic layers were combined, washed with brine, dried over MgSO$_4$ and concentrated under vacuum. Purification by flash column chromatography on silica gel (using 0% to 20% ethyl acetate in cyclohexane as eluent) afforded the product as a yellow oil in 91% yield. $^1$H-NMR (400 MHz, DMSO-D6): 7.77 (d, J 2.1 Hz, 1H, Ar); 7.50 (dd, J 8.3, 2.1 Hz, 1H, Ar); 7.15 (d, J 8.3 Hz, 1H, Ar); 4.40 (s, 2H, CH$_2$); 2.82 (s, 3H, CH$_3$); 1.38 (s, 9H, tert-butyl). M/Z (M[$^{35}$Cl][$^{79}$Br]-tertbutyl)+=280.4.

Compound 33: [4-Chloro-2-(4,4,5,5-tetramethyl-[1,3,2]dioxaborolan-2-yl)-benzyl]-methyl-carbamic acid tert-butyl ester Compound 33 was prepared according to procedure of compound 29, starting from compound 32 and heating at 100° C. for 3 hours. Purification by flash column chromatography on silica gel (using 0% to 40% ethyl acetate in cyclohexane as eluent) afforded the product as a yellow oil in 77% yield. $^1$H-NMR (400 MHz, DMSO-D6): 7.49 (d, J 2.4 Hz, 1H, Ar); 7.42 (dd, J 8.3, 2.4 Hz, 1H, Ar); 7.03 (d, J 8.3 Hz, 1H, Ar); 4.48 (s, 2H, CH$_2$); 2.65 (s, 3H, CH$_3$); 1.29 (s, 9H, tert-butyl); 1.19 (s, 12H, 4CH$_3$). M/Z (M[$^{35}$Cl]-tertbutyl)$^+$=326.5.

General Procedure VII: Preparation of Intermediate C3 by Cross-Coupling Reaction Between Boronic A3 and Ester B2 (Scheme 5)

Under inert atmosphere, tetrakis(triphenylphosphine)palladium (0.10 equiv.) was added to a suspension of boronic acid or ester A3 (1.0 equiv.), halogeno-derivative B2 (1.0 equiv.) in dioxane (0.15 mol·L$^{-1}$) and aqueous K$_2$CO$_3$ (1.2 mol·L$^{-1}$). The reaction mixture was heated at 100° C. for 2 hours. After cooling, the reaction mixture was diluted in water and extracted twice with EtOAc. The organic layers were combined, washed with brine, dried over MgSO$_4$, concentrated and purified to afford the product.

Compound 34: 3-{2-[(tert-Butoxycarbonyl-methyl-amino)-methyl]-5-chloro-phenyl}-pyridine-2-carboxylic acid methyl ester Compound 34 was prepared according to general procedure VII, starting from compound 33 and methyl 3-bromopicolinate. Purification by flash column chromatography on silica gel (using 0% to 50% ethyl acetate in cyclohexane as eluent) afforded the product as a colorless oil in 79% yield. M/Z (M[$^{35}$Cl]-tertbutyl)$^+$=335.5.

General Procedure VIII: Preparation of Cyclized Compound F2 by Protecting Group Removal and Cyclization of Intermediate C3 (Scheme 5 and 6)

Intermediate C3 (1.0 equiv.) was dissolved in dichloromethane (0.15 mol·L$^{-1}$) and TFA was added (0.15 mol·L$^{-1}$). The reaction mixture was stirred at room temperature for 1 hour, before being concentrated under vacuum. The resulting crude oil was dissolved in dioxane (0.10 mol·L$^{-1}$) and triethylamine (3.0 equiv.) and the reaction mixture was heated at 100° C. for 1 hour. After cooling to room temperature, the reaction mixture was hydrolyzed and extracted twice with EtOAc. The organic layers were combined, washed with brine, dried over MgSO$_4$, concentrated and purified to afford the product.

Example 24 (Alternative Preparation: 10-Chloro-6-methyl-6,7-dihydro-4,6-diaza-dibenzo[a, c]cyclohepten-5-one Example 24 was prepared, this time using general procedure VIII and starting from compound 34. Purification by flash column chromatography on silica gel (using 0% to 4% MeOH in dichloromethane as eluent) afforded the product as a white solid in 84% yield. $^1$H-NMR (400 MHz, DMSO-D6): 8.75 (dd, J 4.7, 1.6 Hz, 1H, Ar); 8.16 (d, J 8.1, 1.6 Hz, 1H, Ar); 7.86 (d, J 2.1 Hz, 1H, Ar); 7.66-7.61 (m, 2H, Ar); 7.55 (dd, J 8.1, 2.1 Hz, 1H, Ar); 4.29 (d, J 15.2 Hz, 1H, CHaHb); 4.24 (d, J 15.2 Hz, 1H, CHa<u>Hb</u>); 3.04 (s, 3H, CH$_3$); M/Z (M[$^{35}$Cl]+H)$^+$=259.5.

Example 26: 6-Methyl-10-(2-methyl-pyridin-3-yl)-6,7-dihydro-4,6-diaza-dibenzo[a, c]cyclohepten-5-one

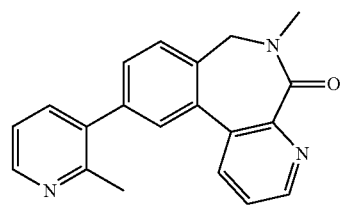 [SMILES: Cc1ncccc1-c1ccc2c(c1)-c1cccnc1C(=O)N(C)C2]

Example 26 was prepared according to general procedure IV(ii), starting from example 24 and 2-methylpyridine-3-boronic acid pinacol ester and heating at 100° C. for 1 hour. Purification by column chromatography on silica gel (using 0% to 6% MeOH in dichloromethane as eluent) and trituration in Et$_2$O afforded example 26 as a brown solid in 97% yield. $^1$H-NMR (400 MHz, DMSO-D6): 8.73 (dd, J 4.5, 1.5 Hz, 1H, Ar); 8.49 (dd, J 4.8, 1.6 Hz, 1H, Ar); 8.19 (d, J 8.1, 1.5 Hz, 1H, Ar); 7.80 (d, J 1.5 Hz, 1H, Ar); 7.75 (dd, J 7.7, 1.5 Hz, 1H, Ar); 7.68 (d, J 7.7 Hz, 1H, Ar); 7.63 (dd, J 8.1, 4.5 Hz, 1H, Ar); 7.53 (dd, J 7.7, 1.6 Hz, 1H, Ar); 7.33 (dd, J 7.7, 4.8 Hz, 1H, Ar); 4.37 (d, J 15.0 Hz, 1H, C<u>Ha</u>Hb); 4.28 (d, J 15.0 Hz, 1H, CHa<u>Hb</u>); 3.10 (s, 3H, CH$_3$); 2.48 (s, 3H, CH$_3$). M/Z (M+H)$^+$=316.5.

Example 27: 10-(6-Fluoro-pyridin-3-yl)-6-methyl-6,7-dihydro-4,6-diaza-dibenzo[a, c]cyclohepten-5-one

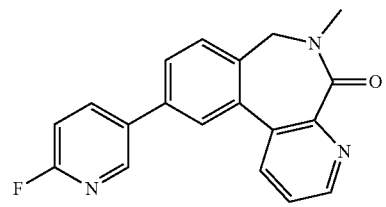 [SMILES: CN1Cc2ccc(-c3ccc(F)nc3)cc2-c2cccnc2C1=O]

Example 27 was prepared according to general procedure IV(i) starting from example 24 in presence of 6-fluoro-3-pyridinylboronic acid and heating at 100° C. for 1 hour. Purification by preparative HPLC afforded example 27 as a white solid in 65% yield. $^1$H-NMR (400 MHz, DMSO-D6): 8.75 (dd, J 4.6, 1.5 Hz, 1H, Ar); 8.70 (d, J 2.4 Hz, 1H, Ar); 8.44 (dt, J 8.0, 2.4 Hz, 1H, Ar); 8.33 (dd, J 8.0, 1.5 Hz, 1H, Ar); 8.09 (d, J 1.7 Hz, 1H, Ar); 7.82 (dd, J 7.8, 1.7 Hz, 1H, Ar); 7.70 (d, J 7.8 Hz, 1H, Ar); 7.66 (dd, J 8.0, 4.6 Hz, 1H, Ar); 7.32 (dd, J 8.6, 2.8 Hz, 1H, Ar); 4.37 (d, J 15.0 Hz, 1H, C<u>Ha</u>Hb); 4.28 (d, J 15.0 Hz, 1H, CHa<u>Hb</u>); 3.08 (s, 3H, CH$_3$). M/Z (M+H)$^+$=320.5.

Example 28: 10-(5-Fluoro-pyridin-2-yl)-6-methyl-6,7-dihydro-4,6-diaza-dibenzo[a, c]cyclohepten-5-one

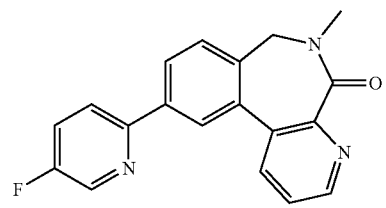 [SMILES: CN1Cc2ccc(-c3ccc(F)cn3)cc2-c2cccnc2C1=O]

Under inert atmosphere, XPhos precatalyst (0.10 equiv.) was added to a suspension of example 24 (1.0 equiv.), bispinacolatodiboron (1.2 equiv.) and potassium acetate (2.7 equiv.) in dioxane (0.15 mol·L$^{-1}$). The reaction mixture was heated at 100° C. for 2 hours. After cooling to room temperature, the mixture was filtered off through celite with EtOAc and the filtrate was concentrated under vacuum. The residue was dissolved in dioxane (0.15 mol·L$^{-1}$) and potassium carbonate (3.0 equiv.) and a solution of 2-bromo-5-fluoropyridine (1.2 equiv.) in dioxane (0.90 mol·L−1) were successively added. Under inert atmosphere, PdCl$_2$(dppf)

.CH$_2$Cl$_2$ (0.10 equiv.) was added and the reaction mixture was heated at 100° C. for 1 hour. After cooling to room temperature, the reaction mixture was hydrolyzed and extracted twice with ethyl acetate. The combined organic extracts were dried with brine and MgSO$_4$, filtered off and concentrated under vacuum. Purification by preparative HPLC afforded example 28 as a white solid in 52% yield. $^1$H-NMR (400 MHz, DMSO-D6): 8.75 (dd, J 4.6, 1.5 Hz, 1H, Ar); 8.69 (d, J 3.0 Hz, 1H, Ar); 8.39 (d, J 1.8 Hz, 1H, Ar); 8.26 (dd, J 8.0, 1.5 Hz, 1H, Ar); 8.22 (d, J 8.7, 4.6 Hz, 1H, Ar); 8.15 (dd, J 7.9, 1.8 Hz, 1H, Ar); 7.87 (dt, J 8.7, 3.0 Hz, 1H, Ar); 7.70 (d, J 7.9 Hz, 1H, Ar); 7.67 (dd, J 8.0, 4.6 Hz, 1H, Ar); 4.37 (d, J 15.0 Hz, 1H, CHaHb); 4.27 (d, J 15.0 Hz, 1H, CHaHb); 3.08 (s, 3H, CH$_3$). M/Z (M+H)$^+$=320.6.

Compound 35: 3-{2-[(tert-Butoxycarbonyl-methyl-amino)-methyl]-5-chloro-phenyl}-6-fluoro-pyridine-2-carboxylic acid methyl ester Compound 35 was prepared according to general procedure VII, starting from compound 33 and methyl 3-bromo-6-fluoropicolinate. Purification by flash column chromatography on silica gel (using 0% to 40% ethyl acetate in cyclohexane as eluent) afforded the product as a colorless oil in 79% yield. M/Z (M[$^{35}$Cl]-boc)$^+$=309.6.

Example 29: 10-Chloro-3-fluoro-6-methyl-6,7-dihydro-4,6-diaza-dibenzo[a,c]cyclohepten-5-one

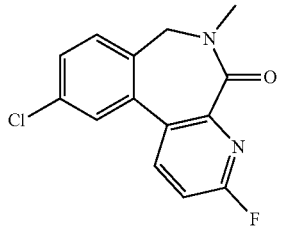 [SMILES: CN1Cc2ccc(Cl)cc2-c2ccc(F)nc2C1=O]

Example 29 was prepared using general procedure VIII and starting from compound 35. Purification by flash column chromatography on silica gel (using 0% to 4% MeOH in dichloromethane as eluent) afforded the product as a yellow oil in quantitative yield. $^1$H-NMR (400 MHz, DMSO-D6): 8.38 (t, J 8.2 Hz, 1H, Ar); 7.87 (s, 1H, Ar); 7.62 (d, J 8.2 Hz, 1H, Ar); 7.55 (d, J 8.1 Hz, 1H, Ar); 7.48 (dd, J 8.2, 2.5 Hz, 1H, Ar); 4.36 (d, J 15.0 Hz, 1H, CHaHb); 4.26 (d, J 15.0 Hz, 1H, CHaHb); 3.04 (s, 3H, CH$_3$); M/Z (M[$^{35}$Cl]+H)$^+$=277.5.

Example 30: 3-Fluoro-6-methyl-10-(2-methyl-pyridin-3-yl)-6,7-dihydro-4,6-diaza-dibenzo[a, c]cyclohepten-5-one

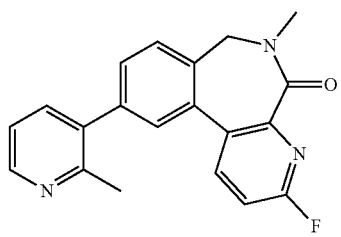 [SMILES: Cc1ncccc1-c1ccc2c(c1)-c1ccc(F)nc1C(=O)N(C)C2]

Example 30 was prepared according to general procedure IV(ii), starting from example 29 and 2-methylpyridine-3-boronic acid pinacol ester and heating at 100° C. for 2 hours. Purification by column chromatography on silica gel (using 0% to 5% MeOH in dichloromethane as eluent) and trituration in iPr$_2$O afforded example 30 as a white solid in 66% yield. $^1$H-NMR (400 MHz, DMSO-D6): 8.49 (dd, J 4.8, 1.6 Hz, 1H, Ar); 8.42 (t, J 8.1 Hz, 1H, Ar); 7.80 (d, J 1.7 Hz, 1H, Ar); 7.74 (dd, J 7.7, 1.7 Hz, 1H, Ar); 7.68 (d, J 7.7 Hz, 1H, Ar); 7.53 (dd, J 7.7, 1.7 Hz, 1H, Ar); 7.46 (dd, J 8.6, 3.3 Hz, 1H, Ar); 7.32 (dd, J 7.7, 4.8 Hz, 1H, Ar); 4.44 (d, J 15.0 Hz, 1H, CHaHb); 4.30 (d, J 15.0 Hz, 1H, CHaHb); 3.09 (s, 3H, CH$_3$); 2.51 (s, 3H, CH$_3$). M/Z (M+H)$^+$=334.7.

Example 31: 3-Fluoro-10-(6-fluoro-pyridin-3-yl)-6-methyl-6,7-dihydro-4,6-diaza-dibenzo[a, c]cyclohepten-5-one

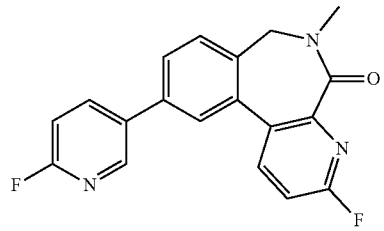 [SMILES: CN1Cc2ccc(-c3ccc(F)nc3)cc2-c2ccc(F)nc2C1=O]

Example 31 was prepared according to general procedure IV(ii) starting from example 29 and 6-fluoro-3-pyridinylboronic acid and heating at 100° C. for 2 hours. Purification by column chromatography on silica gel (using 0% to 100% EtOAc in cyclohexane as eluent) and trituration in iPr$_2$O afforded example 31 as a white solid in 89% yield. $^1$H-NMR (400 MHz, DMSO-D6): 8.70 (d, J 2.6 Hz, 1H, Ar); 8.56 (t, J 8.1 Hz, 1H, Ar); 8.44 (dt, J 8.3, 2.6 Hz, 1H, Ar); 8.09 (d, J 1.7 Hz, 1H, Ar); 7.83 (dd, J 7.8, 1.7 Hz, 1H, Ar); 7.71 (d, J 7.8 Hz, 1H, Ar); 7.51 (dd, J 8.6, 3.3 Hz, 1H, Ar); 7.32 (dd, J 8.6, 2.6 Hz, 1H, Ar); 4.43 (d, J 15.0 Hz, 1H, CHaHb); 4.30 (d, J 15.0 Hz, 1H, CHaHb); 3.07 (s, 3H, CH$_3$). M/Z (M+H)$^+$=338.6.

Example 32: 3-Fluoro-10-(5-fluoro-pyridin-2-yl)-6-methyl-6,7-dihydro-4,6-diaza-dibenzo[a, c]cyclohepten-5-one

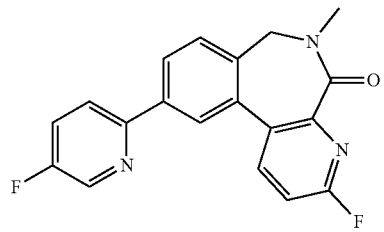 [SMILES: CN1Cc2ccc(-c3ccc(F)cn3)cc2-c2ccc(F)nc2C1=O]

Example 32 was prepared according to procedure of example 28 starting from example 29. Purification by column chromatography on silica gel (using 0% to 4% MeOH in dichloromethane as eluent) and trituration in Et$_2$O afforded example 32 as a white solid in 31% yield. $^1$H-NMR (400 MHz, DMSO-D6): 8.69 (d, J 2.9 Hz, 1H, Ar); 8.48 (t, J 8.2 Hz, 1H, Ar); 8.38 (d, J 1.7 Hz, 1H, Ar); 8.22 (dd, J 8.8, 4.3 Hz, 1H, Ar); 8.15 (dd, J 7.9, 1.7 Hz, 1H, Ar); 7.88 (dt, J 8.8, 2.9 Hz, 1H, Ar); 7.70 (d, J 7.9 Hz, 1H, Ar); 7.50 (dd, J 8.5, 3.4 Hz, 1H, Ar); 4.44 (d, J 15.0 Hz, 1H, CHaHb); 4.29 (d, J 15.0 Hz, 1H, CHaHb); 3.07 (s, 3H, CH$_3$). M/Z (M+H)$^+$=338.5.

Example 33: 10-Chloro-3-methoxy-6-methyl-6,7-dihydro-4,6-diaza-dibenzo[a,c]cyclohepten-5-one

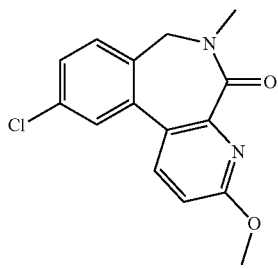 [SMILES: COc1ccc2c(n1)C(=O)N(C)Cc1ccc(Cl)cc1-2]

A solution of example 29 (1.0 equiv.) and sodium methoxide (4.0 equiv.) in anhydrous MeOH (0.20 mol·L$^{-1}$) was stirred at room temperature for 16 hours. The solvent was removed under vacuum and the residue was taken in an aqueous solution of NH$_4$Cl and extracted twice with EtOAc. The combined extracts were dried with brine and MgSO$_4$, filtered and concentrated under vacuum. Purification by column chromatography on silica gel (using EtOAc as eluent) afforded example 33 as a white solid in quantitative yield. M/Z (M$^{[35]}$Cl+H)$^+$=289.6.

Example 34: 10-(5-Fluoro-pyridin-2-yl)-3-methoxy-6-methyl-6,7-dihydro-4,6-diaza-dibenzo[a, c]cyclohepten-5-one

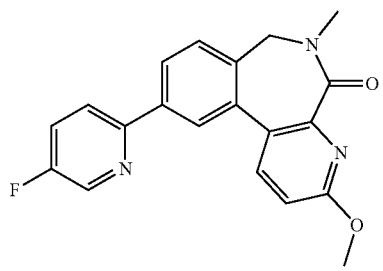 [SMILES: COc1ccc2c(n1)C(=O)N(C)Cc1ccc(-c3ccc(F)cn3)cc1-2]

Example 34 was prepared according to procedure of example 28 starting from example 33. Purification by column chromatography on silica gel (using 0% to 100% EtOAc in cyclohexane as eluent) and trituration in Et$_2$O afforded example 34 as a white solid in 42% yield. $^1$H-NMR (400 MHz, DMSO-D6): 8.68 (d, J 2.9 Hz, 1H, Ar); 8.32 (d, J 1.7 Hz, 1H, Ar); 8.21 (dd, J 8.8, 4.4 Hz, 1H, Ar); 8.17 (d, J 8.6 Hz, 1H, Ar); 8.09 (dd, J 7.9, 1.7 Hz, 1H, Ar); 7.86 (dt, J 8.8, 2.9 Hz, 1H, Ar); 7.67 (d, J 7.9 Hz, 1H, Ar); 7.11 (d, J 8.6 Hz, 1H, Ar); 4.37 (d, J 15.0 Hz, 1H, CHaHb); 4.26 (d, J 15.0 Hz, 1H, CHaHb); 3.95 (s, 3H, CH$_3$); 3.06 (s, 3H, CH$_3$). M/Z (M+H)$^+$=350.5.

Example 35: 10-(6-Fluoro-pyridin-3-yl)-3-methoxy-6-methyl-6,7-dihydro-4,6-diaza-dibenzo[a, c]cyclohepten-5-one

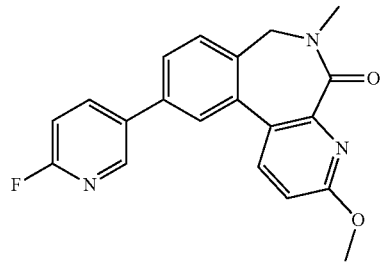 [SMILES: COc1ccc2c(n1)C(=O)N(C)Cc1ccc(-c3ccc(F)nc3)cc1-2]

Example 35 was prepared according to general procedure IV(ii) starting from example 33 and 6-fluoro-3-pyridinylboronic acid and heating at 100° C. for 2 hours. Purification by column chromatography on silica gel (using 0% to 100% EtOAc in cyclohexane as eluent) and trituration in Et$_2$O afforded example 35 as a white solid in 81% yield. $^1$H-NMR (400 MHz, DMSO-D6): 8.68 (d, J 2.6 Hz, 1H, Ar); 8.42 (dt, J 8.2, 2.6 Hz, 1H, Ar); 8.25 (d, J 8.7 Hz, 1H, Ar); 8.02 (d, J 1.7 Hz, 1H, Ar); 7.76 (dd, J 7.9, 1.7 Hz, 1H, Ar); 7.67 (d, J 7.9 Hz, 1H, Ar); 7.31 (dd, J 8.5, 2.8 Hz, 1H, Ar); 7.10 (d, J 8.6 Hz, 1H, Ar); 4.37 (d, J 15.0 Hz, 1H, CHaHb); 4.26 (d, J 15.0 Hz, 1H, CHaHb); 3.95 (s, 3H, CH$_3$); 3.06 (s, 3H, CH$_3$). M/Z (M+H)$^+$=350.5.

Example 36: 3-Methoxy-6-methyl-10-(2-methyl-pyridin-3-yl)-6,7-dihydro-4,6-diaza-dibenzo[a, c]cyclohepten-5-one

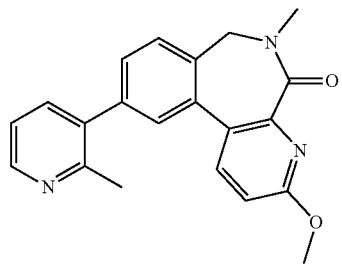 [SMILES: COc1ccc2c(n1)C(=O)N(C)Cc1ccc(-c3cccnc3C)cc1-2]

Example 36 was prepared according to general procedure IV(ii) starting from example 33 and 2-methylpyridine-3-boronic acid pinacol ester and heating at 100° C. for 2 hours. Purification by preparative HPLC and trituration in pentane afforded example 36 as a white solid in 62% yield. $^1$H-NMR (400 MHz, DMSO-D6): 8.49 (dd, J 4.7, 1.5 Hz, 1H, Ar); 8.11 (d, J 8.6 Hz, 1H, Ar); 7.74-7.72 (m, 2H, Ar); 7.65 (d, J 7.8 Hz, 1H, Ar); 7.47 (dd, J 7.6, 1.5 Hz, 1H, Ar); 7.32 (dd, J 7.6, 4.7 Hz, 1H, Ar); 7.07 (d, J 8.6 Hz, 1H, Ar); 4.38 (d, J 15.0 Hz, 1H, CHaHb); 4.27 (d, J 15.0 Hz, 1H, CHaHb); 3.94 (s, 3H, CH$_3$); 3.08 (s, 3H, CH$_3$); 2.49 (s, 3H, CH$_3$). M/Z (M+H)$^+$=346.6.

Example 37: 3-Hydroxy-6-methyl-10-(2-methyl-pyridin-3-yl)-6,7-dihydro-4,6-diaza-dibenzo[a,c]cyclohepten-5-one

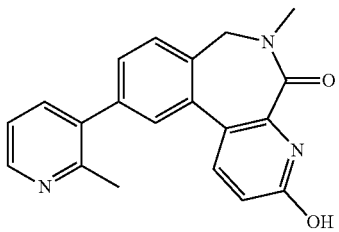 [SMILES: Cc1ncccc1-c1ccc2c(c1)-c1ccc(O)nc1C(=O)N(C)C2]

To a solution of example 30 (1.0 equiv.) in dioxane (0.10 mol·L$^{-1}$) was added a 2M aqueous solution of NaOH (10 equiv.) and the solution was subjected to microwave irradiation at 110° C. for 15 minutes. The reaction mixture was neutralized with an aqueous solution of NH$_4$Cl and extracted twice with ethyl acetate. The combined extracts were dried with brine and MgSO$_4$, filtered off and concentrated under vacuum Purification by column chromatography on silica gel (using 0% to 10% MeOH in dichloromethane as eluent) and trituration in Et$_2$O afforded example 37 as a white solid in 86% yield. $^1$H-NMR (400 MHz, DMSO-D6): 11.49 (bs, 1H, NH or OH); 8.48 (dd, J 4.8, 1.7 Hz, 1H, Ar); 7.90 (d, J 9.6 Hz, 1H, Ar); 7.71 (dd, J 7.7, 1.7 Hz, 1H, Ar); 7.65 (d, J 1.7 Hz, 1H, Ar); 7.62 (d, J 7.7 Hz, 1H, Ar); 7.43 (dd, J 7.7, 1.7 Hz, 1H, Ar); 7.31 (dd, J 7.7, 4.8 Hz, 1H, Ar); 6.61 (d, J 9.6 Hz, 1H, Ar); 4.45 (d, J 14.4 Hz, 1H, CHaHb); 4.32 (d, J 14.4 Hz, 1H, CHaHb); 3.08 (s, 3H, CH$_3$); 2.47 (s, 3H, CH$_3$). M/Z (M+H)$^+$=332.5.

Compound 36: 3-{2-[(tert-Butoxycarbonyl-methyl-amino)-methyl]-5-chloro-phenyl}-6-methyl-pyridine-2-carboxylic acid methyl ester Compound 36 was prepared according to general procedure VII, starting from compound 33 and methyl 3-bromo-6-methylpicolinate. Purification by flash column chromatography on silica gel (using 0% to 50% ethyl acetate in cyclohexane as eluent) afforded the product as a beige oil in 95% yield. $^1$H-NMR (400 MHz, DMSO-D6): 7.66 (d, J 7.9 Hz, 1H, Ar); 7.52-7.46 (m, 2H, Ar); 7.22 (d, J 8.3 Hz, 1H, Ar); 7.14 (d, J 2.1 Hz, 1H, Ar); 4.17 (d, J 15.9 Hz, 1H, CHaHb); 4.06 (d, J 15.9 Hz, 1H, CHaHb); 3.61 (s, 3H, CH$_3$); 2.54 (s, 3H, CH$_3$); 1.29 (bs, 9H, tert-butyl); 1.28 (s, 3H, CH$_3$). M/Z (M[$^{35}$Cl])$^+$=405.6.

Example 38: 10-Chloro-3,6-dimethyl-6,7-dihydro-4,6-diaza-dibenzo[a,c]cyclohepten-5-one

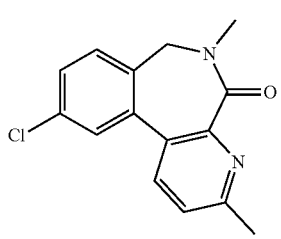 [SMILES: Cc1ccc2c(n1)C(=O)N(C)Cc1ccc(Cl)cc1-2]

Example 38 was prepared using general procedure VIII and starting from compound 36. Purification by flash column chromatography on silica gel (using 0% to 4% MeOH in dichloromethane as eluent) afforded the product as a white solid in 88% yield. 1H-NMR (400 MHz, DMSO-D6): 8.03 (d, J 8.1 Hz, 1H, Ar); 7.82 (d, J 2.0 Hz, 1H, Ar); 7.59 (d, J 8.1 Hz, 1H, Ar); 7.52-7.49 (m, 2H, Ar); 4.27 (d, J 15.0 Hz, 1H, CHaHb); 4.21 (d, J 15.0 Hz, 1H, CHaHb); 3.02 (s, 3H, CH$_3$); 2.57 (s, 3H, CH$_3$); M/Z (M[$^{35}$Cl]+H)$^+$=273.6.

Example 39: 10-(6-Fluoro-pyridin-3-yl)-3,6-dimethyl-6,7-dihydro-4,6-diaza-dibenzo[a,c]cyclohepten-5-one

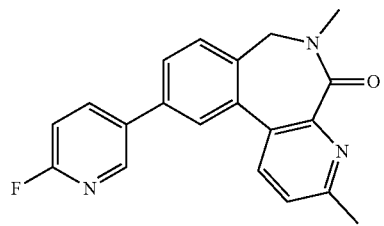 [SMILES: Cc1ccc2c(n1)C(=O)N(C)Cc1ccc(-c3ccc(F)nc3)cc1-2]

Example 39 was prepared according to general procedure IV(ii) starting from example 38 and 6-fluoro-3-pyridinylboronic acid and heating at 100° C. for 2 hours. Purification by column chromatography on silica gel (using 0% to 5% MeOH in dichloromethane as eluent) and trituration in Et$_2$O afforded example 39 as a white solid in 90% yield. $^1$H-NMR (400 MHz, DMSO-D6): 8.69 (d, J 2.6 Hz, 1H, Ar); 8.42 (dt, J 8.2, 2.6 Hz, 1H, Ar); 8.21 (d, J 8.1 Hz, 1H, Ar); 8.05 (d, J 1.7 Hz, 1H, Ar); 7.78 (dd, J 7.8, 1.7 Hz, 1H, Ar); 7.68 (d, J 7.8 Hz, 1H, Ar); 7.52 (d, J 8.1 Hz, 1H, Ar); 7.32 (dd, J 8.6, 2.6 Hz, 1H, Ar); 4.34 (d, J 15.0 Hz, 1H, CHaHb); 4.25 (d, J 15.0 Hz, 1H, CHaHb); 3.06 (s, 3H, CH$_3$); 2.59 (s, 3H, CH$_3$). M/Z (M+H)$^+$=334.6.

Example 40: 10-(5-Fluoro-pyridin-2-yl)-3,6-dimethyl-6,7-dihydro-4,6-diaza-dibenzo[a,c]cyclohepten-5-one

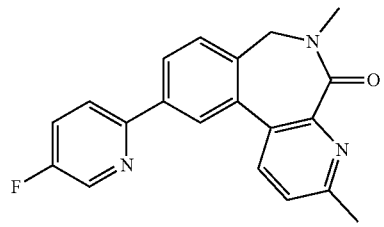 [SMILES: Cc1ccc2c(n1)C(=O)N(C)Cc1ccc(-c3ccc(F)cn3)cc1-2]

Example 40 was prepared according to procedure of example 28 starting from example 38. Purification by column chromatography on silica gel (using 0% to 4% MeOH in dichloromethane as eluent) and trituration in Et$_2$O afforded example 40 as a white solid in 84% yield. $^1$H-NMR (400 MHz, DMSO-D6): 8.69 (d, J 2.9 Hz, 1H, Ar); 8.35 (d, J 1.7 Hz, 1H, Ar); 8.21 (dd, J 8.8, 4.3 Hz, 1H, Ar); 8.14-8.10 (m, 2H, Ar); 7.87 (dt, J 7.8, 1.7 Hz, 1H, Ar); 7.68 (d, J 7.9 Hz, 1H, Ar); 7.53 (d, J 8.1 Hz, 1H, Ar); 4.35 (d, J 15.0 Hz, 1H, CHaHb); 4.25 (d, J 15.0 Hz, 1H, CHaHb); 3.06 (s, 3H, CH$_3$); 2.59 (s, 3H, CH$_3$). M/Z (M+H)$^+$=334.5.

Example 41: 3,6-Dimethyl-10-(2-methyl-pyridin-3-yl)-6,7-dihydro-4,6-diaza-dibenzo[a, c]cyclohepten-5-one

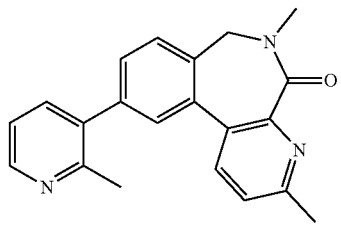 [SMILES: Cc1ccc2c(n1)C(=O)N(C)Cc1ccc(-c3cccnc3C)cc1-2]

Example 41 was prepared according to general procedure IV(ii) starting from example 38 and 2-methylpyridine-3-boronic acid pinacol ester and heating at 100° C. for 2 hours. Purification by column chromatography on silica gel (using 0% to 6% MeOH in dichloromethane as eluent) and trituration in Et$_2$O afforded example 41 as a white solid in 89% yield. $^1$H-NMR (400 MHz, DMSO-D6): 8.48 (dd, J 4.8, 1.7 Hz, 1H, Ar); 8.07 (d, J 8.1 Hz, 1H, Ar); 7.75 (d, J 1.7 Hz, 1H, Ar); 7.73 (dd, J 7.7, 1.7 Hz, 1H, Ar); 7.65 (d, J 7.7 Hz, 1H, Ar); 7.50-7.47 (m, 2H, Ar); 7.32 (d, J 7.7, 4.8 Hz, 1H, Ar); 4.35 (d, J 15.0 Hz, 1H, CHaHb); 4.25 (d, J 15.0 Hz, 1H, CHaHb); 3.08 (s, 3H, CH$_3$); 2.58 (s, 3H, CH$_3$); 2.49 (s, 3H, CH$_3$). M/Z (M+H)$^+$=330.5.

Compound 37: 3-{2-[(tert-Butoxycarbonyl-methyl-amino)-methyl]-5-chloro-phenyl}-5-methyl-pyridine-2-carboxylic acid methyl ester Compound 37 was prepared according to general procedure VII, starting from compound 33 and methyl 3-bromo-5-methylpicolinate. Purification by flash column chromatography on silica gel (using 0% to 100% ethyl acetate in cyclohexane as eluent) afforded the product as a yellow oil in quantitative yield. $^1$H-NMR (400 MHz, DMSO-D6): 8.56 (s, 1H, Ar); 7.65 (s, 1H, Ar); 7.48 (dd, J 8.2, 2.0 Hz, 1H, Ar); 7.22 (d, J 8.2 Hz, 1H, Ar); 7.16 (d, J 2.0 Hz, 1H, Ar); 4.16 (d, J 15.9 Hz, 1H, CHaHb); 4.07 (d, J 15.9 Hz, 1H, CHaHb); 3.62 (s, 3H, CH$_3$); 2.55 (s, 3H, CH$_3$); 2.39 (s, 3H, CH$_3$); 1.32 (bs, 9H, tert-butyl). M/Z (M[$^{35}$Cl])$^+$=405.6.

Example 42: 10-Chloro-2,6-dimethyl-6,7-dihydro-4,6-diaza-dibenzo[a,c]cyclohepten-5-one

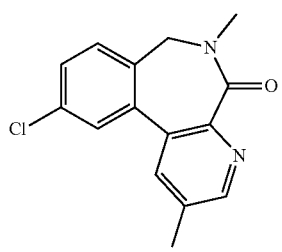 [SMILES: Cc1cnc2c(c1)-c1cc(Cl)ccc1CN(C)C2=O]

Example 42 was prepared using general procedure VIII and starting from compound 37. Purification by flash column chromatography on silica gel (using 0% to 10% MeOH in dichloromethane as eluent) afforded the product as a colorless oil in 79% yield. $^1$H-NMR (400 MHz, DMSO-D6): 8.59 (d, J 2.0 Hz, 1H, Ar); 7.99 (d, J 2.0 Hz, 1H, Ar); 7.86 (d, J 2.1 Hz, 1H, Ar); 7.61 (d, J 8.1 Hz, 1H, Ar); 7.54 (dd, J 8.1, 2.1 Hz, 1H, Ar); 4.28 (d, J 15.0 Hz, 1H, CHaHb); 4.22 (d, J 15.0 Hz, 1H, CHaHb); 3.04 (s, 3H, CH$_3$); 2.44 (s, 3H, CH$_3$); M/Z (M[$^{35}$Cl]+H)$^+$=273.5.

Example 43: 2,6-Dimethyl-10-(2-methyl-pyridin-3-yl)-6,7-dihydro-4,6-diaza-dibenzo[a, c]cyclohepten-5-one

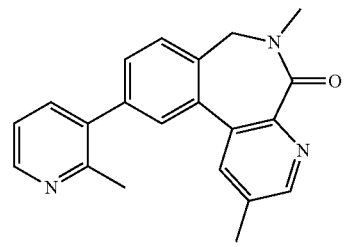 [SMILES: Cc1cnc2c(c1)-c1cc(-c3cccnc3C)ccc1CN(C)C2=O]

Example 43 was prepared according to general procedure IV(ii) starting from example 42 and 2-methylpyridine-3-boronic acid pinacol ester and heating at 100° C. for 1 hour. Purification by preparative HPLC afforded example 43 as a white solid in 25% yield. $^1$H-NMR (400 MHz, DMSO-D6): 8.57 (d, J 1.6 Hz, 1H, Ar); 8.49 (dd, J 4.8, 1.7 Hz, 1H, Ar); 8.02 (d, J 1.6 Hz, 1H, Ar); 7.79 (d, J 1.7 Hz, 1H, Ar); 7.74 (dd, J 7.7, 1.7 Hz, 1H, Ar); 7.66 (d, J 7.7 Hz, 1H, Ar); 7.51 (dd, J 7.7, 1.7 Hz, 1H, Ar); 7.33 (d, J 7.7, 4.8 Hz, 1H, Ar); 4.35 (d, J 15.0 Hz, 1H, CHaHb); 4.26 (d, J 15.0 Hz, 1H, CHaHb); 3.09 (s, 3H, OH$_3$); 2.49 (s, 3H, CH$_3$); 2.42 (s, 3H, OH$_3$). M/Z (M+H)$^+$=330.5.

Example 44: 10-(6-Fluoro-pyridin-3-yl)-2,6-dimethyl-6,7-dihydro-4,6-diaza-dibenzo[a, c]cyclohepten-5-one

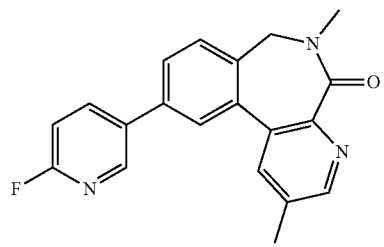 [SMILES: Cc1cnc2c(c1)-c1cc(-c3ccc(F)nc3)ccc1CN(C)C2=O]

Example 44 was prepared according to general procedure IV(ii) starting from example 42 and 6-fluoro-3-pyridinylboronic acid and heating at 100° C. for 1 hour. Purification by column chromatography on silica gel (using 0% to 10% MeOH in dichloromethane as eluent) and trituration in Et$_2$O afforded example 44 as a beige solid in 46% yield. $^1$H-NMR (400 MHz, DMSO-D6): 8.70 (d, J 2.6 Hz, 1H, Ar); 8.59 (d, J 2.0 Hz, 1H, Ar); 8.44 (dt, J 8.1, 2.5 Hz, 1H, Ar); 8.15 (d, J 2.0 Hz, 1H, Ar); 8.08 (d, J 1.7 Hz, 1H, Ar); 7.81 (dd, J 7.8, 1.7 Hz, 1H, Ar); 7.69 (d, J 7.8 Hz, 1H, Ar); 7.33 (dd, J 8.6, 2.6 Hz, 1H, Ar); 4.35 (d, J 15.0 Hz, 1H, CHaHb); 4.25 (d, J 15.0 Hz, 1H, CHaHb); 3.06 (s, 3H, CH$_3$); 2.45 (s, 3H, CH$_3$). M/Z (M+H)$^+$=334.6.

Compound 38: 3-{2-[(tert-Butoxycarbonyl-methyl-amino)-methyl]-5-chloro-phenyl}-5-fluoro-pyridine-2-carboxylic acid methyl ester Compound 38 was prepared according to general procedure VII, starting from compound 33 and methyl 3-bromo-5-fluoropicolinate. Purification by flash column chromatography on silica gel (using 0% to 100% ethyl acetate in cyclohexane as eluent) afforded the product as a yellow oil in 71% yield. $^1$H-NMR (400 MHz, DMSO-D6): 8.78 (bs, 1H, Ar); 7.91 (dd, J 9.1, 2.5 Hz, 1H, Ar); 7.56 (d, J 7.9 Hz, 1H, Ar); 7.34-7.29 (m, 2H, Ar); 4.25 (s, 2H, CH$_2$); 3.69 (s, 3H, CH$_3$); 2.60 (s, 3H, CH$_3$); 1.36 (bs, 9H, tert-butyl). M/Z (M[$^{35}$Cl]-tBu+H)$^+$=353.5.

Example 45: 10-Chloro-2-fluoro-6-methyl-6,7-dihydro-4,6-diaza-dibenzo[a,c]cyclohepten-5-one

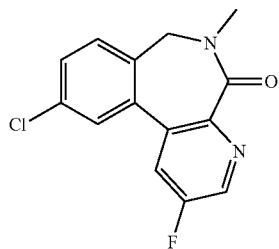 [SMILES: CN1Cc2ccc(Cl)cc2-c2cc(F)cnc2C1=O]

Example 45 was prepared using general procedure VIII and starting from compound 38. Purification by flash column chromatography on silica gel (using 0% to 10% MeOH in dichloromethane as eluent) afforded the product as a colorless oil in quantitative yield. $^1$H-NMR (400 MHz, DMSO-D6): 8.76 (d, J 2.7 Hz, 1H, Ar); 8.16 (dd, J 9.8, 2.7 Hz, 1H, Ar); 7.92 (d, J 2.1 Hz, 1H, Ar); 7.64 (d, J 8.1 Hz, 1H, Ar); 7.58 (dd, J 8.1, 2.1 Hz, 1H, Ar); 4.33 (d, J 15.0 Hz, 1H, C<u>Ha</u>Hb); 4.25 (d, J 15.0 Hz, 1H, CHa<u>Hb</u>); 3.57 (s, 3H, CH$_3$); 3.04 (s, 3H, CH$_3$). M/Z (M[$^{35}$Cl]+H)$^+$=277.5.

Example 46: 2-Fluoro-6-methyl-10-(2-methyl-pyridin-3-yl)-6,7-dihydro-4,6-diaza-dibenzo[a, c]cyclohepten-5-one

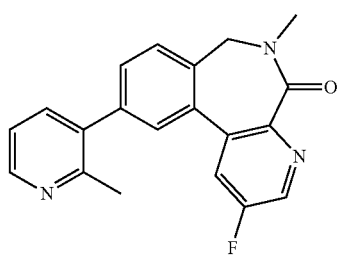 [SMILES: Cc1ncccc1-c1ccc2c(c1)-c1cc(F)cnc1C(=O)N(C)C2]

Example 46 was prepared according to general procedure IV(ii) starting from example 45 and 2-methylpyridine-3-boronic acid pinacol ester and heating at 100° C. for 1 hour. Purification by flash column chromatography on silica gel (using 0% to 10% MeOH in dichloromethane as eluent) and trituration in Et$_2$O afforded example 46 as a beige solid in 46% yield. $^1$H-NMR (400 MHz, DMSO-D6): 8.75 (d, J 2.7 Hz, 1H, Ar); 8.49 (dd, J 4.8, 1.7 Hz, 1H, Ar); 8.18 (d, J 9.8, 2.7 Hz, 1H, Ar); 7.85 (d, J 1.7 Hz, 1H, Ar); 7.76 (dd, J 7.7, 1.7 Hz, 1H, Ar); 7.69 (d, J 7.7 Hz, 1H, Ar); 7.56 (dd, J 7.7, 1.7 Hz, 1H, Ar); 7.33 (d, J 7.7, 4.8 Hz, 1H, Ar); 4.41 (d, J 15.0 Hz, 1H, C<u>Ha</u>Hb); 4.30 (d, J 15.0 Hz, 1H, CHa<u>Hb</u>); 3.11 (s, 3H, CH$_3$); 2.50 (s, 3H, CH$_3$). M/Z (M+H)$^+$334.5.

Example 47: 2-Fluoro-10-(6-fluoro-pyridin-3-yl)-6-methyl-6,7-dihydro-4,6-diaza-dibenzo[a, c]cyclohepten-5-one

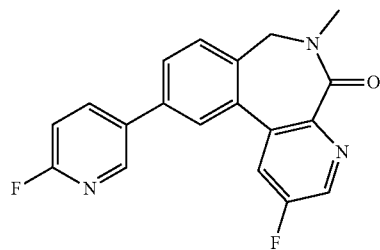 [SMILES: CN1Cc2ccc(-c3ccc(F)nc3)cc2-c2cc(F)cnc2C1=O]

Example 47 was prepared according to general procedure IV(ii) starting from example 45 and 6-fluoro-3-pyridinylboronic acid and heating at 100° C. for 1 hour. Purification by preparative HPLC afforded example 47 as a beige solid in 43% yield. $^1$H-NMR (400 MHz, DMSO-D6): 8.76 (d, J 2.7 Hz, 1H, Ar); 8.73 (d, J 2.6 Hz, 1H, Ar); 8.46 (dt, J 8.2, 2.6 Hz, 1H, Ar); 8.34 (dd, J 9.8, 2.7 Hz, 1H, Ar); 8.13 (d, J 1.7 Hz, 1H, Ar); 7.85 (dd, J 7.8, 1.7 Hz, 1H, Ar); 7.72 (d, J 7.8 Hz, 1H, Ar); 7.33 (dd, J 8.6, 2.6 Hz, 1H, Ar); 4.41 (d, J 15.0 Hz, 1H, C<u>Ha</u>Hb); 4.28 (d, J 15.0 Hz, 1H, CHa<u>Hb</u>); 3.07 (s, 3H, CH$_3$). M/Z (M+H)$^+$=338.5.

Example 48: 2-Methoxy-6-methyl-10-(2-methyl-pyridin-3-yl)-6,7-dihydro-4,6-diaza-dibenzo[a, c]cyclohepten-5-one

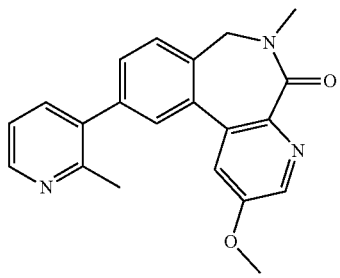 [SMILES: COc1cnc2c(c1)-c1cc(-c3cccnc3C)ccc1CN(C)C2=O]

A solution of example 46 (1.0 equiv.) and sodium methoxide (1.5 equiv.) in anhydrous MeOH (0.20 mol·L−1) was subjected to microwave irradiation at 130° C. for 30 minutes. The solvent was removed under vacuum and the residue was taken in water and extracted twice with EtOAc. The combined extracts were dried with brine and MgSO$_4$, filtered off and concentrated under vacuum to afford example 48 as a white solid in 61% yield. $^1$H-NMR (400 MHz, DMSO-D6): 8.49 (dd, J 4.8, 1.7 Hz, 1H, Ar); 8.43 (d, J 2.8 Hz, 1H, Ar); 7.88 (d, J 1.7 Hz, 1H, Ar); 7.75 (dd, J 7.7, 1.7 Hz, 1H, Ar); 7.67 (d, J 7.7 Hz, 1H, Ar); 7.63 (d, J 2.8 Hz, 1H, Ar); 7.53 (dd, J 7.7, 1.7 Hz, 1H, Ar); 7.33 (d, J 7.7, 4.8 Hz, 1H, Ar); 4.36 (d, J 15.0 Hz, 1H, C<u>Ha</u>Hb); 4.26 (d, J 15.0

Hz, 1H, CHaHb); 3.96 (s, 3H, CH₃); 3.08 (s, 3H, CH₃); 2.51 (s, 3H, CH₃). M/Z (M+H)⁺=346.6.

Compound 39: 1-(4-Chloro-2-iodo-phenyl)-cyclopropanecarboxylic acid

To a solution of 1-(4-chloro-phenyl)-cyclopropanecarboxylic acid (1.0 equiv.) in anhydrous DMF (0.10 mol·L⁻¹) was added [acetoxy(phenyl)-iodanyl]acetate (1.2 equiv.), palladium diacetate (0.15 equiv.) and iodine (1.2 equiv.). The reaction mixture was stirred at 60° C. for 16 hours with foil covered. After cooling to room temperature, the mixture was hydrolyzed with water and extracted twice with ethyl acetate. The combined organic layers were washed with water, dried over Na₂SO₄, filtered off and concentrated under vacuum. Purification by column chromatography on silica gel (using 10% to 50% ethyl acetate in petroleum ether as eluent) afforded compound 39 as a brown solid in 50% yield. M/Z (M[³⁵Cl]+H)⁺=322.9.

Compound 40: 1-(4-Chloro-2-iodo-phenyl)-cyclopropylamine

To a solution of compound 39 (1.0 equiv.) in tert-butanol (0.30 mol·L⁻¹) was added triethylamine (1.1 equiv.) and diphenyl phosphoryl azide (1.1 equiv.) and the reaction mixture was heated at 85° C. for 3 hours. After cooling to room temperature, the mixture was diluted with water and extracted with ethyl acetate. The organic phase was washed with aqueous NaHCO₃, water, dried with Na₂SO₄, filtered off and concentrated under vacuum. The residue was suspended in aqueous HCl (3N, 0.50 mol·L⁻¹) and heated at 85° C. for 16 hours. After cooling to room temperature, pH was adjusted to 8 with aqueous Na₂CO₃ and the mixture was extracted with ethyl acetate. The organic phase was washed with water, dried with Na₂SO₄, filtered off and concentrated under vacuum. Purification by column chromatography on silica gel (using 10% to 25% ethyl acetate in petroleum ether as eluent) afforded compound 40 as a light yellow oil in 27% yield. ¹H-NMR (400 MHz, CDCl₃): 7.84 (d, J 1.6 Hz, 1H, Ar); 7.29-7.23 (m, 2H, Ar); 1.28-1.24 (m, 2H, cyclopropyl), 0.90-0.87 (m, 2H, cyclopropyl). Protons for NH₂ were not observed. M/Z (M[³⁵Cl]-NH₂+H)+=276.7.

Compound 41: [1-(4-Chloro-2-iodo-phenyl)-cyclopropyl]-carbamic acid tert-butyl ester A mixture of compound 40 (1.0 equiv.), triethylamine (1.5 equiv.) and di-tert-butyl dicarbonate (1.1 equiv.) in dichloromethane (0.30 mol·L⁻¹) was stirred at 30° C. for 16 hours. The reaction mixture was washed with water and extracted with dichloromethane. The organic phase was dried over Na₂SO₄ and concentrated under vacuum. Purification by column chromatography on silica gel (using petroleum ether as eluent) afforded compound 41 as a light yellow solid in 55% yield. ¹H-NMR (400 MHz, MeOD-D4): 7.86 (s, 1H, Ar); 7.53 (d, J 8.0 Hz, 1H); 7.32 (d, J 8.0 Hz, 1H); 4.62 (bs, 1H, NH); 1.37 (s, 9H, tert-butyl); 1.24-1.22 (m, 2H, cyclopropyl), 1.09-1.07 (m, 2H, cyclopropyl). M/Z (M[³⁵Cl]-tBu+H)⁺=337.9.

Compound 42: [1-(4-Chloro-2-iodo-phenyl)-cyclopropyl]-methyl-carbamic acid tert-butyl ester At 0° C., to a solution of compound 41 (1.0 equiv.) in anhydrous DMF (0.10 mol·L⁻¹) was added sodium hydride (60% dispersion in oil, 1.3 equiv.) and the reaction mixture was stirred for 15 minutes at 0° C. Iodomethane (1.3 equiv.) was added and the reaction mixture was stirred at room temperature for 1 hour before being neutralized by an aqueous solution of NH₄Cl and extracted twice with EtOAc. The combined extracts were dried with brine and MgSO₄, filtered off and concentrated under vacuum. Purification by flash column chromatography on silica gel (using 0% to 20% ethyl acetate in cyclohexane as eluent) afforded the product as a colorless oil in quantitative yield. ¹H-NMR (400 MHz, DMSO-D6): 7.92 (d, J 2.0 Hz, 1H, Ar); 7.81 (bs, 1H, Ar); 7.48 (d, J 8.4 Hz, 1H, Ar); 3.04 (s, 3H, CH₃); 1.40-1.36 (m, 12H, tert-butyl+cyclopropyl); 1.20-1.17 (m, 1H, cyclopropyl). M/Z (M[³⁵C]-tBu+H)⁺=352.4.

Compound 43: {1-[4-Chloro-2-(2-fluoro-pyridin-3-yl)-phenyl]-cyclopropyl}-methyl-carbamic acid tert-butyl ester Compound 43 was prepared according to general procedure VII, starting from compound 42 and 2-fluoro-3-pyridine boronic acid. Purification by flash column chromatography on silica gel (using 0% to 40% ethyl acetate in cyclohexane as eluent) afforded the product as a yellow oil in 71% yield. ¹H-NMR (400 MHz, DMSO-D6): 8.30 (d, J 4.4 Hz, 1H, Ar); 7.96-7.92 (m, 1H, Ar); 7.65-7.56 (m, 1H, Ar); 7.49-7.44 (m, 2H, Ar); 7.25 (d, J 2.2 Hz, 1H, Ar); 1.90 (bs, 3H, CH₃); 1.28 (s, 9H, tert-butyl); 1.28-1.16 (m, 2H, cyclopropyl); 1.06-0.90 (m, 2H, cyclopropyl). M/Z (M[³⁵Cl]-tBu+H)⁺=321.5.

Compound 44: {1-[4-Chloro-2-(6-cyano-pyridin-2-yl)-phenyl]-cyclopropyl}-methyl-carbamic acid tert-butyl ester A solution of compound 43 (1.0 equiv.) and tetraethylammonium cyanide (5.0 equiv.) in anhydrous DMF (0.15 mol·L⁻¹) was heated at 100° C. for 16 hours. After cooling to room temperature, the reaction mixture was treated with an aqueous solution of NaHCO₃ and extracted twice with EtOAc. The combined extracts were dried with brine and MgSO₄, filtered off and concentrated under vacuum. Purification by flash column chromatography on silica gel (using 0% to 50% ethyl acetate in cyclohexane as eluent) afforded the product as a yellow solid in 84% yield. ¹H-NMR (400 MHz, DMSO-D6): 8.79 (dd, J 4.5, 1.4 Hz, 1H, Ar); 8.06 (dd, J 8.0, 1.4 Hz, 1H, Ar); 7.84 (dd, J 8.0, 4.5 Hz, 1H, Ar); 7.61 (d, J 8.4 Hz, 1H, Ar); 7.52 (dd, J 8.4, 2.3 Hz, 1H, Ar); 7.38 (d, J 2.3 Hz, 1H, Ar); 1.99 (s, 3H, CH₃); 1.27 (s, 9H, tert-butyl); 1.43-1.32 (m, 1H, cyclopropyl); 1.27-1.16 (m, 2H, cyclopropyl); 0.94-0.87 (m, 1H, cyclopropyl). M/Z (M[³⁵Cl]-tBu+H)⁺=328.5.

Compound 45: {1-[2-(6-Carbamoyl-pyridin-2-yl)-4-chloro-phenyl]-cyclopropyl}-methyl-carbamic acid tert-butyl ester To a suspension of compound 44 (1.0 equiv.) and potassium carbonate (0.4 equiv.) in DMSO (0.10 mol·L⁻¹) was added a solution of hydrogen peroxide (30% in water, 3.0 equiv) and the reaction mixture was stirred at room temperature for 16 hours. The mixture was diluted with water and extracted twice with EtOAc. The combined extracts were dried with brine and MgSO₄, filtered off and concentrated under vacuum. Purification by flash column chromatography on silica gel (using 0% to 4% MeOH in dichloromethane as eluent) afforded the product as a white solid in 94% yield. ¹H-NMR (400 MHz, DMSO-D6): 8.65 (dd, J 4.4, 1.8 Hz, 1H, Ar); 7.95 (bs, 1H, NHaHb); 7.68-7.61 (m, 2H, Ar); 7.56 (bs, 1H, NHaHb); 7.33-7.31 (m, 2H, Ar); 6.98 (d, J 2.3 Hz, 1H, Ar); 2.99 (s, 3H, CH₃); 1.30 (s, 9H, tert-butyl); 1.30-1.22 (m, 1H, cyclopropyl); 1.12-1.07 (m, 1H, cyclopropyl); 0.95-0.84 (m, 2H, cyclopropyl). M/Z (M[³⁵Cl]-boc+H)⁺=302.6.

Example: 10-chloro-6-methylspiro[benzo[c]pyrido[3,2-e]azepine-7,1'-cyclopropan]-5(6H)-one

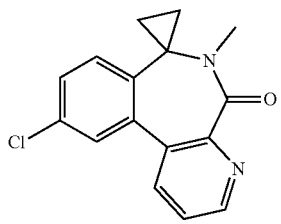 [SMILES: CN1C(=O)c2ncccc2-c2cc(Cl)ccc2C12CC2]

To a solution of compound 45 (1.0 equiv.) in dichloromethane (0.30 mol·L⁻¹) was added TFA (0.30 mol·L⁻¹) and the reaction mixture was subjected to microwave irradiation at 150° C. for 5 minutes. After cooling to room temperature, the reaction mixture was treated with an aqueous solution of NaHCO₃ and extracted twice with EtOAc. The combined extracts were dried with brine and MgSO₄, filtered off and concentrated under vacuum. Purification by flash column chromatography on silica gel (using 0% to 4% MeOH in dichloromethane as eluent) afforded the product as a white solid in quantitative yield. ¹H-NMR (400 MHz, DMSO-D6): 8.73 (dd, J 4.6, 1.4 Hz, 1H, Ar); 8.14 (dd, J 8.0, 1.4 Hz, 1H, Ar); 7.87 (s, 1H, Ar); 7.64 (d, J 8.0, 4.6 Hz, 1H, Ar); 7.52 (d, J 8.0 Hz, 1H, Ar); 7.50 (d, J 8.0 Hz, 1H, Ar); 2.93 (s, 3H, CH₃); 1.45-1.39 (m, 2H, cyclopropyl); 0.85-0.79 (m, 1H, cyclopropyl); 0.35-0.29 (m, 1H, cyclopropyl). M/Z (M[³⁵Cl]+H)⁺=285.5.

Example 50: 10-(6-Fluoro-pyridin-3-yl)-6-methyl-spiro[benzo[c]pyrido[3,2-e]azepine-7,1'-cyclopropan]-5(6H)-one

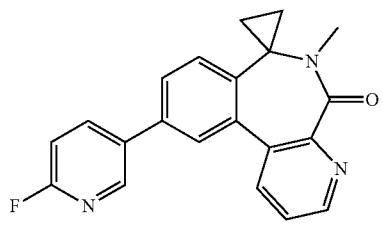 [SMILES: CN1C(=O)c2ncccc2-c2cc(-c3ccc(F)nc3)ccc2C12CC2]

Example 50 was prepared according to general procedure IV(ii) starting from example 49 and 6-fluoro-3-pyridinylboronic acid, at 100° C. for 2 hours. Purification by flash column chromatography on silica gel (using 0% to 5% MeOH in dichloromethane as eluent) and trituration in Et₂O afforded example 50 as a white solid in 87% yield. ¹H-NMR (400 MHz, DMSO-D6): 8.73 (dd, J 4.7, 1.5 Hz, 1H, Ar); 8.68 (d, J 2.6 Hz, 1H, Ar); 8.42 (dt, J 8.2, 2.6 Hz, 1H, Ar); 8.31 (dd, J 8.0, 1.5 Hz, 1H, Ar); 8.10 (d, J 1.8 Hz, 1H, Ar); 7.79 (dd, J 7.9, 1.8 Hz, 1H, Ar); 7.66 (dd, J 8.0, 4.7 Hz, 1H, Ar); 7.60 (d, J 7.9 Hz, 1H, Ar); 7.32 (dd, J 8.6, 2.8 Hz, 1H, Ar); 2.96 (s, 3H, CH₃); 1.51-1.42 (m, 2H, cyclopropyl); 0.89-0.83 (m, 1H, cyclopropyl); 0.38-0.33 (m, 1H, cyclopropyl). M/Z (M+H)⁺=346.6.

Example 51: 10-(5-Fluoro-pyridin-2-yl)-6-methyl-spiro[benzo[c]pyrido[3,2-e]azepine-7,1'-cyclopropan]-5(6H)-one

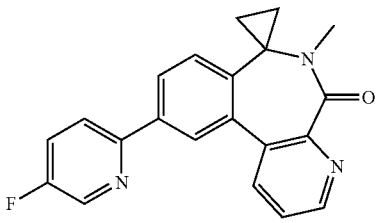 [SMILES: CN1C(=O)c2ncccc2-c2cc(-c3ccc(F)cn3)ccc2C12CC2]

Example 51 was prepared according to procedure of example 28 starting from example 49. Purification by column chromatography on silica gel (using 0% to 5% MeOH in dichloromethane as eluent) and trituration in Et₂O afforded example 51 as a white solid in 87% yield. ¹H-NMR (400 MHz, DMSO-D6): 8.73 (dd, J 4.7, 1.5 Hz, 1H, Ar); 8.69 (d, J 3.0 Hz, 1H, Ar); 8.39 (d, J 1.8 Hz, 1H, Ar); 8.25-8.20 (m, 2H, Ar); 8.13 (dd, J 8.0, 1.8 Hz, 1H, Ar); 7.87 (dt, J 8.7, 3.0 Hz, 1H, Ar); 7.67 (dd, J 8.0, 4.7 Hz, 1H, Ar); 7.60 (d, J 8.0 Hz, 1H, Ar); 2.96 (s, 3H, CH₃); 1.52-1.42 (m, 2H, cyclopropyl); 0.89-0.83 (m, 1H, cyclopropyl); 0.39-0.34 (m, 1H, cyclopropyl). M/Z (M+H)⁺=346.6.

Compound 46: {1-[4-Chloro-2-(6-methoxy-pyridin-3-yl)-phenyl]-cyclopropyl}-methyl-carbamic acid tert-butyl ester Compound 46 was prepared according to general procedure VII, starting from compound 42 and 6-methoxy-3-pyridinyl boronic acid. Purification by flash column chromatography on silica gel (using 0% to 20% ethyl acetate in cyclohexane as eluent) afforded the product as a colorless oil in 87% yield. ¹H-NMR (400 MHz, DMSO-D6): 8.10 (d, J 2.4 Hz, 1H, Ar); 7.67 (dd, J 8.5, 2.4 Hz, 1H, Ar); 7.61 (bs, 1H, Ar); 7.41 (dd, J 8.5, 2.4 Hz, 1H, Ar); 7.13 (d, J 2.4 Hz, 1H, Ar); 6.91 (d, J 8.5 Hz, 1H, Ar); 3.90 (s, 3H, CH₃); 1.98 (bs, 3H, CH₃); 1.29 (s, 11H, tBu+2H cyclopropyl); 1.05-1.01 (m, 2H, cyclopropyl). M/Z (M[³⁵Cl]+H)⁺=389.5.

Compound 47: {1-[4-Chloro-2-(2-cyano-6-methoxy-pyridin-3-yl)-phenyl]-cyclopropyl}-methyl-carbamic acid tert-butyl ester At 0° C., to a solution of compound 46 (1.0 equiv.) in dichloromethane (0.10 mol·L⁻¹) was added 3-chloroperbenzoic acid (3.2 equiv.) and the reaction mixture was stirred at room temperature for 5 days. The reaction mixture was taken in aqueous NaOH (1M) and extracted with dichloromethane. The combined extracts were dried with brine and MgSO₄, filtered off and concentrated under vacuum to give the crude pyridinyl-N-oxide in quantitative yield. M/Z (M[³⁵Cl]+H)⁺=405.6.

To a solution of the crude pyridinyl-N-oxide in anhydrous acetonitrile (0.10 mol·L⁻¹) were added triethylamine (4.0 equiv.) and trimethylsilylcyanide (6.0 equiv.). The reaction mixture was subjected to microwave irradiation at 130° C. for 30 minutes. After cooling to room temperature, the mixture was treated with an aqueous solution of NaHCO₃ and extracted twice with EtOAc. The combined extracts were dried with brine and MgSO₄, filtered off and concentrated under vacuum. Purification by flash column chromatography on silica gel (using 0% to 30% ethyl acetate in cyclohexane as eluent) afforded the product as a yellow solid in 78% yield. ¹H-NMR (400 MHz, DMSO-D6): 7.91 (d, J 8.6 Hz, 1H, Ar); 7.59 (d, J 8.5 Hz, 1H, Ar); 7.49 (dd, J 8.6, 2.3 Hz, 1H, Ar); 7.33 (d, J 2.3 Hz, 1H, Ar); 7.28 (d, J 8.5 Hz, 1H, Ar); 3.94 (s, 3H, CH₃); 1.40 (s, 3H, CH₃); 1.27 (s, 9H, tBu); 1.27-1.15 (m, 2H, cyclopropyl); 1.05-0.90 (m, 2H, cyclopropyl). M/Z (M[$^{35}$Cl]-tBu+H)⁺=358.5.

Compound 48: {1-[2-(2-Carbamoyl-6-methoxy-pyridin-3-yl)-4-chloro-phenyl]-cyclopropyl}-methyl-carbamic acid tert-butyl ester Compound 48 was prepared according to procedure of compound 45, starting from compound 47. Purification by flash column chromatography on silica gel (using 0% to 4% MeOH in dichloromethane as eluent) afforded the product as a white solid in 63% yield. M/Z (M[$^{35}$Cl]-boc+H)⁺=332.5.

Example 52: 10-chloro-3-methoxy-6-methylspiro[benzo[c]pyrido[3,2-e]azepine-7,1'-cyclopropan]-5(6H)-one

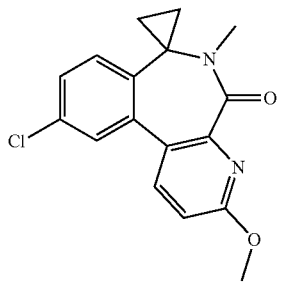 [SMILES: COc1ccc2c(n1)C(=O)N(C)C1(CC1)c1ccc(Cl)cc1-2]

To a solution of compound 48 (1.0 equiv.) in dichloroethane (0.20 mol·L⁻¹) was added TFA (0.20 mol·L⁻¹) and the reaction mixture was heated at 80° C. for 1 hour. After cooling to room temperature, the reaction mixture was treated with an aqueous solution of NaHCO₃ and extracted twice with EtOAc. The combined extracts were dried with brine and MgSO₄, filtered off and concentrated under vacuum. Purification by flash column chromatography on silica gel (0% to 3% MeOH in dichloromethane as eluent) afforded the product as a white solid in 95% yield. ¹H-NMR (400 MHz, DMSO-D6): 8.06 (d, J 8.6 Hz, 1H, Ar); 7.79 (d, J 1.7 Hz, 1H, Ar); 7.48 (d, J 8.0 Hz, 11H, Ar); 7.45 (d, J 8.0, 1.7 Hz, 1H, Ar); 7.07 (d, J 8.6 Hz, 1H, Ar); 3.94 (s, 3H, CH₃); 2.91 (s, 3H, CH₃); 1.47-1.37 (m, 2H, cyclopropyl); 0.93-0.88 (m, 1H, cyclopropyl); 0.37-0.32 (m, 1H, cyclopropyl). M/Z (M[$^{35}$Cl]+H)⁺=315.5.

Example 53: 10-(6-Fluoro-pyridin-3-yl)-3-methoxy-6-methylspiro[benzo[c]pyrido[3,2-e]azepine-7,1'-cyclopropan]-5(6H)-one

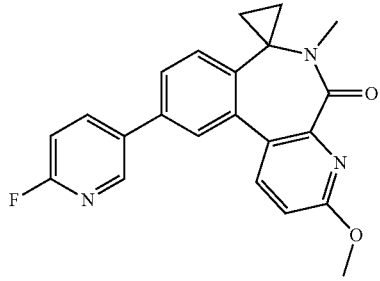 [SMILES: COc1ccc2c(n1)C(=O)N(C)C1(CC1)c1ccc(-c3ccc(F)nc3)cc1-2]

Example 53 was prepared according to general procedure IV(ii) starting from example 52 and 6-fluoro-3-pyridinylboronic acid and heating at 100° C. for 2 hours. Purification by flash column chromatography on silica gel (using 0% to 60% EtOAc in cyclohexane as eluent) and trituration in Et₂O afforded example 53 as a white solid in 80% yield. ¹H-NMR (400 MHz, DMSO-D6): 8.68 (d, J 2.6 Hz, 1H, Ar); 8.42 (dt, J 8.2, 2.6 Hz, 1H, Ar); 8.25 (d, J 8.6 Hz, 1H, Ar); 8.04 (d, J 1.7 Hz, 1H, Ar); 7.74 (dd, J 7.9, 1.7 Hz, 1H, Ar); 7.58 (d, J 7.9 Hz, 1H, Ar); 7.32 (dd, J 8.6, 2.6 Hz, 1H, Ar); 7.11 (d, J 8.6 Hz, 1H, Ar); 3.95 (s, 3H, CH₃); 2.95 (s, 3H, CH₃); 1.52-1.42 (m, 2H, cyclopropyl); 0.97-0.93 (m, 1H, cyclopropyl); 0.41-0.37 (m, 1H, cyclopropyl). M/Z (M+H)⁺=376.5.

General Procedure IX: Preparation of Intermediate C2 from Benzaldehyde Boronic Acid or Ester A2 and (Hetero)Aromatic Halide B2 (Scheme 4)

Under inert atmosphere, a mixture of benzaldehyde boronic acid or ester A2 (1.0 equiv.), (hetero)aromatic halide B2 (1.0 equiv.) and PdCl₂(dppf)·CH₂Cl₂ (0.10 equiv.) in a mixture of dioxane (0.10 mol·L) and aqueous K₃PO₄ (1.2 mol·L¹) was heated at 80° C. for 1 hour. After cooling to room temperature, the reaction mixture was hydrolysed and extracted twice with EtOAc. The organic layers were combined, washed with brine, dried over MgSO₄, concentrated and purified to afford the product.

General Procedure X: Preparation of Cyclized Compound F2 by Reductive Amination of Intermediate C2 (Scheme 4)

A mixture of intermediate C2 (1.0 equiv.), acetic acid (1.0 equiv.), primary amine E2 (5.0 equiv.) and sodium acetoxyborohydride (5.0 equiv.) in MeOH (0.20 mol·L¹) and THF (0.20 mol·L⁻¹) was stirred at room temperature overnight, then heated at 60° C. for 3 hours. Several additions of E2 and sodium acetoxyborohydride are often required until reaction completion. After cooling to room temperature, the reaction mixture was hydrolyzed with sodium bicarbonate and extracted twice with EtOAc. The organic layers were combined, washed with brine, dried over MgSO₄, concentrated and purified to afford the product.

Compound 49: 3-(5-Chloro-2-formyl-phenyl)-thiophene-2-carboxylic acid methyl ester Compound 49 was prepared according to general procedure IX, starting from compound 29 and methyl 3-bromo-

Example 54: 9-Chloro-5-methyl-5,6-dihydro-3-thia-5-aza-benzo[e]azulen-4-one

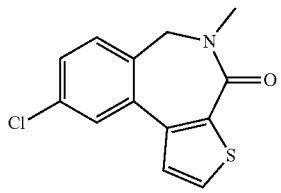 [SMILES: CN1Cc2ccc(Cl)cc2-c2ccsc2C1=O]

Example 54 was prepared according to general procedure X, starting from compound 49 and methylamine. Purification by column chromatography on silica gel (using 0% to 50% ethyl acetate in cyclohexane as eluent) afforded example 54 as a white solid in 33% yield. $^1$H-NMR (400 MHz, DMSO-D6): 7.92 (d, J 5.3 Hz, 1H, Ar); 7.81 (d, J 2.1 Hz, 1H, Ar); 7.63-7.60 (m, 2H, Ar); 7.50 (dd, J 8.1, 2.1 Hz, 1H, Ar); 4.32 (s, 2H, CH$_2$); 3.89 (s, 3H, CH$_3$). M/Z (M[$^{35}$Cl]+H)$^+$=264.5.

Example 55: 5-Methyl-9-(2-methyl-pyridin-3-yl)-5,6-dihydro-3-thia-5-aza-benzo[e]azulen-4-one

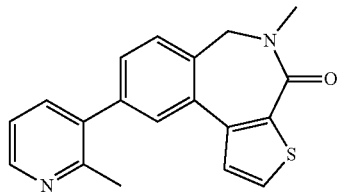 [SMILES: Cc1ncccc1-c1ccc2c(c1)-c1ccsc1C(=O)N(C)C2]

Example 55 was prepared according to general procedure IV(ii), starting from example 54 and 2-methylpyridine-3-boronic acid pinacol ester and heating at 100° C. for 1 hour. Purification by column chromatography on silica gel (using 0% to 10% MeOH in dichloromethane as eluent) afforded example 55 as a brown solid in 26% yield. $^1$H-NMR (400 MHz, DMSO-D6): 8.55 (dd, J 4.9, 1.7 Hz, 1H, Ar); 7.96 (d, J 5.2 Hz, 1H, Ar); 7.81 (d, J 1.7 Hz, 1H, Ar); 7.77-7.73 (m, 2H, Ar); 7.69 (d, J 5.2 Hz, 1H, Ar); 7.54 (dd, J 7.7, 1.7 Hz, 1H, Ar); 7.39 (dd, J 7.7, 4.9 Hz, 1H, Ar); 4.45 (s, 2H, CH$_2$); 3.20 (s, 3H, CH$_3$); 2.53 (s, 3H, CH$_3$). M/Z (M+H)$^+$=321.5.

Example 56: 3-(5-Methyl-4-oxo-5,6-dihydro-4H-3-thia-5-aza-benzo[e]azulen-9-yl)-benzonitrile

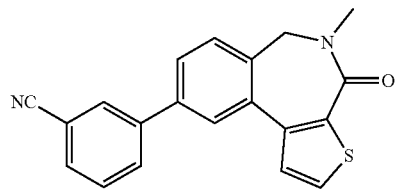 [SMILES: CN1Cc2ccc(-c3cccc(C#N)c3)cc2-c2ccsc2C1=O]

Example 56 was prepared according to general procedure IV(ii), starting from example 55 and 3-cyanophenylboronic acid. Purification by column chromatography on silica gel (using 0% to 10% MeOH in dichloromethane as eluent) and trituration in iPr$_2$O afforded example 56 as a beige solid in 47% yield. $^1$H-NMR (400 MHz, DMSO-D6): 8.34 (m, 1H, Ar); 8.14 (m, 1H, Ar); 8.08 (d, J 1.8 Hz, 1H, Ar); 7.94 (d, J 5.2 Hz, 1H, Ar); 7.86 (m, 1H, Ar); 7.82-7.79 (m, 2H, Ar); 7.72-7.67 (m, 2H, Ar); 4.38 (s, 2H, OH$_2$); 3.12 (s, 3H, CH$_3$). M/Z (M+H)$^+$=331.5.

Compound 50: 4-Iodo-1-(2-trimethylsilanyl-ethoxymethyl)-1H-pyrazole-3-carboxylic acid ethyl ester At 0° C., to a solution of 4-iodo-1H-pyrazole-3-carboxylic acid ethyl ester (1.0 equiv.) in anhydrous THF (0.20 mol·L$^{-1}$), sodium hydride (60% in oil, 1.5 equiv.) was slowly added. The reaction mixture was stirred at 0° C. for 30 minutes, before dropwise addition of 2-(trimethylsilyl)ethoxymethyl chloride (1.1 equiv.). The reaction mixture was stirred at room temperature for 3 hours before being hydrolysed with aqueous sodium bicarbonate and extracted twice with EtOAc. The organic layers were combined, washed with brine, dried over MgSO$_4$ and concentrated under vacuum. Purification by flash column chromatography on silica gel (using 0% to 3% MeOH in dichloromethane as eluent) afforded the product as a yellow oil in 96% yield. $^1$H-NMR (400 MHz, DMSO-D6): 8.25 (s, 1H, Ar); 5.46 (s, 2H, CH$_2$); 4.28 (q, J 7.3 Hz, 2H, C$\underline{H}$—CH$_3$); 3.54 (m, 2H, CH$_2$); 1.30 (t, J 7.3 Hz, 3H, CH$_2$—C$\underline{H}_3$); 0.83 (m, 2H, CH$_2$); −0.04 (s, 9H, TMS). M/Z (M+H)$^+$=397.4.

Compound 51: 4-(5-Chloro-2-formyl-phenyl)-1-(2-trimethylsilanyl-ethoxymethyl)-1H-pyrazole-3-carboxylic acid ethyl ester Compound 51 was prepared according to general procedure IX, starting from compound 29 and compound 50. Purification by column chromatography on silica gel (using 0% to 40% ethyl acetate in cyclohexane as eluent) afforded the product as a yellow oil in 46% yield. M/Z (M[$^{35}$Cl]+H)$^+$=409.5.

Compound 52: 9-Chloro-5-methyl-2-(2-trimethylsilanyl-ethoxymethyl)-5,6-dihydro-2H-2,3,5-triaza-benzo[e]azulen-4-one Compound 52 was prepared according to general procedure X, starting from compound 51 and methylamine. Purification by column chromatography on silica gel (using 0% to 2% MeOH in dichloromethane as eluent) afforded the product as a brown oil in 21% yield. $^1$H-NMR (400 MHz, DMSO-D6): 8.54 (s, 1H, Ar); 7.70 (d, J 2.1 Hz, 1H, Ar); 7.57 (d, J 8.2 Hz, 1H, Ar); 7.39 (dd, J 8.2, 2.1 Hz, 1H, Ar); 5.53 (s, 2H, CH$_2$); 4.27 (s, 2H, CH$_2$); 3.63 (m, 2H, CH$_2$); 3.07 (s, 3H, CH$_3$); 0.87 (m, 2H, CH$_2$); −0.04 (s, 9H, TMS). M/Z (M[$^{35}$Cl]+H)$^+$=378.4.

Example 57: 5-Methyl-9-(2-methyl-pyridin-3-yl)-5,6-dihydro-2H-2,3,5-triaza-benzo[e]azulen-4-one

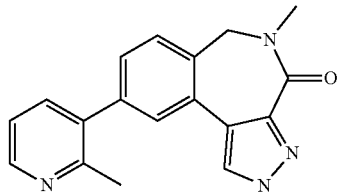 [SMILES: Cc1ncccc1-c1ccc2c(c1)-c1c[nH]nc1C(=O)N(C)C2]

Example 57 was prepared according to general procedure IV(ii), starting from compound 52 and 2-methylpyridine-3-boronic acid pinacol ester and heating at 80° C. for 2 hours. Purification by column chromatography on silica gel (using 0% to 50% ethyl acetate in cyclohexane as eluent) afforded the SEM-protected intermediate as a beige solid in 52% yield. M/Z (M+H)$^+$=435.7.

SEM removal was performed by heating the SEM-protected intermediate in a mixture of ethanol (0.02 mol·L$^{-1}$) and aqueous HCl (3N, 0.06 mol·L$^{-1}$) at 80° C. overnight. After cooling to room temperature, the reaction mixture was neutralysed with aqueous sodium bicarbonate and extracted twice with EtOAc. The organic layers were combined, washed with brine, dried over MgSO$_4$ and concentrated under vacuum. Purification by flash column chromatography on silica gel (using 0% to 10% MeOH in dichloromethane as eluent) afforded example 57 as a beige solid in 37% yield. $^1$H-NMR (400 MHz, DMSO-D6): 13.85 (bs, 1H, NH); 8.48 (dd, J 4.9, 1.7 Hz, 1H, Ar); 8.17 (bs, 1H, Ar); 7.72 (s, 1H, Ar); 7.66 (dd, J 7.7, 1.7 Hz, 1H, Ar); 7.63 (d, J 7.7 Hz, 1H, Ar); 7.36 (dd, J 7.7, 1.7 Hz, 1H, Ar); 7.32 (dd, J 7.7, 4.9 Hz, 1H, Ar); 4.36 (s, 2H, CH$_2$); 3.13 (s, 3H, CH$_3$); 2.46 (s, 3H, CH$_3$). M/Z (M+H)$^+$=305.6.

Compound 53: 3-(5-Chloro-2-formyl-phenyl)-1H-pyrrole-2-carboxylic acid methyl ester Compound 53 was prepared according to general procedure IX, starting from compound 29 and methyl 3-bromopyrrole-2-carboxylate and heating at 100° C. for 1 hour. Purification by column chromatography on silica gel (using 0% to 45% ethyl acetate in cyclohexane as eluent) afforded the product as a yellow oil in 63% yield. $^1$H-NMR (400 MHz, DMSO-D6): 12.26 (bs, 1H, NH); 9.80 (s, 1H, CHO); 7.85 (d, J 8.4 Hz, 1H, Ar); 7.57 (dd, J 8.4, 2.1 Hz, 1H, Ar); 7.47 (d, J 2.1 Hz, 1H, Ar); 7.16 (d, J 2.1 Hz, 1H, Ar); 6.39 (d, J 2.1 Hz, 1H, Ar); 3.60 (s, 3H, CH$_3$); M/Z (M[$^{35}$Cl]+H)$^+$=264.5.

Example 58: 9-Chloro-5-methyl-5,6-dihydro-3H-3,5-diaza-benzo[e]azulen-4-one

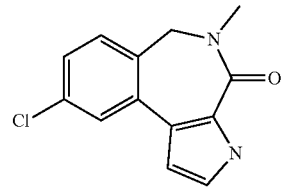 [SMILES: CN1Cc2ccc(Cl)cc2-c2cc[nH]c2C1=O]

Example 58 was prepared according to general procedure X, starting from compound 53 and methylamine. Purification by column chromatography on silica gel (using 0% to 2% MeOH in dichloromethane as eluent) afforded the product as a beige solid in 54% yield. $^1$H-NMR (400 MHz, DMSO-D6): 11.90 (bs, 1H, NH); 7.66 (d, J 2.2 Hz, 1H, Ar); 7.52 (d, J 8.1 Hz, 1H, Ar); 7.32 (dd, J 8.1, 2.2 Hz, 1H, Ar); 7.05 (t, J 2.9 Hz, 1H, Ar); 6.65 (t, J 2.6 Hz, 1H, Ar); 4.25 (s, 2H, CH$_2$); 3.06 (s, 3H, CH$_3$); M/Z (M[$^{35}$Cl]+H)$^+$=247.5.

Example 59: 5-Methyl-9-(2-methyl-pyridin-3-yl)-5,6-dihydro-3H-3,5-diaza-benzo[e]azulen-4-one

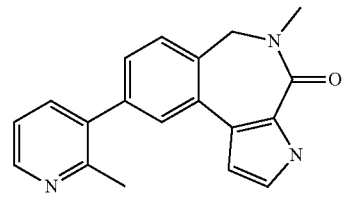 [SMILES: Cc1ncccc1-c1ccc2c(c1)-c1cc[nH]c1C(=O)N(C)C2]

Example 59 was prepared according to general procedure IV(ii), starting from example 58 and 2-methylpyridine-3-boronic acid pinacol ester and heating at 100° C. for 1 hour. Purification by column chromatography on silica gel (using 0% to 10% MeOH in dichloromethane as eluent) and trituration in Et$_2$O afforded example 59 as a brown solid in 64% yield. $^1$H-NMR (400 MHz, DMSO-D6): 11.83 (bs, 1H, NH); 8.48 (d, J 4.9, 1.7 Hz, 1H, Ar); 7.68 (d, J 7.7 Hz, 1H, Ar); 7.62 (d, J 1.7 Hz, 1H, Ar); 7.58 (d, J 7.7 Hz, 1H, Ar); 7.33 (dd, J 7.7, 4.9 Hz, 1H, Ar); 7.29 (dd, J 7.7, 1.7 Hz, 1H, Ar); 7.04 (t, J 2.8 Hz, 1H, Ar); 6.64 (t, J 2.6 Hz, 1H, Ar); 4.32 (s, 2H, CH$_2$); 3.10 (s, 3H, CH$_3$); 2.46 (s, 3H, CH$_3$). M/Z (M+H)$^+$=304.5.

Example 60: 6-Methyl-O-(2-methyl-pyridin-3-yl)-6,7-dihydro-1,6-diaza-dibenzo[a, c]cyclohepten-5-one

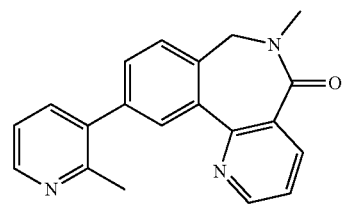 [SMILES: Cc1ncccc1-c1ccc2c(c1)-c1ncccc1C(=O)N(C)C2]

Example 60 was obtained according to synthetic route of scheme 5, in a similar way as for example 26, and starting from compound 33 and methyl 2-bromopyridine-3-carboxylate. Purification by column chromatography on silica gel (using 0% to 5% MeOH in dichloromethane as eluent) and trituration in Et$_2$O afforded example 60 as a white solid in 88% yield. $^1$H-NMR (400 MHz, DMSO-D6): 8.84 (dd, J 4.6, 1.7 Hz, 1H, Ar); 8.49 (dd, J 4.7, 1.6 Hz, 1H, Ar); 8.24 (d, J 8.0, 1.7 Hz, 1H, Ar); 7.98 (d, J 1.7 Hz, 1H, Ar); 7.70-7.66 (m, 2H, Ar); 7.58-7.55 (m, 2H, Ar); 7.32 (dd, J 7.7, 4.7 Hz, 1H, Ar); 4.39 (m, 2H, CH$_2$); 3.15 (s, 3H, CH$_3$); 2.50 (s, 3H, CH$_3$). M/Z (M+H)$^+$=316.6.

Example 61: 3-(6-Methyl-5-oxo-6,7-dihydro-5H-1,6-diaza-dibenzo[a,c]cyclohepten-10-yl)-benzonitrile

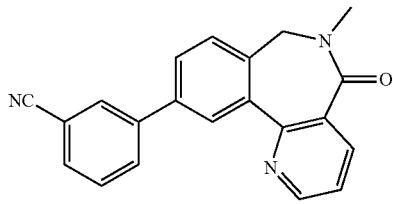 [SMILES: CN1Cc2ccc(-c3cccc(C#N)c3)cc2-c2ncccc2C1=O]

Example 61 was obtained according to synthetic route of scheme 5 in a similar way as for example 60 and using 3-benzonitrile boronic acid in the last step with general procedure IV(ii). Purification by column chromatography on silica gel (using 0% to 3% MeOH in dichloromethane as eluent) and trituration in Et$_2$O afforded example 61 as a white solid in 87% yield. $^1$H-NMR (400 MHz, DMSO-D6): 8.88 (dd, J 4.7, 1.8 Hz, 1H, Ar); 8.30 (d, J 1.8 Hz, 1H, Ar); 8.25-8.22 (m, 2H, Ar); 8.09 (m, 1H, Ar); 7.90-7.85 (m, 2H, Ar); 7.72-7.68 (m, 2H, Ar); 7.59 (dd, J 7.8, 4.7 Hz, 1H, Ar); 4.39 (m, 2H, CH$_2$); 3.13 (s, 3H, CH$_3$). M/Z (M+H)$^+$=326.5.

Example 62: 6-Methyl-10-(2-methyl-pyridin-3-yl)-6,7-dihydro-3,6-diaza-dibenzo[a, c]cyclohepten-5-one

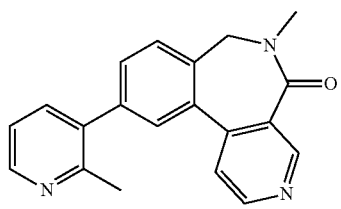 [SMILES: Cc1ncccc1-c1ccc2c(c1)-c1ccncc1C(=O)N(C)C2]

Example 62 was obtained according to synthetic route of scheme 5 in a similar way as for example 26 and starting from compound 33 and methyl 4-bromopyridine-3-carboxylate. Purification by column chromatography on silica gel (using 0% to 4% MeOH in dichloromethane as eluent) and trituration in Et$_2$O afforded example 62 as a white solid in 71% yield. $^1$H-NMR (400 MHz, DMSO-D6): 8.95 (s, 1H, Ar); 8.73 (d, J 5.3 Hz, 1H, Ar); 8.49 (dd, J 4.7, 1.6 Hz, 1H, Ar); 7.82 (d, J 1.7 Hz, 1H, Ar); 7.76-7.63 (m, 2H, Ar); 7.70 (d, J 7.7 Hz, 1H, Ar); 7.59 (dd, J 7.7, 1.7 Hz, 1H, Ar); 7.33 (dd, J 7.7, 4.7 Hz, 1H, Ar); 4.40 (d, J 14.8 Hz, 1H, CHaHb); 4.31 (d, J 14.8 Hz, 1H, CHaHb); 3.13 (s, 3H, CH$_3$); 2.50 (s, 3H, CH$_3$). M/Z (M+H)$^+$=316.5.

Example 63: 6-Methyl-10-(2-methyl-pyridin-3-yl)-6,7-dihydro-2,6-diaza-dibenzo[a, c]cyclohepten-5-one

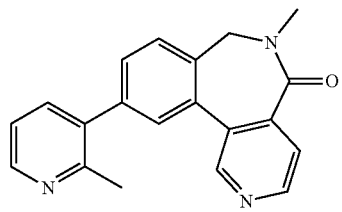 [SMILES: Cc1ncccc1-c1ccc2c(c1)-c1cnccc1C(=O)N(C)C2]

Example 63 was obtained according to synthetic route of scheme 4 in a similar way as for example 55 and starting from compound 29 and 3-bromo-isonicotinic acid ethyl ester. Purification by column chromatography on silica gel (using 0% to 5% MeOH in dichloromethane as eluent) afforded example 63 as a white solid in 44% yield. $^1$H-NMR (400 MHz, DMSO-D6): 8.99 (s, 1H, Ar); 8.73 (d, J 5.0 Hz, 1H, Ar); 8.49 (dd, J 4.8, 1.7 Hz, 1H, Ar); 7.86 (d, J 1.7 Hz, 1H, Ar); 7.77-7.74 (m, 2H, Ar); 7.70 (d, J 7.7 Hz, 1H, Ar); 7.55 (dd, J 7.7, 1.7 Hz, 1H, Ar); 7.33 (dd, J 7.7, 4.8 Hz, 1H, Ar); 4.35 (d, J 14.8 Hz, 1H, CHaHb); 4.30 (d, J 14.8 Hz, 1H, CHaHb); 3.13 (s, 3H, CH$_3$); 2.48 (s, 3H, CH$_3$). M/Z (M+H)$^+$=316.6.

Compound 54: 4-Iodo-1-methoxymethyl-1H-pyrazole-3-carboxylic acid ethyl ester

Compound 54 was prepared according to procedure of compound 50, using methoxymethyl chloride instead of 2-(trimethylsilyl)ethoxymethyl chloride. Purification by flash column chromatography on silica gel (using 0% to 50% ethyl acetate in cyclohexane as eluent) afforded the product as a colorless oil in 20% yield (minor isomer). $^1$H-NMR (400 MHz, DMSO-D6): 8.27 (s, 1H, Ar); 5.43 (s, 2H, CH$_2$); 4.29 (q, J 7.1 Hz, 2H, CH$_2$—CH$_3$); 3.25 (s, 3H, CH$_3$); 1.31 (t, J 7.1 Hz, 3H, CH$_2$—CH$_3$). NOESY $^1$H/$^1$H NMR (400 MHz, DMSO-D6): correlation observed between CH$_2$ of methoxymethyl and CH of pyrazole. M/Z (M+H)$^+$=311.5.

Compound 55: 4-{2-[(tert-Butoxycarbonyl-methyl-amino)-methyl]-5-chloro-phenyl}-1-methoxymethyl-1H-pyrazole-3-carboxylic acid ethyl ester Compound 55 was prepared according to general procedure VII, starting from compounds 54 and 33 and heating at 80° C. for 17 hours. Purification by flash column chromatography on silica gel (using 0% to 50% ethyl acetate in cyclohexane as eluent) afforded the product as a yellow oil in 50% yield. $^1$H-NMR (400 MHz, DMSO-D6): 8.12 (s, 1H, Ar); 7.46 (dd, J 8.1, 2.1 Hz, 1H, Ar); 7.25 (d, J 2.1 Hz, 1H, Ar); 7.18 (d, J 8.1 Hz, 1H, Ar); 5.48 (s, 2H, CH$_2$); 4.20 (s, 2H, CH$_2$); 4.12 (q, J 7.1 Hz, 2H, CH$_2$—CH$_3$); 3.31 (s, 3H, CH$_3$); 2.58 (s, 3H, CH$_3$); 1.37 (s, 9H, tert-butyl); 1.10 (t, J 7.1 Hz, 3H, CH$_2$—CH$_3$). M/Z (M[$^{35}$Cl]-boc+H)$^+$=338.4.

Example 64: 9-Chloro-2-methoxymethyl-5-methyl-5,6-dihydro-2H-2,3,5-triaza-benzo[e]azulen-4-one

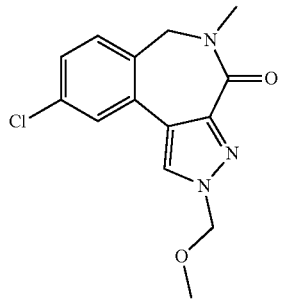 [SMILES: COCn1cc2c(n1)C(=O)N(C)Cc1ccc(Cl)cc1-2]

Example 64 was prepared according to general procedure XI, starting from compound 55 and heating at 110° C. for 4 hours. Purification by flash column chromatography on silica gel (using 0% to 1% MeOH in dichloromethane as eluent) afforded example 64 as a beige solid in 71% yield. $^1$H-NMR (400 MHz, DMSO-D6): 8.55 (s, 1H, Ar); 7.73 (d, J 2.1 Hz, 1H, Ar); 7.57 (d, J 8.0 Hz, 1H, Ar); 7.39 (dd, J 8.0, 2.1 Hz, 1H, Ar); 5.50 (s, 2H, CH$_2$); 4.29 (s, 2H, CH$_2$); 3.34 (s, 3H, CH$_3$); 3.07 (s, 3H, CH$_3$). M/Z (M[$^{35}$Cl]+H)$^+$=292.5.

Example 65: 2-Methoxymethyl-5-methyl-9-(2-methyl-pyridin-3-yl)-5,6-dihydro-2H-2,3,5-triaza-benzo[e]azulen-4-one

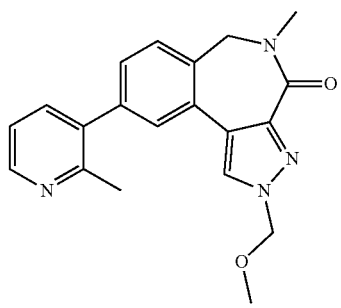 [SMILES: COCn1cc2c(n1)C(=O)N(C)Cc1ccc(-c3cccnc3C)cc1-2]

Example 65 was prepared according to general procedure IV(ii), starting from example 64 and 2-methylpyridine-3-boronic acid pinacol ester and heating at 100° C. for 1 hour. Purification by column chromatography on silica gel (using 0% to 10% MeOH in dichloromethane as eluent) and trituration in iPr$_2$O afforded example 65 as a beige solid in 73% yield. $^1$H-NMR (400 MHz, DMSO-D6): 8.53 (s, 1H, Ar); 8.48 (dd, J 4.8, 1.7 Hz, 1H, Ar); 7.68-7.66 (m, 2H, Ar); 7.63 (d, J 7.7 Hz, 1H, Ar); 7.37 (dd, J 7.7, 1.7 Hz, 1H, Ar); 7.32 (dd, J 7.7, 4.8 Hz, 1H, Ar); 5.50 (s, 2H, CH$_2$); 4.37 (s, 2H, CH$_2$); 3.33 (s, 3H, CH$_3$); 3.12 (s, 3H, CH$_3$). NOESY $^1$H/$^1$H NMR (400 MHz, DMSO-D6): correlation observed between CH$_2$ of methoxymethyl and CH of pyrazole. M/Z (M+H)$^+$=349.5.

Example 66: 2-Methoxymethyl-5-methyl-9-(6-fluoro-pyridin-3-yl)-5,6-dihydro-2H-2,3,5-triaza-benzo[e]azulen-4-one

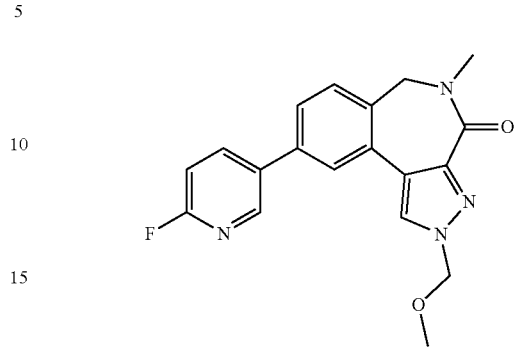

Example 66 was prepared according to general procedure IV(ii), starting from example 64 and 6-fluoro-3-pyridinylboronic acid and heating at 100° C. for 1 hour. Purification by preparative HPLC afforded example 66 as a white solid in 20% yield. $^1$H-NMR (400 MHz, DMSO-D6): 8.65 (d, J 2.0 Hz, 1H, Ar); 8.60 (s, 1H, Ar); 8.38 (dt, J 8.3, 2.7 Hz, 1H, Ar); 8.00 (d, J 1.7 Hz, 1H, Ar); 7.69 (dd, J 7.8, 1.7 Hz, 1H, Ar); 7.65 (d, J 7.8 Hz, 1H, Ar); 7.32 (dd, J 8.5, 2.7 Hz, 1H, Ar); 5.53 (s, 2H, CH$_2$); 4.35 (s, 2H, CH$_2$); 3.35 (s, 3H, CH$_3$); 3.10 (s, 3H, CH$_3$). M/Z (M+H)$^+$=353.5.

Example 67: 2-Methoxymethyl-5-methyl-9-(6-fluoro-pyridin-2-yl)-5,6-dihydro-2H-2,3,5-triaza-benzo[e]azulen-4-one

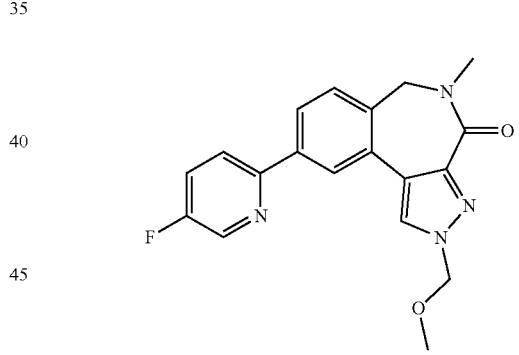

Under inert atmosphere, XPhos precatalyst (0.10 equiv.) was added to a suspension of example 64 (1.0 equiv.), bispinacolatodiboron (1.2 equiv.) and potassium acetate (2.7 equiv.) in dioxane (0.15 mol·L$^{-1}$). The reaction mixture was heated at 100° C. for 1 hour. After cooling to room temperature, the mixture was filtered off on celite with ethyl acetate and the filtrate was concentrated under vacuum. Potassium carbonate (3.0 equiv.), a solution of 2-bromo-5-fluoropyridine (1.2 equiv.) in dioxane (0.10 mol·L$^{-1}$) and PdCl$_2$(dppf).CH$_2$Cl$_2$ (0.10 equiv.) were successively added. The reaction mixture was heated at 100° C. for 15 minutes. After cooling to room temperature, the reaction mixture was treated with water and extracted twice with dichloromethane. The combined organic extracts were dried with brine and MgSO$_4$, filtered off and concentrated under vacuum. Purification by preparative HPLC afforded example 67 as a white solid in 38% yield. $^1$H-NMR (400 MHz, DMSO-D6): 8.68 (d, J 2.9 Hz, 1H, Ar); 8.61 (s, 1H, Ar); 8.30 (d, J 1.8 Hz, 1H, Ar); 8.16 (dd, J 8.8, 4.4 Hz, 1H, Ar); 8.01 (dd, J 7.9, 1.8 Hz, 1H, Ar); 7.87 (dt, J 8.8, 2.9 Hz, 1H, Ar); 7.65 (d, J 7.9 Hz, 1H, Ar); 5.53 (s, 2H, CH$_2$); 4.35 (s, 2H, CH$_2$); 3.35 (s, 3H, CH$_3$); 3.11 (s, 3H, CH$_3$). M/Z (M+H)$^+$=353.5. MP=97-99° C.

Example 68: 2,5-Dimethyl-9-(2-methyl-pyridin-3-yl)-5,6-dihydro-2H-2,3,5-triaza-benzo[e]azulen-4-one

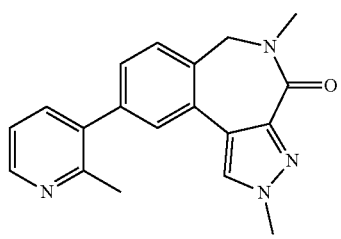 [SMILES: Cc1ncccc1-c1ccc2c(c1)-c1cn(C)nc1C(=O)N(C)C2]

At 0° C., to a solution of example 57 (1.0 equiv.) in anhydrous DMF (0.10 mol·L$^{-1}$) was added sodium hydride (60% suspension in oil, 1.3 equiv.) and the reaction mixture was stirred for 1 hour at room temperature. Iodomethane (1.1 equiv.) was added and the reaction mixture was stirred for 1 hour at room temperature before being treated with an aqueous solution of NaHCO$_3$ and extracted twice with EtOAc. The combined extracts were dried with brine and MgSO$_4$, filtered off and concentrated under vacuum. Purification by preparative HPLC afforded example 68 as a white solid in 12% yield. $^1$H-NMR (400 MHz, DMSO-D6): 8.56 (dd, J 4.8, 1.6 Hz, 1H, Ar); 8.37 (s, 1H, Ar); 7.75 (dd, J 7.5 Hz, 1.6 Hz, 1H, Ar); 7.68-7.66 (m, 2H, Ar); 7.42-7.39 (m, 2H, Ar); 4.38 (s, 2H, CH$_2$); 4.03 (s, 3H, CH$_3$); 3.16 (s, 3H, CH$_3$); 2.53 (s, 3H, COH$_3$). NOESY $^1$H/$^1$H NMR (400 MHz, DMSO-D6): correlation observed between N—CH$_3$ of pyrazole and OH of pyrazole. M/Z (M+H)$^+$=319.6.

Example 69: 3,5-Dimethyl-9-(2-methyl-pyridin-3-yl)-5,6-dihydro-2H-2,3,5-triaza-benzo[e]azulen-4-one

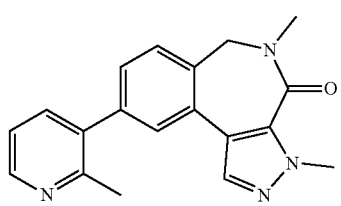 [SMILES: Cc1ncccc1-c1ccc2c(c1)-c1cnn(C)c1C(=O)N(C)C2]

Example 69 was obtained as example 68 regioisomer in the same procedure. Purification by preparative HPLC afforded example 69 as a white solid in 6% yield. $^1$H-NMR (400 MHz, DMSO-D6): 8.49 (dd, J 4.8, 1.7 Hz, 1H, Ar); 8.06 (s, 1H, Ar); 7.73 (d, J 1.7 Hz, 1H, Ar); 7.67 (dd, J 7.7, 1.7 Hz, 1H, Ar); 7.63 (d, J=7.7 Hz, 1H, Ar); 7.38 (dd, J 7.7, 1.7 Hz, 1H, Ar); 7.32 (dd, J 7.7, 4.8 Hz, 1H, Ar); 4.37 (s, 2H, CH$_2$); 4.10 (s, 3H, CH$_3$); 3.12 (s, 3H, CH$_3$); 2.47 (s, 3H, CH$_3$). NOESY $^1$H/$^1$H NMR (400 MHz, DMSO-D6): absence of correlation between N—CH$_3$ of pyrazole and CH of pyrazole. M/Z (M+H)$^+$=319.6.

Example 70: 2-Ethyl-5-methyl-9-(2-methyl-pyridin-3-yl)-5,6-dihydro-2H-2,3,5-triaza-benzo[e]azulen-4-one

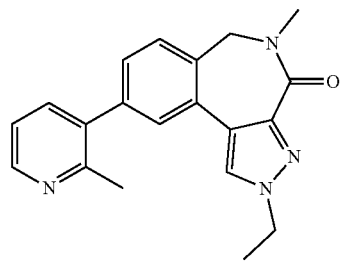 [SMILES: CCn1cc2c(n1)C(=O)N(C)Cc1ccc(-c3cccnc3C)cc1-2]

A suspension of example 57 (1.0 equiv.), potassium carbonate (2.5 equiv.) and iodoethane (1.2 equiv.) in anhydrous DMF (0.10 mol·L$^{-1}$) was heated at 100° C. for 1 hour. After cooling to room temperature, the reaction mixture was treated with an aqueous solution of NaHCO$_3$ and extracted twice with EtOAc. The combined extracts were dried with brine and MgSO$_4$, filtered and concentrated under vacuum. Purification by preparative HPLC afforded example 70 as a white solid in 3% yield. $^1$H-NMR (400 MHz, DMSO-D6): 8.57 (dd, J 4.8, 1.6 Hz, 1H, Ar); 8.38 (s, 1H, Ar); 7.82 (d, J 7.7 Hz 1H, Ar); 7.64-7.62 (m, 2H, Ar); 7.45 (dd, J 7.5, 4.8 Hz, 1H, Ar); 7.37 (dd, J 7.5, 1.6 Hz, 1H, Ar); 4.34 (s, 2H, CH$_2$); 4.26 (q, J 7.2 Hz, 2H, CH$_2$—CH$_3$); 3.11 (s, 3H, CH$_3$); 2.51 (s, 3H, CH$_3$); 1.47 (t, J 7.2 Hz, 3H, CH$_2$—CH$_3$). NOESY $^1$H/$^1$H NMR (400 MHz, DMSO-D6): correlation observed between N—CH$_2$ of pyrazole and CH of pyrazole. M/Z (M+H)+=333.6.

Example 71: 3-Ethyl-5-methyl-9-(2-methyl-pyridin-3-yl)-5,6-dihydro-2H-2,3,5-triaza-benzo[e]azulen-4-one

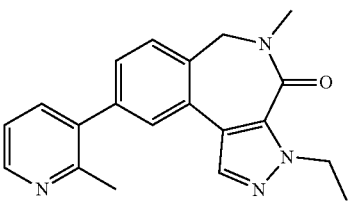 [SMILES: CCn1ncc2c1C(=O)N(C)Cc1ccc(-c3cccnc3C)cc1-2]

Example 71 was obtained as example 70 regioisomer in the same procedure. Purification by preparative HPLC afforded example 71 as a white solid in 2% yield. $^1$H-NMR (400 MHz, DMSO-D6): 8.54 (dd, J 4.8, 1.6 Hz, 1H, Ar); 8.08 (s, 1H, Ar); 7.80-7.75 (m, 2H, Ar); 7.65 (d, J 7.7 Hz, 1H, Ar); 7.43-7.39 (m, 2H, Ar); 4.49 (q, J 7.2 Hz, 2H, CH$_2$—CH$_3$); 4.37 (s, 2H, CH$_2$); 3.13 (s, 3H, CH$_3$); 2.51 (s, 3H, CH$_3$); 1.42 (t, J 7.2 Hz, 3H, CH$_2$—CH$_3$). NOESY $^1$H/$^1$H NMR (400 MHz, DMSO-D6): absence of correlation between N—CH$_2$ of pyrazole and CH of pyrazole. M/Z (M+H)$^+$=333.6.

Example 72: 2-(2-Methoxy-ethyl)-5-methyl-9-(2-methyl-pyridin-3-yl)-5,6-dihydro-2H-2,3,5-triaza-benzo[e]azulen-4-one

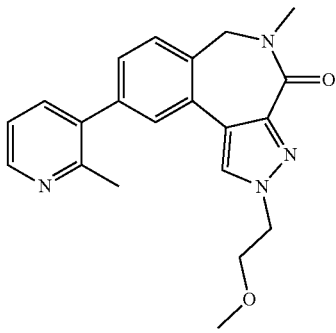 [SMILES: COCCn1cc2c(n1)C(=O)N(C)Cc1ccc(-c3cccnc3C)cc1-2]

Example 72 was prepared according to procedure of example 68, using 2-bromoethyl methyl ether instead of iodomethane. Purification by preparative HPLC afforded example 72 as a white solid in 26% yield. $^1$H-NMR (400 MHz, DMSO-D6): 8.54 (dd, J 4.8, 1.5 Hz, 1H, Ar); 8.35 (s, 1H, Ar); 7.79 (d, J 7.7 Hz 1H, Ar); 7.64-7.62 (m, 2H, Ar); 7.42 (dd, J 7.5, 4.8 Hz, 1H, Ar); 7.37 (dd, J 7.5, 1.5 Hz, 1H, Ar); 4.39 (t, J 5.0 Hz, 2H, C$\underline{H}_2$—CH$_2$); 4.34 (s, 2H, CH$_2$); 3.78 (t, J 5.0 Hz, 2H, CH—C$\underline{H}_2$); 3.26 (s, 3H, CH$_3$); 3.11 (s, 3H, CH$_3$); 2.50 (s, 3H, CH$_3$). NOESY $^1$H/$^1$H NMR (400 MHz, DMSO-D6): correlation observed between N—CH$_2$ of pyrazole and CH of pyrazole. M/Z (M+H)$^+$=363.6.

Example 72: 3-(2-Methoxy-ethyl)-5-methyl-9-(2-methyl-pyridin-3-yl)-5,6-dihydro-2H-2,3,5-triaza-benzo[e]azulen-4-one

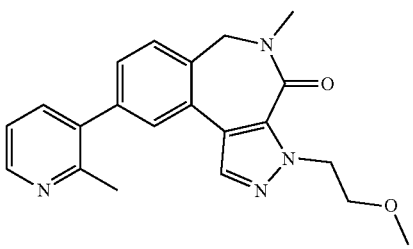 [SMILES: COCCn1ncc2c1C(=O)N(C)Cc1ccc(-c3cccnc3C)cc1-2]

Example 73 was obtained as example 72 regioisomer in the same procedure. Purification by preparative HPLC afforded example 73 as a white solid in 16% yield. $^1$H-NMR (400 MHz, DMSO-D6): 8.53 (dd, J 4.8, 1.5 Hz, 1H, Ar); 8.09 (s, 1H, Ar); 7.78-7.75 (m, 2H, Ar); 7.67-7.62 (m, 1H, Ar); 7.41-7.39 (m, 2H, Ar); 4.67 (bs, 2H, C$\underline{H}_2$—CH$_2$); 4.35 (s, 2H, CH$_2$); 3.71 (t, J 5.1 Hz, 2H, C$\underline{H}_2$—CH$_2$); 3.22 (s, 3H, CH$_3$); 3.12 (s, 3H, CH$_3$); 2.50 (s, 3H, CH$_3$). NOESY $^1$H/$^1$H NMR (400 MHz, DMSO-D6): absence of correlation between N—CH$_2$ of pyrazole and CH of pyrazole. M/Z (M+H)$^+$=363.6.

Compound 56: (3-(ethoxycarbonyl)-1-(methoxymethyl)-1H-pyrazol-4-yl)boronic acid Under dry atmosphere, at –78° C., to a solution of compound 54 (1.0 equiv.) and 2-isopropyl-4,4,5,5-tetramethyl-1,2,3-dioxaborolane (3.0 equiv.) in anhydrous THF (0.10 mol·L$^{11}$) was added butyllithium (1.6N in hexanes, 2.9 equiv.) dropwise. The reaction mixture was stirred for 2 hours at –78° C. before being hydrolyzed by an aqueous solution of K$_2$CO$_3$ and washed with EtOAc. The aqueous phase was acidified with aqueous HCl (1N) and extracted twice with dichloromethane. The combined extracts were dried with brine and MgSO$_4$, filtered off and concentrated under vacuum to afford compound 56 as a yellow oil in 93% yield. $^1$H-NMR (400 MHz, DMSO-D6): 8.12 (s, 1H, Ar); 5.43 (s, 2H, CH$_2$); 4.26 (q, J 7.2 Hz, 2H, C$\underline{H}_2$—CH$_3$); 3.23 (s, 3H, CH$_3$); 1.29 (t, J 7.2 Hz, 3H, CH$_2$—C$\underline{H}_3$). M/Z (M+H)$^+$=229.6.

Compound 57: 3-[2-(1-tert-Butoxycarbonylamino-cyclopropyl)-5-chloro-phenyl]-1-methoxymethyl-1H-pyrazole-4-carboxylic acid ethyl ester Under inert atmosphere, a suspension of compound 41 (1.0 equiv.), compound 56 (1.3 equiv.) and tetrakis(triphenylphosphine)palladium (0.1 equiv.) in aqueous potassium carbonate (1.2M, 3.0 equiv) and dioxane (0.20 mol·L$^{-1}$) was heated at 100° C. for 2 hours. After cooling to room temperature, the mixture was diluted with water and extracted twice with ethyl acetate. The combined organic phases were dried with brine and over MgSO$_4$, filtered off and concentrated under vacuum. Purification by column chromatography on silica gel (using 0% to 20% EtOAc in cyclohexane as eluent) afforded compound 57 as a light yellow solid in 92% yield. $^1$H-NMR (400 MHz, DMSO-D6): 8.07 (s, 1H, Ar); 7.66-7.63 (m, 1H, Ar); 7.33 (dd, J 8.4, 2.3 Hz, 1H, Ar); 7.13 (d, J 2.3 Hz, 1H, Ar); 6.75 (bs, 1H, NH); 5.49 (s, 2H, CH$_2$); 4.06 (q, J 7.0 Hz, 2H, CH—OH$_3$); 3.33 (s, 3H, CH$_3$); 1.30 (s, 9H, tert-butyl); 1.03 (t, J 7.0 Hz, 3H, CH$_2$—CH$_3$); 1.45-0.70 (m, 3H, cyclopropyl); 0.51-0.30 (m, 1H, cyclopropyl). M/Z (M[$^{31}$Cl]-boc+H)$^+$=350.6.

Compound 58: 9-Chloro-2-(methoxymethyl)-2H-spiro[benzo[c]pyrazolo[4,3-e]azepine-6,1'-cyclopropan]-4(5H)-one Compound 58 was prepared according to general procedure XI, starting from compound 57 and heating at 100° C. for 16 hours. Purification by column chromatography on silica gel (using 0% to 4% MeOH in dichloromethane as eluent) afforded compound 58 as a beige solid in 80% yield. $^1$H-NMR (400 MHz, DMSO-D6): 8.62 (s, 1H, NH); 8.56 (s, 1H, Ar); 7.71 (d, J 2.1 Hz, 1H, Ar); 7.37 (d, J 8.1 Hz, 1H, Ar); 7.32 (dd, J 8.1, 2.1 Hz, 1H, Ar); 5.51 (s, 2H, CH$_2$); 3.43 (s, 3H, CH$_3$); 1.40-0.71 (m, 3H, cyclopropyl); 0.48-0.18 (m, 1H, cyclopropyl). M/Z (M[$^{35}$Cl]+H)+=304.5.

Example 74: 9-Chloro-2-(methoxymethyl)-5-methyl-2H-spiro[benzo[c]pyrazolo[4,3-e]azepine-6,1'-cyclopropan]-4(5H)-one

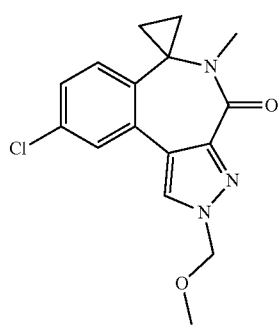 [SMILES: COCn1cc2c(n1)C(=O)N(C)C1(CC1)c1ccc(Cl)cc1-2]

Example 74 was obtained according to general procedure III, starting from compound 58 in presence of iodomethane. The reaction mixture was stirred at room temperature for 1 hour. Purification by column chromatography on silica gel (using 0% to 3% MeOH in dichloromethane as eluent) afforded the product as a white solid in 98% yield. $^1$H-NMR (400 MHz, DMSO-D6): 8.53 (s, 1H, Ar); 7.72 (d, J 2.1 Hz, 1H, Ar); 7.47 (d, J 8.2 Hz, 1H, Ar); 7.35 (dd, J 8.2, 2.1 Hz, 1H, Ar); 5.51 (s, 2H, $CH_2$); 3.33 (s, 3H, $CH_3$); 2.93 (s, 3H, $CH_3$); 1.49-1.39 (m, 2H, cyclopropyl); 0.97-0.91 (m, 1H, cyclopropyl); 0.42-0.37 (m, 1H, cyclopropyl). M/Z $(M[^{35}Cl]+H)^+=318.5$.

Example 75: 2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one

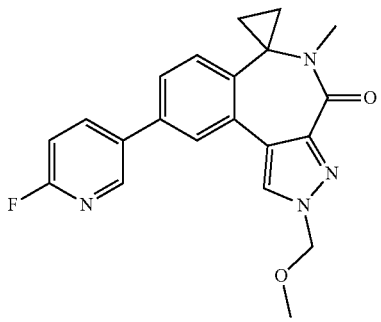 [SMILES: COCn1cc2c(n1)C(=O)N(C)C1(CC1)c1ccc(-c3ccc(F)nc3)cc1-2]

Example 75 was prepared according to general procedure IV(ii), starting from example 74 and 6-fluoro-3-pyridinyl-boronic acid and heating at 100° C. for 2 hours. Purification by column chromatography on silica gel (using EtOAc as eluent) afforded the product as a white solid in 85% yield. $^1$H-NMR (400 MHz, DMSO-D6): 8.63 (d, J 2.6 Hz, 1H, Ar); 8.59 (s, 1H, Ar); 8.36 (dt, J 8.1, 2.6 Hz, 1H, Ar); 8.00 (d, J 1.9 Hz, 1H, Ar); 7.65 (dd, J 7.8, 1.9 Hz, 1H, Ar); 7.56 (d, J 7.8 Hz, 1H, Ar); 7.31 (dd, J 8.5, 2.6 Hz, 1H, Ar); 5.54 (AB system, J 10.6 Hz, 2H, $CH_2$); 3.35 (s, 3H, $CH_3$); 2.96 (s, 3H, $CH_3$); 1.55-1.42 (m, 2H, cyclopropyl); 1.00-0.95 (m, 1H, cyclopropyl); 0.46-0.41 (m, 1H, cyclopropyl). M/Z $(M+H)^+=379.5$. MP=198-200° C.

Example 76: 2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one

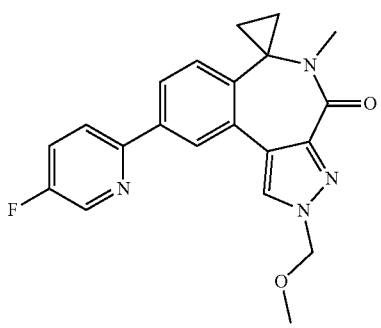 [SMILES: COCn1cc2c(n1)C(=O)N(C)C1(CC1)c1ccc(-c3ccc(F)cn3)cc1-2]

Example 76 was prepared according to procedure of example 67, starting from example 74. Purification by preparative HPLC afforded the product as a white solid in 36% yield. $^1$H-NMR (400 MHz, DMSO-D6): 8.67 (d, J 2.9 Hz, 1H, Ar); 8.60 (s, 1H, Ar); 8.29 (d, J 1.8 Hz, 1H, Ar); 8.14 (dd, J 8.8, 4.5 Hz, 1H, Ar); 7.98 (dd, J 8.0, 1.8 Hz, 1H, Ar); 7.86 (dt, J 8.8, 2.9 Hz, 1H, Ar); 7.55 (d, J 8.0 Hz, 1H, Ar); 5.54 (s, 2H, $CH_2$); 3.35 (s, 3H, $CH_3$); 2.97 (s, 3H, $CH_3$); 1.55-1.42 (m, 2H, cyclopropyl); 1.00-0.95 (m, 1H, cyclopropyl); 0.47-0.41 (m, 1H, cyclopropyl). M/Z $(M+H)^+=379.5$. MP=219-223° C.

Compound 59: 2-(5-Chloro-2-formyl-phenyl)-pyrrole-1-carboxylic acid tert-butyl ester Compound 59 was prepared according to general procedure IX, starting from 2-bromo-4-chlorobenzaldehyde and N-boc-2-pyrroleboronic acid and heating at 80° C. for 3 hours. Purification by column chromatography on silica gel (using 0% to 20% ethyl acetate in cyclohexane as eluent) afforded the product as a yellow oil in 68% yield. M/Z $(M[^{35}Cl]-boc+H)^+=205.9$.

Compound 60: 2-(5-Chloro-2-methylaminomethyl-phenyl)-pyrrole-1-carboxylic acid tert-butyl ester A solution of compound 59 (1.0 equiv.) and 40% aqueous methylamine (1.5 equiv.) in MeOH (0.1 mol·L$^{-1}$) was stirred for 2 hours at room temperature, before addition of sodium borohydride (1.5 equiv.). The reaction mixture was stirred at room temperature for 3 hours before being hydrolyzed with aqueous ammonium chloride and extracted twice with dichloromethane. The organic layers were combined, washed with brine, dried over $MgSO_4$ and concentrated under vacuum to give the product as a white solid in 90% yield. $^1$H-NMR (400 MHz, DMSO-D6): 11.20 (s, 1H, NH); 7.46 (d, J 2.2 Hz, 1H, Ar); 7.34 (dd, J 8.3, 2.2 Hz, 1H, Ar); 7.11 (d, J 8.3 Hz, 1H, Ar); 6.91 (m, 1H, Ar), 6.24 (m, 1H, Ar); 6.17 (m, 1H, Ar); 4.52 (s, 2H, $CH_2$); 2.72 (s, 3H, $CH_3$); 1.32 (s, 9H, tert-butyl).

Compound 61: [4-Chloro-2-(1H-pyrrol-2-yl)-benzyl]-methyl-amine

To a solution of compound 60 (1.0 equiv.) in dichloromethane (0.10 mol·L$^{-1}$), TFA (0.20 mol·L$^{-1}$) was added dropwise and the reaction mixture was stirred at room temperature for 30 minutes. TFA was neutralized by slow addition of aqueous sodium bicarbonate and the mixture was extracted twice with dichloromethane. The organic layers were combined, washed with brine, dried over $MgSO_4$ and concentrated under vacuum. Purification by column chromatography on silica gel (using 0% to 5% MeOH in dichloromethane as eluent) afforded the product as a brown oil in 44% yield. M/Z $(M[^{35}Cl]+H)^+=220.9$.

Example 77: 10-Chloro-6-methyl-6,7-dihydro-benzo[e]pyrrolo[1,2-c][1,3]diazepin-5-one

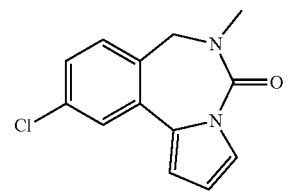

At 0° C., to a solution of compound 61 (1.0 equiv.) in anhydrous DMA (0.10 mol·L⁻¹), sodium hydride (60% in oil, 3.0 equiv.) was slowly added. The reaction mixture was stirred at 0° C. for 5 minutes, before addition of 1,1'-carbonyldiimidazole (1.5 equiv.). The reaction mixture was stirred at room temperature for 1 hour, before being hydrolyzed and extracted twice with EtOAc. The organic layers were combined, washed with brine, dried over MgSO₄ and concentrated under vacuum. Purification by trituration in pentane afforded example 77 as a white solid in 67% yield. ¹H-NMR (400 MHz, DMSO-D6): 7.70 (d, J 2.1 Hz, 1H, Ar); 7.51 (d, J 8.0 Hz, 1H, Ar); 7.46 (dd, J 3.1, 1.8 Hz, 1H, Ar); 7.36 (dd, J 8.0, 2.1 Hz, 1H, Ar); 6.79 (dd, J 3.5, 1.8 Hz, 1H, Ar), 6.39 (t, J 3.3 Hz, 1H, Ar); 4.30 (s, 2H, CH₂); 3.10 (s, 3H, CH₃); M/Z (M[³⁵Cl]+H)⁺=246.9.

Example 78: 10-(6-Fluoro-pyridin-3-yl)-6-methyl-6,7-dihydro-benzo[e]pyrrolo[1,2-c][1,3]diazepin-5-one

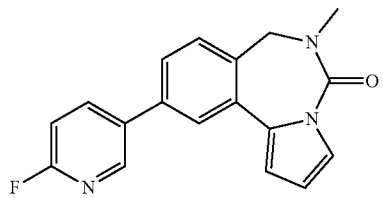 [SMILES: CN1Cc2ccc(-c3ccc(F)nc3)cc2-c2cccn2C1=O]

Example 78 was prepared according to general procedure IV(ii), starting from example 77 and 6-fluoro-3-pyridinylboronic acid. Purification by column chromatography on silica gel (using 0% to 5% MeOH in dichloromethane as eluent) and trituration in Et₂O afforded example 78 as a yellow solid in 72% yield. ¹H-NMR (400 MHz, DMSO-D6): 8.64 (d, J 2.2 Hz, 1H, Ar); 8.38 (td, J 8.2, 2.2 Hz, 1H, Ar); 7.95 (d, J 1.5 Hz, 1H, Ar); 7.65 (dd, J 7.8, 1.5 Hz, 1H, Ar); 7.60 (d, J 7.8 Hz, 1H, Ar), 7.46 (dd, J 3.1, 1.8 Hz, 1H, Ar); 7.31 (dd, J 8.6, 2.8 Hz, 1H, Ar); 6.89 (dd, J 3.5, 1.8 Hz, 1H, Ar); 6.40 (t, J 3.3 Hz, 1H, Ar); 4.36 (s, 2H, CH₂); 3.13 (s, 3H, CH₃); M/Z (M+H)⁺=308.0.

Example 79: 6-Methyl-O-(2-methyl-pyridin-3-yl)-6,7-dihydro-benzo[e]pyrrolo[1,2-c][1,3]diazepin-5-one, hydrochloride

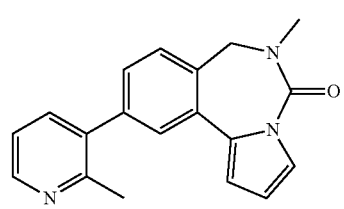 [SMILES: Cc1ncccc1-c1ccc2c(c1)-c1cccn1C(=O)N(C)C2]

Example 79 was prepared according to general procedure IV(ii), starting from example 77 and 2-methylpyridine-3-boronic acid pinacol ester. Purification by column chromatography on silica gel (using 0% to 4% MeOH in dichloromethane as eluent) afforded example 79 as a beige powder in 71% yield. Salt formation was performed according to method V(i). ¹H-NMR (400 MHz, DMSO-D6): 8.77 (dd, J 5.6, 1.3 Hz, 1H, Ar); 8.37 (d, J 7.7 Hz, 1H, Ar); 7.87 (dd, J 7.7, 5.6 Hz, 1H, Ar); 7.76 (d, J 1.7 Hz, 1H, Ar); 7.65 (d, J 7.7 Hz, 1H, Ar); 7.48 (dd, J 3.1, 1.8 Hz, 1H, Ar); 7.44 (dd, J 7.7, 1.7 Hz, 1H, Ar), 6.77 (dd, J 3.5, 1.8 Hz, 1H, Ar); 6.40 (t, J 3.3 Hz, 1H, Ar); 4.39 (s, 2H, CH₂); 3.15 (s, 3H, CH₃); 2.68 (s, 3H, CH₃); M/Z (M+H)⁺=304.0.

Compound 62: {[(2-Bromo-4-chloro-benzyl)-methyl-carbamoyl]-methyl}-carbamic acid tert-butyl ester A mixture of (2-bromo-4-chloro-benzyl)-methylamine (1 equiv., prepared as described in the procedure of compound 32), N-(tert-butoxycarbonyl)glycine (1.1 equiv.), BOP (1.1 equiv.) and diisopropylethylamine (2.2 equiv.) in dichloromethane (0.15 mol·L⁻¹) was stirred at room temperature for 5 hours. The reaction mixture was hydrolyzed and extracted twice with dichloromethane. The organic layers were combined, washed with brine, dried over MgSO₄ and concentrated under vacuum. Purification by column chromatography on silica gel (using 0% to 1% MeOH in dichloromethane as eluent) afforded the product as a yellow oil in quantitative yield. ¹H-NMR (400 MHz, DMSO-D6): 7.77 (d, J 2.0 Hz, 1H, Ar); 7.44 (dd, J 8.4, 2.0 Hz, 1H, Ar); 7.16 (d, J 8.4 Hz, 1H, Ar); 6.78 (t, J 5.6 Hz, 1H, NH); 4.50 (s, 2H, CH₂); 3.91 (d, J 5.6 Hz, 2H, CH₂); 2.98 (s, 3H, CH₃), 1.35 (s, 9H, tert-butyl). M/Z (M[³⁵C][⁸⁰Br]-Boc)⁺=293.5.

Compound 63: 8-Chloro-4-methyl-3-oxo-2,3,4,5-tetrahydro-benzo[e][1,4]diazepine-1-carboxylic acid tert-butyl ester Under inert atmosphere, a mixture of compound 62 (1.0 equiv.), cesium carbonate (1.5 equiv.) and XantPhos precatalyst (0.05 equiv.) in toluene (0.20 mol·L⁻¹) was heated at 100° C. for 16 hours. After cooling to room temperature, the reaction mixture was hydrolyzed with sodium bicarbonate and extracted twice with EtOAc. The organic layers were combined, washed with brine, dried over MgSO₄ and concentrated under vacuum. Purification by flash column chromatography on silica gel (using 0% to 100% ethyl acetate in cyclohexane as eluent) and trituration in pentane afforded the product as a yellow solid in 64% yield. ¹H-NMR (400 MHz, DMSO-D6): 7.52 (d, J 8.1 Hz, 1H, Ar); 7.42 (d, J 2.2 Hz, 1H, Ar); 7.38 (d, J 8.1, 2.2 Hz, 1H, Ar); 4.40 (s, 2H, CH₂); 4.31 (s, 2H, CH₂); 2.99 (s, 3H, CH₃); 1.37 (s, 9H, tertbutyl). M/Z (M[³⁵Cl]+H-tBu)⁺=255.5.

Compound 64: 4-Methyl-8-(2-methyl-pyridin-3-yl)-3-oxo-2,3,4,5-tetrahydro-benzo[e][1,4]diazepine-1-carboxylic acid tert-butyl ester Compound 64 was prepared according to general procedure IV(ii), starting from compound 63 and 2-methylpyridine-3-boronic acid pinacol ester. Purification by column chromatography on silica gel (using 0% to 10% MeOH in dichloromethane as eluent) afforded the product as a brown oil in 94% yield. ¹H-NMR (400 MHz, DMSO-D6): 8.48 (dd, J 4.8, 1.7 Hz, 1H, Ar); 7.60-7.58 (m, 2H, Ar); 7.35-7.30 (m, 3H, Ar); 4.46 (s, 2H, CH₂); 4.34 (s, 2H, CH₂); 3.04 (s, 3H, CH); 2.44 (s, 3H, CH₃); 1.36 (s, 9H, tertbutyl). M/Z (M+H)⁺=368.4.

Example 80: 4-Methyl-8-(2-methyl-pyridin-3-yl)-1,2,4,5-tetrahydro-benzo[e][1,4]diazepin-3-one

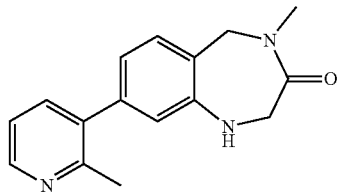 [SMILES: Cc1ncccc1-c1ccc2c(c1)NCC(=O)N(C)C2]

To a solution of compound 64 (1.0 equiv.) in dichloromethane (0.10 mol·L$^{-1}$) was added a 4N solution of HCl in dioxane (10 equiv.) and the reaction mixture was stirred at room temperature for 16 hours. The reaction mixture was neutralized with aqueous sodium bicarbonate and extracted twice with EtOAc. The organic layers were combined, washed with brine, dried over MgSO$_4$ and concentrated under vacuum to afford example 80 as a beige solid in 82% yield. $^1$H-NMR (400 MHz, DMSO-D6): 8.41 (dd, J 4.8, 1.7 Hz, 1H, Ar); 7.51 (dd, J 7.7, 1.7 Hz, 1H, Ar); 7.25 (d, J 7.7, 4.8 Hz, 1H, Ar); 7.01 (d, J 7.4 Hz, 1H, Ar); 6.46-6.44 (m, 2H, Ar); 6.31 (t, J 5.1 Hz, 1H, NH); 4.67 (s, 2H, CH$_2$); 4.09 (d, J 5.1 Hz, 2H, CH$_2$); 3.00 (s, 3H, CH$_3$); 2.47 (s, 3H, CH$_3$). M/Z (M+H)$^+$=268.6.

Example 81: 4-Methyl-8-(2-methyl-pyridin-3-yl)-1-phenethyl-1,2,4,5-tetrahydro-benzo[e][1,4]diazepin-3-one

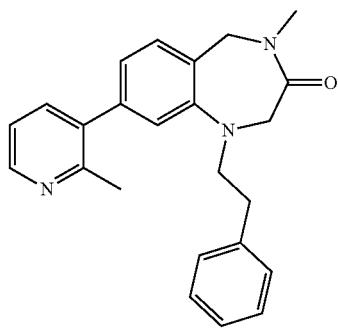 [SMILES: Cc1ncccc1-c1ccc2c(c1)N(CCc1ccccc1)CC(=O)N(C)C2]

To a solution of example 80 (1.0 equiv.), phenylacetaldehyde (3.0 equiv.) and acetic acid (1.0 equiv.) in anhydrous THF (0.20 mol·L$^{-1}$), was added sodium triacetoxyborohydride (3.0 equiv.) portionwise. The reaction mixture was stirred at room temperature for 2 days, before being hydrolyzed and extracted twice with EtOAc. The organic layers were combined, washed with brine, dried over MgSO$_4$ and concentrated under vacuum. Purification by preparative HPLC afforded example 81 as a colorless oil in 6% yield. $^1$H-NMR (400 MHz, DMSO-D6): 8.50 (dd, J 4.8, 1.8 Hz, 1H, Ar); 7.56 (dd, J 7.7, 1.8 Hz, 1H, Ar); 7.35-7.19 (m, 7H, Ar); 6.76-6.72 (m, 2H, Ar); 4.65 (s, 2H, CH$_2$); 4.14 (s, 2H, CH$_2$); 3.57 (t, J 7.5 Hz, 2H, CH$_2$); 3.02 (s, 3H, CH$_3$); 2.90 (t, J 7.5 Hz, 2H, CH$_2$); 2.47 (s, 3H, CH$_3$). M/Z (M+H)$^+$=372.5.

Example 82: 1-Benzyl-4-methyl-8-(2-methyl-pyridin-3-yl)-1,2,4,5-tetrahydro-benzo[e][1,4]diazepin-3-one

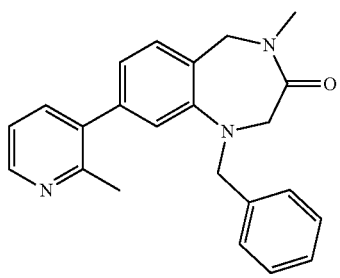 [SMILES: Cc1ncccc1-c1ccc2c(c1)N(Cc1ccccc1)CC(=O)N(C)C2]

Example 82 was prepared according to procedure of example 81, using benzaldehyde instead of phenylacetaldehyde. Purification by preparative HPLC afforded example 82 as a beige solid in 37% yield. $^1$H-NMR (400 MHz, DMSO-D6): 8.39 (dd, J 4.8, 1.7 Hz, 1H, Ar); 7.46 (dd, J 7.7, 1.8 Hz, 1H, Ar); 7.35-7.30 (m, 4H, Ar); 7.26-7.20 (m, 3H, Ar); 6.71 (dd, J 7.6, 1.6 Hz, 1H, Ar); 6.66 (d, J 1.6 Hz, 1H, Ar); 4.70 (s, 2H, CH$_2$); 4.51 (s, 2H, CH$_2$); 4.11 (s, 2H, CH$_2$); 3.01 (s, 3H, CH$_3$); 2.18 (s, 3H, CH$_3$). M/Z (M+H)$^+$=358.5.

Example 83: 4-Methyl-8-(2-methyl-pyridin-3-yl)-1-pyridin-4-yl-1,2,4,5-tetrahydro-benzo[e][1,4]diazepin-3-one

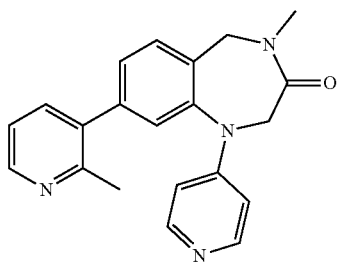 [SMILES: Cc1ncccc1-c1ccc2c(c1)N(c1ccncc1)CC(=O)N(C)C2]

Under inert atmosphere, a mixture of example 80 (1.0 equiv.), 4-bromopyridine (1.2 equiv.), potassium tertbutoxide (3.0 equiv.), Ruphos ligand (0.1 equiv.) and Pd$_2$dba$_3$ (0.1 equiv.) in dioxane (0.10 mol·L$^{-1}$) was heated at 80° C. for 1 hour. After cooling, the reaction mixture was hydrolyzed and extracted twice with EtOAc. The organic layers were combined, washed with brine, dried over MgSO$_4$ and concentrated under vacuum. Purification by preparative HPLC afforded example 83 as a brown solid in 3% yield. $^1$H-NMR (400 MHz, DMSO-D6): 8.47 (dd, J 4.8, 1.7 Hz, 1H, Ar); 8.23 (d, J 6.4 Hz, 2H, Ar); 7.70 (d, J 7.7 Hz, 1H, Ar); 7.66 (dd, J 7.7, 1.7 Hz, 1H, Ar); 7.43 (dd, J 7.7, 1.7 Hz, 1H, Ar); 7.37 (d, J 1.7 Hz, 1H, Ar); 7.31 (dd, J 7.7, 4.8 Hz, 1H, Ar); 6.78 (d, J 6.4 Hz, 2H, Ar); 4.52 (s, 2H, CH$_2$); 4.41 (s, 2H, CH$_2$); 3.00 (s, 3H, CH$_3$); 2.47 (s, 3H, CH$_3$). M/Z (M+H)$^+$=345.0.

Example 84: 4-Methyl-8-(2-methyl-pyridin-3-yl)-1-phenyl-1,2,4,5-tetrahydro-benzo[e][1,4]diazepin-3-one

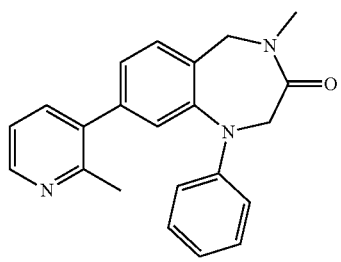 [SMILES: Cc1ncccc1-c1ccc2c(c1)N(c1ccccc1)CC(=O)N(C)C2]

Example 84 was obtained according to procedure of example 83, using bromobenzene instead of 4-bromopyridine and heating at 100° C. for 1 hour. Purification by preparative HPLC afforded example 84 as a brown solid in 10% yield. $^1$H-NMR (400 MHz, DMSO-D6): 8.41 (dd, J 4.8, 1.7 Hz, 1H, Ar); 7.52 (dd, J 7.7, 1.7 Hz, 1H, Ar); 7.46 (dd, J 7.7 Hz, 1H, Ar); 7.29-7.22 (m, 3H, Ar); 7.07 (dd, J 7.7, 1.8 Hz, 1H, Ar); 6.99-6.92 (m, 3H, Ar); 6.83 (d, J 1.8 Hz, 1H, Ar); 4.58 (s, 2H, CH$_2$); 4.42 (s, 2H, CH$_2$); 2.99 (s, 3H, CH$_3$); 2.34 (s, 3H, CH$_3$). M/Z (M+H)$^+$=344.5.

Example 85: 8-(2-Fluoro-pyridin-3-yl)-4-methyl-1,2,4,5-tetrahydro-benzo[e][1,4]diazepin-3-one

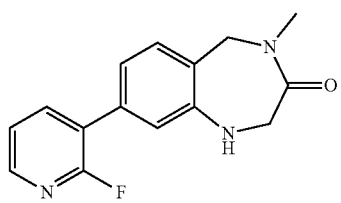 [SMILES: CN1Cc2ccc(-c3cccnc3F)cc2NCC1=O]

Example 85 was prepared in a similar sequence as for example 82, starting from compound 63 and 2-fluoro-3-pyridineboronic acid. Example 85 was isolated as an orange solid in 82% yield. $^1$H-NMR (400 MHz, DMSO-D6): 8.21-8.18 (m, 1H, Ar); 8.02-7.97 (m, 1H, Ar); 7.45-7.41 (m, 1H, Ar); 7.06 (d, J 7.7 Hz, 1H, Ar); 6.71-6.65 (m, 2H, Ar); 6.34 (bs, 1H, Ar); 4.61 (s, 2H, CH$_2$); 4.04 (s, 2H, CH$_2$); 2.93 (s, 3H, CH$_3$). M/Z (M+H)$^+$=272.0.

Example 86: 8-(2-Fluoro-pyridin-3-yl)-1,4-dimethyl-1,2,4,5-tetrahydro-benzo[e][1,4]diazepin-3-one

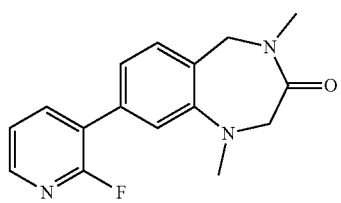 [SMILES: CN1Cc2ccc(-c3cccnc3F)cc2N(C)CC1=O]

Example 86 was prepared according to general procedure ill, starting from example 85 and iodomethane. Purification by column chromatography on silica gel (using 50% to 100% ethyl acetate in cyclohexane as eluent) afforded example 86 as a white solid in 65% yield. $^1$H-NMR (400 MHz, DMSO-D6): 8.24-8.21 (m, 1H, Ar); 8.13-8.08 (m, 1H, Ar); 7.47-7.43 (m, 1H, Ar); 7.24 (d, J 7.7 Hz, 1H, Ar); 7.00-6.96 (m, 2H, Ar); 4.60 (s, 2H, CH$_2$); 4.01 (s, 2H, CH$_2$); 2.96 (s, 3H, CH$_3$); 2.95 (s, 3H, CH$_3$). M/Z (M+H)$^+$=286.0.

Example 87: 8-(6-Fluoro-pyridin-3-yl)-4-methyl-1,2,4,5-tetrahydro-benzo[e][1,4]diazepin-3-one

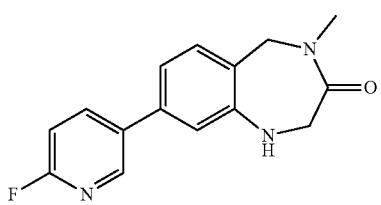 [SMILES: CN1Cc2ccc(-c3ccc(F)nc3)cc2NCC1=O]

Example 87 was prepared in a similar sequence as for example 80, starting from compound 63 and 2-fluoro-5-pyridineboronic acid. Example 87 was isolated as a red solid in 7% yield. $^1$H-NMR (400 MHz, DMSO-D6): 8.39-8.38 (m, 1H, Ar); 8.13-8.09 (m, 1H, Ar); 7.25-7.22 (m, 1H, Ar); 7.06 (d, J 8.3 Hz, 1H, Ar); 6.77-6.75 (m, 2H, Ar); 4.60 (s, 2H, CH$_2$); 4.04 (s, 2H, CH$_2$); 2.92 (s, 3H, CH$_3$). Proton for NH not observed. M/Z (M+H)$^+$=271.9.

Example 88: 1-Acetyl-8-(6-fluoro-pyridin-3-yl)-4-methy-1,2,4,5-tetrahydro-benzo[e][1,4]diazepin-3-one

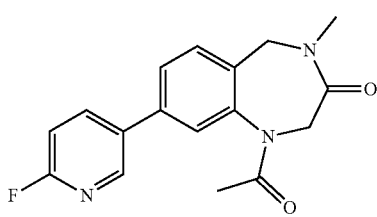 [SMILES: CC(=O)N1CC(=O)N(C)Cc2ccc(-c3ccc(F)nc3)cc21]

To a solution of example 87 (1.0 equiv.) and diisopropylethylamine (3.0 equiv.) in anhydrous DMA (0.10 mol·L$^{-1}$), acetyl chloride (3.0 equiv.) was added and the reaction mixture was stirred at room temperature for 1 hour. The reaction mixture was hydrolyzed and extracted twice with EtOAc. The organic layers were combined, washed with brine, dried over MgSO$_4$ and concentrated under vacuum. Purification by column chromatography on silica gel (using 0% to 8% MeOH in dichloromethane as eluent) afforded example 88 as a beige solid in 45% yield. $^1$H-NMR (400 MHz, DMSO-D6): 8.64 (m, 1H, Ar); 8.37 (m, 1H, Ar); 7.91 (s, 1H, Ar); 7.79 (d, J 7.5 Hz, 1H, Ar); 7.71 (d, J 7.5 Hz, 1H, Ar); 7.31 (dd, J 8.3, 2.2 Hz, 1H, Ar); 4.48 (bs, 4H, 2CH$_2$); 3.03 (s, 3H, CH$_3$); 1.90 (s, 3H, CH$_3$). M/Z (M+H)$^+$=314.0.

Example 89: Human mGluR3 Positive Allosteric Modulator Evaluation Using Ca++ Functional Assay Compounds of the present invention were tested successively for their agonist and positive allosteric modulator activities on human mGluR3 (hmGluR3) transiently overexpressed in HEK-293 cells. Compounds exert agonist activity if they are able to activate hmGluR3 by themselves, i.e., in absence of the endogenous agonist glutamate; and they exert positive allosteric modulator activity if they increase the action of the endogenous agonist glutamate.

Cell Culture and Transfection:

HEK-293 cells were maintained in Modified Eagle's Medium supplemented with 10% Foetal Calf Serum, 1% Penicillin/Streptomycin and 1% non-essential amino acids at 37° C./5% $CO_2$. Cells were co-transfected by electroporation with four DNA plasmids encoding hmGluR3, a chimeric G protein allowing redirection of the activation signal toward intracellular calcium pathway, and two glutamate transporters so as to decrease extracellular glutamate levels and avoid receptor desensitization (Brabet I et al., Neuropharmacology 37(8), 1043-51, 1998). After transfection, cells were seeded in 75 $cm^2$ culture flasks, and cultured for 24 h.

Calcium Assa EC50 determination:

Receptor activity was detected by changes in intracellular calcium measured using the fluorescent $Ca^{2+}$ sensitive dye, Fluo4AM (Molecular Probes).

The day of the assay, medium was aspirated and replaced during 3 hrs by freshly prepared buffer B (HBSS 1×, Hepes 20 mM, $MgSO_4$-$7H_2O$ 1 mM, $Na_2CO_3$ 3.3 mM, $CaCl_2$-$2H_2O$ 1.3 mM, 0.5% BSA, Probenecid 2.5 mM). Then, cells were loaded at 37° C./5% $CO_2$ for 1.5 hrs with buffer B containing 1 µM Fluo4AM, 0.1 mg/mL Pluronic Acid, 7 µg/mL Glutamate Pyruvate Transaminase and 2 mM sodium pyruvate. Afterwards cells were washed with buffer B. Cells were then detached from the 75 $cm^2$ culture flasks with Accutase® (5 min incubation at 37° C.), centrifuged (5 min at 840 rpm), resuspended in buffer B and finally seeded at a density of 30,000 cells/well in black-walled clear-bottom 384-well plates. Addition of compounds on cells and intracellular $Ca^{2+}$ measurements (excitation 485 nm, emission 525 nm) were performed by the fluorescence microplate reader FLIPR Tetra (Molecular Devices).

Agonist and positive allosteric modulator activities of compounds were consecutively evaluated on the same cells plate. Agonist activity was first tested during 10 min with the addition of compound alone on the cells. Then, the cells were stimulated by an EC50 glutamate concentration and fluorescence was recorded for additional 3 min. EC50 glutamate concentration is the concentration giving 50% of the maximal glutamate response. Agonist and/or positive allosteric modulator activity(ies) were evaluated in comparison to basal signal or signal evoked by EC50 glutamate concentration alone, respectively.

For potency determination, a dose-response test was performed using 20 concentrations of each compound of the invention. Dose-response curves were fitted using the sigmoïdal dose-response (variable slope) analysis in XLfit Scientific Curve Fitting for Excel (IDBS). EC50 of agonist/EC50 of positive allosteric modulator activity(ies) were calculated. Dose-response experiments were all performed in duplicate, two times independently.

The compounds of the present invention were found to have no agonist activity on hmGluR3. The EC50 of the hmGluR3 positive allosteric modulator compounds of the present invention are preferably 1 µM or less.

The following list represents selected examples of the compounds of the present invention showing mGluR3 positive allosteric modulator activity with an EC50>10 µM:
Examples: 6, 11 and 12.

The following list represents selected examples of the compounds of the present invention showing mGluR3 positive allosteric modulator activity with 1 µM<EC50<10 µM:
Examples: 3, 7, 22, 30, 31, 32, 43, 46, 57, 68, 72.

The following list represents selected examples of the compounds of the present invention showing mGluR3 positive allosteric modulator activity with 0.1 µM<EC50<1 µM:
Examples: 17, 18, 21, 23, 25, 26, 27, 28, 34, 36, 39, 40, 41, 44, 47, 48, 52, 55, 59, 65, 66, 67, 70.

The following list represents selected examples of the compounds of the present invention showing mGluR3 positive allosteric modulator activity with an EC50<0.1 µM:
Examples: 16, 35, 50, 51, 53, 75, 76.

The invention claimed is:
1. A compound of formula (Ia):

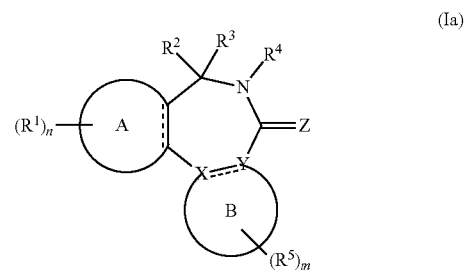

wherein:
  A is phenyl;
  B is a heteroaryl group;
  X and Y are each C;
  Z is O, S or N(—$R^Z$);
  each ═══ is independently a single bond or a double bond;
  $R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;
  each $R^1$ is independently a group -$L^1$-$R^{11}$;
  each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —NR$^{12}$COR$^{12}$, —SR$^{12}$, —SOR$^{12}$, —SO$_2$R$^{12}$, —SO$_2$NR$^{12}$R$^{12}$, and —NR$^{12}$SO$_2$R$^{12}$, and further wherein one or more —CH$_2$— units comprised in said alkylene, said alkenylene or said alkynylene are each optionally replaced by a group independently selected from —O—, —NR$^{12}$—, —CO—, —S—, —SO—, and —SO$_2$—;

each R$^{11}$ is independently selected from aryl, heteroaryl, cycloalkyl, heterocycloalkyl, cycloalkenyl, heterocycloalkenyl, halogen, C$_1$-C$_1$ haloalkyl, —CN, C$_1$-C$_{10}$ alkyl, C$_2$-C$_{10}$ alkenyl, C$_2$-C$_{10}$ alkynyl, —NR$^{12}$R$^{12}$, —OR$^{12}$, —SR$^{12}$, —SOR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, —NR$^{12}$SO$_2$R$^{12}$, and —SO$_3$R$^{12}$, wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$, and further wherein, if R$^{11}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$;

each R$^{12}$ is independently selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, wherein if R$^{12}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further if two groups R$^{12}$ are attached to the same nitrogen atom, then these two groups R$^{12}$ may also together form a C$_2$-C$_8$ alkylene;

each L$^{11}$ is independently selected from a bond, C$_1$-C$_{10}$ alkylene, C$_2$-C$_{10}$ alkenylene, and C$_2$-C$_{10}$ alkynylene, wherein one or more —CH$_2$— units comprised in said alkylene, said alkenylene or said alkynylene are each optionally replaced by a group independently selected from —O—, —NH—, —N(C$_1$-C$_{10}$ alkyl)-, —CO—, —S—, —SO—, and —SO$_2$—;

each R$^{13}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NH$_2$, —NH(C$_1$-C$_{10}$ alkyl), —N(C$_1$-C$_{10}$ alkyl)(C$_1$-C$_{10}$ alkyl), —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —SH, and —S(C$_1$-C$_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl;

n is an integer of 0 to 4;

R$^2$ and R$^3$ are mutually linked to form, together with the carbon atom that they are attached to, a cycloalkyl or a heterocycloalkyl;

R$^4$ is selected from C$_1$-C$_{10}$ alkyl, C$_2$-C$_{10}$ alkenyl, C$_2$-C$_{10}$ alkynyl, cycloalkyl, and heterocycloalkyl, wherein said alkyl, said alkenyl and said alkynyl are each optionally substituted with one or more groups independently selected from halogen, C$_1$-C$_{10}$ haloalkyl, —O—(C$_1$-C$_{10}$ haloalkyl), —CN, —OH, —O(C$_1$-C$_{10}$ alkyl), and cycloalkyl, and further wherein, if R$^4$ is cycloalkyl or heterocycloalkyl, then said cycloalkyl or said heterocycloalkyl is optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), and cycloalkyl;

each R$^5$ is independently a group -L$^5$-R$^{51}$;

each L$^5$ is independently selected from a bond, C$_1$-C$_{10}$ alkylene, C$_2$-C$_{10}$ alkenylene, and C$_2$-C$_{10}$ alkynylene, wherein said alkylene, said alkenylene and said alkynylene are each optionally substituted with one or more groups independently selected from halogen, C$_1$-C$_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—;

each R$^{51}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$, and further wherein, if R$^{51}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$;

each R$^{52}$ is independently selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, wherein if R$^{52}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further if two groups R$^{52}$ are attached to the same nitrogen atom, then these two groups R$^{52}$ may also together form a C$_2$-C$_8$ alkylene;

each L$^{51}$ is independently selected from a bond, C$_1$-C$_{10}$ alkylene, C$_2$-C$_{10}$ alkenylene, and C$_2$-C$_{10}$ alkynylene, wherein one or more —CH$_2$— units comprised in said alkylene, said alkenylene or said alkynylene are each optionally replaced by a group independently selected from —O—, —NH—, —N(C$_1$-C$_{10}$ alkyl)-, —CO—, —S—, —SO—, and —SO$_2$—;

each R$^{53}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NH$_2$, —NH(C$_1$-C$_{10}$ alkyl), —N(C$_1$-C$_{10}$ alkyl)(C$_1$-C$_{10}$ alkyl), —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —SH, and —S(C$_1$-C$_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl; and m is an integer of 0 to 3;

or a pharmaceutically acceptable salt, solvate or prodrug thereof.

2. The compound of claim 1, wherein said compound is selected from:

10-chloro-6-methylspiro[benzo[c]pyrido[3,2-e]azepine-7,1'-cyclopropan]-5(6H)-one;

10-(6-Fluoro-pyridin-3-yl)-6-methylspiro[benzo[c]pyrido[3,2-e]azepine-7,1'-cyclopropan]-5(6H)-one;

10-(5-Fluoro-pyridin-2-yl)-6-methylspiro[benzo[c]pyrido[3,2-e]azepine-7,1'-cyclopropan]-5(6H)-one;

10-chloro-3-methoxy-6-methylspiro[benzo[c]pyrido[3,2-e]azepine-7,1'-cyclopropan]-5(6H)-one;

10-(6-Fluoro-pyridin-3-yl)-3-methoxy-6-methylspiro[benzo[c]pyrido[3,2-e]azepine-7,1'-cyclopropan]-5(6H)-one;

9-Chloro-2-(methoxymethyl)-5-methyl-2H-spiro[benzo[c]pyrazolo[4,3-e]azepine-6,1'-cyclopropan]-4(5H)-one;

2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;

2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;

and pharmaceutically acceptable salts, solvates and prodrugs thereof.

3. A compound of formula (Ia):

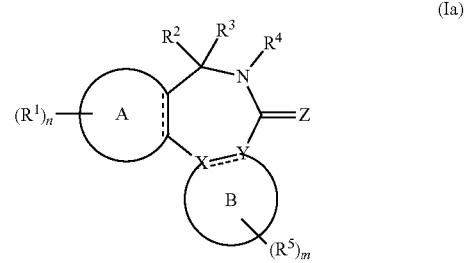

(Ia)

wherein:

A is phenyl;

B is a heteroaryl group, said heteroaryl group being different from indolyl and from 1,3-benzodioxolyl, X and Y are each C;

Z is O, S or N(—R$^Z$);

each ═ is independently a single bond or a double bond;

R$^Z$ is selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_1$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;

each $R^1$ is independently a group -$L^1$-$R^{11}$;

each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —$CH_2$— units comprised in said alkylene, said alkenylene or said alkynylene are each optionally replaced by a group independently selected from —O—, —$NR^{12}$—, —CO—, —S—, —SO—, and —$SO_2$—;

each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{12}R^{12}$, —$OR^{12}$, —$SR^{12}$, —$SOR^{12}$, —$SO_2R^{12}$, —$COR^{12}$, —$COOR^{12}$, —$OCOR^{12}$, —$CONR^{12}R^{12}$, —$NR^{12}COR^{12}$, —$SO_2NR^{12}R^{12}$, —$NR^{12}SO_2R^{12}$, and —$SO_3R^{12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$;

each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene;

each $L^{11}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—;

each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

$R^2$ and $R^3$ are mutually linked to form, together with the carbon atom that they are attached to, a cycloalkyl or a heterocycloalkyl;

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each $R^5$ is independently a group -$L^5$-$R^{51}$;

each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^5$—, —CO—, —S—, —SO—, and —SO$_2$—;

each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SOR$^{52}$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$;

each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene;

each $L^{51}$ is independently selected from a bond, $C_1$-$C_{10}$ alkylene, $C_2$-$C_{10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—;

each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; and m is an integer of 0 to 3;

or a pharmaceutically acceptable salt, solvate or prodrug thereof.

4. The compound of claim 3, wherein said compound is selected from:

10-chloro-6-methylspiro[benzo[c]pyrido[3,2-e]azepine-7,1'-cyclopropan]-5(6H)-one;

10-(6-Fluoro-pyridin-3-yl)-6-methylspiro[benzo[c]pyrido[3,2-e]azepine-7,1'-cyclopropan]-5(6H)-one;

10-(5-Fluoro-pyridin-2-yl)-6-methylspiro[benzo[c]pyrido[3,2-e]azepine-7,1'-cyclopropan]-5(6H)-one;

10-chloro-3-methoxy-6-methylspiro[benzo[c]pyrido[3,2-e]azepine-7,1-cyclopropan]-5(6H)-one;

10-(6-Fluoro-pyridin-3-yl)-3-methoxy-6-methylspiro[benzo[c]pyrido[3,2-e]azepine-7,1'-cyclopropan]-5(6H)-one;

9-Chloro-2-(methoxymethyl)-5-methyl-2H-spiro[benzo[c]pyrazolo[4,3-e]azepine-6,1'-cyclopropan]-4(5H)-one;

2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;

2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;

and pharmaceutically acceptable salts, solvates and prodrugs thereof.

5. A pharmaceutical composition comprising a compound of formula (Ia):

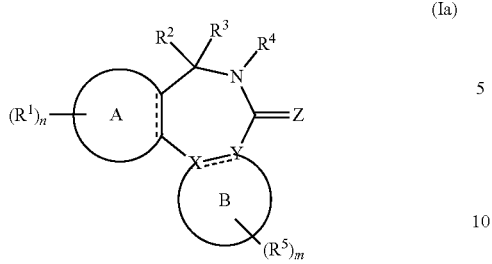

(Ia)

wherein:

A is phenyl;

B is a heteroaryl group, said heteroaryl group being different from indolyl and from 1,3-benzodioxolyl;

X and Y are each C;

Z is O, S or N(—$R^Z$);

each ═══ is independently a single bond or a double bond;

$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;

each $R^1$ is independently a group -$L^1$-$R^{11}$;

each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —$CH_2$— units comprised in said alkylene, said alkenylene or said alkynylene are each optionally replaced by a group independently selected from —O—, —$NR^{12}$—, —CO—, —S—, —SO—, and —$SO_2$—;

each $R^{11}$ is independently selected from aryl, heteroaryl, cycloalkyl, heterocycloalkyl, cycloalkenyl, heterocycloalkenyl, halogen, $C_1$-$C_1$ haloalkyl, —CN, $C_1$-$C_{10}$ alkyl, $C_2$-$C_{10}$ alkenyl, $C_2$-$C_{10}$ alkynyl, —$NR^{12}R^{12}$, —$OR^{12}$, —$SR^{12}$, —$SOR^{12}$, —$SO_2R^{12}$, —$COR^{12}$, —$COOR^{12}$, —$OCOR^{12}$, —$CONR^{12}R^{12}$, —$NR^{12}COR^{12}$, —$SO_2NR^{12}R^{12}$, —$NR^{12}SO_2R^{12}$, and —$SO_3R^{12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$;

each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene;

each $L^{11}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—;

each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

$R^2$ and $R^3$ are mutually linked to form, together with the carbon atom that they are attached to, a cycloalkyl or a heterocycloalkyl;

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each $R^5$ is independently a group -$L^5$-$R^5$1;

each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$ and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—;

each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$;

each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene;

each $L^{51}$ is independently selected from a bond, $C_1$-$C_{10}$ alkylene, $C_2$-$C_{10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—;

each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; and m is an integer of 0 to 3;

or a pharmaceutically acceptable salt, solvate or prodrug thereof;

and optionally a pharmaceutically acceptable excipient.

6. A method of treating a condition in a subject, the method comprising the administration of a compound of the general formula (Ia):

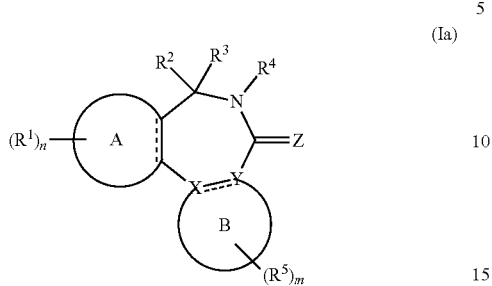

wherein:
A is phenyl;
B is a heteroaryl group;
X and Y are each C;
Z is O, S or N(—$R^Z$);
each === is independently a single bond or a double bond;
$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;
each $R^1$ is independently a group -$L^1$-$R^{11}$;
each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$ and —$NR^{12}SO_2R^{12}$, and further wherein one or more —$CH_2$— units comprised in said alkylene, said alkenylene or said alkynylene are each optionally replaced by a group independently selected from —O—, —$NR^{12}$—, —CO—, —S—, —SO—, and —$SO_2$—;
each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{12}R^{12}$, —$OR^{12}$, —$SR^{12}$, —$SOR^{12}$, —$SO_2R^{12}$, —$COR^{12}$, —$COOR^{12}$, —$OCOR^{12}$, —$CONR^{12}R^{12}$, —$NR^{12}COR^{12}$, —$SO_2NR^{12}R^{12}$, —$NR^{12}SO_2R^{12}$, and —$SO_3R^{12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$;
each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene;
each $L^{11}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—;
each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-

$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

$R^2$ and $R^3$ are mutually linked to form, together with the carbon atom that they are attached to, a cycloalkyl or a heterocycloalkyl;

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each $R^5$ is independently a group -$L^5$-$R^{51}$;

each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{52}$, —$NR^{52}R^{52}$, —$COR^{52}$, —$COOR^{52}$, —$OCOR^{52}$, —$CONR^{52}R^{52}$, —$NR^{52}COR^{52}$, —$SR^{52}$, —$SOR^{52}$, —$SO_2R^{52}$, —$SO_2NR^{52}R^{52}$ and —$NR^{52}SO_2R^{52}$, and further wherein one or more —$CH_2$— units comprised in said alkylene, said alkenylene or said alkynylene are each optionally replaced by a group independently selected from —O—, —$NR^{52}$—, —CO—, —S—, —SO—, and —$SO_2$—;

each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{52}R^{52}$, —$OR^{52}$, —$SR^{52}$, —$SOR^{52}$, —$SO_2R^{52}$, —$COR^{52}$, —$COOR^{52}$, —$OCOR^{52}$, —$CONR^{52}R^{52}$, —$NR^{52}COR^{52}$, —$SO_2NR^{52}R^{52}$, —$NR^{52}SO_2R^{52}$, and —$SO_3R^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$;

each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene;

each $L^{51}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—;

each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl; and m is an integer of 0 to 3;

or a pharmaceutically acceptable salt, solvate or prodrug thereof;

b to a subject in need thereof, wherein the condition is selected from: epilepsy; Alzheimer's disease; Parkinson's disease; Huntington's disease; Amyotrophic lateral sclerosis; schizophrenia; anxiety; and chronic pain.

7. The method of claim 6, wherein the condition is Parkinson's disease.

8. The method of claim 6, wherein B is a monocyclic 5- or 6-membered heteroaryl.

9. The method of claim 6, wherein $R^2$ and $R^3$ are mutually linked to form, together with the carbon atom that they are attached to, a $C_3$-$C_5$ cycloalkyl.

10. The method of claim 6, wherein $R^4$ is $C_1$-$C_4$ alkyl, wherein said alkyl is optionally substituted with one or more groups independently selected from halogen, $C_1$-$C_4$ haloalkyl, —O—($C_1$-$C_4$ haloalkyl), —CN, —OH and —O($C_1$-$C_4$ alkyl).

11. The method of claim 6, wherein said compound is selected from:
- 10-chloro-6-methylspiro[benzo[c]pyrido[3,2-e]azepine-7,1'-cyclopropan]-5(6H)-one;
- 10-(6-Fluoro-pyridin-3-yl)-6-methylspiro[benzo[c]pyrido[3,2-e]azepine-7,1'-cyclopropan]-5(6H)-one;
- 10-(5-Fluoro-pyridin-2-yl)-6-methylspiro[benzo[c]pyrido[3,2-e]azepine-7,1'-cyclopropan]-5(6H)-one;
- 10-chloro-3-methoxy-6-methylspiro[benzo[c]pyrido[3,2-e]azepine-7,1'-cyclopropan]-5(6H)-one;
- 10-(6-Fluoro-pyridin-3-yl)-3-methoxy-6-methylspiro[benzo[c]pyrido[3,2-e]azepine-7,1'-cyclopropan]-5(6H)-one;
- 9-Chloro-2-(methoxymethyl)-5-methyl-2H-spiro[benzo[c]pyrazolo[4,3-e]azepine-6,1'-cyclopropan]-4(5H)-one;
- 2-(Methoxymethyl)-5-methyl-9-(6-fluoro-pyridin-3-yl)-2H-spiro[benzo[c]pyrazolo[4,3-e]azepine-6,1'-cyclopropan]-4(5H)-one;
- 2-(Methoxymethyl)-5-methyl-9-(5-fluoro-pyridin-2-yl)-2H-spiro[benzo[c]pyrazolo[4,3-e]azepine-6,1'-cyclopropan]-4(5H)-one;

and pharmaceutically acceptable salts, solvates and prodrugs thereof.

12. The method of claim 6, wherein the subject to be treated is a human.

13. The method of claim 6, wherein the method comprises administering orally said compound to the subject.

14. A method of treating a condition in a subject, the method comprising the administration of a compound as defined in claim 3 or a pharmaceutical composition comprising said compound and optionally a pharmaceutically acceptable excipient, to a subject in need thereof, wherein said condition is selected from: epilepsy; Alzheimer's disease; Parkinson's disease; Huntington's disease; Amyotrophic lateral sclerosis; schizophrenia; anxiety; and chronic pain.

* * * * *

UNITED STATES PATENT AND TRADEMARK OFFICE
CERTIFICATE OF CORRECTION

PATENT NO. : 11,472,806 B2
APPLICATION NO. : 16/612866
DATED : October 18, 2022
INVENTOR(S) : Anne-Laure Blayo et al.

It is certified that error appears in the above-identified patent and that said Letters Patent is hereby corrected as shown below:

On the Title Page

Item (30), delete "17170865" and insert --17170865.4-- therefore.

In the Claims

In Claim 1, Column 255, Line 10, delete "$C_1$-$C_1$" and insert --$C_1$-$C_{10}$-- therefore.

In Claim 5, Column 263, Line 58, delete "$C_1$-$C_1$" and insert --$C_1$-$C_{10}$-- therefore.

In Claim 5, Column 265, Line 27, delete "-$L^5$-$R^5$1" and insert -- -$L^5$-$R^{51}$-- therefore.

In Claim 6, Column 271, Line 3, delete the "b" at the beginning of the line.

Signed and Sealed this
Twenty-first Day of February, 2023

Katherine Kelly Vidal
*Director of the United States Patent and Trademark Office*